(12) United States Patent
Abraham et al.

(10) Patent No.: US 7,166,716 B2
(45) Date of Patent: Jan. 23, 2007

(54) ATM RELATED KINASE ATX, NUCLEIC ACIDS ENCODING SAME AND METHODS OF USE

(75) Inventors: Robert T. Abraham, San Diego, CA (US); Diane M. Otterness, San Diego, CA (US)

(73) Assignee: The Burnham Institute, La Jolla, CA (US)

(*) Notice: Subject to any disclaimer, the term of this patent is extended or adjusted under 35 U.S.C. 154(b) by 152 days.

(21) Appl. No.: 10/456,238

(22) Filed: Jun. 6, 2003

(65) Prior Publication Data

US 2004/0248244 A1    Dec. 9, 2004

Related U.S. Application Data

(60) Provisional application No. 60/813,607, filed on Jun. 6, 2002.

(51) Int. Cl.
*C07H 21/04* (2006.01)
*C07H 21/02* (2006.01)
*C12N 1/20* (2006.01)
*C12N 15/00* (2006.01)
*C12N 9/12* (2006.01)

(52) U.S. Cl. ............... 536/23.2; 536/23.1; 435/194; 435/320.1; 435/252.3

(58) Field of Classification Search .......... 536/23.2, 536/23.1; 435/194, 252.3, 320.1
See application file for complete search history.

(56) References Cited

U.S. PATENT DOCUMENTS

| | | | |
|---|---|---|---|
| 6,344,549 B1 | 2/2002 | Loughney et al. | |
| 6,348,311 B1 | 2/2002 | Kastan et al. | |
| 2005/0032725 A1* | 2/2005 | Rao et al. ................ | 514/44 |

OTHER PUBLICATIONS

Dias et al., EST Database, Accession No. AF395444, Jul. 1994.*
Brumbaugh et al., GenEMbl Database, Accession No. AF395444, Jul. 2002.*
Abraham, "Cell cycle checkpoint signaling through the ATM and ATR kinases," *Genes Dev.* 15(17):2177-2196 (2001).
Ahn et al., "Threonine 68 phosphorylation by ataxia telangiectasia mutated is required for efficient activation of Chk2 in response to ionizing radiation," *Cancer Res.* 60(21):5934-5936 (2000).
Andegeko et al., "Nuclear retention of ATM at sites of DNA double strand breaks," *J. Biol. Chem.* 276(41):38224-38230 (2001).
Banin et al., "Enhanced phosphorylation of p53 by ATM in response to DNA damage," *Science.* 281(5383):1674-1677 (1998).
Brummelkamp et al., "A system for stable expression of short interfering RNAs in mammalian cells," *Science.* 296(5567):550-553 (2002).
Bunz et al., "Disruption of p53 in human cancer cells alters the responses to therapeutic agents," *J Clin Invest.* 104(3):263-269 (1999).

Canman et al., "Activation of the ATM kinase by ionizing radiation and phosphorylation of p53," *Science.* 281(5383):1677-1679 (1998).
Capecchi, "Altering the genome by homologous recombination," *Science.* 244(4910):1288-1292 (1989).
Chen et al., "Identification of an 11-kDa FKBP12-rapamycin-binding domain within the 289-kDa FKBP12-rapamycin-associated protein and characterization of a critical serine residue," *Proc Natl Acad Sci U S A.* 92(11):4947-4951 (1995).
Cliby et al., "Overexpression of a kinase-inactive ATR protein causes sensitivity to DNA-damaging agents and defects in cell cycle checkpoints," *EMBO J.* 17(1):159-169 (1998).
Danenberg et al. "Thymidylate synthase inhibitors," *Semin Oncol.* 26(6):621-631 (1999).
Denning et al., "Cloning of a novel phosphatidylinositol kinase-related kinase: characterization of the human SMG-1 RNA surveillance protein," *J. Biol. Chem.*, 276:22709-22714 (2001).
Dumaz et al., "Serine15 phosphorylation stimulated p53 transactivation but does not directly influence interaction with HDM2", *EMBO J.* 18(24):7002-7010 (1999).
Durocher and Jackson, "DNA-PK, ATM and ATR as sensors of DNA damage: variations on a theme?" *Curr. Opin. Cell Biol.*, 13:225-231 (2001).
Elbashir et al., "Duplexes of 21-nucleotide RNAs mediate RNA interference in cultured mammalian cells," *Nature.* 411(6836):494-498 (2001).
Giaccia et al., "The complexity of p53 modulation: emerging patterns from divergent signals," *Genes Dev.* 12(19):2973-2983 (1998).
Grem, "5-Fluorouracil: forty-plus and still ticking. A review of its preclinical and clinical development," *Invest New Drugs.* 18(4):299-313 (2000).
Hunter, T., "When is a lipid kinase not a lipid kinase? When it is a protein kinase," *Cell*, 83:1-4 (1995).

(Continued)

Primary Examiner—Maryam Monshipouri
(74) Attorney, Agent, or Firm—McDermott Will & Emery, LLP

(57) ABSTRACT

The invention provides an isolated nucleic acid molecule having substantially the same nucleotide sequence as SEQ ID NO:1. Also provided is an isolated oligonucleotide having at least 15 contiguous nucleotides of a nucleotide sequence referenced as SEQ ID NO:11. An isolated polypeptide having substantially the same amino acid sequence as SEQ ID NO:2 is further provided as well as an antibody, or antigen binding fragment thereof, which specifically binds to an ATX polypeptide and has an amino acid sequence as referenced in SEQ ID NO:2. A method for identifying an ATX-modulatory compound is additionally provided. The method consists of measuring the level of an ATX polypeptide in the presence of a test compound, wherein a difference in the level of said ATX polypeptide in the presence of said test compound compared to in the absence of said test compound indicating that said test compound is an ATX-modulatory compound, and wherein said ATX-modulatory compound is not caffeine or wortmannin.

6 Claims, 19 Drawing Sheets

OTHER PUBLICATIONS

Ishigaki et al., "Evidence for a pioneer round of mRNA translation: mRNAs subject to nonsense-mediated decay in mammalian cells are bound by CBP80 and CBP20," *Cell*, 106:607-617 (2001).

Karabinos et al., "Essential roles for four cytoplasmic intermediate filament proteins in *Caenorhabditis elegans* development," *Proc. Natl. Acad. Sci.*, 98:7863-7868 (2001).

Ko et al., "p53: puzzle and paradigm," *Genes Dev.* 10(9):1054-1072 (1996).

Lehmann and Carr, "The ataxia-telangiectasia gene: a link between checkpoint controls, neurodegeneration and cancer," *Trends in Genet.*, 11:375-377 (1995).

Melchionna et al., "Threonine 68 is required for radiation-induced phosphorylation and activation of Cds1," *Nat Cell Biol.* 2(10):762-765 (2000).

North et al., "p53 and cell-cycle control: a finger in every pie," *Pathol Biol.* 48(3):255-270 (2000).

O'Neill et al., "Utilization of oriented peptide libraries to identify substrate motifs selected by ATM," *J. Biol. Chem.* 275(30):22719-22727 (2000).

Pal et al., "Evidence that Phosphorylation of human Upf1 protein varies with intracellular location and is mediated by a wortmannin-sensitive and rapamycin-sensitive PI 3-kinase-related kinase signaling pathway," *RNA*, 7:5-15 (2001).

Powell et al., "Differential sensitivity of p53(−) and p53(+) cells to caffeine-induced radiosensitization and override of G2 delay," *Cancer Res.* 55(8):1643-1648 (1995).

Rotman and Shiloh, "ATM: from gene to function," *Human Mol. Gen.*, 7:1555-1563 (1998).

Rotman et al., "ATM: a mediator of multiple responses to genotoxic stress," *Oncogene*. 18(45):6135-6144 (1999).

Russell et al., "Abrogation of the G2 checkpoint results in differential radiosensitization of G1 checkpoint-deficient and G1 checkpoint-competent cells," *Cancer Res.* 55(8):1639-1642 (1995).

Ryan et al., "Regulation and function of the p53 tumor suppressor protein," *Curr Opin Cell Biol.* 13(3):332-337 (2001).

Sarkaria et al., "Inhibition of phosphoinositide 3-kinase related kinases by the radiosensitizing agent wortmannin," *Cancer Res.* 58(19):4375-4382 (1998).

Siliciano et al., "DNA damage induces phosphorylation of the amino terminus of p53," *Genes Dev.* 11(24):3471-3481 (1997).

Sun et al., "A mutated human homologue to yeast Upf1 protein has a dominant-negative effect on the decay of nonsense-containing mRNAs in mammalian cells," *Proc Natl Acad Sci U S A.* 95(17):10009-10014 (1998).

Tibbetts et al., "A role for ATR in the DNA damage-induced phosphorylation of p53.," *Genes Dev.* 13(2):152-157 (1999).

Tibbetts et al., "Functional interactions between BRCA1 and the checkpoint kinase ATR during genotoxic stress," *Genes Dev.* 14(23):2989-3002 (2000).

Vassilev et al., "The 400 kDa subunit of the PCAF histone acetylase complex belongs to the ATM superfamily," *Mol. Cell*, 2:869-875 (1998).

Waldman et al., "p21 is necessary for the p53-mediated G1 arrest in human cancer cells," *Cancer Res.* 55(22):5187-5190 (1995).

Walker et al., "Structural determinants of phosphoinositide 3-kinase inhibition by wortmannin, LY294002, quercetin, myricetin, and staurosporine," *Mol Cell*. 6(4):909-919 (2000).

Yamashita et al., "Human SMG-1, a novel phosphatidylinositol 3-kinase-related protein kinase, associates with components of the mRNA surveillance complex and is involved in the regulation of nonsense-mediated mRNA decay," *Genes Dev.* 15(17):2215-2228 (2001).

Yao et al., "Selective radiosensitization of p53-deficient cells by caffeine-mediated activation of p34cdc2 kinase," *Nat Med.* 2(10):1140-1143 (1996).

Zamore, P., "RNA interference: listening to the sound of silence," *Nat. Struct. Biol.*, 8:746-750 (2001).

Zhang et al., "A p53 amino-terminal nuclear export signal inhibited by DNA damage-induced phosphorylation," *Science.* 292(5523):1910-1915 (2001).

Genbank Accession No. AB007881, May 2002.

Genbank Accession No. AB040413, Dec. 2000.

Genbank Accession No. D86974, Jan. 2004.

Genbank Accession No. U32581, Jul. 1999.

Cali et al., "mRNA surveillance mitigates genetic dominance in *Caenorhabditis elegans*," *Mol Gen Genet.* 260(2-3):176-184 (1998).

Diaz-Meco et al., "Lambda-interacting protein, a novel protein that specifically interacts with the zinc finger domain of the atypical protein kinase C isotype lambda/iota and stimulates its kinase activity in vitro and in vivo," *Mol Cell Biol.* 16(1):105-14 (1996).

Hodgkin et al., "A new kind of informational suppression in the Nematode *Caenorhabditis elegans*," *Genetics* 123:301-313 (1989).

Page et al., "SMG-2 is a phosphorylated protein required for mRNA surveillance in *Caenorhabditis elegans* and related to Upf1p of yeast," *Mol Cell Biol.* 19(9):5943-5951 (1999).

Pulak et al., "mRNA surveillance by the *Caenorhabditis elegans* smg genes," *Genes Dev.* 7(10):1885-1897 (1993).

* cited by examiner

B

A

SEQUENCE LISTING

```
<160> NUMBER OF SEQ ID NOS: 11

<210> SEQ ID NO 1
<211> LENGTH: 12464
<212> TYPE: DNA
<213> ORGANISM: Homo sapiens
<220> FEATURE:
<221> NAME/KEY: CDS
<222> LOCATION: (91)...(10656)

<400> SEQUENCE: 1
caaccttcaa attcagctgt ggtgtctcgg caaaggcacg atgataccag agtccacgct         60
gacatacaga atgacgaaaa ggagagatcg atg tct tat tgt gat gag tct cga        114
                                 Met Ser Tyr Cys Asp Glu Ser Arg
                                  1               5 ctg tcg aat ctt ctt cgg agg atc acc cgg gaa gac gac aga gac cga         162
Leu Ser Asn Leu Leu Arg Arg Ile Thr Arg Glu Asp Asp Arg Asp Arg
       10                  15                  20 aga ttg gct act gta aag cag ttg aaa gaa ttt att cag caa cca gaa         210
Arg Leu Ala Thr Val Lys Gln Leu Lys Glu Phe Ile Gln Gln Pro Glu
 25                  30                  35                  40 aat aag ctg gta cta gtt aaa caa ttg gat aat atc ttg gct gct gta         258
Asn Lys Leu Val Leu Val Lys Gln Leu Asp Asn Ile Leu Ala Ala Val
                 45                  50                  55 cat gac gtg ctt aat gaa agt agc aaa ttg ctt cag gag ttg aga cag         306
His Asp Val Leu Asn Glu Ser Ser Lys Leu Leu Gln Glu Leu Arg Gln
             60                  65                  70 gag gga gct tgc tgt ctt ggc ctt ctt tgt gct tct ctg agc tat gag         354
Glu Gly Ala Cys Cys Leu Gly Leu Leu Cys Ala Ser Leu Ser Tyr Glu
         75                  80                  85 gct gag aag atc ttc aag tgg att ttt agc aaa ttt agc tca tct gca         402
Ala Glu Lys Ile Phe Lys Trp Ile Phe Ser Lys Phe Ser Ser Ser Ala
     90                  95                 100 aaa gat gaa gtt aaa ctc ctc tac tta tgt gcc acc tac aaa gca cta         450
Lys Asp Glu Val Lys Leu Leu Tyr Leu Cys Ala Thr Tyr Lys Ala Leu
105                 110                 115                 120 gag act gta gga gaa aag aaa gcc ttt tca tct gta atg cag ctt gta         498
Glu Thr Val Gly Glu Lys Lys Ala Phe Ser Ser Val Met Gln Leu Val
                125                 130                 135 atg acc agc ctg cag tct att ctt gaa aat gtg gat aca cca gaa ttg         546
Met Thr Ser Leu Gln Ser Ile Leu Glu Asn Val Asp Thr Pro Glu Leu
            140                 145                 150 ctt tgt aaa tgt gtt aag tgc att ctt ttg gtg gct cga tgt tac cct         594
Leu Cys Lys Cys Val Lys Cys Ile Leu Leu Val Ala Arg Cys Tyr Pro
        155                 160                 165 cat att ttc agc act aat ttt agg gat aca gtt gat ata tta gtt gga         642
His Ile Phe Ser Thr Asn Phe Arg Asp Thr Val Asp Ile Leu Val Gly
    170                 175                 180 tgg cat ata gat cat act cag aaa cct tcg ctc acg cag cag gta tct         690
Trp His Ile Asp His Thr Gln Lys Pro Ser Leu Thr Gln Gln Val Ser
185                 190                 195                 200
```

```
                                                              -continued ggg tgg ttg cag agt ttg gag cca ttt tgg gta gct gat ctt gca ttt        738
Gly Trp Leu Gln Ser Leu Glu Pro Phe Trp Val Ala Asp Leu Ala Phe
            205                 210                 215 tct act act ctt ctt ggt cag ttt ctg gaa gac atg gaa gca tat gct        786
Ser Thr Thr Leu Leu Gly Gln Phe Leu Glu Asp Met Glu Ala Tyr Ala
            220                 225                 230 gag gac ctc agc cat gtg gcc tct ggg gaa tca gtg gat gaa gat gtc        834
Glu Asp Leu Ser His Val Ala Ser Gly Glu Ser Val Asp Glu Asp Val
            235                 240                 245 cct cct cca tca gtg tca tta cca aag ctg gct gca ctt ctc cgg gta        882
Pro Pro Pro Ser Val Ser Leu Pro Lys Leu Ala Ala Leu Leu Arg Val
250                 255                 260 ttt agt act gtg gtg agg agc att ggg gaa cgc ttc agc cca att cgg       930
Phe Ser Thr Val Val Arg Ser Ile Gly Glu Arg Phe Ser Pro Ile Arg
265                 270                 275                 280 ggt cct cca att act gag gca tat gta aca gat gtt ctg tac aga gta       978
Gly Pro Pro Ile Thr Glu Ala Tyr Val Thr Asp Val Leu Tyr Arg Val
                285                 290                 295 atg aga tgt gtg acg gct gca aac cag gtg ttt ttt tct gag gct gtg      1026
Met Arg Cys Val Thr Ala Ala Asn Gln Val Phe Phe Ser Glu Ala Val
            300                 305                 310 ttg aca gct gct aat gag tgt gtt ggt gtt ttg ctc ggc agc ttg gat      1074
Leu Thr Ala Ala Asn Glu Cys Val Gly Val Leu Leu Gly Ser Leu Asp
            315                 320                 325 cct agc atg act ata cat tgt gac atg gtc att aca tat gga tta gac      1122
Pro Ser Met Thr Ile His Cys Asp Met Val Ile Thr Tyr Gly Leu Asp
330                 335                 340 caa ctg gag aat tgc cag act tgt ggt acc gat tat atc atc tca gtc      1170
Gln Leu Glu Asn Cys Gln Thr Cys Gly Thr Asp Tyr Ile Ile Ser Val
345                 350                 355                 360 ttg aat tta ctc acg ctg att gtt gaa cag ata aat acg aaa ctg cca      1218
Leu Asn Leu Leu Thr Leu Ile Val Glu Gln Ile Asn Thr Lys Leu Pro
                365                 370                 375 tca tca ttt gta gaa aaa ctg ttt ata cca tca tct aaa cta cta ttc      1266
Ser Ser Phe Val Glu Lys Leu Phe Ile Pro Ser Ser Lys Leu Leu Phe
            380                 385                 390 ttg cgt tat cat aaa gaa aaa gag gtt gtt gct gta gcc cat gct gtt      1314
Leu Arg Tyr His Lys Glu Lys Glu Val Val Ala Val Ala His Ala Val
            395                 400                 405 tat caa gca gtg ctc agc ttg aag aat att cct gtt ttg gag act gcc      1362
Tyr Gln Ala Val Leu Ser Leu Lys Asn Ile Pro Val Leu Glu Thr Ala
410                 415                 420 tat aag tta ata ttg gga gaa atg act tgt gcc cta aac aac ctc cta      1410
Tyr Lys Leu Ile Leu Gly Glu Met Thr Cys Ala Leu Asn Asn Leu Leu
425                 430                 435                 440 cac agt cta caa ctt cct gag gcc tgt tct gaa ata aaa cat gag gct      1458
His Ser Leu Gln Leu Pro Glu Ala Cys Ser Glu Ile Lys His Glu Ala
                445                 450                 455 ttt aag aat cat gtg ttc aat gta gac aat gca aaa ttt gta gtt ata      1506
Phe Lys Asn His Val Phe Asn Val Asp Asn Ala Lys Phe Val Val Ile
            460                 465                 470 ttt gac ctc agt gcc ctg act aca att gga aat gcc aaa aac tca cta      1554
Phe Asp Leu Ser Ala Leu Thr Thr Ile Gly Asn Ala Lys Asn Ser Leu
            475                 480                 485 ata ggg atg tgg gcg cta tct cca act gtc ttt gca ctt ctg agt aag      1602
Ile Gly Met Trp Ala Leu Ser Pro Thr Val Phe Ala Leu Leu Ser Lys
490                 495                 500 aat ctg atg att gtg cac agt gac ctg gct gtt cac ttc cct gcc att      1650
Asn Leu Met Ile Val His Ser Asp Leu Ala Val His Phe Pro Ala Ile
```

```
                    -continued
505                 510                 515                 520 cag tat gct gtg ctc tac aca ttg tat tct cat tgt acc agg cat gat    1698
Gln Tyr Ala Val Leu Tyr Thr Leu Tyr Ser His Cys Thr Arg His Asp
                525                 530                 535 cac ttt atc tct agt agc ctc agt tct tcc tct cct tct ttg ttt gat    1746
His Phe Ile Ser Ser Ser Leu Ser Ser Ser Pro Ser Leu Phe Asp
            540                 545                 550 gga gct gtg att agc act gta act acg gct aca aag aaa cat ttc tca    1794
Gly Ala Val Ile Ser Thr Val Thr Thr Ala Thr Lys Lys His Phe Ser
        555                 560                 565 att ata tta aat ctt ctg gga ata tta ctt aag aaa gat aac ctt aac    1842
Ile Ile Leu Asn Leu Leu Gly Ile Leu Leu Lys Lys Asp Asn Leu Asn
    570                 575                 580 cag gac acg agg aaa ctg tta atg act tgg gct ttg gaa gca gct gtt    1890
Gln Asp Thr Arg Lys Leu Leu Met Thr Trp Ala Leu Glu Ala Ala Val
585                 590                 595                 600 tta atg aag aag tct gaa aca tac gca cct tta ttc tct ctt ccg tct    1938
Leu Met Lys Lys Ser Glu Thr Tyr Ala Pro Leu Phe Ser Leu Pro Ser
                605                 610                 615 ttc cat aaa ttt tgc aaa ggc ctt tta gcc aac act ctc gtt gaa gat    1986
Phe His Lys Phe Cys Lys Gly Leu Leu Ala Asn Thr Leu Val Glu Asp
            620                 625                 630 gtg aat atc tgt ctg cag gca tgc agc agt cta cat gct ctg tcc tct    2034
Val Asn Ile Cys Leu Gln Ala Cys Ser Ser Leu His Ala Leu Ser Ser
        635                 640                 645 tcc ttg cca gat gat ctt tta cag aga tgt gtc gat gtt tgc cgt gtt    2082
Ser Leu Pro Asp Asp Leu Leu Gln Arg Cys Val Asp Val Cys Arg Val
    650                 655                 660 caa cta gtg cac agt gga act cgt att cga caa gca ttt gga aaa ctg    2130
Gln Leu Val His Ser Gly Thr Arg Ile Arg Gln Ala Phe Gly Lys Leu
665                 670                 675                 680 ttg aaa tca att cct tta gat gtt gtc cta agc aat aac aat cac aca    2178
Leu Lys Ser Ile Pro Leu Asp Val Val Leu Ser Asn Asn Asn His Thr
                685                 690                 695 gaa att caa gaa att tct tta gca tta aga agt cac atg agt aaa gca    2226
Glu Ile Gln Glu Ile Ser Leu Ala Leu Arg Ser His Met Ser Lys Ala
            700                 705                 710 cca agt aat aca ttc cac ccc caa gat ttc tct gat gtt att agt ttt    2274
Pro Ser Asn Thr Phe His Pro Gln Asp Phe Ser Asp Val Ile Ser Phe
        715                 720                 725 att ttg tat ggg aac tct cat aga aca ggg aag gac aat tgg ttg gaa    2322
Ile Leu Tyr Gly Asn Ser His Arg Thr Gly Lys Asp Asn Trp Leu Glu
    730                 735                 740 aga ctg ttc tat agc tgc cag aga ctg gat aag cgt gac cag tca aca    2370
Arg Leu Phe Tyr Ser Cys Gln Arg Leu Asp Lys Arg Asp Gln Ser Thr
745                 750                 755                 760 att cca cgc aat ctc ctg aag aca gat gct gtc ctt tgg cag tgg gcc    2418
Ile Pro Arg Asn Leu Leu Lys Thr Asp Ala Val Leu Trp Gln Trp Ala
                765                 770                 775 ata tgg gaa gct gca caa ttc act gtt ctt tct aag ctg aga acc cca    2466
Ile Trp Glu Ala Ala Gln Phe Thr Val Leu Ser Lys Leu Arg Thr Pro
            780                 785                 790 ctg ggc aga gct caa gac acc ttc cag aca att gaa ggt atc att cga    2514
Leu Gly Arg Ala Gln Asp Thr Phe Gln Thr Ile Glu Gly Ile Ile Arg
        795                 800                 805 agt ctc gca gct cac aca tta aac cct gat cag gat gtt agt cag tgg    2562
Ser Leu Ala Ala His Thr Leu Asn Pro Asp Gln Asp Val Ser Gln Trp
    810                 815                 820 aca act gca gac aat gat gaa ggc cat ggt aac aac caa ctt aga ctt    2610
```

|  |  |
|---|---|
| Thr Thr Ala Asp Asn Asp Glu Gly His Gly Asn Asn Gln Leu Arg Leu<br>825                        830                   835                 840 |  |
| gtt ctt ctt ctg cag tat ctg gaa aat ctg gag aaa tta atg tat aat<br>Val Leu Leu Leu Gln Tyr Leu Glu Asn Leu Glu Lys Leu Met Tyr Asn<br>                         845                   850                 855 | 2658 |
| gca tac gag gga tgt gct aat gca tta act tca cct ccc aag gtc att<br>Ala Tyr Glu Gly Cys Ala Asn Ala Leu Thr Ser Pro Pro Lys Val Ile<br>                  860                   865                 870 | 2706 |
| aga act ttt ttc tat acc aat cgc caa act tgt cag gac tgg cta acg<br>Arg Thr Phe Phe Tyr Thr Asn Arg Gln Thr Cys Gln Asp Trp Leu Thr<br>         875                   880                 885 | 2754 |
| cgg att cga ctc tcc atc atg agg gta gga ttg ttg gca ggc cag cct<br>Arg Ile Arg Leu Ser Ile Met Arg Val Gly Leu Leu Ala Gly Gln Pro<br>890                        895                   900 | 2802 |
| gca gtg aca gtg aga cat ggc ttt gac ttg ctt aca gag atg aaa aca<br>Ala Val Thr Val Arg His Gly Phe Asp Leu Leu Thr Glu Met Lys Thr<br>905                        910                   915               920 | 2850 |
| acc agc cta tct cag ggg aat gaa ttg gaa gta acc att atg atg gtg<br>Thr Ser Leu Ser Gln Gly Asn Glu Leu Glu Val Thr Ile Met Met Val<br>                  925                   930                 935 | 2898 |
| gta gaa gca tta tgt gaa ctt cat tgt cct gaa gct ata cag gga att<br>Val Glu Ala Leu Cys Glu Leu His Cys Pro Glu Ala Ile Gln Gly Ile<br>             940                   945                 950 | 2946 |
| gct gtc tgg tca tca tct att gtt gga aaa aat ctt ctg tgg att aac<br>Ala Val Trp Ser Ser Ser Ile Val Gly Lys Asn Leu Leu Trp Ile Asn<br>         955                   960                 965 | 2994 |
| tca gtg gct caa cag gct gaa ggg agg ttt gaa aag gcc tct gtg gag<br>Ser Val Ala Gln Gln Ala Glu Gly Arg Phe Glu Lys Ala Ser Val Glu<br>970                        975                   980 | 3042 |
| tac cag gaa cac ctg tgt gcc atg aca ggt gtt gat tgc tgc atc tcc<br>Tyr Gln Glu His Leu Cys Ala Met Thr Gly Val Asp Cys Cys Ile Ser<br>985                        990                   995              1000 | 3090 |
| agc ttt gac aaa tcg gtg ctc acc tta gcc aat gct ggg cgt aac agt<br>Ser Phe Asp Lys Ser Val Leu Thr Leu Ala Asn Ala Gly Arg Asn Ser<br>                 1005                1010                1015 | 3138 |
| gcc agc ccg aaa cat tct ctg aat ggt gaa tcc aga aaa act gtg ctg<br>Ala Ser Pro Lys His Ser Leu Asn Gly Glu Ser Arg Lys Thr Val Leu<br>1020                   1025                1030 | 3186 |
| tcc aaa ccg act gac tct tcc cct gag gtt ata aat tat tta gga aat<br>Ser Lys Pro Thr Asp Ser Ser Pro Glu Val Ile Asn Tyr Leu Gly Asn<br>                 1035                1040                1045 | 3234 |
| aaa gca tgt gag tgc tac atc tca att gcc gat tgg gct gct gtg cag<br>Lys Ala Cys Glu Cys Tyr Ile Ser Ile Ala Asp Trp Ala Ala Val Gln<br>1050                   1055                1060 | 3282 |
| gaa tgg cag aac gct atc cat gac ttg aaa aag agt acc agt agc act<br>Glu Trp Gln Asn Ala Ile His Asp Leu Lys Lys Ser Thr Ser Ser Thr<br>1065                   1070                1075                1080 | 3330 |
| tcc ctc aac ctg aaa gct gac ttc aac tat ata aaa tca tta agc agc<br>Ser Leu Asn Leu Lys Ala Asp Phe Asn Tyr Ile Lys Ser Leu Ser Ser<br>                 1085                1090                1095 | 3378 |
| ttt gag tct gga aaa ttt gtt gaa tgt acc gag caa tta gaa ttg tta<br>Phe Glu Ser Gly Lys Phe Val Glu Cys Thr Glu Gln Leu Glu Leu Leu<br>1100                   1105                1110 | 3426 |
| cca gga gaa aat atc aat cta ctt gct gga gga tca aaa gaa aaa ata<br>Pro Gly Glu Asn Ile Asn Leu Leu Ala Gly Gly Ser Lys Glu Lys Ile<br>1115                   1120                1125 | 3474 |
| gac atg aaa aaa ctg ctt cct aac atg tta agt ccg gat ccg agg gaa<br>Asp Met Lys Lys Leu Leu Pro Asn Met Leu Ser Pro Asp Pro Arg Glu<br>1130                   1135                1140 | 3522 |

-continued

| | | |
|---|---|---|
| ctt cag aaa tcc att gaa gtt caa ttg tta aga agt tct gtt tgt ttg<br>Leu Gln Lys Ser Ile Glu Val Gln Leu Leu Arg Ser Ser Val Cys Leu<br>1145                1150                1155                1160 | | 3570 |
| gca act gct tta aac ccg ata gaa caa gat cag aag tgg cag tct ata<br>Ala Thr Ala Leu Asn Pro Ile Glu Gln Asp Gln Lys Trp Gln Ser Ile<br>                1165                1170                1175 | | 3618 |
| act gaa aat gtg gta aag tac ttg aag caa aca tcc cgc atc gct att<br>Thr Glu Asn Val Val Lys Tyr Leu Lys Gln Thr Ser Arg Ile Ala Ile<br>1180                1185                1190 | | 3666 |
| gga cct ctg aga ctt tct act tta aca gtt tca cag tct ttg cca gtt<br>Gly Pro Leu Arg Leu Ser Thr Leu Thr Val Ser Gln Ser Leu Pro Val<br>                1195                1200                1205 | | 3714 |
| cta agt acc ttg cag ctg tat tgc tca tct gct ttg gag aac aca gtt<br>Leu Ser Thr Leu Gln Leu Tyr Cys Ser Ser Ala Leu Glu Asn Thr Val<br>1210                1215                1220 | | 3762 |
| tct aac aga ctt tca aca gag gac tgt ctt att cca ctc ttc agt gaa<br>Ser Asn Arg Leu Ser Thr Glu Asp Cys Leu Ile Pro Leu Phe Ser Glu<br>1225                1230                1235                1240 | | 3810 |
| gct tta cgt tca tgt aaa cag cat gac gtg agg cca tgg atg cag gca<br>Ala Leu Arg Ser Cys Lys Gln His Asp Val Arg Pro Trp Met Gln Ala<br>                1245                1250                1255 | | 3858 |
| tta agg tat act atg tac cag aat cag ttg ttg gag aaa att aaa gaa<br>Leu Arg Tyr Thr Met Tyr Gln Asn Gln Leu Leu Glu Lys Ile Lys Glu<br>1260                1265                1270 | | 3906 |
| caa aca gtc cca att aga agc cat ctc atg gaa tta ggt cta aca gca<br>Gln Thr Val Pro Ile Arg Ser His Leu Met Glu Leu Gly Leu Thr Ala<br>                1275                1280                1285 | | 3954 |
| gca aaa ttt gct aga aaa cga ggg aat gtg tcc ctt gca aca aga ctg<br>Ala Lys Phe Ala Arg Lys Arg Gly Asn Val Ser Leu Ala Thr Arg Leu<br>1290                1295                1300 | | 4002 |
| ctg gca cag tgc agt gaa gtt cag ctg gga aag acc act act gca cag<br>Leu Ala Gln Cys Ser Glu Val Gln Leu Gly Lys Thr Thr Thr Ala Gln<br>1305                1310                1315                1320 | | 4050 |
| gat tta gtc caa cat ttt aaa aaa cta tca acc caa ggt caa gtg gat<br>Asp Leu Val Gln His Phe Lys Lys Leu Ser Thr Gln Gly Gln Val Asp<br>                1325                1330                1335 | | 4098 |
| gaa aaa tgg ggg ccc gaa ctt gat att gaa aaa acc aaa ttg ctt tat<br>Glu Lys Trp Gly Pro Glu Leu Asp Ile Glu Lys Thr Lys Leu Leu Tyr<br>                1340                1345                1350 | | 4146 |
| aca gca ggc cag tca aca cat gca atg gaa atg ttg agt tct tgt gcc<br>Thr Ala Gly Gln Ser Thr His Ala Met Glu Met Leu Ser Ser Cys Ala<br>                1355                1360                1365 | | 4194 |
| ata tct ttc tgc aag tct gtg aaa gct gaa tat gca gtt gct aaa tca<br>Ile Ser Phe Cys Lys Ser Val Lys Ala Glu Tyr Ala Val Ala Lys Ser<br>1370                1375                1380 | | 4242 |
| att ctg aca ctg gct aaa tgg atc cag gca gaa tgg aaa gag att tca<br>Ile Leu Thr Leu Ala Lys Trp Ile Gln Ala Glu Trp Lys Glu Ile Ser<br>1385                1390                1395                1400 | | 4290 |
| gga cag ctg aaa cag gtt tac aga gct cag cac caa cag aac ttc aca<br>Gly Gln Leu Lys Gln Val Tyr Arg Ala Gln His Gln Gln Asn Phe Thr<br>                1405                1410                1415 | | 4338 |
| ggt ctt tct act ttg tct aaa aac ata ctc act cta ata gaa ctg cca<br>Gly Leu Ser Thr Leu Ser Lys Asn Ile Leu Thr Leu Ile Glu Leu Pro<br>1420                1425                1430 | | 4386 |
| tct gtt aat acg atg gaa gaa gag tat cct cgg atc gag agt gaa tct<br>Ser Val Asn Thr Met Glu Glu Glu Tyr Pro Arg Ile Glu Ser Glu Ser<br>                1435                1440                1445 | | 4434 |
| aca gtg cat att gga gtt gga gaa cct gac ttc att ttg gga cag ttg<br>Thr Val His Ile Gly Val Gly Glu Pro Asp Phe Ile Leu Gly Gln Leu<br>1450                1455                1460 | | 4482 |

```
tat cac ctg tct tca gta cag gca cct gaa gta gcc aaa tct tgg gca    4530
Tyr His Leu Ser Ser Val Gln Ala Pro Glu Val Ala Lys Ser Trp Ala
1465                1470                1475                1480 gcg ttg gcc agc tgg gct tat agg tgg ggc aga aag gtg gtt gac aat    4578
Ala Leu Ala Ser Trp Ala Tyr Arg Trp Gly Arg Lys Val Val Asp Asn
                1485                1490                1495 gcc agt cag gga gaa ggt gtt cgt ctg ctg cct aga gaa aaa tct gaa    4626
Ala Ser Gln Gly Glu Gly Val Arg Leu Leu Pro Arg Glu Lys Ser Glu
            1500                1505                1510 gtt cag aat cta ctt cca gac act ata act gag gaa gag aaa gag aga    4674
Val Gln Asn Leu Leu Pro Asp Thr Ile Thr Glu Glu Glu Lys Glu Arg
        1515                1520                1525 ata tat ggt att ctt gga cag gct gtg tgt cgg ccg gcg ggg att cag    4722
Ile Tyr Gly Ile Leu Gly Gln Ala Val Cys Arg Pro Ala Gly Ile Gln
    1530                1535                1540 gat gaa gat ata aca ctt cag ata act gag agt gaa gac aac gaa gaa    4770
Asp Glu Asp Ile Thr Leu Gln Ile Thr Glu Ser Glu Asp Asn Glu Glu
1545                1550                1555                1560 gat gac atg gtt gat gtt atc tgg cgt cag ttg ata tca agc tgc cca    4818
Asp Asp Met Val Asp Val Ile Trp Arg Gln Leu Ile Ser Ser Cys Pro
                1565                1570                1575 tgg ctt tca gaa ctt gat gaa agt gca act gaa gga gtt att aaa gtg    4866
Trp Leu Ser Glu Leu Asp Glu Ser Ala Thr Glu Gly Val Ile Lys Val
            1580                1585                1590 tgg agg aaa gtt gta gat aga ata ttc agc ctg tac aaa ctc tct tgc    4914
Trp Arg Lys Val Val Asp Arg Ile Phe Ser Leu Tyr Lys Leu Ser Cys
        1595                1600                1605 agt gca tac ttt act ttc ctt aaa ctc aac gct ggt caa att cct tta    4962
Ser Ala Tyr Phe Thr Phe Leu Lys Leu Asn Ala Gly Gln Ile Pro Leu
    1610                1615                1620 gat gag gat gac cct agg ctg cat tta agt cac aga gtg gaa cag agc    5010
Asp Glu Asp Asp Pro Arg Leu His Leu Ser His Arg Val Glu Gln Ser
1625                1630                1635                1640 act gat gac atg att gtg atg gcc aca ttg cgc ctg ctg cgg ttg ctc    5058
Thr Asp Asp Met Ile Val Met Ala Thr Leu Arg Leu Leu Arg Leu Leu
                1645                1650                1655 gtg aag cat gct ggt gag ctt cgg cag tat ctg gag cac ggc ttg gag    5106
Val Lys His Ala Gly Glu Leu Arg Gln Tyr Leu Glu His Gly Leu Glu
            1660                1665                1670 aca aca ccc act gca cca tgg aga gga att att ccg caa ctt ttc tca    5154
Thr Thr Pro Thr Ala Pro Trp Arg Gly Ile Ile Pro Gln Leu Phe Ser
        1675                1680                1685 cgc tta aac cac cct gaa gtg tat gtg cgc caa agt att tgt aac ctt    5202
Arg Leu Asn His Pro Glu Val Tyr Val Arg Gln Ser Ile Cys Asn Leu
    1690                1695                1700 ctc tgc cgt gtg gct caa gat tcc cca cat ctc ata ttg tat cct gca    5250
Leu Cys Arg Val Ala Gln Asp Ser Pro His Leu Ile Leu Tyr Pro Ala
1705                1710                1715                1720 ata gtg ggt acc ata tcg ctt agt agt gaa tcc cag gct tca gga aat    5298
Ile Val Gly Thr Ile Ser Leu Ser Ser Glu Ser Gln Ala Ser Gly Asn
                1725                1730                1735 aaa ttt tcc act gca att cca act tta ctt ggc aat att caa gga gaa    5346
Lys Phe Ser Thr Ala Ile Pro Thr Leu Leu Gly Asn Ile Gln Gly Glu
            1740                1745                1750 gaa ttg ctg gtt tct gaa tgt gag gga gga agt cct cct gca tct cag    5394
Glu Leu Leu Val Ser Glu Cys Glu Gly Gly Ser Pro Pro Ala Ser Gln
        1755                1760                1765 gat agc aat aag gat gaa cct aaa agt gga tta aat gaa gac caa gcc    5442
Asp Ser Asn Lys Asp Glu Pro Lys Ser Gly Leu Asn Glu Asp Gln Ala
```

-continued

|  | 1770 |  |  |  | 1775 |  |  |  | 1780 |  |  |  |
|---|---|---|---|---|---|---|---|---|---|---|---|---|
| atg | atg | cag | gat | tgt | tac | agc | aaa | att | gta | gat | aag | ctg | tcc | tct | gca | 5490 |
| Met | Met | Gln | Asp | Cys | Tyr | Ser | Lys | Ile | Val | Asp | Lys | Leu | Ser | Ser | Ala |  |
| 1785 |  |  |  | 1790 |  |  |  | 1795 |  |  |  | 1800 | aac ccc acc atg gta tta cag gtt cag atg ctc gtg gct gaa ctg cgc       5538
Asn Pro Thr Met Val Leu Gln Val Gln Met Leu Val Ala Glu Leu Arg
                1805                1810                1815 agg gtc act gtg ctc tgg gat gag ctc tgg ctg gga gtt ttg ctg caa       5586
Arg Val Thr Val Leu Trp Asp Glu Leu Trp Leu Gly Val Leu Leu Gln
        1820                1825                1830 caa cac atg tat gtc ctg aga cga att cag cag ctt gaa gat gag gtg       5634
Gln His Met Tyr Val Leu Arg Arg Ile Gln Gln Leu Glu Asp Glu Val
        1835                1840                1845 aag aga gtc cag aac aac aac acc tta cgc aaa gaa gag aaa att gca       5682
Lys Arg Val Gln Asn Asn Asn Thr Leu Arg Lys Glu Glu Lys Ile Ala
        1850                1855                1860 atc atg agg gag aag cac aca gct ttg atg aag ccc atc gta ttt gct       5730
Ile Met Arg Glu Lys His Thr Ala Leu Met Lys Pro Ile Val Phe Ala
1865                1870                1875                1880 ttg gag cat gtg agg agt atc aca gcg gct cct gca gaa aca cct cat       5778
Leu Glu His Val Arg Ser Ile Thr Ala Ala Pro Ala Glu Thr Pro His
                1885                1890                1895 gaa aaa tgg ttt cag gat aac tat ggt gat gcc att gaa aat gcc cta       5826
Glu Lys Trp Phe Gln Asp Asn Tyr Gly Asp Ala Ile Glu Asn Ala Leu
        1900                1905                1910 gaa aaa ctg aag act cca ttg aac cct gca aag cct ggg agc agc tgg       5874
Glu Lys Leu Lys Thr Pro Leu Asn Pro Ala Lys Pro Gly Ser Ser Trp
        1915                1920                1925 att cca ttt aaa gag ata atg cta agt ttg caa cag aga gca cag aaa       5922
Ile Pro Phe Lys Glu Ile Met Leu Ser Leu Gln Gln Arg Ala Gln Lys
        1930                1935                1940 cgt gca agt tac atc ttg cgt ctt gaa gaa atc agt cca tgg ttg gct       5970
Arg Ala Ser Tyr Ile Leu Arg Leu Glu Glu Ile Ser Pro Trp Leu Ala
1945                1950                1955                1960 gcc atg act aac act gaa att gct ctt cct ggg gaa gtc tca gcc aga       6018
Ala Met Thr Asn Thr Glu Ile Ala Leu Pro Gly Glu Val Ser Ala Arg
                1965                1970                1975 gac act gtc aca atc cat agt gtg ggc gga acc atc aca atc tta ccg       6066
Asp Thr Val Thr Ile His Ser Val Gly Gly Thr Ile Thr Ile Leu Pro
        1980                1985                1990 act aaa acc aag cca aag aaa ctt ctc ttt ctt gga tca gat ggg aag       6114
Thr Lys Thr Lys Pro Lys Lys Leu Leu Phe Leu Gly Ser Asp Gly Lys
        1995                2000                2005 agc tat cct tat ctt ttc aaa gga ctg gag gat tta cat ctg gat gag       6162
Ser Tyr Pro Tyr Leu Phe Lys Gly Leu Glu Asp Leu His Leu Asp Glu
        2010                2015                2020 aga ata atg cag ttc cta tct att gtg aat acc atg ttt gct aca att       6210
Arg Ile Met Gln Phe Leu Ser Ile Val Asn Thr Met Phe Ala Thr Ile
2025                2030                2035                2040 aat cgc caa gaa aca ccc cgg ttc cat gct cga cac tat tct gta aca       6258
Asn Arg Gln Glu Thr Pro Arg Phe His Ala Arg His Tyr Ser Val Thr
                2045                2050                2055 cca cta gga aca aga tca gga cta atc cag tgg gta gat gga gcc aca       6306
Pro Leu Gly Thr Arg Ser Gly Leu Ile Gln Trp Val Asp Gly Ala Thr
        2060                2065                2070 ccc tta ttt ggt ctt tac aaa cga tgg caa caa cgg gaa gct gcc tta       6354
Pro Leu Phe Gly Leu Tyr Lys Arg Trp Gln Gln Arg Glu Ala Ala Leu
        2075                2080                2085 caa gca caa aag gcc caa gat tcc tac caa act cct cag aat cct gga       6402

|                                                                                                     |      |
|-----------------------------------------------------------------------------------------------------|------|
| Gln Ala Gln Lys Ala Gln Asp Ser Tyr Gln Thr Pro Gln Asn Pro Gly<br>    2090            2095                2100                |      |
| att gta ccc cgt cct agt gaa ctt tat tac agt aaa att ggc cct gct<br>Ile Val Pro Arg Pro Ser Glu Leu Tyr Tyr Ser Lys Ile Gly Pro Ala<br>2105            2110                2115                2120 | 6450 |
| ttg aaa aca gtt ggg ctt agc ctg gat gtg tcc cgt cgg gat tgg cct<br>Leu Lys Thr Val Gly Leu Ser Leu Asp Val Ser Arg Arg Asp Trp Pro<br>    2125                2130                2135          | 6498 |
| ctt cat gta atg aag gca gta ttg gaa gag tta atg gag gcc aca ccc<br>Leu His Val Met Lys Ala Val Leu Glu Glu Leu Met Glu Ala Thr Pro<br>    2140                2145                2150          | 6546 |
| ccg aat ctc ctt gcc aaa gag ctc tgg tca tct tgc aca aca cct gat<br>Pro Asn Leu Leu Ala Lys Glu Leu Trp Ser Ser Cys Thr Thr Pro Asp<br>    2155                2160                2165          | 6594 |
| gaa tgg tgg aga gtt acg cag tct tat gca aga tct act gca gtc atg<br>Glu Trp Trp Arg Val Thr Gln Ser Tyr Ala Arg Ser Thr Ala Val Met<br>    2170                2175                2180          | 6642 |
| tct atg gtt gga tac ata att ggc ctt gga gac aga cat ctg gat aat<br>Ser Met Val Gly Tyr Ile Ile Gly Leu Gly Asp Arg His Leu Asp Asn<br>2185            2190                2195                2200 | 6690 |
| gtt ctt ata gat atg acg act gga gaa gtt gtt cac ata gat tac aat<br>Val Leu Ile Asp Met Thr Thr Gly Glu Val Val His Ile Asp Tyr Asn<br>        2205            2210                2215          | 6738 |
| gtt tgc ttt gaa aaa ggt aaa agc ctt aga gtt cct gag aaa gta cct<br>Val Cys Phe Glu Lys Gly Lys Ser Leu Arg Val Pro Glu Lys Val Pro<br>    2220                2225                2230          | 6786 |
| ttt cga atg aca caa aac att gaa aca gca ctg ggt gta act gga gta<br>Phe Arg Met Thr Gln Asn Ile Glu Thr Ala Leu Gly Val Thr Gly Val<br>    2235                2240                2245          | 6834 |
| gaa ggt gta ttt agg ctt tca tgt gag cag gtt tta cac att atg cgg<br>Glu Gly Val Phe Arg Leu Ser Cys Glu Gln Val Leu His Ile Met Arg<br>    2250                2255                2260          | 6882 |
| cgt ggc aga gag acc ctg ctg acg ctg ctg gag gcc ttt gtg tac gac<br>Arg Gly Arg Glu Thr Leu Leu Thr Leu Leu Glu Ala Phe Val Tyr Asp<br>2265            2270                2275                2280 | 6930 |
| cct ctg gtg gac tgg aca gca gga ggc gag gct ggg ttt gct ggt gct<br>Pro Leu Val Asp Trp Thr Ala Gly Gly Glu Ala Gly Phe Ala Gly Ala<br>        2285            2290                2295          | 6978 |
| gtc tat ggt gga ggt ggc cag cag gcc gag agc aag cag agc aag aga<br>Val Tyr Gly Gly Gly Gly Gln Gln Ala Glu Ser Lys Gln Ser Lys Arg<br>    2300                2305                2310          | 7026 |
| gag atg gag cga gag atc acc cgc agc ctg ttt tct tct aga gta gct<br>Glu Met Glu Arg Glu Ile Thr Arg Ser Leu Phe Ser Ser Arg Val Ala<br>    2315                2320                2325          | 7074 |
| gag att aag gtg aac tgg ttt aag aat aga gat gag atg ctg gtt gtg<br>Glu Ile Lys Val Asn Trp Phe Lys Asn Arg Asp Glu Met Leu Val Val<br>    2330                2335                2340          | 7122 |
| ctt ccc aag ttg gac ggt agc tta gat gaa tac cta agc ttg caa gag<br>Leu Pro Lys Leu Asp Gly Ser Leu Asp Glu Tyr Leu Ser Leu Gln Glu<br>2345            2350                2355                2360 | 7170 |
| caa ctg aca gat gtg gaa aaa ctg cag ggc aaa cta ctg gag gaa ata<br>Gln Leu Thr Asp Val Glu Lys Leu Gln Gly Lys Leu Leu Glu Glu Ile<br>        2365            2370                2375          | 7218 |
| gag ttt cta gaa gga gct gaa ggg gtg gat cat cct tct cat act ctg<br>Glu Phe Leu Glu Gly Ala Glu Gly Val Asp His Pro Ser His Thr Leu<br>    2380                2385                2390          | 7266 |
| caa cac agg tat tct gag cac acc caa cta cag act cag caa aga gct<br>Gln His Arg Tyr Ser Glu His Thr Gln Leu Gln Thr Gln Gln Arg Ala<br>    2395                2400                2405          | 7314 |

```
                                                    -continued
gtt cag gaa gca atc cag gtg aag ctg aat gaa ttt gaa caa tgg ata    7362
Val Gln Glu Ala Ile Gln Val Lys Leu Asn Glu Phe Glu Gln Trp Ile
    2410                2415                2420 aca cat tat cag gct gca ttc aat aat tta gaa gca aca cag ctt gca    7410
Thr His Tyr Gln Ala Ala Phe Asn Asn Leu Glu Ala Thr Gln Leu Ala
2425                2430                2435                2440 agc ttg ctt caa gag ata agc aca caa atg gac ctt ggt cct cca agt    7458
Ser Leu Leu Gln Glu Ile Ser Thr Gln Met Asp Leu Gly Pro Pro Ser
            2445                2450                2455 tac gtg cca gca aca gcc ttt ctg cag aat gct ggt cag gcc cac ttg    7506
Tyr Val Pro Ala Thr Ala Phe Leu Gln Asn Ala Gly Gln Ala His Leu
        2460                2465                2470 att agc cag tgc gag cag ctg gag ggg gag gtt ggt gct ctc ctg cag    7554
Ile Ser Gln Cys Glu Gln Leu Glu Gly Glu Val Gly Ala Leu Leu Gln
    2475                2480                2485 cag agg cgc tcc gtg ctc cgt ggc tgt ctg gag caa ctg cat cac tat    7602
Gln Arg Arg Ser Val Leu Arg Gly Cys Leu Glu Gln Leu His His Tyr
2490                2495                2500 gca acc gtg gcc ctg cag tat ccg aag gcc ata ttt cag aaa cat cga    7650
Ala Thr Val Ala Leu Gln Tyr Pro Lys Ala Ile Phe Gln Lys His Arg
2505                2510                2515                2520 att gaa cag tgg aag acc tgg atg gaa gag ctc atc tgt aac acc aca    7698
Ile Glu Gln Trp Lys Thr Trp Met Glu Glu Leu Ile Cys Asn Thr Thr
            2525                2530                2535 gta gag cgt tgt caa gag ctc tat agg aaa tat gaa atg caa tat gct    7746
Val Glu Arg Cys Gln Glu Leu Tyr Arg Lys Tyr Glu Met Gln Tyr Ala
        2540                2545                2550 ccc cag cca ccc cca aca gtg tgt cag ttc atc act gcc act gaa atg    7794
Pro Gln Pro Pro Pro Thr Val Cys Gln Phe Ile Thr Ala Thr Glu Met
    2555                2560                2565 acc ctg cag cga tac gca gca gac atc aac agc aga ctt att aga caa    7842
Thr Leu Gln Arg Tyr Ala Ala Asp Ile Asn Ser Arg Leu Ile Arg Gln
2570                2575                2580 gtg gaa cgc ttg aaa cag gaa gct gtc act gtg cca gtt tgt gaa gat    7890
Val Glu Arg Leu Lys Gln Glu Ala Val Thr Val Pro Val Cys Glu Asp
2585                2590                2595                2600 cag ttg aaa gaa att gaa cgt tgc att aaa gtt ttc ctt cat gag aat    7938
Gln Leu Lys Glu Ile Glu Arg Cys Ile Lys Val Phe Leu His Glu Asn
            2605                2610                2615 gga gaa gaa gga tct ttg agt cta gca agt gtt att att tct gcc ctt    7986
Gly Glu Glu Gly Ser Leu Ser Leu Ala Ser Val Ile Ile Ser Ala Leu
        2620                2625                2630 tgt acc ctt aca agg cgt aac ctg atg atg gaa ggt gca gcg tca agt    8034
Cys Thr Leu Thr Arg Arg Asn Leu Met Met Glu Gly Ala Ala Ser Ser
    2635                2640                2645 gct gga gaa cag ctg gtt gat ctg act tct cgg gat gga gcc tgg ttc    8082
Ala Gly Glu Gln Leu Val Asp Leu Thr Ser Arg Asp Gly Ala Trp Phe
2650                2655                2660 ttg gag gaa ctc tgc agt atg agc gga aac gtc acc tgc ttg gtt cag    8130
Leu Glu Glu Leu Cys Ser Met Ser Gly Asn Val Thr Cys Leu Val Gln
2665                2670                2675                2680 tta ctg aag cag tgc cac ctg gtg cca cag gac tta gat atc ccg aac    8178
Leu Leu Lys Gln Cys His Leu Val Pro Gln Asp Leu Asp Ile Pro Asn
            2685                2690                2695 ccc atg gaa gcg tct gag aca gtt cac tta gcc aat gga gtg tat acc    8226
Pro Met Glu Ala Ser Glu Thr Val His Leu Ala Asn Gly Val Tyr Thr
        2700                2705                2710 tca ctt cag gaa ttg aat tcg aat ttc cgg caa atc ata ttt cca gaa    8274
Ser Leu Gln Glu Leu Asn Ser Asn Phe Arg Gln Ile Ile Phe Pro Glu
    2715                2720                2725
```

```
gca ctt cga tgt tta atg aaa ggg gaa tac acg tta gaa agt atg ctg      8322
Ala Leu Arg Cys Leu Met Lys Gly Glu Tyr Thr Leu Glu Ser Met Leu
    2730                2735                2740 cat gaa ctg gac ggt ctt att gag cag acc acc gat ggc gtt ccc ctg      8370
His Glu Leu Asp Gly Leu Ile Glu Gln Thr Thr Asp Gly Val Pro Leu
2745                2750                2755                2760 cag act cta gtg gaa tct ctt cag gcc tac tta aga aac gca gct atg      8418
Gln Thr Leu Val Glu Ser Leu Gln Ala Tyr Leu Arg Asn Ala Ala Met
            2765                2770                2775 gga ctg gaa gaa gaa aca cat gct cat tac atc gat gtt gcc aga cta      8466
Gly Leu Glu Glu Glu Thr His Ala His Tyr Ile Asp Val Ala Arg Leu
        2780                2785                2790 cta cat gct cag tac ggt gaa tta atc caa ccg aga aat ggt tca gtt      8514
Leu His Ala Gln Tyr Gly Glu Leu Ile Gln Pro Arg Asn Gly Ser Val
    2795                2800                2805 gat gaa aca ccc aaa atg tca gct ggc cag atg ctt ttg gta gca ttc      8562
Asp Glu Thr Pro Lys Met Ser Ala Gly Gln Met Leu Leu Val Ala Phe
2810                2815                2820 gat ggc atg ttt gct caa gtt gaa act gct ttc agc tta tta gtt gaa      8610
Asp Gly Met Phe Ala Gln Val Glu Thr Ala Phe Ser Leu Leu Val Glu
2825                2830                2835                2840 aag ttg aac aag atg gaa att ccc ata gct tgg cga aag att gac atc      8658
Lys Leu Asn Lys Met Glu Ile Pro Ile Ala Trp Arg Lys Ile Asp Ile
            2845                2850                2855 ata agg gaa gcc agg agt act caa gtt aat ttt ttt gat gat gat aat      8706
Ile Arg Glu Ala Arg Ser Thr Gln Val Asn Phe Phe Asp Asp Asp Asn
        2860                2865                2870 cac cgg cag gtg cta gaa gag att ttc ttt cta aaa aga cta cag act      8754
His Arg Gln Val Leu Glu Glu Ile Phe Phe Leu Lys Arg Leu Gln Thr
    2875                2880                2885 att aag gag ttc ttc agg ctc tgt ggt acc ttt tct aaa aca ttg tca      8802
Ile Lys Glu Phe Phe Arg Leu Cys Gly Thr Phe Ser Lys Thr Leu Ser
2890                2895                2900 gga tca agt tca ctt gaa gat cag aat act gtg aat ggg cct gta cag      8850
Gly Ser Ser Ser Leu Glu Asp Gln Asn Thr Val Asn Gly Pro Val Gln
2905                2910                2915                2920 att gtc aat gtg aaa acc ctt ttt aga aac tct tgt ttc agt gaa gac      8898
Ile Val Asn Val Lys Thr Leu Phe Arg Asn Ser Cys Phe Ser Glu Asp
            2925                2930                2935 caa atg gcc aaa cct atc aag gca ttc aca gct gac ttt gtg agg cag      8946
Gln Met Ala Lys Pro Ile Lys Ala Phe Thr Ala Asp Phe Val Arg Gln
        2940                2945                2950 ctc ttg ata ggg cta ccc aac caa gcc ctc gga ctc aca ctg tgc agt      8994
Leu Leu Ile Gly Leu Pro Asn Gln Ala Leu Gly Leu Thr Leu Cys Ser
    2955                2960                2965 ttt atc agt gct ctg ggt gta gac atc att gct caa gta gag gca aag      9042
Phe Ile Ser Ala Leu Gly Val Asp Ile Ile Ala Gln Val Glu Ala Lys
2970                2975                2980 gac ttt ggt gcc gaa agc aaa gtt tct gtt gat gat ctc tgt aag aaa      9090
Asp Phe Gly Ala Glu Ser Lys Val Ser Val Asp Asp Leu Cys Lys Lys
2985                2990                2995                3000 gcg gtg gaa cat aac atc cag ata ggg aag ttc tct cag ctg gtt atg      9138
Ala Val Glu His Asn Ile Gln Ile Gly Lys Phe Ser Gln Leu Val Met
            3005                3010                3015 aac agg gca act gtg tta gca agt tct tac gac act gcc tgg aag aag      9186
Asn Arg Ala Thr Val Leu Ala Ser Ser Tyr Asp Thr Ala Trp Lys Lys
        3020                3025                3030 cat gac ttg gtg cga agg cta gaa acc agt att tct tct tgt aag aca      9234
His Asp Leu Val Arg Arg Leu Glu Thr Ser Ile Ser Ser Cys Lys Thr
```

-continued

| | | |
|---|---|---|
| agc ctg cag cgg gtt cag ctg cat att gcc atg ttt cag tgg caa cat<br>Ser Leu Gln Arg Val Gln Leu His Ile Ala Met Phe Gln Trp Gln His<br>    3050               3055               3060 | | 9282 |
| gaa gat cta ctt atc aat aga cca caa gcc atg tca gtc aca cct ccc<br>Glu Asp Leu Leu Ile Asn Arg Pro Gln Ala Met Ser Val Thr Pro Pro<br>3065               3070               3075               3080 | | 9330 |
| cca cgg tct gct atc cta acc agc atg aaa aag aag ctg cat acc ctg<br>Pro Arg Ser Ala Ile Leu Thr Ser Met Lys Lys Lys Leu His Thr Leu<br>                3085               3090               3095 | | 9378 |
| agc cag att gaa act tct att gca aca gtt cag gag aag cta gct gca<br>Ser Gln Ile Glu Thr Ser Ile Ala Thr Val Gln Glu Lys Leu Ala Ala<br>    3100               3105               3110 | | 9426 |
| ctt gaa tca agt att gaa cag cga ctc aag tgg gca ggt ggt gcc aac<br>Leu Glu Ser Ser Ile Glu Gln Arg Leu Lys Trp Ala Gly Gly Ala Asn<br>3115               3120               3125 | | 9474 |
| cct gca ttg gcc cct gta cta caa gat ttt gaa gca acg ata gct gaa<br>Pro Ala Leu Ala Pro Val Leu Gln Asp Phe Glu Ala Thr Ile Ala Glu<br>    3130               3135               3140 | | 9522 |
| aga aga aat ctt gtc ctt aaa gag agc caa aga gca agt cag gtc aca<br>Arg Arg Asn Leu Val Leu Lys Glu Ser Gln Arg Ala Ser Gln Val Thr<br>3145               3150               3155               3160 | | 9570 |
| ttt ctc tgc agc aat atc att cat ttt gaa agt tta cga aca aga act<br>Phe Leu Cys Ser Asn Ile Ile His Phe Glu Ser Leu Arg Thr Arg Thr<br>                3165               3170               3175 | | 9618 |
| gca gaa gcc tta aac ctg gat gcg gcg tta ttt gaa cta atc aag cga<br>Ala Glu Ala Leu Asn Leu Asp Ala Ala Leu Phe Glu Leu Ile Lys Arg<br>    3180               3185               3190 | | 9666 |
| tgt cag cag atg tgt tcg ttt gca tca cag ttt aac agt tca gtg tct<br>Cys Gln Gln Met Cys Ser Phe Ala Ser Gln Phe Asn Ser Ser Val Ser<br>    3195               3200               3205 | | 9714 |
| gag tta gag ctt cgt tta tta cag aga gtg gac act ggt ctt gaa cat<br>Glu Leu Glu Leu Arg Leu Leu Gln Arg Val Asp Thr Gly Leu Glu His<br>    3210               3215               3220 | | 9762 |
| cct att ggc agc tct gaa tgg ctt ttg tca gca cac aaa cag ttg acc<br>Pro Ile Gly Ser Ser Glu Trp Leu Leu Ser Ala His Lys Gln Leu Thr<br>3225               3230               3235               3240 | | 9810 |
| cag gat atg tct act cag agg gca att cag aca gag aaa gag cag cag<br>Gln Asp Met Ser Thr Gln Arg Ala Ile Gln Thr Glu Lys Glu Gln Gln<br>                3245               3250               3255 | | 9858 |
| ata gaa acg gtc tgt gaa aca att cag aat ctg gtt gat aat ata aag<br>Ile Glu Thr Val Cys Glu Thr Ile Gln Asn Leu Val Asp Asn Ile Lys<br>    3260               3265               3270 | | 9906 |
| act gtg ctc act ggt cat aac cga cag ctt gga gat gtc aaa cat ctc<br>Thr Val Leu Thr Gly His Asn Arg Gln Leu Gly Asp Val Lys His Leu<br>    3275               3280               3285 | | 9954 |
| ttg aaa gct atg gct aag gat gaa gaa gct gct ctg gca gat ggt gaa<br>Leu Lys Ala Met Ala Lys Asp Glu Glu Ala Ala Leu Ala Asp Gly Glu<br>    3290               3295               3300 | | 10002 |
| gat gtt ccc tat gag aac agt gtt agg cag ttt ttg ggt gaa tat aaa<br>Asp Val Pro Tyr Glu Asn Ser Val Arg Gln Phe Leu Gly Glu Tyr Lys<br>3305               3310               3315               3320 | | 10050 |
| tca tgg caa gac aac att caa aca gtt cta ttt aca tta gtc cag gct<br>Ser Trp Gln Asp Asn Ile Gln Thr Val Leu Phe Thr Leu Val Gln Ala<br>                3325               3330               3335 | | 10098 |
| atg ggt cag gtt cga agt caa gaa cac gtt gaa atg ctc cag gaa atc<br>Met Gly Gln Val Arg Ser Gln Glu His Val Glu Met Leu Gln Glu Ile<br>    3340               3345               3350 | | 10146 |
| act ccc acc ttg aaa gaa ctg aaa aca caa agt cag agt atc tat aat | | 10194 |

-continued

| | | |
|---|---|---|
| Thr Pro Thr Leu Lys Glu Leu Lys Thr Gln Ser Gln Ser Ile Tyr Asn<br>              3355                   3360                 3365 | | |
| aat tta gtg agt ttt gca tca ccc tta gtc acc gat gca aca aat gaa<br>Asn Leu Val Ser Phe Ala Ser Pro Leu Val Thr Asp Ala Thr Asn Glu<br>3370                  3375                   3380 | 10242 |
| tgt tcg agt cca acg tca tct gct act tat cag cca tcc ttc gct gca<br>Cys Ser Ser Pro Thr Ser Ser Ala Thr Tyr Gln Pro Ser Phe Ala Ala<br>3385                  3390                   3395               3400 | 10290 |
| gca gtc cgg agt aac act ggc cag aag act cag cct gat gtc atg tca<br>Ala Val Arg Ser Asn Thr Gly Gln Lys Thr Gln Pro Asp Val Met Ser<br>               3405                  3410               3415 | 10338 |
| cag aat gct aga aag ctg atc cag aaa aat ctt gct aca tca gct gat<br>Gln Asn Ala Arg Lys Leu Ile Gln Lys Asn Leu Ala Thr Ser Ala Asp<br>3420                  3425                   3430 | 10386 |
| act cca cca agc acc gtt cca gga act ggc aag agt gtt gct tgt agt<br>Thr Pro Pro Ser Thr Val Pro Gly Thr Gly Lys Ser Val Ala Cys Ser<br>               3435                  3440               3445 | 10434 |
| cct aaa aag gca gtc aga gac cct aaa act ggg aaa gcg gtg caa gag<br>Pro Lys Lys Ala Val Arg Asp Pro Lys Thr Gly Lys Ala Val Gln Glu<br>3450                  3455                   3460 | 10482 |
| aga aac tcc tat gca gtg agt gtg tgg aag aga gtg aaa gcc aag tta<br>Arg Asn Ser Tyr Ala Val Ser Val Trp Lys Arg Val Lys Ala Lys Leu<br>3465                  3470                   3475               3480 | 10530 |
| gag ggc cga gat gtt gat ccg aat agg agg atg tca gtt gct gaa cag<br>Glu Gly Arg Asp Val Asp Pro Asn Arg Arg Met Ser Val Ala Glu Gln<br>               3485                  3490               3495 | 10578 |
| gtt gac tat gtc att aag gaa gca act aat cta gat aac ttg gct cag<br>Val Asp Tyr Val Ile Lys Glu Ala Thr Asn Leu Asp Asn Leu Ala Gln<br>3500                  3505                   3510 | 10626 |
| ctg tat gaa ggt tgg aca gcc tgg gtg tga atggcaagac agtagatgag<br>Leu Tyr Glu Gly Trp Thr Ala Trp Val *<br>               3515                  3520 | 10676 |
| tctggttaag cgaggtcaga catccaccag aatcaactca gcctcaggca tccaaagcca | 10736 |
| caccacagtc ggtggtgatg caactggggg cttactctga ggaaacctag gaaatctcgg | 10796 |
| tgcactagga agtgaatccc gcaggacagc tgcactcagg gatacgccca acaccatggc | 10856 |
| ctgcaacccc agggtcaagg gtgaaggaaa gcaagctcac cgcctgaaca cggagattgt | 10916 |
| cttttctgcca cagaacagca gcagacgtgt cgggaggtta gctgcggaaa gaaatcggga | 10976 |
| tgccgcggag cacagagtga tttggaactc cattccacct gaccctgtgt gtacaatcca | 11036 |
| ggaaaaaaac aaacccccact cagaaacaga gaaaactggg gtcgcgaaga aatcacagcc | 11096 |
| aaggaagatt tgatgcattc agattctcgt gtaacacttg ttgcttggca acagtactgg | 11156 |
| ttgggttgac cagtaagtag aaaaaggcta aggctatgc gatatgaatt tcagaaatgg | 11216 |
| actgaaaatg gagagctatg taacagatac actacagtag aagaacttac ttctgaaatg | 11276 |
| aagggaaaaa aaccacccca tcgttcccta ctcctcccca ccacttaccc gttccccctt | 11336 |
| tacctaatct agtagattag ccatctttca aattcacttt tatttcagtc cttatatttc | 11396 |
| atatacttcc gtctcgatgc tgttaacaac ttctgataac atggaaaatt caaggattgt | 11456 |
| ttaaaggtct gatgatcaca cacaaaatgt aattccggtt atttaagtca tttctgtgat | 11516 |
| tctatcatgt acagtttcca gaattgtcac tgtgcattca aaagtaatga atctaacaga | 11576 |
| catttgattt aatgtacact cccttttgct tatagtgtgc attttttttg gaggtcattc | 11636 |
| aaatttccc tcttctgtga tagctgtagt ttctttcata gaaagtagct aatccagtgt | 11696 |
| aatctttac ctttttaaaa accaagatag agtatctatt agagtttac attgttgatg | 11756 |

-continued

```
atagattaac aataaagtga tgttctggtg gaggtagact gaaatttttt taattcatgt    11816
ttttcatttg atacttttaa tttacactta gtaaattaaa agttgtttaa tttacttggc    11876
attttaggac atgtacatga aacagtgaaa atgagatcca ccaacatctt ttattaagtt    11936
cagttattag tctgtgaagt gctttacttt ttgcacaatt ttaatagctt gctattcagt    11996
aatacattat agtgaattca tgatcaaggt ttccttaaat ttagcattgc atttcagtac    12056
tgactgtgta agctaaattg ctgatccaaa ataaaaaccc agactagaat agggttctta    12116
aaatcaagta tcaatacaaa atagaacaca attaaaatct taattgttgg ctgggcacag    12176
tggctcacgc ctgtaatccc agcactttgg gaggccgagg cgggcggatc atgaggttag    12236
gagagcgaga ccatcctggc taacacggtg aaaccccgtc tttactaaaa tacaaaaaaa    12296
attagccggg tgtggtggcg gcgcctgta gtcccagcta ctcgggaggc tgaggcagga    12356
gaatggcgtg aacccaggag gcggagcttg cagtgagccg agattgtgcc actgcactcc    12416
agcctgggca acagagctag actctgtgtc aaaataaat gactagat                 12464
```

<210> SEQ ID NO 2
<211> LENGTH: 3521
<212> TYPE: PRT
<213> ORGANISM: Homo sapiens
<400> SEQUENCE: 2

```
Met Ser Tyr Cys Asp Glu Ser Arg Leu Ser Asn Leu Leu Arg Arg Ile
  1               5                  10                  15

Thr Arg Glu Asp Asp Arg Asp Arg Arg Leu Ala Thr Val Lys Gln Leu
             20                  25                  30

Lys Glu Phe Ile Gln Gln Pro Glu Asn Lys Leu Val Leu Val Lys Gln
         35                  40                  45

Leu Asp Asn Ile Leu Ala Ala Val His Asp Val Leu Asn Glu Ser Ser
     50                  55                  60

Lys Leu Leu Gln Glu Leu Arg Gln Glu Gly Ala Cys Cys Leu Gly Leu
 65                  70                  75                  80

Leu Cys Ala Ser Leu Ser Tyr Glu Ala Glu Lys Ile Phe Lys Trp Ile
                 85                  90                  95

Phe Ser Lys Phe Ser Ser Ala Lys Asp Glu Val Lys Leu Leu Tyr
            100                 105                 110

Leu Cys Ala Thr Tyr Lys Ala Leu Glu Thr Val Gly Glu Lys Lys Ala
        115                 120                 125

Phe Ser Ser Val Met Gln Leu Val Met Thr Ser Leu Gln Ser Ile Leu
    130                 135                 140

Glu Asn Val Asp Thr Pro Glu Leu Leu Cys Lys Cys Val Lys Cys Ile
145                 150                 155                 160

Leu Leu Val Ala Arg Cys Tyr Pro His Ile Phe Ser Thr Asn Phe Arg
                165                 170                 175

Asp Thr Val Asp Ile Leu Val Gly Trp His Ile Asp His Thr Gln Lys
            180                 185                 190

Pro Ser Leu Thr Gln Gln Val Ser Gly Trp Leu Gln Ser Leu Glu Pro
        195                 200                 205

Phe Trp Val Ala Asp Leu Ala Phe Ser Thr Thr Leu Leu Gly Gln Phe
    210                 215                 220

Leu Glu Asp Met Glu Ala Tyr Ala Glu Asp Leu Ser His Val Ala Ser
225                 230                 235                 240

Gly Glu Ser Val Asp Glu Asp Val Pro Pro Ser Val Ser Leu Pro
                245                 250                 255
```

-continued

Lys Leu Ala Ala Leu Leu Arg Val Phe Ser Thr Val Val Arg Ser Ile
    260                 265                 270

Gly Glu Arg Phe Ser Pro Ile Arg Gly Pro Pro Ile Thr Glu Ala Tyr
        275                 280                 285

Val Thr Asp Val Leu Tyr Arg Val Met Arg Cys Val Thr Ala Ala Asn
    290                 295                 300

Gln Val Phe Phe Ser Glu Ala Val Leu Thr Ala Ala Asn Glu Cys Val
305                 310                 315                 320

Gly Val Leu Leu Gly Ser Leu Asp Pro Ser Met Thr Ile His Cys Asp
                325                 330                 335

Met Val Ile Thr Tyr Gly Leu Asp Gln Leu Glu Asn Cys Gln Thr Cys
                340                 345                 350

Gly Thr Asp Tyr Ile Ile Ser Val Leu Asn Leu Leu Thr Leu Ile Val
            355                 360                 365

Glu Gln Ile Asn Thr Lys Leu Pro Ser Ser Phe Val Glu Lys Leu Phe
        370                 375                 380

Ile Pro Ser Ser Lys Leu Leu Phe Leu Arg Tyr His Lys Glu Lys Glu
385                 390                 395                 400

Val Val Ala Val Ala His Ala Val Tyr Gln Ala Val Leu Ser Leu Lys
                405                 410                 415

Asn Ile Pro Val Leu Glu Thr Ala Tyr Lys Leu Ile Leu Gly Glu Met
            420                 425                 430

Thr Cys Ala Leu Asn Asn Leu Leu His Ser Leu Gln Leu Pro Glu Ala
        435                 440                 445

Cys Ser Glu Ile Lys His Glu Ala Phe Lys Asn His Val Phe Asn Val
    450                 455                 460

Asp Asn Ala Lys Phe Val Ile Phe Asp Leu Ser Ala Leu Thr Thr
465                 470                 475                 480

Ile Gly Asn Ala Lys Asn Ser Leu Ile Gly Met Trp Ala Leu Ser Pro
                485                 490                 495

Thr Val Phe Ala Leu Leu Ser Lys Asn Leu Met Ile Val His Ser Asp
            500                 505                 510

Leu Ala Val His Phe Pro Ala Ile Gln Tyr Ala Val Leu Tyr Thr Leu
        515                 520                 525

Tyr Ser His Cys Thr Arg His Asp His Phe Ile Ser Ser Ser Leu Ser
    530                 535                 540

Ser Ser Ser Pro Ser Leu Phe Asp Gly Ala Val Ile Ser Thr Val Thr
545                 550                 555                 560

Thr Ala Thr Lys Lys His Phe Ser Ile Ile Leu Asn Leu Leu Gly Ile
                565                 570                 575

Leu Leu Lys Lys Asp Asn Leu Asn Gln Asp Thr Arg Lys Leu Leu Met
            580                 585                 590

Thr Trp Ala Leu Glu Ala Ala Val Leu Met Lys Lys Ser Glu Thr Tyr
        595                 600                 605

Ala Pro Leu Phe Ser Leu Pro Ser Phe His Lys Phe Cys Lys Gly Leu
    610                 615                 620

Leu Ala Asn Thr Leu Val Glu Asp Val Asn Ile Cys Leu Gln Ala Cys
625                 630                 635                 640

Ser Ser Leu His Ala Leu Ser Ser Ser Leu Pro Asp Asp Leu Leu Gln
                645                 650                 655

Arg Cys Val Asp Val Cys Arg Val Gln Leu Val His Ser Gly Thr Arg
            660                 665                 670

-continued

```
Ile Arg Gln Ala Phe Gly Lys Leu Leu Lys Ser Ile Pro Leu Asp Val
            675                 680                 685

Val Leu Ser Asn Asn Asn His Thr Glu Ile Gln Glu Ile Ser Leu Ala
690                 695                 700

Leu Arg Ser His Met Ser Lys Ala Pro Ser Asn Thr Phe His Pro Gln
705                 710                 715                 720

Asp Phe Ser Asp Val Ile Ser Phe Ile Leu Tyr Gly Asn Ser His Arg
            725                 730                 735

Thr Gly Lys Asp Asn Trp Leu Glu Arg Leu Phe Tyr Ser Cys Gln Arg
            740                 745                 750

Leu Asp Lys Arg Asp Gln Ser Thr Ile Pro Arg Asn Leu Leu Lys Thr
            755                 760                 765

Asp Ala Val Leu Trp Gln Trp Ala Ile Trp Glu Ala Ala Gln Phe Thr
770                 775                 780

Val Leu Ser Lys Leu Arg Thr Pro Leu Gly Arg Ala Gln Asp Thr Phe
785                 790                 795                 800

Gln Thr Ile Glu Gly Ile Ile Arg Ser Leu Ala Ala His Thr Leu Asn
            805                 810                 815

Pro Asp Gln Asp Val Ser Gln Trp Thr Thr Ala Asp Asn Asp Glu Gly
            820                 825                 830

His Gly Asn Asn Gln Leu Arg Leu Val Leu Leu Gln Tyr Leu Glu
            835                 840                 845

Asn Leu Glu Lys Leu Met Tyr Asn Ala Tyr Glu Gly Cys Ala Asn Ala
850                 855                 860

Leu Thr Ser Pro Pro Lys Val Ile Arg Thr Phe Phe Tyr Thr Asn Arg
865                 870                 875                 880

Gln Thr Cys Gln Asp Trp Leu Thr Arg Ile Arg Leu Ser Ile Met Arg
            885                 890                 895

Val Gly Leu Leu Ala Gly Gln Pro Ala Val Thr Val Arg His Gly Phe
            900                 905                 910

Asp Leu Leu Thr Glu Met Lys Thr Thr Ser Leu Ser Gln Gly Asn Glu
            915                 920                 925

Leu Glu Val Thr Ile Met Met Val Val Glu Ala Leu Cys Glu Leu His
930                 935                 940

Cys Pro Glu Ala Ile Gln Gly Ile Ala Val Trp Ser Ser Ile Val
945                 950                 955                 960

Gly Lys Asn Leu Leu Trp Ile Asn Ser Val Ala Gln Gln Ala Glu Gly
            965                 970                 975

Arg Phe Glu Lys Ala Ser Val Glu Tyr Gln Glu His Leu Cys Ala Met
            980                 985                 990

Thr Gly Val Asp Cys Cys Ile Ser Ser Phe Asp Lys Ser Val Leu Thr
            995                 1000                1005

Leu Ala Asn Ala Gly Arg Asn Ser Ala Ser Pro Lys His Ser Leu Asn
     1010                1015                1020

Gly Glu Ser Arg Lys Thr Val Leu Ser Lys Pro Thr Asp Ser Ser Pro
1025                1030                1035                1040

Glu Val Ile Asn Tyr Leu Gly Asn Lys Ala Cys Glu Cys Tyr Ile Ser
               1045                1050                1055

Ile Ala Asp Trp Ala Ala Val Gln Glu Trp Gln Asn Ala Ile His Asp
               1060                1065                1070

Leu Lys Lys Ser Thr Ser Ser Thr Ser Leu Asn Leu Lys Ala Asp Phe
     1075                1080                1085

Asn Tyr Ile Lys Ser Leu Ser Ser Phe Glu Ser Gly Lys Phe Val Glu
```

```
                1090             1095             1100
Cys Thr Glu Gln Leu Glu Leu Leu Pro Gly Glu Asn Ile Asn Leu Leu
1105                 1110                 1115                 1120
Ala Gly Gly Ser Lys Glu Lys Ile Asp Met Lys Lys Leu Leu Pro Asn
                 1125                 1130                 1135
Met Leu Ser Pro Asp Pro Arg Glu Leu Gln Lys Ser Ile Glu Val Gln
                     1140                 1145                 1150
Leu Leu Arg Ser Ser Val Cys Leu Ala Thr Ala Leu Asn Pro Ile Glu
            1155                 1160                 1165
Gln Asp Gln Lys Trp Gln Ser Ile Thr Glu Asn Val Val Lys Tyr Leu
    1170                 1175                 1180
Lys Gln Thr Ser Arg Ile Ala Ile Gly Pro Leu Arg Leu Ser Thr Leu
1185                 1190                 1195                 1200
Thr Val Ser Gln Ser Leu Pro Val Leu Ser Thr Leu Gln Leu Tyr Cys
                     1205                 1210                 1215
Ser Ser Ala Leu Glu Asn Thr Val Ser Asn Arg Leu Ser Thr Glu Asp
                 1220                 1225                 1230
Cys Leu Ile Pro Leu Phe Ser Glu Ala Leu Arg Ser Cys Lys Gln His
            1235                 1240                 1245
Asp Val Arg Pro Trp Met Gln Ala Leu Arg Tyr Thr Met Tyr Gln Asn
        1250                 1255                 1260
Gln Leu Leu Glu Lys Ile Lys Glu Gln Thr Val Pro Ile Arg Ser His
1265                 1270                 1275                 1280
Leu Met Glu Leu Gly Leu Thr Ala Ala Lys Phe Ala Arg Lys Arg Gly
                 1285                 1290                 1295
Asn Val Ser Leu Ala Thr Arg Leu Leu Ala Gln Cys Ser Glu Val Gln
                 1300                 1305                 1310
Leu Gly Lys Thr Thr Thr Ala Gln Asp Leu Val Gln His Phe Lys Lys
            1315                 1320                 1325
Leu Ser Thr Gln Gly Gln Val Asp Glu Lys Trp Gly Pro Glu Leu Asp
        1330                 1335                 1340
Ile Glu Lys Thr Lys Leu Leu Tyr Thr Ala Gly Gln Ser Thr His Ala
1345                 1350                 1355                 1360
Met Glu Met Leu Ser Ser Cys Ala Ile Ser Phe Cys Lys Ser Val Lys
                 1365                 1370                 1375
Ala Glu Tyr Ala Val Ala Lys Ser Ile Leu Thr Leu Ala Lys Trp Ile
                 1380                 1385                 1390
Gln Ala Glu Trp Lys Glu Ile Ser Gly Gln Leu Lys Gln Val Tyr Arg
            1395                 1400                 1405
Ala Gln His Gln Gln Asn Phe Thr Gly Leu Ser Thr Leu Ser Lys Asn
        1410                 1415                 1420
Ile Leu Thr Leu Ile Glu Leu Pro Ser Val Asn Thr Met Glu Glu Glu
1425                 1430                 1435                 1440
Tyr Pro Arg Ile Glu Ser Glu Ser Thr Val His Ile Gly Val Gly Glu
                 1445                 1450                 1455
Pro Asp Phe Ile Leu Gly Gln Leu Tyr His Leu Ser Ser Val Gln Ala
                 1460                 1465                 1470
Pro Glu Val Ala Lys Ser Trp Ala Ala Leu Ala Ser Trp Ala Tyr Arg
            1475                 1480                 1485
Trp Gly Arg Lys Val Val Asp Asn Ala Ser Gln Gly Glu Gly Val Arg
        1490                 1495                 1500
Leu Leu Pro Arg Glu Lys Ser Glu Val Gln Asn Leu Leu Pro Asp Thr
1505                 1510                 1515                 1520
```

```
Ile Thr Glu Glu Glu Lys Glu Arg Ile Tyr Gly Ile Leu Gly Gln Ala
            1525                1530                1535

Val Cys Arg Pro Ala Gly Ile Gln Asp Glu Asp Ile Thr Leu Gln Ile
        1540                1545                1550

Thr Glu Ser Glu Asp Asn Glu Asp Asp Met Val Asp Val Ile Trp
    1555                1560                1565

Arg Gln Leu Ile Ser Ser Cys Pro Trp Leu Ser Glu Leu Asp Glu Ser
    1570                1575                1580

Ala Thr Glu Gly Val Ile Lys Val Trp Arg Lys Val Val Asp Arg Ile
1585                1590                1595                1600

Phe Ser Leu Tyr Lys Leu Ser Cys Ser Ala Tyr Phe Thr Phe Leu Lys
            1605                1610                1615

Leu Asn Ala Gly Gln Ile Pro Leu Asp Glu Asp Pro Arg Leu His
            1620                1625                1630

Leu Ser His Arg Val Glu Gln Ser Thr Asp Asp Met Ile Val Met Ala
            1635                1640                1645

Thr Leu Arg Leu Leu Arg Leu Leu Val Lys His Ala Gly Glu Leu Arg
    1650                1655                1660

Gln Tyr Leu Glu His Gly Leu Glu Thr Thr Pro Thr Ala Pro Trp Arg
1665                1670                1675                1680

Gly Ile Ile Pro Gln Leu Phe Ser Arg Leu Asn His Pro Glu Val Tyr
            1685                1690                1695

Val Arg Gln Ser Ile Cys Asn Leu Leu Cys Arg Val Ala Gln Asp Ser
                1700                1705                1710

Pro His Leu Ile Leu Tyr Pro Ala Ile Val Gly Thr Ile Ser Leu Ser
        1715                1720                1725

Ser Glu Ser Gln Ala Ser Gly Asn Lys Phe Ser Thr Ala Ile Pro Thr
1730                1735                1740

Leu Leu Gly Asn Ile Gln Gly Glu Glu Leu Leu Val Ser Glu Cys Glu
1745                1750                1755                1760

Gly Gly Ser Pro Pro Ala Ser Gln Asp Ser Asn Lys Asp Glu Pro Lys
        1765                1770                1775

Ser Gly Leu Asn Glu Asp Gln Ala Met Met Gln Asp Cys Tyr Ser Lys
            1780                1785                1790

Ile Val Asp Lys Leu Ser Ser Ala Asn Pro Thr Met Val Leu Gln Val
        1795                1800                1805

Gln Met Leu Val Ala Glu Leu Arg Arg Val Thr Val Leu Trp Asp Glu
    1810                1815                1820

Leu Trp Leu Gly Val Leu Leu Gln Gln His Met Tyr Val Leu Arg Arg
1825                1830                1835                1840

Ile Gln Gln Leu Glu Asp Glu Val Lys Arg Val Gln Asn Asn Asn Thr
            1845                1850                1855

Leu Arg Lys Glu Glu Lys Ile Ala Ile Met Arg Glu Lys His Thr Ala
        1860                1865                1870

Leu Met Lys Pro Ile Val Phe Ala Leu Glu His Val Arg Ser Ile Thr
    1875                1880                1885

Ala Ala Pro Ala Glu Thr Pro His Glu Lys Trp Phe Gln Asp Asn Tyr
1890                1895                1900

Gly Asp Ala Ile Glu Asn Ala Leu Glu Lys Leu Lys Thr Pro Leu Asn
1905                1910                1915                1920

Pro Ala Lys Pro Gly Ser Ser Trp Ile Pro Phe Lys Glu Ile Met Leu
            1925                1930                1935
```

-continued

```
Ser Leu Gln Gln Arg Ala Gln Lys Arg Ala Ser Tyr Ile Leu Arg Leu
            1940                1945                1950

Glu Glu Ile Ser Pro Trp Leu Ala Ala Met Thr Asn Thr Glu Ile Ala
            1955                1960                1965

Leu Pro Gly Glu Val Ser Ala Arg Asp Thr Val Thr Ile His Ser Val
            1970                1975                1980

Gly Gly Thr Ile Thr Ile Leu Pro Thr Lys Thr Lys Pro Lys Lys Leu
1985                1990                1995                2000

Leu Phe Leu Gly Ser Asp Gly Lys Ser Tyr Pro Tyr Leu Phe Lys Gly
            2005                2010                2015

Leu Glu Asp Leu His Leu Asp Glu Arg Ile Met Gln Phe Leu Ser Ile
            2020                2025                2030

Val Asn Thr Met Phe Ala Thr Ile Asn Arg Gln Glu Thr Pro Arg Phe
            2035                2040                2045

His Ala Arg His Tyr Ser Val Thr Pro Leu Gly Thr Arg Ser Gly Leu
            2050                2055                2060

Ile Gln Trp Val Asp Gly Ala Thr Pro Leu Phe Gly Leu Tyr Lys Arg
2065                2070                2075                2080

Trp Gln Gln Arg Glu Ala Ala Leu Gln Ala Lys Ala Gln Asp Ser
            2085                2090                2095

Tyr Gln Thr Pro Gln Asn Pro Gly Ile Val Pro Arg Pro Ser Glu Leu
            2100                2105                2110

Tyr Tyr Ser Lys Ile Gly Pro Ala Leu Lys Thr Val Gly Leu Ser Leu
            2115                2120                2125

Asp Val Ser Arg Arg Asp Trp Pro Leu His Val Met Lys Ala Val Leu
            2130                2135                2140

Glu Glu Leu Met Glu Ala Thr Pro Pro Asn Leu Leu Ala Lys Glu Leu
2145                2150                2155                2160

Trp Ser Ser Cys Thr Thr Pro Asp Glu Trp Trp Arg Val Thr Gln Ser
            2165                2170                2175

Tyr Ala Arg Ser Thr Ala Val Met Ser Met Val Gly Tyr Ile Ile Gly
            2180                2185                2190

Leu Gly Asp Arg His Leu Asp Asn Val Leu Ile Asp Met Thr Thr Gly
            2195                2200                2205

Glu Val Val His Ile Asp Tyr Asn Val Cys Phe Glu Lys Gly Lys Ser
            2210                2215                2220

Leu Arg Val Pro Glu Lys Val Pro Phe Arg Met Thr Gln Asn Ile Glu
2225                2230                2235                2240

Thr Ala Leu Gly Val Thr Gly Val Glu Gly Val Phe Arg Leu Ser Cys
            2245                2250                2255

Glu Gln Val Leu His Ile Met Arg Arg Gly Arg Glu Thr Leu Leu Thr
            2260                2265                2270

Leu Leu Glu Ala Phe Val Tyr Asp Pro Leu Val Asp Trp Thr Ala Gly
            2275                2280                2285

Gly Glu Ala Gly Phe Ala Gly Ala Val Tyr Gly Gly Gly Gln Gln
            2290                2295                2300

Ala Glu Ser Lys Gln Ser Lys Arg Glu Met Glu Arg Glu Ile Thr Arg
2305                2310                2315                2320

Ser Leu Phe Ser Ser Arg Val Ala Glu Ile Lys Val Asn Trp Phe Lys
            2325                2330                2335

Asn Arg Asp Glu Met Leu Val Val Leu Pro Lys Leu Asp Gly Ser Leu
            2340                2345                2350

Asp Glu Tyr Leu Ser Leu Gln Glu Gln Leu Thr Asp Val Glu Lys Leu
```

-continued

| | 2355 | | | 2360 | | | 2365 | |

Gln Gly Lys Leu Leu Glu Glu Ile Glu Phe Leu Glu Gly Ala Glu Gly
              2370                2375                2380

Val Asp His Pro Ser His Thr Leu Gln His Arg Tyr Ser Glu His Thr
2385                2390                2395                2400

Gln Leu Gln Thr Gln Gln Arg Ala Val Gln Glu Ala Ile Gln Val Lys
              2405                2410                2415

Leu Asn Glu Phe Glu Gln Trp Ile Thr His Tyr Gln Ala Ala Phe Asn
              2420                2425                2430

Asn Leu Glu Ala Thr Gln Leu Ala Ser Leu Leu Gln Glu Ile Ser Thr
              2435                2440                2445

Gln Met Asp Leu Gly Pro Pro Ser Tyr Val Pro Ala Thr Ala Phe Leu
              2450                2455                2460

Gln Asn Ala Gly Gln Ala His Leu Ile Ser Gln Cys Glu Gln Leu Glu
2465                2470                2475                2480

Gly Glu Val Gly Ala Leu Leu Gln Gln Arg Arg Ser Val Leu Arg Gly
              2485                2490                2495

Cys Leu Glu Gln Leu His His Tyr Ala Thr Val Ala Leu Gln Tyr Pro
              2500                2505                2510

Lys Ala Ile Phe Gln Lys His Arg Ile Glu Gln Trp Lys Thr Trp Met
              2515                2520                2525

Glu Glu Leu Ile Cys Asn Thr Thr Val Glu Arg Cys Gln Glu Leu Tyr
              2530                2535                2540

Arg Lys Tyr Glu Met Gln Tyr Ala Pro Gln Pro Pro Thr Val Cys
2545                2550                2555                2560

Gln Phe Ile Thr Ala Thr Glu Met Thr Leu Gln Arg Tyr Ala Ala Asp
              2565                2570                2575

Ile Asn Ser Arg Leu Ile Arg Gln Val Glu Arg Leu Lys Gln Glu Ala
              2580                2585                2590

Val Thr Val Pro Val Cys Glu Asp Gln Leu Lys Glu Ile Glu Arg Cys
              2595                2600                2605

Ile Lys Val Phe Leu His Glu Asn Gly Glu Gly Ser Leu Ser Leu
              2610                2615                2620

Ala Ser Val Ile Ile Ser Ala Leu Cys Thr Leu Thr Arg Arg Asn Leu
2625                2630                2635                2640

Met Met Glu Gly Ala Ala Ser Ser Ala Gly Glu Gln Leu Val Asp Leu
              2645                2650                2655

Thr Ser Arg Asp Gly Ala Trp Phe Leu Glu Glu Leu Cys Ser Met Ser
              2660                2665                2670

Gly Asn Val Thr Cys Leu Val Gln Leu Leu Lys Gln Cys His Leu Val
              2675                2680                2685

Pro Gln Asp Leu Asp Ile Pro Asn Pro Met Glu Ala Ser Glu Thr Val
              2690                2695                2700

His Leu Ala Asn Gly Val Tyr Thr Ser Leu Gln Glu Leu Asn Ser Asn
2705                2710                2715                2720

Phe Arg Gln Ile Ile Phe Pro Glu Ala Leu Arg Cys Leu Met Lys Gly
              2725                2730                2735

Glu Tyr Thr Leu Glu Ser Met Leu His Glu Leu Asp Gly Leu Ile Glu
              2740                2745                2750

Gln Thr Thr Asp Gly Val Pro Leu Gln Thr Leu Val Glu Ser Leu Gln
              2755                2760                2765

Ala Tyr Leu Arg Asn Ala Ala Met Gly Leu Glu Glu Glu Thr His Ala
              2770                2775                2780

```
His Tyr Ile Asp Val Ala Arg Leu Leu His Ala Gln Tyr Gly Glu Leu
2785                2790                2795                2800

Ile Gln Pro Arg Asn Gly Ser Val Asp Glu Thr Pro Lys Met Ser Ala
        2805                2810                2815

Gly Gln Met Leu Leu Val Ala Phe Asp Gly Met Phe Ala Gln Val Glu
            2820                2825                2830

Thr Ala Phe Ser Leu Leu Val Glu Lys Leu Asn Lys Met Glu Ile Pro
        2835                2840                2845

Ile Ala Trp Arg Lys Ile Asp Ile Ile Arg Glu Ala Arg Ser Thr Gln
        2850                2855                2860

Val Asn Phe Phe Asp Asp Asn His Arg Gln Val Leu Glu Glu Ile
2865                2870                2875                2880

Phe Phe Leu Lys Arg Leu Gln Thr Ile Lys Glu Phe Phe Arg Leu Cys
                2885                2890                2895

Gly Thr Phe Ser Lys Thr Leu Ser Gly Ser Ser Ser Leu Glu Asp Gln
            2900                2905                2910

Asn Thr Val Asn Gly Pro Val Gln Ile Val Asn Val Lys Thr Leu Phe
        2915                2920                2925

Arg Asn Ser Cys Phe Ser Glu Asp Gln Met Ala Lys Pro Ile Lys Ala
        2930                2935                2940

Phe Thr Ala Asp Phe Val Arg Gln Leu Leu Ile Gly Leu Pro Asn Gln
2945                2950                2955                2960

Ala Leu Gly Leu Thr Leu Cys Ser Phe Ile Ser Ala Leu Gly Val Asp
            2965                2970                2975

Ile Ile Ala Gln Val Glu Ala Lys Asp Phe Gly Ala Glu Ser Lys Val
        2980                2985                2990

Ser Val Asp Asp Leu Cys Lys Lys Ala Val Glu His Asn Ile Gln Ile
        2995                3000                3005

Gly Lys Phe Ser Gln Leu Val Met Asn Arg Ala Thr Val Leu Ala Ser
        3010                3015                3020

Ser Tyr Asp Thr Ala Trp Lys Lys His Asp Leu Val Arg Arg Leu Glu
3025                3030                3035                3040

Thr Ser Ile Ser Ser Cys Lys Thr Ser Leu Gln Arg Val Gln Leu His
            3045                3050                3055

Ile Ala Met Phe Gln Trp Gln His Glu Asp Leu Leu Ile Asn Arg Pro
        3060                3065                3070

Gln Ala Met Ser Val Thr Pro Pro Arg Ser Ala Ile Leu Thr Ser
        3075                3080                3085

Met Lys Lys Lys Leu His Thr Leu Ser Gln Ile Glu Thr Ser Ile Ala
        3090                3095                3100

Thr Val Gln Glu Lys Leu Ala Ala Leu Glu Ser Ser Ile Glu Gln Arg
3105                3110                3115                3120

Leu Lys Trp Ala Gly Gly Ala Asn Pro Ala Leu Ala Pro Val Leu Gln
            3125                3130                3135

Asp Phe Glu Ala Thr Ile Ala Glu Arg Arg Asn Leu Val Leu Lys Glu
            3140                3145                3150

Ser Gln Arg Ala Ser Gln Val Thr Phe Leu Cys Ser Asn Ile Ile His
        3155                3160                3165

Phe Glu Ser Leu Arg Thr Arg Thr Ala Glu Ala Leu Asn Leu Asp Ala
        3170                3175                3180

Ala Leu Phe Glu Leu Ile Lys Arg Cys Gln Gln Met Cys Ser Phe Ala
        3185                3190                3195                3200
```

-continued

Ser Gln Phe Asn Ser Ser Val Ser Glu Leu Glu Leu Arg Leu Leu Gln
            3205                3210                3215
Arg Val Asp Thr Gly Leu Glu His Pro Ile Gly Ser Ser Glu Trp Leu
        3220                3225                3230
Leu Ser Ala His Lys Gln Leu Thr Gln Asp Met Ser Thr Gln Arg Ala
    3235                3240                3245
Ile Gln Thr Glu Lys Glu Gln Gln Ile Glu Thr Val Cys Glu Thr Ile
3250                3255                3260
Gln Asn Leu Val Asp Asn Ile Lys Thr Val Leu Thr Gly His Asn Arg
3265                3270                3275                3280
Gln Leu Gly Asp Val Lys His Leu Leu Lys Ala Met Ala Lys Asp Glu
            3285                3290                3295
Glu Ala Ala Leu Ala Asp Gly Glu Asp Val Pro Tyr Glu Asn Ser Val
        3300                3305                3310
Arg Gln Phe Leu Gly Glu Tyr Lys Ser Trp Gln Asp Asn Ile Gln Thr
    3315                3320                3325
Val Leu Phe Thr Leu Val Gln Ala Met Gly Gln Val Arg Ser Gln Glu
3330                3335                3340
His Val Glu Met Leu Gln Glu Ile Thr Pro Thr Leu Lys Glu Leu Lys
3345                3350                3355                3360
Thr Gln Ser Gln Ser Ile Tyr Asn Asn Leu Val Ser Phe Ala Ser Pro
            3365                3370                3375
Leu Val Thr Asp Ala Thr Asn Glu Cys Ser Ser Pro Thr Ser Ser Ala
        3380                3385                3390
Thr Tyr Gln Pro Ser Phe Ala Ala Val Arg Ser Asn Thr Gly Gln
    3395                3400                3405
Lys Thr Gln Pro Asp Val Met Ser Gln Asn Ala Arg Lys Leu Ile Gln
3410                3415                3420
Lys Asn Leu Ala Thr Ser Ala Asp Thr Pro Pro Ser Thr Val Pro Gly
3425                3430                3435                3440
Thr Gly Lys Ser Val Ala Cys Ser Pro Lys Lys Ala Val Arg Asp Pro
            3445                3450                3455
Lys Thr Gly Lys Ala Val Gln Glu Arg Asn Ser Tyr Ala Val Ser Val
        3460                3465                3470
Trp Lys Arg Val Lys Ala Lys Leu Glu Gly Arg Asp Val Asp Pro Asn
    3475                3480                3485
Arg Arg Met Ser Val Ala Glu Gln Val Asp Tyr Val Ile Lys Glu Ala
3490                3495                3500
Thr Asn Leu Asp Asn Leu Ala Gln Leu Tyr Glu Gly Trp Thr Ala Trp
3505                3510                3515                3520
Val

<210> SEQ ID NO 3
<211> LENGTH: 2629
<212> TYPE: DNA
<213> ORGANISM: Homo sapiens
<220> FEATURE:
<221> NAME/KEY: CDS
<222> LOCATION: (252)...(1433)

<400> SEQUENCE: 3
acttgtcatg gcgactgtcc agctttgtgc caggagcctc gcaggggttg atgggattgg      60
ggttttcccc tcccatgtgc tcaagactgg cgctaaaagt tttgagcttc tcaaagtct     120 agagccaccg tccagggagc aggtagctgc tgggctccgg ggacactttg cgttcgggct    180

-continued

```
gggagcgtgc tttccacgac ggtgacacgc ttccctggat tggcagccag actgccttcc    240
gggtcactgc c atg gag gag ccg cag tca gat cct agc gtc gag ccc cct    290
            Met Glu Glu Pro Gln Ser Asp Pro Ser Val Glu Pro Pro
              1               5                  10 ctg agt cag gaa aca ttt tca gac cta tgg aaa cta ctt cct gaa aac    338
Leu Ser Gln Glu Thr Phe Ser Asp Leu Trp Lys Leu Leu Pro Glu Asn
 15              20                  25 aac gtt ctg tcc ccc ttg ccg tcc caa gca atg gat gat ttg atg ctg    386
Asn Val Leu Ser Pro Leu Pro Ser Gln Ala Met Asp Asp Leu Met Leu
 30              35                  40                  45 tcc ccg gac gat att gaa caa tgg ttc act gaa gac cca ggt cca gat    434
Ser Pro Asp Asp Ile Glu Gln Trp Phe Thr Glu Asp Pro Gly Pro Asp
                 50                  55                  60 gaa gct ccc aga atg cca gag gct gct ccc cgc gtg gcc cct gca cca    482
Glu Ala Pro Arg Met Pro Glu Ala Ala Pro Arg Val Ala Pro Ala Pro
                 65                  70                  75 gca gct cct aca ccg gcg gcc cct gca cca gcc ccc tcc tgg ccc ctg    530
Ala Ala Pro Thr Pro Ala Ala Pro Ala Pro Ala Pro Ser Trp Pro Leu
             80                  85                  90 tca tct tct gtc cct tcc cag aaa acc tac cag ggc agc tac ggt ttc    578
Ser Ser Ser Val Pro Ser Gln Lys Thr Tyr Gln Gly Ser Tyr Gly Phe
 95                 100                 105 cgt ctg ggc ttc ttg cat tct ggg aca gcc aag tct gtg act tgc acg    626
Arg Leu Gly Phe Leu His Ser Gly Thr Ala Lys Ser Val Thr Cys Thr
110             115                 120                 125 tac tcc cct gcc ctc aac aag atg ttt tgc caa ctg gcc aag acc tgc    674
Tyr Ser Pro Ala Leu Asn Lys Met Phe Cys Gln Leu Ala Lys Thr Cys
                130                 135                 140 cct gtg cag ctg tgg gtt gat tcc aca ccc ccg ccc ggc acc cgc gtc    722
Pro Val Gln Leu Trp Val Asp Ser Thr Pro Pro Pro Gly Thr Arg Val
                145                 150                 155 cgc gcc atg gcc atc tac aag cag tca cag cac atg acg gag gtt gtg    770
Arg Ala Met Ala Ile Tyr Lys Gln Ser Gln His Met Thr Glu Val Val
            160                 165                 170 agg cgc tgc ccc cac cat gag cgc tgc tca gat agc gat ggt ctg gcc    818
Arg Arg Cys Pro His His Glu Arg Cys Ser Asp Ser Asp Gly Leu Ala
175             180                 185 cct cct cag cat ctt atc cga gtg gaa gga aat ttg cgt gtg gag tat    866
Pro Pro Gln His Leu Ile Arg Val Glu Gly Asn Leu Arg Val Glu Tyr
190             195                 200                 205 ttg gat gac aga aac act ttt cga cat agt gtg gtg gtg ccc tat gag    914
Leu Asp Asp Arg Asn Thr Phe Arg His Ser Val Val Val Pro Tyr Glu
                210                 215                 220 ccg cct gag gtt ggc tct gac tgt acc acc atc cac tac aac tac atg    962
Pro Pro Glu Val Gly Ser Asp Cys Thr Thr Ile His Tyr Asn Tyr Met
                225                 230                 235 tgt aac agt tcc tgc atg ggc ggc atg aac cgg agg ccc atc ctc acc    1010
Cys Asn Ser Ser Cys Met Gly Gly Met Asn Arg Arg Pro Ile Leu Thr
                240                 245                 250 atc atc aca ctg gaa gac tcc agt ggt aat cta ctg gga cgg aac agc    1058
Ile Ile Thr Leu Glu Asp Ser Ser Gly Asn Leu Leu Gly Arg Asn Ser
 255                 260                 265 ttt gag gtg cgt gtt tgt gcc tgt cct ggg aga gac cgg cgc aca gag    1106
Phe Glu Val Arg Val Cys Ala Cys Pro Gly Arg Asp Arg Arg Thr Glu
270             275                 280                 285 gaa gag aat ctc cgc aag aaa ggg gag cct cac cac gag ctg ccc cca    1154
Glu Glu Asn Leu Arg Lys Lys Gly Glu Pro His His Glu Leu Pro Pro
                290                 295                 300 ggg agc act aag cga gca ctg ccc aac aac acc agc tcc tct ccc cag    1202
```

```
Gly Ser Thr Lys Arg Ala Leu Pro Asn Asn Thr Ser Ser Pro Gln
            305                 310                 315 cca aag aag aaa cca ctg gat gga gaa tat ttc acc ctt cag atc cgt    1250
Pro Lys Lys Lys Pro Leu Asp Gly Glu Tyr Phe Thr Leu Gln Ile Arg
            320                 325                 330 ggg cgt gag cgc ttc gag atg ttc cga gag ctg aat gag gcc ttg gaa    1298
Gly Arg Glu Arg Phe Glu Met Phe Arg Glu Leu Asn Glu Ala Leu Glu
        335                 340                 345 ctc aag gat gcc cag gct ggg aag gag cca ggg ggg agc agg gct cac    1346
Leu Lys Asp Ala Gln Ala Gly Lys Glu Pro Gly Gly Ser Arg Ala His
350                 355                 360                 365 tcc agc cac ctg aag tcc aaa aag ggt cag tct acc tcc cgc cat aaa    1394
Ser Ser His Leu Lys Ser Lys Lys Gly Gln Ser Thr Ser Arg His Lys
                370                 375                 380 aaa ctc atg ttc aag aca gaa ggg cct gac tca gac tga cattctccac     1443
Lys Leu Met Phe Lys Thr Glu Gly Pro Asp Ser Asp  *
            385                 390 ttcttgttcc ccactgacag cctcccaccc ccatctctcc ctccctgcc attttgggtt   1503
ttgggtcttt gaacccttgc ttgcaatagg tgtgcgtcag aagcacccag gacttccatt  1563
tgctttgtcc cggggctcca ctgaacaagt tggcctgcac tggtgttttg ttgtggggag  1623
gaggatgggg agtaggacat accagcttag attttaaggt ttttactgtg agggatgttt  1683
gggagatgta agaaatgttc ttgcagttaa gggttagttt acaatcagcc acattctagg  1743
taggtagggg cccacttcac cgtactaacc agggaagctg tccctcatgt tgaattttct  1803
ctaacttcaa ggcccatatc tgtgaaatgc tggcatttgc acctacctca cagagtgcat  1863
tgtgagggtt aatgaaataa tgtacatctg gccttgaaac cacctttat tacatggggt   1923
ctaaaacttg accccttga gggtgcctgt tccctctccc tctccctgtt ggctggtggg   1983
ttggtagttt ctacagttgg gcagctggtt aggtagaggg agttgtcaag tcttgctggc  2043
ccagccaaac cctgtctgac aacctcttgg tcgaccttag tacctaaaag gaaatctcac  2103
cccatcccac accctggagg atttcatctc ttgtatatga tgatctggat ccaccaagac  2163
ttgtttatg ctcagggtca attcttttt tctttttttt ttttttttt cttttcttt     2223
gagactgggt ctcgctttgt tgcccaggct ggagtggagt ggcgtgatct tggcttactg  2283
cagccttttgc ctccccggct cgagcagtcc tgcctcagcc tccggagtag ctgggaccac  2343
aggttcatgc caccatggcc agccaacttt tgcatgtttt gtagagatgg ggtctcacag  2403
tgttgcccag gctggtctca aactcctggg ctcaggcgat ccacctgtct cagcctccca  2463
gagtgctggg attacaattg tgagccacca cgtggagctg aagggtcaa catcttttac   2523
attctgcaag cacatctgca ttttcacccc acccttcccc tccttctccc tttttatatc  2583
ccattttttat atcgatctct tatttttacaa taaaactttg ctgcca             2629

<210> SEQ ID NO 4
<211> LENGTH: 393
<212> TYPE: PRT
<213> ORGANISM: Homo sapiens

<400> SEQUENCE: 4

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45
```

```
Asp Ile Glu Gln Trp Phe Thr Glu Asp Pro Gly Pro Asp Glu Ala Pro
        50                  55                  60

Arg Met Pro Glu Ala Ala Pro Arg Val Ala Pro Ala Pro Ala Ala Pro
 65                  70                  75                  80

Thr Pro Ala Ala Pro Ala Pro Ala Pro Ser Trp Pro Leu Ser Ser Ser
                    85                  90                  95

Val Pro Ser Gln Lys Thr Tyr Gln Gly Ser Tyr Gly Phe Arg Leu Gly
                100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
        130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
370                 375                 380

Phe Lys Thr Glu Gly Pro Asp Ser Asp
385                 390

<210> SEQ ID NO 5
<211> LENGTH: 12606
<212> TYPE: DNA
<213> ORGANISM: Homo sapiens
<220> FEATURE:
<221> NAME/KEY: CDS
<222> LOCATION: (1703)...(10798)

<400> SEQUENCE: 5
attgacttga tgcacaacat cacaaaggcg attttttgaga actgatagtg catcagccga    60
```

-continued

```
cccaggtaat ttaaaatatt cttcatccag agatagaggt ggttcttcct cttacggact      120
gcaaccttca aattcagctg tggtgtctcg gcaaaggcac gatgatacca gagtccacgc      180
tgacatacag aatgacgaaa aggagagatc gatgtcttat tgtgatgagt ctcgactgtc      240
gaatcttctt cggaggatca cccgggaaga cgacagagac cgaagattgg ctactgtaaa      300
gcagttgaaa gaatttattc agcaaccaga aaataagctg gtactagtta aacaattgga      360
taatatcttg gctgctgtac atgacgtgct taatgaaagt agcaaattgc ttcaggagtt      420
gagacaggag ggagcttgct gtcttggcct tctttgtgct tctctgagct atgaggctga      480
gaagatcttc aagtggattt ttagcaaaat tagctcatct gcaaagatg aagttaaact       540 cctctactta tgtgccacct acaaagcact agagactgta ggagaaaaga aagcctttc       600 atctgtaatg cagcttgtaa tgaccagcct gcagtctatt cttgaaaatg tggatacacc      660
agaattgctt tgtaaatgtg ttaagtgcat tcttttggtg gctcgatgtt accctcatat      720
tttcagcact aattttaggg atacagttga tatattagtt ggatggcata tagatcatac      780
tcagaaacct tcgctcacgc agcaggtatc tgggtggttg cagagtttgg agccattttg      840
ggtagctgat cttgcatttt ctactactct tcttggtcag tttctggaag acatggaagc      900
atatgctgag gacctcagcc atgtggcctc tggggaatca gtggatgaag atgtccctcc      960
tccatcagtg tcattaccaa agctggctgc acttctccgg gtatttagta ctgtggtgag     1020
gagcattggg gaacgcttca gcccaattcg gggtcctcca attactgagg catatgtaac     1080
agatgttctg tacagagtaa tgagatgtgt gacggctgca aaccaggtgt ttttttctga     1140
ggctgtgttg acagctgcta atgagtgtgt tggtgttttg ctcggcagct tggatcctag     1200
catgactata cattgtgaca tggtcattac atatggatta gaccaactgg agaattgcca     1260
gacttgtggt accgattata tcatctcagt cttgaattta ctcacgctga ttgttgaaca     1320
gataaatacg aaactgccat catcatttgt agaaaaactg tttataccat catctaaact     1380
actattcttg cgttatcata aagaaaaaga ggttgttgct gtagcccatg ctgtttatca     1440
agcagtgctc agcttgaaga atattcctgt tttggagact gcctataagt taatattggg     1500
agaaatgact tgtgccctaa caacctcct acacagtcta caacttcctg aggcctgttc      1560
tgaaataaaa catgaggctt ttaagaatca tgtgttcaat gtagacaatg caaaatttgt     1620
agttatattt gacctcaatt gactacaaaa tttgtagtta aatttgacta caattggaaa     1680
tgccaaaaac tcactaatag gg atg tgg gcg cta tct cca act gtc ttt gca      1732
                        Met Trp Ala Leu Ser Pro Thr Val Phe Ala
                         1               5                  10 ctt ctg agt aag aat ctg atg att gtg cac agt gac ctg gct gtt cac       1780
Leu Leu Ser Lys Asn Leu Met Ile Val His Ser Asp Leu Ala Val His
            15                  20                  25 ttc cct gcc att cag tat gct gtg ctc tac aca ttg tat tct cat tgt       1828
Phe Pro Ala Ile Gln Tyr Ala Val Leu Tyr Thr Leu Tyr Ser His Cys
        30                  35                  40 acc agg cat gat cac ttt atc tct agt agc ctc agt tct tcc tct cct       1876
Thr Arg His Asp His Phe Ile Ser Ser Ser Leu Ser Ser Ser Ser Pro
    45                  50                  55 tct ttg ttt gat gga gct gtg att agc act gta act acg gct aca aag       1924
Ser Leu Phe Asp Gly Ala Val Ile Ser Thr Val Thr Thr Ala Thr Lys
60                  65                  70 aaa cat ttc tca att ata tta aat ctt ctg gga ata tta ctt aag aaa       1972
Lys His Phe Ser Ile Ile Leu Asn Leu Leu Gly Ile Leu Leu Lys Lys
75                  80                  85                  90
```

```
                                             -continued gat aac ctt aac cag gac acg agg aaa ctg tta atg act tgg gct ttg    2020
Asp Asn Leu Asn Gln Asp Thr Arg Lys Leu Leu Met Thr Trp Ala Leu
                 95                 100                 105 gaa gca gct gtt tta atg aag aag tct gaa aca tac gca cct tta ttc    2068
Glu Ala Ala Val Leu Met Lys Lys Ser Glu Thr Tyr Ala Pro Leu Phe
             110                 115                 120 tct ctt ccg tct ttc cat aaa ttt tgc aaa ggc ctt tta gcc aac act    2116
Ser Leu Pro Ser Phe His Lys Phe Cys Lys Gly Leu Leu Ala Asn Thr
         125                 130                 135 ctc gtt gaa gat gtg aat atc tgt ctg cag gca tgc agc agt cta cat    2164
Leu Val Glu Asp Val Asn Ile Cys Leu Gln Ala Cys Ser Ser Leu His
     140                 145                 150 gct ctg tcc tct tcc ttg cca gat gat ctt tta cag aga tgt gtc gat    2212
Ala Leu Ser Ser Ser Leu Pro Asp Asp Leu Leu Gln Arg Cys Val Asp
155                 160                 165                 170 gtt tgc cgt gtt caa cta gtg cac agt gga act cgt att cga caa gca    2260
Val Cys Arg Val Gln Leu Val His Ser Gly Thr Arg Ile Arg Gln Ala
                 175                 180                 185 ttt gga aaa ctg ttg aaa tca att cct tta gat gtt gtc cta agc aat    2308
Phe Gly Lys Leu Leu Lys Ser Ile Pro Leu Asp Val Val Leu Ser Asn
             190                 195                 200 aac aat cac aca gaa att caa gaa att tct tta gca tta aga agt cac    2356
Asn Asn His Thr Glu Ile Gln Glu Ile Ser Leu Ala Leu Arg Ser His
         205                 210                 215 atg agt aaa gca cca agt aat aca ttc cac ccc caa gat ttc tct gat    2404
Met Ser Lys Ala Pro Ser Asn Thr Phe His Pro Gln Asp Phe Ser Asp
     220                 225                 230 gtt att agt ttt att ttg tat ggg aac tct cat aga aca ggg aag gac    2452
Val Ile Ser Phe Ile Leu Tyr Gly Asn Ser His Arg Thr Gly Lys Asp
235                 240                 245                 250 aat tgg ttg gaa aga ctg ttc tat agc tgc cag aga ctg gat aag cgt    2500
Asn Trp Leu Glu Arg Leu Phe Tyr Ser Cys Gln Arg Leu Asp Lys Arg
                 255                 260                 265 gac cag tca aca att cca cgc aat ctc ctg aag aca gat gct gtc ctt    2548
Asp Gln Ser Thr Ile Pro Arg Asn Leu Leu Lys Thr Asp Ala Val Leu
             270                 275                 280 tgg cag tgg gcc ata tgg gaa gct gca caa ttc act gtt ctt tct aag    2596
Trp Gln Trp Ala Ile Trp Glu Ala Ala Gln Phe Thr Val Leu Ser Lys
         285                 290                 295 ctg aga acc cca ctg ggc aga gct caa gac acc ttc cag aca att gaa    2644
Leu Arg Thr Pro Leu Gly Arg Ala Gln Asp Thr Phe Gln Thr Ile Glu
     300                 305                 310 ggt atc att cga agt ctc gca gct cac aca tta aac cct gat cag gat    2692
Gly Ile Ile Arg Ser Leu Ala Ala His Thr Leu Asn Pro Asp Gln Asp
315                 320                 325                 330 gtt agt cag tgg aca act gca gac aat gat gaa ggc cat ggt aac aac    2740
Val Ser Gln Trp Thr Thr Ala Asp Asn Asp Glu Gly His Gly Asn Asn
                 335                 340                 345 caa ctt aga ctt gtt ctt ctt ctg cag tat ctg gaa aat ctg gag aaa    2788
Gln Leu Arg Leu Val Leu Leu Leu Gln Tyr Leu Glu Asn Leu Glu Lys
             350                 355                 360 tta atg tat aat gca tac gag gga tgt gct aat gca tta act tca cct    2836
Leu Met Tyr Asn Ala Tyr Glu Gly Cys Ala Asn Ala Leu Thr Ser Pro
         365                 370                 375 ccc aag gtc att aga act ttt ttc tat acc aat cgc caa act tgt cag    2884
Pro Lys Val Ile Arg Thr Phe Phe Tyr Thr Asn Arg Gln Thr Cys Gln
     380                 385                 390 gac tgg cta acg cgg att cga ctc tcc atc atg agg gta gga ttg ttg    2932
Asp Trp Leu Thr Arg Ile Arg Leu Ser Ile Met Arg Val Gly Leu Leu
395                 400                 405                 410
```

```
gca ggc cag cct gca gtg aca gtg aga cat ggc ttt gac ttg ctt aca    2980
Ala Gly Gln Pro Ala Val Thr Val Arg His Gly Phe Asp Leu Leu Thr
            415                 420                 425 gag atg aaa aca acc agc cta tct cag ggg aat gaa ttg gaa gta acc    3028
Glu Met Lys Thr Thr Ser Leu Ser Gln Gly Asn Glu Leu Glu Val Thr
        430                 435                 440 att atg atg gtg gta gaa gca tta tgt gaa ctt cat tgt cct gaa gct    3076
Ile Met Met Val Val Glu Ala Leu Cys Glu Leu His Cys Pro Glu Ala
                445                 450                 455 ata cag gga att gct gtc tgg tca tca tct att gtt gga aaa aat ctt    3124
Ile Gln Gly Ile Ala Val Trp Ser Ser Ser Ile Val Gly Lys Asn Leu
            460                 465                 470 ctg tgg att aac tca gtg gct caa cag gct gaa ggg agg ttt gaa aag    3172
Leu Trp Ile Asn Ser Val Ala Gln Gln Ala Glu Gly Arg Phe Glu Lys
475                 480                 485                 490 gcc tct gtg gag tac cag gaa cac ctg tgt gcc atg aca ggt gtt gat    3220
Ala Ser Val Glu Tyr Gln Glu His Leu Cys Ala Met Thr Gly Val Asp
                495                 500                 505 tgc tgc atc tcc agc ttt gac aaa tcg gtg ctc acc tta gcc aat gct    3268
Cys Cys Ile Ser Ser Phe Asp Lys Ser Val Leu Thr Leu Ala Asn Ala
            510                 515                 520 ggg cgt aac agt gcc agc ccg aaa cat tct ctg aat ggt gaa tcc aga    3316
Gly Arg Asn Ser Ala Ser Pro Lys His Ser Leu Asn Gly Glu Ser Arg
        525                 530                 535 aaa act gtg ctg tcc aaa ccg act gac tct tcc cct gag gtt ata aat    3364
Lys Thr Val Leu Ser Lys Pro Thr Asp Ser Ser Pro Glu Val Ile Asn
540                 545                 550 tat tta gga aat aaa gca tgt gag tgc tac atc tca att gcc gat tgg    3412
Tyr Leu Gly Asn Lys Ala Cys Glu Cys Tyr Ile Ser Ile Ala Asp Trp
555                 560                 565                 570 gct gct gtg cag gaa tgg cag aac gct atc cat gac ttg aaa aag agt    3460
Ala Ala Val Gln Glu Trp Gln Asn Ala Ile His Asp Leu Lys Lys Ser
                575                 580                 585 acc agt agc act tcc ctc aac ctg aaa gct gac ttc aac tat ata aaa    3508
Thr Ser Ser Thr Ser Leu Asn Leu Lys Ala Asp Phe Asn Tyr Ile Lys
            590                 595                 600 tca tta agc agc ttt gag tct gga aaa ttt gtt gaa tgt acc gag caa    3556
Ser Leu Ser Ser Phe Glu Ser Gly Lys Phe Val Glu Cys Thr Glu Gln
        605                 610                 615 tta gaa ttg tta cca gga gaa aat atc aat cta ctt gct gga gga tca    3604
Leu Glu Leu Leu Pro Gly Glu Asn Ile Asn Leu Leu Ala Gly Gly Ser
620                 625                 630 aaa gaa aaa ata gac atg aaa aaa ctg ctt cct aac atg tta agt ccg    3652
Lys Glu Lys Ile Asp Met Lys Lys Leu Leu Pro Asn Met Leu Ser Pro
635                 640                 645                 650 gat ccg agg gaa ctt cag aaa tcc att gaa gtt caa ttg tta aga agt    3700
Asp Pro Arg Glu Leu Gln Lys Ser Ile Glu Val Gln Leu Leu Arg Ser
                655                 660                 665 tct gtt tgt ttg gca act gct tta aac ccg ata gaa caa gat cag aag    3748
Ser Val Cys Leu Ala Thr Ala Leu Asn Pro Ile Glu Gln Asp Gln Lys
            670                 675                 680 tgg cag tct ata act gaa aat gtg gta aag tac ttg aag caa aca tcc    3796
Trp Gln Ser Ile Thr Glu Asn Val Val Lys Tyr Leu Lys Gln Thr Ser
        685                 690                 695 cgc atc gct att gga cct ctg aga ctt tct act tta aca gtt tca cag    3844
Arg Ile Ala Ile Gly Pro Leu Arg Leu Ser Thr Leu Thr Val Ser Gln
700                 705                 710 tct ttg cca gtt cta agt acc ttg cag ctg tat tgc tca tct gct ttg    3892
Ser Leu Pro Val Leu Ser Thr Leu Gln Leu Tyr Cys Ser Ser Ala Leu
```

```
                715               720               725               730
gag aac aca gtt tct aac aga ctt tca aca gag gac tgt ctt att cca       3940
Glu Asn Thr Val Ser Asn Arg Leu Ser Thr Glu Asp Cys Leu Ile Pro
                    735               740               745 ctc ttc agt gaa gct tta cgt tca tgt aaa cag cat gac gtg agg cca       3988
Leu Phe Ser Glu Ala Leu Arg Ser Cys Lys Gln His Asp Val Arg Pro
            750               755               760 tgg atg cag gca tta agg tat act atg tac cag aat cag ttg ttg gag       4036
Trp Met Gln Ala Leu Arg Tyr Thr Met Tyr Gln Asn Gln Leu Leu Glu
        765               770               775 aaa att aaa gaa caa aca gtc cca att aga agc cat ctc atg gaa tta       4084
Lys Ile Lys Glu Gln Thr Val Pro Ile Arg Ser His Leu Met Glu Leu
    780               785               790 ggt cta aca gca gca aaa ttt gct aga aaa cga ggg aat gtg tcc ctt       4132
Gly Leu Thr Ala Ala Lys Phe Ala Arg Lys Arg Gly Asn Val Ser Leu
795               800               805               810 gca aca aga ctg ctg gca cag tgc agt gaa gtt cag ctg gga aag acc       4180
Ala Thr Arg Leu Leu Ala Gln Cys Ser Glu Val Gln Leu Gly Lys Thr
                    815               820               825 acc act gca cag gat tta gtc caa cat ttt aaa aaa cta tca acc caa       4228
Thr Thr Ala Gln Asp Leu Val Gln His Phe Lys Lys Leu Ser Thr Gln
            830               835               840 ggt caa gtg gat gaa aaa tgg ggg ccc gaa ctt gat att gaa aaa acc       4276
Gly Gln Val Asp Glu Lys Trp Gly Pro Glu Leu Asp Ile Glu Lys Thr
        845               850               855 aaa ttg ctt tat aca gca ggc cag tca aca cat gca atg gaa atg ttg       4324
Lys Leu Leu Tyr Thr Ala Gly Gln Ser Thr His Ala Met Glu Met Leu
    860               865               870 agt tct tgt gcc ata tct ttc tgc aag tct gtg aaa gct gaa tat gca       4372
Ser Ser Cys Ala Ile Ser Phe Cys Lys Ser Val Lys Ala Glu Tyr Ala
875               880               885               890 gtt gct aaa tca att ctg aca ctg gct aaa tgg atc cag gca gaa tgg       4420
Val Ala Lys Ser Ile Leu Thr Leu Ala Lys Trp Ile Gln Ala Glu Trp
                    895               900               905 aaa gag att tca gga cag ctg aaa cag gtt tac aga gct cag cac caa       4468
Lys Glu Ile Ser Gly Gln Leu Lys Gln Val Tyr Arg Ala Gln His Gln
            910               915               920 cag aac ttc aca ggt ctt tct act ttg tct aaa aac ata ctc act cta       4516
Gln Asn Phe Thr Gly Leu Ser Thr Leu Ser Lys Asn Ile Leu Thr Leu
        925               930               935 ata gaa ctg cca tct gtt aat acg atg gaa gaa gag tat cct cgg atc       4564
Ile Glu Leu Pro Ser Val Asn Thr Met Glu Glu Glu Tyr Pro Arg Ile
    940               945               950 gag agt gaa tct aca gtg cat att gga gtt gga gaa cct gac ttc att       4612
Glu Ser Glu Ser Thr Val His Ile Gly Val Gly Glu Pro Asp Phe Ile
955               960               965               970 ttg gga cag ttg tat cac ctg tct tca gta cag gca cct gaa gta gcc       4660
Leu Gly Gln Leu Tyr His Leu Ser Ser Val Gln Ala Pro Glu Val Ala
                    975               980               985 aaa tct tgg gca gcg ttg gcc agc tgg gct tat agg tgg ggc aga aag       4708
Lys Ser Trp Ala Ala Leu Ala Ser Trp Ala Tyr Arg Trp Gly Arg Lys
            990               995               1000 gtg gtt gac aat gcc agt cag gga gaa ggt gtt cgt ctg ctg cct aga       4756
Val Val Asp Asn Ala Ser Gln Gly Glu Gly Val Arg Leu Leu Pro Arg
        1005              1010              1015 gaa aaa tct gaa gtt cag aat cta ctt cca gac act ata act gag gaa       4804
Glu Lys Ser Glu Val Gln Asn Leu Leu Pro Asp Thr Ile Thr Glu Glu
    1020              1025              1030 gag aaa gag aga ata tat ggt att ctt gga cag gct gtg tgt cgg ccg       4852
```

```
Glu Lys Glu Arg Ile Tyr Gly Ile Leu Gly Gln Ala Val Cys Arg Pro
1035                1040                1045                1050 gcg ggg att cag gat gaa gat ata aca ctt cag ata act gag agt gaa       4900
Ala Gly Ile Gln Asp Glu Asp Ile Thr Leu Gln Ile Thr Glu Ser Glu
                1055                1060                1065 gac aac gaa gaa gat gac atg gtt gat gtt atc tgg cgt cag ttg ata       4948
Asp Asn Glu Glu Asp Asp Met Val Asp Val Ile Trp Arg Gln Leu Ile
            1070                1075                1080 tca agc tgc cca tgg ctt tca gaa ctt gat gaa agt gca act gaa gga       4996
Ser Ser Cys Pro Trp Leu Ser Glu Leu Asp Glu Ser Ala Thr Glu Gly
        1085                1090                1095 gtt att aaa gtg tgg agg aaa gtt gta gat aga ata ttc agc ctg tac       5044
Val Ile Lys Val Trp Arg Lys Val Val Asp Arg Ile Phe Ser Leu Tyr
    1100                1105                1110 aaa ctc tct tgc agt gca tac ttt act ttc ctt aaa ctc aac gct ggt       5092
Lys Leu Ser Cys Ser Ala Tyr Phe Thr Phe Leu Lys Leu Asn Ala Gly
1115                1120                1125                1130 caa att cct tta gat gag gat gac cct agg ctg cat tta agt cac aga       5140
Gln Ile Pro Leu Asp Glu Asp Asp Pro Arg Leu His Leu Ser His Arg
                1135                1140                1145 gtg gaa cag agc act gat gac atg att gtg atg gcc aca ttg cgc ctg       5188
Val Glu Gln Ser Thr Asp Asp Met Ile Val Met Ala Thr Leu Arg Leu
            1150                1155                1160 ctg cgg ttg ctc gtg aag cat gct ggt gag ctt cgg cag tat ctg gag       5236
Leu Arg Leu Leu Val Lys His Ala Gly Glu Leu Arg Gln Tyr Leu Glu
        1165                1170                1175 cac ggc ttg gag aca aca ccc act gca cca tgg aga gga att att ccg       5284
His Gly Leu Glu Thr Thr Pro Thr Ala Pro Trp Arg Gly Ile Ile Pro
    1180                1185                1190 caa ctt ttc tca cgc tta aac cac cct gaa gtg tat gtg cgc caa agt       5332
Gln Leu Phe Ser Arg Leu Asn His Pro Glu Val Tyr Val Arg Gln Ser
1195                1200                1205                1210 att tgt aac ctt ctc tgc cgt gtg gct caa gat tcc cca cat ctc ata       5380
Ile Cys Asn Leu Leu Cys Arg Val Ala Gln Asp Ser Pro His Leu Ile
                1215                1220                1225 ttg tat cct gca ata gtg ggt acc ata tcg ctt agt agt gaa tcc cag       5428
Leu Tyr Pro Ala Ile Val Gly Thr Ile Ser Leu Ser Ser Glu Ser Gln
            1230                1235                1240 gct tca gga aat aaa ttt tcc act gca att cca act tta ctt ggc aat       5476
Ala Ser Gly Asn Lys Phe Ser Thr Ala Ile Pro Thr Leu Leu Gly Asn
        1245                1250                1255 att caa gga gaa gaa ttg ctg gtt tct gaa tgt gag gga gga agt cct       5524
Ile Gln Gly Glu Glu Leu Leu Val Ser Glu Cys Glu Gly Gly Ser Pro
    1260                1265                1270 cct gca tct cag gat agc aat aag gat gaa cct aaa agt gga tta aat       5572
Pro Ala Ser Gln Asp Ser Asn Lys Asp Glu Pro Lys Ser Gly Leu Asn
1275                1280                1285                1290 gaa gac caa gcc atg atg cag gat tgt tac agc aaa att gta gat aag       5620
Glu Asp Gln Ala Met Met Gln Asp Cys Tyr Ser Lys Ile Val Asp Lys
                1295                1300                1305 ctg tcc tct gca aac ccc acc atg gta tta cag gtt cag atg ctc gtg       5668
Leu Ser Ser Ala Asn Pro Thr Met Val Leu Gln Val Gln Met Leu Val
            1310                1315                1320 gct gaa ctg cgc agg gtc act gtg ctc tgg gat gag ctc tgg ctg gga       5716
Ala Glu Leu Arg Arg Val Thr Val Leu Trp Asp Glu Leu Trp Leu Gly
        1325                1330                1335 gtt ttg ctg caa caa cac atg tat gtc ctg aga cga att cag cag ctt       5764
Val Leu Leu Gln Gln His Met Tyr Val Leu Arg Arg Ile Gln Gln Leu
    1340                1345                1350
```

-continued

| | | |
|---|---|---|
| gaa gat gag gtg aag aga gtc cag aac aac aac acc tta cgc aaa gaa<br>Glu Asp Glu Val Lys Arg Val Gln Asn Asn Asn Thr Leu Arg Lys Glu<br>1355                      1360                      1365                      1370 | 5812 |
| gag aaa att gca atc atg agg gag aag cac aca gct ttg atg aag ccc<br>Glu Lys Ile Ala Ile Met Arg Glu Lys His Thr Ala Leu Met Lys Pro<br>                      1375                      1380                      1385 | 5860 |
| atc gta ttt gct ttg gag cat gtg agg agt atc aca gcg gct cct gca<br>Ile Val Phe Ala Leu Glu His Val Arg Ser Ile Thr Ala Ala Pro Ala<br>1390                      1395                      1400 | 5908 |
| gaa aca cct cat gaa aaa tgg ttt cag gat aac tat ggt gat gcc att<br>Glu Thr Pro His Glu Lys Trp Phe Gln Asp Asn Tyr Gly Asp Ala Ile<br>                      1405                      1410                      1415 | 5956 |
| gaa aat gcc cta gaa aaa ctg aag act cca ttg aac cct gca aag cct<br>Glu Asn Ala Leu Glu Lys Leu Lys Thr Pro Leu Asn Pro Ala Lys Pro<br>1420                      1425                      1430 | 6004 |
| ggg agc agc tgg att cca ttt aaa gag ata atg cta agt ttg caa cag<br>Gly Ser Ser Trp Ile Pro Phe Lys Glu Ile Met Leu Ser Leu Gln Gln<br>1435                      1440                      1445                      1450 | 6052 |
| aga gca cag aaa cgt gca agt tac atc ttg cgt ctt gaa gaa atc agt<br>Arg Ala Gln Lys Arg Ala Ser Tyr Ile Leu Arg Leu Glu Glu Ile Ser<br>                      1455                      1460                      1465 | 6100 |
| cca tgg ttg gct gcc atg act aac act gaa att gct ctt cct ggg gaa<br>Pro Trp Leu Ala Ala Met Thr Asn Thr Glu Ile Ala Leu Pro Gly Glu<br>1470                      1475                      1480 | 6148 |
| gtc tca gcc aga gac act gtc aca atc cat agt gtg ggc gga acc atc<br>Val Ser Ala Arg Asp Thr Val Thr Ile His Ser Val Gly Gly Thr Ile<br>                      1485                      1490                      1495 | 6196 |
| aca atc tta ccg act aaa acc aag cca aag aaa ctt ctc ttt ctt gga<br>Thr Ile Leu Pro Thr Lys Thr Lys Pro Lys Lys Leu Leu Phe Leu Gly<br>1500                      1505                      1510 | 6244 |
| tca gat ggg aag agc tat cct tat ctt ttc aaa gga ctg gag gat tta<br>Ser Asp Gly Lys Ser Tyr Pro Tyr Leu Phe Lys Gly Leu Glu Asp Leu<br>1515                      1520                      1525                      1530 | 6292 |
| cat ctg gat gag aga ata atg cag ttc cta tct att gtg aat acc atg<br>His Leu Asp Glu Arg Ile Met Gln Phe Leu Ser Ile Val Asn Thr Met<br>                      1535                      1540                      1545 | 6340 |
| ttt gct aca att aat cgc caa gaa aca ccc cgg ttc cat gct cga cac<br>Phe Ala Thr Ile Asn Arg Gln Glu Thr Pro Arg Phe His Ala Arg His<br>1550                      1555                      1560 | 6388 |
| tat tct gta aca cca cta gga aca aga tca gga cta atc cag tgg gta<br>Tyr Ser Val Thr Pro Leu Gly Thr Arg Ser Gly Leu Ile Gln Trp Val<br>                      1565                      1570                      1575 | 6436 |
| gat gga gcc aca ccc tta ttt ggt ctt tac aaa cga tgg caa caa cgg<br>Asp Gly Ala Thr Pro Leu Phe Gly Leu Tyr Lys Arg Trp Gln Gln Arg<br>1580                      1585                      1590 | 6484 |
| gaa gct gcc tta caa gca caa aag gcc caa gat tcc tac caa act cct<br>Glu Ala Ala Leu Gln Ala Gln Lys Ala Gln Asp Ser Tyr Gln Thr Pro<br>1595                      1600                      1605                      1610 | 6532 |
| cag aat cct gga att gta ccc cgt cct agt gaa ctt tat tac agt aaa<br>Gln Asn Pro Gly Ile Val Pro Arg Pro Ser Glu Leu Tyr Tyr Ser Lys<br>                      1615                      1620                      1625 | 6580 |
| att ggc cct gct ttg aaa aca gtt ggg ctt agc ctg gat gtg tcc cgt<br>Ile Gly Pro Ala Leu Lys Thr Val Gly Leu Ser Leu Asp Val Ser Arg<br>1630                      1635                      1640 | 6628 |
| cgg gat tgg cct ctt cat gta atg aag gca gta ttg gaa gag tta atg<br>Arg Asp Trp Pro Leu His Val Met Lys Ala Val Leu Glu Glu Leu Met<br>                      1645                      1650                      1655 | 6676 |
| gag gcc aca ccc ccg aat ctc ctt gcc aaa gag ctc tgg tca tct tgc<br>Glu Ala Thr Pro Pro Asn Leu Leu Ala Lys Glu Leu Trp Ser Ser Cys<br>1660                      1665                      1670 | 6724 |

-continued

| | | |
|---|---|---|
| aca aca cct gat gaa tgg tgg aga gtt acg cag tct tat gca aga tct<br>Thr Thr Pro Asp Glu Trp Trp Arg Val Thr Gln Ser Tyr Ala Arg Ser<br>1675                   1680                   1685                   1690 | 6772 |
| act gca gtc atg tct atg gtt gga tac ata att ggc ctt gga gac aga<br>Thr Ala Val Met Ser Met Val Gly Tyr Ile Ile Gly Leu Gly Asp Arg<br>                 1695                   1700                   1705 | 6820 |
| cat ctg gat aat gtt ctt ata gat atg acg act gga gaa gtt gtt cac<br>His Leu Asp Asn Val Leu Ile Asp Met Thr Thr Gly Glu Val Val His<br>            1710                   1715                   1720 | 6868 |
| ata gat tac aat gtt tgc ttt gaa aaa ggt aaa agc ctt aga gtt cct<br>Ile Asp Tyr Asn Val Cys Phe Glu Lys Gly Lys Ser Leu Arg Val Pro<br>1725                   1730                   1735 | 6916 |
| gag aaa gta cct ttt cga atg aca caa aac att gaa aca gca ctg ggt<br>Glu Lys Val Pro Phe Arg Met Thr Gln Asn Ile Glu Thr Ala Leu Gly<br>           1740                   1745                   1750 | 6964 |
| gta act gga gta gaa ggt gta ttt agg ctt tca tgt gag cag gtt tta<br>Val Thr Gly Val Glu Gly Val Phe Arg Leu Ser Cys Glu Gln Val Leu<br>1755                   1760                   1765                   1770 | 7012 |
| cac att atg cgg cgt ggc aga gag acc ctg ctg acg ctg ctg gag gcc<br>His Ile Met Arg Arg Gly Arg Glu Thr Leu Leu Thr Leu Leu Glu Ala<br>                 1775                   1780                   1785 | 7060 |
| ttt gtg tac gac cct ctg gtg gac tgg aca gca gga ggc gag gct ggg<br>Phe Val Tyr Asp Pro Leu Val Asp Trp Thr Ala Gly Gly Glu Ala Gly<br>            1790                   1795                   1800 | 7108 |
| ttt gct ggt gct gtc tat ggt gga ggt ggc cag cag gcc gag agc aag<br>Phe Ala Gly Ala Val Tyr Gly Gly Gly Gly Gln Gln Ala Glu Ser Lys<br>1805                   1810                   1815 | 7156 |
| cag agc aag aga gag atg gag cga gag atc acc cgc agc ctg ttt tct<br>Gln Ser Lys Arg Glu Met Glu Arg Glu Ile Thr Arg Ser Leu Phe Ser<br>                 1820                   1825                   1830 | 7204 |
| tct aga gta gct gag att aag gtg aac tgg ttt aag aat aga gat gag<br>Ser Arg Val Ala Glu Ile Lys Val Asn Trp Phe Lys Asn Arg Asp Glu<br>1835                   1840                   1845                   1850 | 7252 |
| atg ctg gtt gtg ctt ccc aag ttg gac ggt agc tta gat gaa tac cta<br>Met Leu Val Val Leu Pro Lys Leu Asp Gly Ser Leu Asp Glu Tyr Leu<br>            1855                   1860                   1865 | 7300 |
| agc ttg caa gag caa ctg aca gat gtg gaa aaa ctg cag ggc aaa cta<br>Ser Leu Gln Glu Gln Leu Thr Asp Val Glu Lys Leu Gln Gly Lys Leu<br>           1870                   1875                   1880 | 7348 |
| ctg gag gaa ata gag ttt cta gaa gga gct gaa ggg gtg gat cat cct<br>Leu Glu Glu Ile Glu Phe Leu Glu Gly Ala Glu Gly Val Asp His Pro<br>1885                   1890                   1895 | 7396 |
| tct cat act ctg caa cac agg tat tct gag cac acc caa cta cag act<br>Ser His Thr Leu Gln His Arg Tyr Ser Glu His Thr Gln Leu Gln Thr<br>            1900                   1905                   1910 | 7444 |
| cag caa aga gct gtt cag gaa gca atc cag gtg aag ctg aat gaa ttt<br>Gln Gln Arg Ala Val Gln Glu Ala Ile Gln Val Lys Leu Asn Glu Phe<br>1915                   1920                   1925                   1930 | 7492 |
| gaa caa tgg ata aca cat tat cag gct gca ttc aat aat tta gaa gca<br>Glu Gln Trp Ile Thr His Tyr Gln Ala Ala Phe Asn Asn Leu Glu Ala<br>                 1935                   1940                   1945 | 7540 |
| aca cag ctt gca agc ttg ctt caa gag ata agc aca caa atg gac ctt<br>Thr Gln Leu Ala Ser Leu Leu Gln Glu Ile Ser Thr Gln Met Asp Leu<br>            1950                   1955                   1960 | 7588 |
| ggt cct cca agt tac gtg cca gca aca gcc ttt ctg cag aat gct ggt<br>Gly Pro Pro Ser Tyr Val Pro Ala Thr Ala Phe Leu Gln Asn Ala Gly<br>           1965                   1970                   1975 | 7636 |
| cag gcc cac ttg att agc cag tgc gag cag ctg gag ggg gag gtt ggt<br>Gln Ala His Leu Ile Ser Gln Cys Glu Gln Leu Glu Gly Glu Val Gly | 7684 |

|     |     |     |     |     |     |     |     |     |     |     |     |     |     |     |      |
| --- | --- | --- | --- | --- | --- | --- | --- | --- | --- | --- | --- | --- | --- | --- | ---- |
|     | 1980|     |     |     | 1985|     |     |     | 1990|     |     |     |     |     |      |
| gct | ctc | ctg | cag | cag | agg | cgc | tcc | gtg | ctc | cgt | ggc | tgt | ctg | gag | caa  | 7732 |
| Ala | Leu | Leu | Gln | Gln | Arg | Arg | Ser | Val | Leu | Arg | Gly | Cys | Leu | Glu | Gln  |      |
| 1995|     |     |     | 2000|     |     |     | 2005|     |     |     |     | 2010|     |      |
| ctg | cat | cac | tat | gca | acc | gtg | gcc | ctg | cag | tat | ccg | aag | gcc | ata | ttt  | 7780 |
| Leu | His | His | Tyr | Ala | Thr | Val | Ala | Leu | Gln | Tyr | Pro | Lys | Ala | Ile | Phe  |      |
|     |     |     |     | 2015|     |     |     |     | 2020|     |     |     |     | 2025|      |
| cag | aaa | cat | cga | att | gaa | cag | tgg | aag | acc | tgg | atg | gaa | gag | ctc | atc  | 7828 |
| Gln | Lys | His | Arg | Ile | Glu | Gln | Trp | Lys | Thr | Trp | Met | Glu | Glu | Leu | Ile  |      |
|     |     |     | 2030|     |     |     |     | 2035|     |     |     |     | 2040|     |      |
| tgt | aac | acc | aca | gta | gag | cgt | tgt | caa | gag | ctc | tat | agg | aaa | tat | gaa  | 7876 |
| Cys | Asn | Thr | Thr | Val | Glu | Arg | Cys | Gln | Glu | Leu | Tyr | Arg | Lys | Tyr | Glu  |      |
|     |     |     | 2045|     |     |     |     | 2050|     |     |     |     | 2055|     |      |
| atg | caa | tat | gct | ccc | cag | cca | ccc | cca | aca | gtg | tgt | cag | ttc | atc | act  | 7924 |
| Met | Gln | Tyr | Ala | Pro | Gln | Pro | Pro | Pro | Thr | Val | Cys | Gln | Phe | Ile | Thr  |      |
|     |     |     | 2060|     |     |     | 2065|     |     |     |     | 2070|     |     |      |
| gcc | act | gaa | atg | acc | ctg | cag | cga | tac | gca | gca | gac | atc | aac | agc | aga  | 7972 |
| Ala | Thr | Glu | Met | Thr | Leu | Gln | Arg | Tyr | Ala | Ala | Asp | Ile | Asn | Ser | Arg  |      |
| 2075|     |     |     | 2080|     |     |     | 2085|     |     |     |     |     | 2090|      |
| ctt | att | aga | caa | gtg | gaa | cgc | ttg | aaa | cag | gaa | gct | gtc | act | gtg | cca  | 8020 |
| Leu | Ile | Arg | Gln | Val | Glu | Arg | Leu | Lys | Gln | Glu | Ala | Val | Thr | Val | Pro  |      |
|     |     |     | 2095|     |     |     |     | 2100|     |     |     |     | 2105|     |      |
| gtt | tgt | gaa | gat | cag | ttg | aaa | gaa | att | gaa | cgt | tgc | att | aaa | gtt | ttc  | 8068 |
| Val | Cys | Glu | Asp | Gln | Leu | Lys | Glu | Ile | Glu | Arg | Cys | Ile | Lys | Val | Phe  |      |
|     |     |     | 2110|     |     |     |     | 2115|     |     |     |     | 2120|     |      |
| ctt | cat | gag | aat | gga | gaa | gaa | gga | tct | ttg | agt | cta | gca | agt | gtt | att  | 8116 |
| Leu | His | Glu | Asn | Gly | Glu | Glu | Gly | Ser | Leu | Ser | Leu | Ala | Ser | Val | Ile  |      |
|     |     |     | 2125|     |     |     |     | 2130|     |     |     |     | 2135|     |      |
| att | tct | gcc | ctt | tgt | acc | ctt | aca | agg | cgt | aac | ctg | atg | atg | gaa | ggt  | 8164 |
| Ile | Ser | Ala | Leu | Cys | Thr | Leu | Thr | Arg | Arg | Asn | Leu | Met | Met | Glu | Gly  |      |
|     |     |     | 2140|     |     |     | 2145|     |     |     |     | 2150|     |     |      |
| gca | gcg | tca | agt | gct | gga | gaa | cag | ctg | gtt | gat | ctg | act | tct | cgg | gat  | 8212 |
| Ala | Ala | Ser | Ser | Ala | Gly | Glu | Gln | Leu | Val | Asp | Leu | Thr | Ser | Arg | Asp  |      |
| 2155|     |     |     | 2160|     |     |     | 2165|     |     |     |     |     | 2170|      |
| gga | gcc | tgg | ttc | ttg | gag | gaa | ctc | tgc | agt | atg | agc | gga | aac | gtc | acc  | 8260 |
| Gly | Ala | Trp | Phe | Leu | Glu | Glu | Leu | Cys | Ser | Met | Ser | Gly | Asn | Val | Thr  |      |
|     |     |     |     | 2175|     |     |     | 2180|     |     |     |     | 2185|     |      |
| tgc | ttg | gtt | cag | tta | ctg | aag | cag | tgc | cac | ctg | gtg | cca | cag | gac | tta  | 8308 |
| Cys | Leu | Val | Gln | Leu | Leu | Lys | Gln | Cys | His | Leu | Val | Pro | Gln | Asp | Leu  |      |
|     |     |     | 2190|     |     |     |     | 2195|     |     |     |     | 2200|     |      |
| gat | atc | ccg | aac | ccc | atg | gaa | gcg | tct | gag | aca | gtt | cac | tta | gcc | aat  | 8356 |
| Asp | Ile | Pro | Asn | Pro | Met | Glu | Ala | Ser | Glu | Thr | Val | His | Leu | Ala | Asn  |      |
|     |     |     | 2205|     |     |     |     | 2210|     |     |     |     | 2215|     |      |
| gga | gtg | tat | acc | tca | ctt | cag | gaa | ttg | aat | tcg | aat | ttc | cgg | caa | atc  | 8404 |
| Gly | Val | Tyr | Thr | Ser | Leu | Gln | Glu | Leu | Asn | Ser | Asn | Phe | Arg | Gln | Ile  |      |
|     |     |     | 2220|     |     |     | 2225|     |     |     |     | 2230|     |     |      |
| ata | ttt | cca | gaa | gca | ctt | cga | tgt | tta | atg | aaa | ggg | gaa | tac | acg | tta  | 8452 |
| Ile | Phe | Pro | Glu | Ala | Leu | Arg | Cys | Leu | Met | Lys | Gly | Glu | Tyr | Thr | Leu  |      |
| 2235|     |     |     | 2240|     |     |     | 2245|     |     |     |     |     | 2250|      |
| gaa | agt | atg | ctg | cat | gaa | ctg | gac | ggt | ctt | att | gag | cag | acc | acc | gat  | 8500 |
| Glu | Ser | Met | Leu | His | Glu | Leu | Asp | Gly | Leu | Ile | Glu | Gln | Thr | Thr | Asp  |      |
|     |     |     | 2255|     |     |     |     | 2260|     |     |     |     | 2265|     |      |
| ggc | gtt | ccc | ctg | cag | act | cta | gtg | gaa | tct | ctt | cag | gcc | tac | tta | aga  | 8548 |
| Gly | Val | Pro | Leu | Gln | Thr | Leu | Val | Glu | Ser | Leu | Gln | Ala | Tyr | Leu | Arg  |      |
|     |     |     | 2270|     |     |     | 2275|     |     |     |     | 2280|     |     |      |
| aac | gca | gct | atg | gga | ctg | gaa | gaa | gaa | aca | cat | gct | cat | tac | atc | gat  | 8596 |
| Asn | Ala | Ala | Met | Gly | Leu | Glu | Glu | Glu | Thr | His | Ala | His | Tyr | Ile | Asp  |      |
|     |     |     | 2285|     |     |     |     | 2290|     |     |     |     | 2295|     |      |
| gtt | gcc | aga | cta | cta | cat | gct | cag | tac | ggt | gaa | tta | atc | caa | ccg | aga  | 8644 |

```
                                                               -continued

Val Ala Arg Leu Leu His Ala Gln Tyr Gly Glu Leu Ile Gln Pro Arg
    2300                2305                2310 aat ggt tca gtt gat gaa aca ccc aaa atg tca gct ggc cag atg ctt    8692
Asn Gly Ser Val Asp Glu Thr Pro Lys Met Ser Ala Gly Gln Met Leu
2315                2320                2325                2330 ttg gta gca ttc gat ggc atg ttt gct caa gtt gaa act gct ttc agc    8740
Leu Val Ala Phe Asp Gly Met Phe Ala Gln Val Glu Thr Ala Phe Ser
                2335                2340                2345 tta tta gtt gaa aag ttg aac aag atg gaa att ccc ata gct tgg cga    8788
Leu Leu Val Glu Lys Leu Asn Lys Met Glu Ile Pro Ile Ala Trp Arg
            2350                2355                2360 aag att gac atc ata agg gaa gcc agg agt act caa gtt aat ttt ttt    8836
Lys Ile Asp Ile Ile Arg Glu Ala Arg Ser Thr Gln Val Asn Phe Phe
        2365                2370                2375 gat gat gat aat cac cgg cag gtg cta gaa gag att ttc ttt cta aaa    8884
Asp Asp Asp Asn His Arg Gln Val Leu Glu Glu Ile Phe Phe Leu Lys
    2380                2385                2390 aga cta cag act att aag gag ttc ttc agg ctc tgt ggt acc ttt tct    8932
Arg Leu Gln Thr Ile Lys Glu Phe Phe Arg Leu Cys Gly Thr Phe Ser
2395                2400                2405                2410 aaa aca ttg tca gga tca agt tca ctt gaa gat cag aat act gtg aat    8980
Lys Thr Leu Ser Gly Ser Ser Ser Leu Glu Asp Gln Asn Thr Val Asn
                2415                2420                2425 ggg cct gta cag att gtc aat gtg aaa acc ctt ttt aga aac tct tgt    9028
Gly Pro Val Gln Ile Val Asn Val Lys Thr Leu Phe Arg Asn Ser Cys
            2430                2435                2440 ttc agt gaa gac caa atg gcc aaa cct atc aag gca ttc aca gct gac    9076
Phe Ser Glu Asp Gln Met Ala Lys Pro Ile Lys Ala Phe Thr Ala Asp
        2445                2450                2455 ttt gtg agg cag ctc ttg ata ggg cta ccc aac caa gcc ctc gga ctc    9124
Phe Val Arg Gln Leu Leu Ile Gly Leu Pro Asn Gln Ala Leu Gly Leu
    2460                2465                2470 aca ctg tgc agt ttt atc agt gct ctg ggt gta gac atc att gct caa    9172
Thr Leu Cys Ser Phe Ile Ser Ala Leu Gly Val Asp Ile Ile Ala Gln
2475                2480                2485                2490 gta gag gca aag gac ttt ggt gcc gaa agc aaa gtt tct gtt gat gat    9220
Val Glu Ala Lys Asp Phe Gly Ala Glu Ser Lys Val Ser Val Asp Asp
                2495                2500                2505 ctc tgt aag aaa gcg gtg gaa cat aac atc cag ata ggg aag ttc tct    9268
Leu Cys Lys Lys Ala Val Glu His Asn Ile Gln Ile Gly Lys Phe Ser
            2510                2515                2520 cag ctg gtt atg aac agg gca act gtg tta gca agt tct tac gac act    9316
Gln Leu Val Met Asn Arg Ala Thr Val Leu Ala Ser Ser Tyr Asp Thr
        2525                2530                2535 gcc tgg aag aag cat gac ttg gtg cga agg cta gaa acc agt att tct    9364
Ala Trp Lys Lys His Asp Leu Val Arg Arg Leu Glu Thr Ser Ile Ser
    2540                2545                2550 tct tgt aag aca agc ctg cag cgg gtt cag ctg cat att gcc atg ttt    9412
Ser Cys Lys Thr Ser Leu Gln Arg Val Gln Leu His Ile Ala Met Phe
2555                2560                2565                2570 cag tgg caa cat gaa gat cta ctt atc aat aga cca caa gcc atg tca    9460
Gln Trp Gln His Glu Asp Leu Leu Ile Asn Arg Pro Gln Ala Met Ser
                2575                2580                2585 gtc aca cct ccc cca cgg tct gct atc cta acc agc atg aaa aag aag    9508
Val Thr Pro Pro Pro Arg Ser Ala Ile Leu Thr Ser Met Lys Lys Lys
            2590                2595                2600 ctg cat acc ctg agc cag att gaa act tct att gca aca gtt cag gag    9556
Leu His Thr Leu Ser Gln Ile Glu Thr Ser Ile Ala Thr Val Gln Glu
        2605                2610                2615
```

-continued

| | |
|---|---|
| aag cta gct gca ctt gaa tca agt att gaa cag cga ctc aag tgg gca<br>Lys Leu Ala Ala Leu Glu Ser Ser Ile Glu Gln Arg Leu Lys Trp Ala<br>    2620                    2625                    2630 | 9604 |
| ggt ggt gcc aac cct gca ttg gcc cct gta cta caa gat ttt gaa gca<br>Gly Gly Ala Asn Pro Ala Leu Ala Pro Val Leu Gln Asp Phe Glu Ala<br>2635                    2640                    2645                    2650 | 9652 |
| acg ata gct gaa aga aga aat ctt gtc ctt aaa gag agc caa aga gca<br>Thr Ile Ala Glu Arg Arg Asn Leu Val Leu Lys Glu Ser Gln Arg Ala<br>    2655                    2660                    2665 | 9700 |
| agt cag gtc aca ttt ctc tgc agc aat atc att cat ttt gaa agt tta<br>Ser Gln Val Thr Phe Leu Cys Ser Asn Ile Ile His Phe Glu Ser Leu<br>2670                    2675                    2680 | 9748 |
| cga aca aga act gca gaa gcc tta aac ctg gat gcg gcg tta ttt gaa<br>Arg Thr Arg Thr Ala Glu Ala Leu Asn Leu Asp Ala Ala Leu Phe Glu<br>    2685                    2690                    2695 | 9796 |
| cta atc aag cga tgt cag cag atg tgt tcg ttt gca tca cag ttt aac<br>Leu Ile Lys Arg Cys Gln Gln Met Cys Ser Phe Ala Ser Gln Phe Asn<br>2700                    2705                    2710 | 9844 |
| agt tca gtg tct gag tta gag ctt cgt tta tta cag aga gtg gac act<br>Ser Ser Val Ser Glu Leu Glu Leu Arg Leu Leu Gln Arg Val Asp Thr<br>2715                    2720                    2725                    2730 | 9892 |
| ggt ctt gaa cat cct att ggc agc tct gaa tgg ctt ttg tca gca cac<br>Gly Leu Glu His Pro Ile Gly Ser Ser Glu Trp Leu Leu Ser Ala His<br>                2735                    2740                    2745 | 9940 |
| aaa cag ttg acc cag gat atg tct act cag agg gca att cag aca gag<br>Lys Gln Leu Thr Gln Asp Met Ser Thr Gln Arg Ala Ile Gln Thr Glu<br>    2750                    2755                    2760 | 9988 |
| aaa gag cag cag ata gaa acg gtc tgt gaa aca att cag aat ctg gtt<br>Lys Glu Gln Gln Ile Glu Thr Val Cys Glu Thr Ile Gln Asn Leu Val<br>2765                    2770                    2775 | 10036 |
| gat aat ata aag act gtg ctc act ggt cat aac cga cag ctt gga gat<br>Asp Asn Ile Lys Thr Val Leu Thr Gly His Asn Arg Gln Leu Gly Asp<br>    2780                    2785                    2790 | 10084 |
| gtc aaa cat ctc ttg aaa gct atg gct aag gat gaa gaa gct gct ctg<br>Val Lys His Leu Leu Lys Ala Met Ala Lys Asp Glu Glu Ala Ala Leu<br>2795                    2800                    2805                    2810 | 10132 |
| gca gat ggt gaa gat gtt ccc tat gag aac agt gtt agg cag ttt ttg<br>Ala Asp Gly Glu Asp Val Pro Tyr Glu Asn Ser Val Arg Gln Phe Leu<br>                2815                    2820                    2825 | 10180 |
| ggt gaa tat aaa tca tgg caa gac aac att caa aca gtt cta ttt aca<br>Gly Glu Tyr Lys Ser Trp Gln Asp Asn Ile Gln Thr Val Leu Phe Thr<br>                2830                    2835                    2840 | 10228 |
| tta gtc cag gct atg ggt cag gtt cga agt caa gaa cac gtt gaa atg<br>Leu Val Gln Ala Met Gly Gln Val Arg Ser Gln Glu His Val Glu Met<br>2845                    2850                    2855 | 10276 |
| ctc cag gaa atc act ccc acc ttg aaa gaa ctg aaa aca caa agt cag<br>Leu Gln Glu Ile Thr Pro Thr Leu Lys Glu Leu Lys Thr Gln Ser Gln<br>    2860                    2865                    2870 | 10324 |
| agt atc tat aat aat tta gtg agt ttt gca tca ccc tta gtc acc gat<br>Ser Ile Tyr Asn Asn Leu Val Ser Phe Ala Ser Pro Leu Val Thr Asp<br>2875                    2880                    2885                    2890 | 10372 |
| gca aca aat gaa tgt tcg agt cca acg tca tct gct act tat cag cca<br>Ala Thr Asn Glu Cys Ser Ser Pro Thr Ser Ser Ala Thr Tyr Gln Pro<br>                2895                    2900                    2905 | 10420 |
| tcc ttc gct gca gca gtc cgg agt aac act ggc cag aag act cag cct<br>Ser Phe Ala Ala Ala Val Arg Ser Asn Thr Gly Gln Lys Thr Gln Pro<br>    2910                    2915                    2920 | 10468 |
| gat gtc atg tca cag aat gct aga aag ctg atc cag aaa aat ctt gct<br>Asp Val Met Ser Gln Asn Ala Arg Lys Leu Ile Gln Lys Asn Leu Ala<br>2925                    2930                    2935 | 10516 |

-continued

| | | |
|---|---|---|
| aca tca gct gat act cca cca agc acc gtt cca gga act ggc aag agt<br>Thr Ser Ala Asp Thr Pro Pro Ser Thr Val Pro Gly Thr Gly Lys Ser<br>2940                  2945                    2950 | | 10564 |
| gtt gct tgt agt cct aaa aag gca gtc aga gac cct aaa act ggg aaa<br>Val Ala Cys Ser Pro Lys Lys Ala Val Arg Asp Pro Lys Thr Gly Lys<br>2955                  2960                  2965                  2970 | | 10612 |
| gcg gtg caa gag aga aac tcc tat gca gtg agt gtg tgg aag aga gtg<br>Ala Val Gln Glu Arg Asn Ser Tyr Ala Val Ser Val Trp Lys Arg Val<br>              2975                  2980                  2985 | | 10660 |
| aaa gcc aag tta gag ggc cga gat gtt gat ccg aat agg agg atg tca<br>Lys Ala Lys Leu Glu Gly Arg Asp Val Asp Pro Asn Arg Arg Met Ser<br>2990                  2995                  3000 | | 10708 |
| gtt gct gaa cag gtt gac tat gtc att aag gaa gca act aat cta gat<br>Val Ala Glu Gln Val Asp Tyr Val Ile Lys Glu Ala Thr Asn Leu Asp<br>3005                  3010                  3015 | | 10756 |
| aac ttg gct cag ctg tat gaa ggt tgg aca gcc tgg gtg tga<br>Asn Leu Ala Gln Leu Tyr Glu Gly Trp Thr Ala Trp Val *<br>3020                  3025                  3030 | | 10798 |
| atggcaagac agtagatgag tctggttaag cgaggtcaga catccaccag aatcaactca | | 10858 |
| gcctcaggca tccaaagcca caccacagtc ggtggtgatg caactggggg cttactctga | | 10918 |
| ggaaacctag gaaatctcgg tgcactagga agtgaatccc gcaggacagc tgcactcagg | | 10978 |
| gatacgccca acaccatggc ctgcaacccc agggtcaagg gtgaaggaaa gcaagctcac | | 11038 |
| cgcctgaaca cggagattgt ctttctgcca cagaacagca gcagacgtgt cgggaggtta | | 11098 |
| gctgcggaaa gaaatcggga tgccgcggag cacagagtga tttggaactc cattccacct | | 11158 |
| gaccctgtgt gtacaatcca ggaaaaaaac aaacccccact cagaaacaga gaaaactggg | | 11218 |
| gtcgcgaaga aatcacagcc aaggaagatt tgatgcattc agattctcgt gtaacacttg | | 11278 |
| ttgcttggca acagtactgg ttgggttgac cagtaagtag aaaaaggcta aggctatgc | | 11338 |
| gatatgaatt tcagaaatgg actgaaaatg gagagctatg taacagatac actacagtag | | 11398 |
| aagaacttac ttctgaaatg aagggaaaaa accaccccca tcgttcccta ctcctcccca | | 11458 |
| ccacttaccc gttcccccctt tacctaatct agtagattac ccatctttca aattcacttt | | 11518 |
| tatttcagtc cttatatttc atatacttcc gtctcgatgc tgttaacaac ttctgataac | | 11578 |
| atggaaaatt caaggattgt ttaaaggtct gatgatcaca cacaaaatgt aattccggtt | | 11638 |
| atttaagtca tttctgtgat tctatcatgt acagtttcca gaattgtcac tgtgcattca | | 11698 |
| aaagtaatga atctaacaga catttgattt aatgtacact ccctttttgct tatagtgtgc | | 11758 |
| attttttttg gaggtcattc aaattttccc tcttctgtga tagctgtagt ttctttcata | | 11818 |
| gaaagtagct aatccagtgt aatcttttac ctttttaaaa accaagatag agtatctatt | | 11878 |
| agagttttac attgttgatg atagattaac aataaagtga tgttctggtg gaggtagact | | 11938 |
| gaaattttt taattcatgt ttttcatttg atactttaa tttacactta gtaaattaaa | | 11998 |
| agttgtttaa tttacttggc attttaggac atgtacatga aacagtgaaa atgagatcca | | 12058 |
| ccaacatctt ttattaagtt cagttattag tctgtgaagt gctttacttt ttgcacaatt | | 12118 |
| ttaatagctt gctattcagt aatacattat agtgaattca tgatcaaggt ttccttaaat | | 12178 |
| ttagcattgc atttcagtac tgactgtgta agctaaattg ctgatccaaa ataaaaaccc | | 12238 |
| agactagaat agggttctta aaatcaagta tcaatacaaa atagaacaca attaaaatct | | 12298 |
| taattgttgg ctgggcacag tggctcacgc ctgtaatccc agcactttgg gaggccgagg | | 12358 |
| cgggcggatc atgaggttag gagagcgaga ccatcctggc taacacggtg aaaccccgtc | | 12418 |

-continued

```
tttactaaaa tacaaaaaaa attagccggg tgtggtggcg ggcgcctgta gtcccagcta    12478
ctcgggaggc tgaggcagga gaatggcgtg aacccaggag gcggagcttg cagtgagccg    12538
agattgtgcc actgcactcc agcctgggca acagagctag actctgtgtc aaaaataaat    12598
gactagat                                                             12606
```

<210> SEQ ID NO 6
<211> LENGTH: 3031
<212> TYPE: PRT
<213> ORGANISM: Homo sapiens

<400> SEQUENCE: 6

```
Met Trp Ala Leu Ser Pro Thr Val Phe Ala Leu Leu Ser Lys Asn Leu
 1               5                  10                  15

Met Ile Val His Ser Asp Leu Ala Val His Phe Pro Ala Ile Gln Tyr
             20                  25                  30

Ala Val Leu Tyr Thr Leu Tyr Ser His Cys Thr Arg His Asp His Phe
         35                  40                  45

Ile Ser Ser Ser Leu Ser Ser Ser Pro Ser Leu Phe Asp Gly Ala
     50                  55                  60

Val Ile Ser Thr Val Thr Thr Ala Thr Lys Lys His Phe Ser Ile Ile
 65                  70                  75                  80

Leu Asn Leu Leu Gly Ile Leu Leu Lys Lys Asp Asn Leu Asn Gln Asp
                 85                  90                  95

Thr Arg Lys Leu Leu Met Thr Trp Ala Leu Glu Ala Ala Val Leu Met
            100                 105                 110

Lys Lys Ser Glu Thr Tyr Ala Pro Leu Phe Ser Leu Pro Ser Phe His
        115                 120                 125

Lys Phe Cys Lys Gly Leu Leu Ala Asn Thr Leu Val Glu Asp Val Asn
    130                 135                 140

Ile Cys Leu Gln Ala Cys Ser Ser Leu His Ala Leu Ser Ser Ser Leu
145                 150                 155                 160

Pro Asp Asp Leu Leu Gln Arg Cys Val Asp Val Cys Arg Val Gln Leu
                165                 170                 175

Val His Ser Gly Thr Arg Ile Arg Gln Ala Phe Gly Lys Leu Leu Lys
            180                 185                 190

Ser Ile Pro Leu Asp Val Val Leu Ser Asn Asn His Thr Glu Ile
        195                 200                 205

Gln Glu Ile Ser Leu Ala Leu Arg Ser His Met Ser Lys Ala Pro Ser
    210                 215                 220

Asn Thr Phe His Pro Gln Asp Phe Ser Asp Val Ile Ser Phe Ile Leu
225                 230                 235                 240

Tyr Gly Asn Ser His Arg Thr Gly Lys Asp Asn Trp Leu Glu Arg Leu
                245                 250                 255

Phe Tyr Ser Cys Gln Arg Leu Asp Lys Arg Asp Gln Ser Thr Ile Pro
            260                 265                 270

Arg Asn Leu Leu Lys Thr Asp Ala Val Leu Trp Gln Trp Ala Ile Trp
        275                 280                 285

Glu Ala Ala Gln Phe Thr Val Leu Ser Lys Leu Arg Thr Pro Leu Gly
    290                 295                 300

Arg Ala Gln Asp Thr Phe Gln Thr Ile Glu Gly Ile Ile Arg Ser Leu
305                 310                 315                 320

Ala Ala His Thr Leu Asn Pro Asp Gln Asp Val Ser Gln Trp Thr Thr
                325                 330                 335
```

-continued

```
Ala Asp Asn Asp Glu Gly His Gly Asn Asn Gln Leu Arg Leu Val Leu
            340                 345                 350

Leu Leu Gln Tyr Leu Glu Asn Leu Glu Lys Leu Met Tyr Asn Ala Tyr
            355                 360                 365

Glu Gly Cys Ala Asn Ala Leu Thr Ser Pro Pro Lys Val Ile Arg Thr
            370                 375                 380

Phe Phe Tyr Thr Asn Arg Gln Thr Cys Gln Asp Trp Leu Thr Arg Ile
385                 390                 395                 400

Arg Leu Ser Ile Met Arg Val Gly Leu Leu Ala Gly Gln Pro Ala Val
                405                 410                 415

Thr Val Arg His Gly Phe Asp Leu Leu Thr Glu Met Lys Thr Thr Ser
            420                 425                 430

Leu Ser Gln Gly Asn Glu Leu Glu Val Thr Ile Met Met Val Val Glu
            435                 440                 445

Ala Leu Cys Glu Leu His Cys Pro Glu Ala Ile Gln Gly Ile Ala Val
450                 455                 460

Trp Ser Ser Ser Ile Val Gly Lys Asn Leu Leu Trp Ile Asn Ser Val
465                 470                 475                 480

Ala Gln Gln Ala Glu Gly Arg Phe Glu Lys Ala Ser Val Glu Tyr Gln
            485                 490                 495

Glu His Leu Cys Ala Met Thr Gly Val Asp Cys Cys Ile Ser Ser Phe
            500                 505                 510

Asp Lys Ser Val Leu Thr Leu Ala Asn Ala Gly Arg Asn Ser Ala Ser
            515                 520                 525

Pro Lys His Ser Leu Asn Gly Glu Ser Arg Lys Thr Val Leu Ser Lys
            530                 535                 540

Pro Thr Asp Ser Ser Pro Glu Val Ile Asn Tyr Leu Gly Asn Lys Ala
545                 550                 555                 560

Cys Glu Cys Tyr Ile Ser Ile Ala Asp Trp Ala Ala Val Gln Glu Trp
                565                 570                 575

Gln Asn Ala Ile His Asp Leu Lys Lys Ser Thr Ser Ser Thr Ser Leu
            580                 585                 590

Asn Leu Lys Ala Asp Phe Asn Tyr Ile Lys Ser Leu Ser Ser Phe Glu
            595                 600                 605

Ser Gly Lys Phe Val Glu Cys Thr Glu Gln Leu Glu Leu Leu Pro Gly
            610                 615                 620

Glu Asn Ile Asn Leu Leu Ala Gly Gly Ser Lys Glu Lys Ile Asp Met
625                 630                 635                 640

Lys Lys Leu Leu Pro Asn Met Leu Ser Pro Asp Pro Arg Glu Leu Gln
                645                 650                 655

Lys Ser Ile Glu Val Gln Leu Leu Arg Ser Ser Val Cys Leu Ala Thr
            660                 665                 670

Ala Leu Asn Pro Ile Glu Gln Asp Gln Lys Trp Gln Ser Ile Thr Glu
            675                 680                 685

Asn Val Val Lys Tyr Leu Lys Gln Thr Ser Arg Ile Ala Ile Gly Pro
            690                 695                 700

Leu Arg Leu Ser Thr Leu Thr Val Ser Gln Ser Leu Pro Val Leu Ser
705                 710                 715                 720

Thr Leu Gln Leu Tyr Cys Ser Ser Ala Leu Glu Asn Thr Val Ser Asn
                725                 730                 735

Arg Leu Ser Thr Glu Asp Cys Leu Ile Pro Leu Phe Ser Glu Ala Leu
            740                 745                 750

Arg Ser Cys Lys Gln His Asp Val Arg Pro Trp Met Gln Ala Leu Arg
```

```
                755                 760                 765
Tyr Thr Met Tyr Gln Asn Gln Leu Leu Glu Lys Ile Lys Glu Gln Thr
770                 775                 780

Val Pro Ile Arg Ser His Leu Met Glu Leu Gly Leu Thr Ala Ala Lys
785                 790                 795                 800

Phe Ala Arg Lys Arg Gly Asn Val Ser Leu Ala Thr Arg Leu Leu Ala
                805                 810                 815

Gln Cys Ser Glu Val Gln Leu Gly Lys Thr Thr Ala Gln Asp Leu
                820                 825                 830

Val Gln His Phe Lys Lys Leu Ser Thr Gln Gly Gln Val Asp Glu Lys
                835                 840                 845

Trp Gly Pro Glu Leu Asp Ile Glu Lys Thr Lys Leu Leu Tyr Thr Ala
                850                 855                 860

Gly Gln Ser Thr His Ala Met Glu Met Leu Ser Ser Cys Ala Ile Ser
865                 870                 875                 880

Phe Cys Lys Ser Val Lys Ala Glu Tyr Ala Val Ala Lys Ser Ile Leu
                885                 890                 895

Thr Leu Ala Lys Trp Ile Gln Ala Glu Trp Lys Glu Ile Ser Gly Gln
                900                 905                 910

Leu Lys Gln Val Tyr Arg Ala Gln His Gln Asn Phe Thr Gly Leu
                915                 920                 925

Ser Thr Leu Ser Lys Asn Ile Leu Thr Leu Ile Glu Leu Pro Ser Val
                930                 935                 940

Asn Thr Met Glu Glu Tyr Pro Arg Ile Glu Ser Glu Ser Thr Val
945                 950                 955                 960

His Ile Gly Val Gly Glu Pro Asp Phe Ile Leu Gly Gln Leu Tyr His
                965                 970                 975

Leu Ser Ser Val Gln Ala Pro Glu Val Ala Lys Ser Trp Ala Ala Leu
                980                 985                 990

Ala Ser Trp Ala Tyr Arg Trp Gly Arg Lys Val Val Asp Asn Ala Ser
                995                 1000                1005

Gln Gly Glu Gly Val Arg Leu Leu Pro Arg Glu Lys Ser Glu Val Gln
1010                1015                1020

Asn Leu Leu Pro Asp Thr Ile Thr Glu Glu Lys Glu Arg Ile Tyr
1025                1030                1035                1040

Gly Ile Leu Gly Gln Ala Val Cys Arg Pro Ala Gly Ile Gln Asp Glu
                1045                1050                1055

Asp Ile Thr Leu Gln Ile Thr Glu Ser Glu Asp Asn Glu Glu Asp Asp
                1060                1065                1070

Met Val Asp Val Ile Trp Arg Gln Leu Ile Ser Ser Cys Pro Trp Leu
                1075                1080                1085

Ser Glu Leu Asp Glu Ser Ala Thr Glu Gly Val Ile Lys Val Trp Arg
                1090                1095                1100

Lys Val Val Asp Arg Ile Phe Ser Leu Tyr Lys Leu Ser Cys Ser Ala
1105                1110                1115                1120

Tyr Phe Thr Phe Leu Lys Leu Asn Ala Gly Gln Ile Pro Leu Asp Glu
                1125                1130                1135

Asp Asp Pro Arg Leu His Leu Ser His Arg Val Glu Gln Ser Thr Asp
                1140                1145                1150

Asp Met Ile Val Met Ala Thr Leu Arg Leu Leu Arg Leu Leu Val Lys
                1155                1160                1165

His Ala Gly Glu Leu Arg Gln Tyr Leu Glu His Gly Leu Glu Thr Thr
                1170                1175                1180
```

```
Pro Thr Ala Pro Trp Arg Gly Ile Ile Pro Gln Leu Phe Ser Arg Leu
1185                1190                1195                1200

Asn His Pro Glu Val Tyr Val Arg Gln Ser Ile Cys Asn Leu Leu Cys
            1205                1210                1215

Arg Val Ala Gln Asp Ser Pro His Leu Ile Leu Tyr Pro Ala Ile Val
                1220                1225                1230

Gly Thr Ile Ser Leu Ser Ser Glu Ser Gln Ala Ser Gly Asn Lys Phe
            1235                1240                1245

Ser Thr Ala Ile Pro Thr Leu Leu Gly Asn Ile Gln Gly Glu Glu Leu
        1250                1255                1260

Leu Val Ser Glu Cys Glu Gly Gly Ser Pro Pro Ala Ser Gln Asp Ser
1265                1270                1275                1280

Asn Lys Asp Glu Pro Lys Ser Gly Leu Asn Glu Asp Gln Ala Met Met
            1285                1290                1295

Gln Asp Cys Tyr Ser Lys Ile Val Asp Lys Leu Ser Ser Ala Asn Pro
                1300                1305                1310

Thr Met Val Leu Gln Val Gln Met Leu Val Ala Glu Leu Arg Arg Val
            1315                1320                1325

Thr Val Leu Trp Asp Glu Leu Trp Leu Gly Val Leu Leu Gln Gln His
1330                1335                1340

Met Tyr Val Leu Arg Arg Ile Gln Gln Leu Glu Asp Glu Val Lys Arg
1345                1350                1355                1360

Val Gln Asn Asn Asn Thr Leu Arg Lys Glu Glu Lys Ile Ala Ile Met
                1365                1370                1375

Arg Glu Lys His Thr Ala Leu Met Lys Pro Ile Val Phe Ala Leu Glu
            1380                1385                1390

His Val Arg Ser Ile Thr Ala Ala Pro Ala Glu Thr Pro His Glu Lys
            1395                1400                1405

Trp Phe Gln Asp Asn Tyr Gly Asp Ala Ile Glu Asn Ala Leu Glu Lys
            1410                1415                1420

Leu Lys Thr Pro Leu Asn Pro Ala Lys Pro Gly Ser Ser Trp Ile Pro
1425                1430                1435                1440

Phe Lys Glu Ile Met Leu Ser Leu Gln Gln Arg Ala Gln Lys Arg Ala
                1445                1450                1455

Ser Tyr Ile Leu Arg Leu Glu Glu Ile Ser Pro Trp Leu Ala Ala Met
            1460                1465                1470

Thr Asn Thr Glu Ile Ala Leu Pro Gly Glu Val Ser Ala Arg Asp Thr
            1475                1480                1485

Val Thr Ile His Ser Val Gly Gly Thr Ile Thr Ile Leu Pro Thr Lys
        1490                1495                1500

Thr Lys Pro Lys Lys Leu Leu Phe Leu Gly Ser Asp Gly Lys Ser Tyr
1505                1510                1515                1520

Pro Tyr Leu Phe Lys Gly Leu Glu Asp Leu His Leu Asp Glu Arg Ile
                1525                1530                1535

Met Gln Phe Leu Ser Ile Val Asn Thr Met Phe Ala Thr Ile Asn Arg
            1540                1545                1550

Gln Glu Thr Pro Arg Phe His Ala Arg His Tyr Ser Val Thr Pro Leu
            1555                1560                1565

Gly Thr Arg Ser Gly Leu Ile Gln Trp Val Asp Gly Ala Thr Pro Leu
        1570                1575                1580

Phe Gly Leu Tyr Lys Arg Trp Gln Gln Arg Glu Ala Ala Leu Gln Ala
1585                1590                1595                1600
```

-continued

Gln Lys Ala Gln Asp Ser Tyr Gln Thr Pro Gln Asn Pro Gly Ile Val
            1605                1610                1615

Pro Arg Pro Ser Glu Leu Tyr Tyr Ser Lys Ile Gly Pro Ala Leu Lys
            1620                1625                1630

Thr Val Gly Leu Ser Leu Asp Val Ser Arg Arg Asp Trp Pro Leu His
            1635                1640                1645

Val Met Lys Ala Val Leu Glu Glu Leu Met Glu Ala Thr Pro Pro Asn
            1650                1655                1660

Leu Leu Ala Lys Glu Leu Trp Ser Ser Cys Thr Thr Pro Asp Glu Trp
1665                1670                1675                1680

Trp Arg Val Thr Gln Ser Tyr Ala Arg Ser Thr Ala Val Met Ser Met
            1685                1690                1695

Val Gly Tyr Ile Ile Gly Leu Gly Asp Arg His Leu Asp Asn Val Leu
            1700                1705                1710

Ile Asp Met Thr Thr Gly Glu Val Val His Ile Asp Tyr Asn Val Cys
            1715                1720                1725

Phe Glu Lys Gly Lys Ser Leu Arg Val Pro Glu Lys Val Pro Phe Arg
            1730                1735                1740

Met Thr Gln Asn Ile Glu Thr Ala Leu Gly Val Thr Gly Val Glu Gly
1745                1750                1755                1760

Val Phe Arg Leu Ser Cys Glu Gln Val Leu His Ile Met Arg Arg Gly
            1765                1770                1775

Arg Glu Thr Leu Leu Thr Leu Leu Glu Ala Phe Val Tyr Asp Pro Leu
            1780                1785                1790

Val Asp Trp Thr Ala Gly Gly Glu Ala Gly Phe Ala Gly Ala Val Tyr
            1795                1800                1805

Gly Gly Gly Gly Gln Gln Ala Glu Ser Lys Gln Ser Lys Arg Glu Met
            1810                1815                1820

Glu Arg Glu Ile Thr Arg Ser Leu Phe Ser Ser Arg Val Ala Glu Ile
1825                1830                1835                1840

Lys Val Asn Trp Phe Lys Asn Arg Asp Glu Met Leu Val Val Leu Pro
            1845                1850                1855

Lys Leu Asp Gly Ser Leu Asp Glu Tyr Leu Ser Leu Gln Glu Gln Leu
            1860                1865                1870

Thr Asp Val Glu Lys Leu Gln Gly Lys Leu Leu Glu Glu Ile Glu Phe
            1875                1880                1885

Leu Glu Gly Ala Glu Gly Val Asp His Pro Ser His Thr Leu Gln His
            1890                1895                1900

Arg Tyr Ser Glu His Thr Gln Leu Gln Thr Gln Gln Arg Ala Val Gln
1905                1910                1915                1920

Glu Ala Ile Gln Val Lys Leu Asn Glu Phe Glu Gln Trp Ile Thr His
            1925                1930                1935

Tyr Gln Ala Ala Phe Asn Asn Leu Glu Ala Thr Gln Leu Ala Ser Leu
            1940                1945                1950

Leu Gln Glu Ile Ser Thr Gln Met Asp Leu Gly Pro Pro Ser Tyr Val
            1955                1960                1965

Pro Ala Thr Ala Phe Leu Gln Asn Ala Gly Gln Ala His Leu Ile Ser
            1970                1975                1980

Gln Cys Glu Gln Leu Glu Gly Glu Val Gly Ala Leu Leu Gln Gln Arg
1985                1990                1995                2000

Arg Ser Val Leu Arg Gly Cys Leu Glu Gln Leu His His Tyr Ala Thr
            2005                2010                2015

Val Ala Leu Gln Tyr Pro Lys Ala Ile Phe Gln Lys His Arg Ile Glu

-continued

Gln Trp Lys Thr Trp Met Glu Glu Leu Ile Cys Asn Thr Thr Val Glu
        2020            2025            2030
                    2035            2040            2045

Arg Cys Gln Glu Leu Tyr Arg Lys Tyr Glu Met Gln Tyr Ala Pro Gln
                    2050            2055            2060

Pro Pro Pro Thr Val Cys Gln Phe Ile Thr Ala Thr Glu Met Thr Leu
2065            2070            2075            2080

Gln Arg Tyr Ala Ala Asp Ile Asn Ser Arg Leu Ile Arg Gln Val Glu
                    2085            2090            2095

Arg Leu Lys Gln Glu Ala Val Thr Val Pro Val Cys Glu Asp Gln Leu
                    2100            2105            2110

Lys Glu Ile Glu Arg Cys Ile Lys Val Phe Leu His Glu Asn Gly Glu
                    2115            2120            2125

Glu Gly Ser Leu Ser Leu Ala Ser Val Ile Ile Ser Ala Leu Cys Thr
                    2130            2135            2140

Leu Thr Arg Arg Asn Leu Met Met Glu Gly Ala Ala Ser Ser Ala Gly
2145            2150            2155            2160

Glu Gln Leu Val Asp Leu Thr Ser Arg Asp Gly Ala Trp Phe Leu Glu
                    2165            2170            2175

Glu Leu Cys Ser Met Ser Gly Asn Val Thr Cys Leu Val Gln Leu Leu
                    2180            2185            2190

Lys Gln Cys His Leu Val Pro Gln Asp Leu Asp Ile Pro Asn Pro Met
                    2195            2200            2205

Glu Ala Ser Glu Thr Val His Leu Ala Asn Gly Val Tyr Thr Ser Leu
                    2210            2215            2220

Gln Glu Leu Asn Ser Asn Phe Arg Gln Ile Ile Phe Pro Glu Ala Leu
2225            2230            2235            2240

Arg Cys Leu Met Lys Gly Glu Tyr Thr Leu Glu Ser Met Leu His Glu
                    2245            2250            2255

Leu Asp Gly Leu Ile Glu Gln Thr Thr Asp Gly Val Pro Leu Gln Thr
                    2260            2265            2270

Leu Val Glu Ser Leu Gln Ala Tyr Leu Arg Asn Ala Ala Met Gly Leu
                    2275            2280            2285

Glu Glu Glu Thr His Ala His Tyr Ile Asp Val Ala Arg Leu Leu His
                    2290            2295            2300

Ala Gln Tyr Gly Glu Leu Ile Gln Pro Arg Asn Gly Ser Val Asp Glu
2305            2310            2315            2320

Thr Pro Lys Met Ser Ala Gly Gln Met Leu Leu Val Ala Phe Asp Gly
                    2325            2330            2335

Met Phe Ala Gln Val Glu Thr Ala Phe Ser Leu Leu Val Glu Lys Leu
                    2340            2345            2350

Asn Lys Met Glu Ile Pro Ile Ala Trp Arg Lys Ile Asp Ile Ile Arg
                    2355            2360            2365

Glu Ala Arg Ser Thr Gln Val Asn Phe Asp Asp Asp Asn His Arg
                    2370            2375            2380

Gln Val Leu Glu Glu Ile Phe Phe Leu Lys Arg Leu Gln Thr Ile Lys
2385            2390            2395            2400

Glu Phe Phe Arg Leu Cys Gly Thr Phe Ser Lys Thr Leu Ser Gly Ser
                    2405            2410            2415

Ser Ser Leu Glu Asp Gln Asn Thr Val Asn Gly Pro Val Gln Ile Val
                    2420            2425            2430

Asn Val Lys Thr Leu Phe Arg Asn Ser Cys Phe Ser Glu Asp Gln Met
                    2435            2440            2445

```
Ala Lys Pro Ile Lys Ala Phe Thr Ala Asp Phe Val Arg Gln Leu Leu
    2450                2455                2460

Ile Gly Leu Pro Asn Gln Ala Leu Gly Leu Thr Leu Cys Ser Phe Ile
2465                2470                2475                2480

Ser Ala Leu Gly Val Asp Ile Ile Ala Gln Val Glu Ala Lys Asp Phe
        2485                2490                2495

Gly Ala Glu Ser Lys Val Ser Val Asp Asp Leu Cys Lys Lys Ala Val
            2500                2505                2510

Glu His Asn Ile Gln Ile Gly Lys Phe Ser Gln Leu Val Met Asn Arg
        2515                2520                2525

Ala Thr Val Leu Ala Ser Ser Tyr Asp Thr Ala Trp Lys Lys His Asp
    2530                2535                2540

Leu Val Arg Arg Leu Glu Thr Ser Ile Ser Ser Cys Lys Thr Ser Leu
2545                2550                2555                2560

Gln Arg Val Gln Leu His Ile Ala Met Phe Gln Trp Gln His Glu Asp
        2565                2570                2575

Leu Leu Ile Asn Arg Pro Gln Ala Met Ser Val Thr Pro Pro Pro Arg
        2580                2585                2590

Ser Ala Ile Leu Thr Ser Met Lys Lys Lys Leu His Thr Leu Ser Gln
        2595                2600                2605

Ile Glu Thr Ser Ile Ala Thr Val Gln Glu Lys Leu Ala Ala Leu Glu
    2610                2615                2620

Ser Ser Ile Glu Gln Arg Leu Lys Trp Ala Gly Gly Ala Asn Pro Ala
2625                2630                2635                2640

Leu Ala Pro Val Leu Gln Asp Phe Glu Ala Thr Ile Ala Glu Arg Arg
        2645                2650                2655

Asn Leu Val Leu Lys Glu Ser Gln Arg Ala Ser Gln Val Thr Phe Leu
        2660                2665                2670

Cys Ser Asn Ile Ile His Phe Glu Ser Leu Arg Thr Arg Thr Ala Glu
        2675                2680                2685

Ala Leu Asn Leu Asp Ala Ala Leu Phe Glu Leu Ile Lys Arg Cys Gln
    2690                2695                2700

Gln Met Cys Ser Phe Ala Ser Gln Phe Asn Ser Ser Val Ser Glu Leu
2705                2710                2715                2720

Glu Leu Arg Leu Leu Gln Arg Val Asp Thr Gly Leu Glu His Pro Ile
            2725                2730                2735

Gly Ser Ser Glu Trp Leu Leu Ser Ala His Lys Gln Leu Thr Gln Asp
            2740                2745                2750

Met Ser Thr Gln Arg Ala Ile Gln Thr Glu Lys Glu Gln Gln Ile Glu
        2755                2760                2765

Thr Val Cys Glu Thr Ile Gln Asn Leu Val Asp Asn Ile Lys Thr Val
    2770                2775                2780

Leu Thr Gly His Asn Arg Gln Leu Gly Asp Val Lys His Leu Leu Lys
2785                2790                2795                2800

Ala Met Ala Lys Asp Glu Glu Ala Ala Leu Ala Asp Gly Glu Asp Val
            2805                2810                2815

Pro Tyr Glu Asn Ser Val Arg Gln Phe Leu Gly Glu Tyr Lys Ser Trp
        2820                2825                2830

Gln Asp Asn Ile Gln Thr Val Leu Phe Thr Leu Val Gln Ala Met Gly
        2835                2840                2845

Gln Val Arg Ser Gln Glu His Val Glu Met Leu Gln Glu Ile Thr Pro
    2850                2855                2860
```

-continued

| | | | | | | | | | | | |
|---|---|---|---|---|---|---|---|---|---|---|---|
| Thr | Leu | Lys | Glu | Leu | Lys | Thr | Gln | Ser | Gln | Ser | Ile | Tyr | Asn | Asn | Leu |
| 2865 | | | | 2870 | | | | | 2875 | | | | 2880 | | |

Val Ser Phe Ala Ser Pro Leu Val Thr Asp Ala Thr Asn Glu Cys Ser
                    2885                        2890                    2895

Ser Pro Thr Ser Ser Ala Thr Tyr Gln Pro Ser Phe Ala Ala Ala Val
                    2900                        2905                    2910

Arg Ser Asn Thr Gly Gln Lys Thr Gln Pro Asp Val Met Ser Gln Asn
                    2915                        2920                    2925

Ala Arg Lys Leu Ile Gln Lys Asn Leu Ala Thr Ser Ala Asp Thr Pro
    2930                    2935                        2940

Pro Ser Thr Val Pro Gly Thr Gly Lys Ser Val Ala Cys Ser Pro Lys
2945                    2950                        2955                    2960

Lys Ala Val Arg Asp Pro Lys Thr Gly Lys Ala Val Gln Glu Arg Asn
                    2965                        2970                    2975

Ser Tyr Ala Val Ser Val Trp Lys Arg Val Lys Ala Lys Leu Glu Gly
                    2980                        2985                    2990

Arg Asp Val Asp Pro Asn Arg Arg Met Ser Val Ala Glu Gln Val Asp
                    2995                        3000                    3005

Tyr Val Ile Lys Glu Ala Thr Asn Leu Asp Asn Leu Ala Gln Leu Tyr
    3010                    3015                        3020

Glu Gly Trp Thr Ala Trp Val
3025                    3030

<210> SEQ ID NO 7
<211> LENGTH: 12539
<212> TYPE: DNA
<213> ORGANISM: Homo sapiens
<220> FEATURE:
<221> NAME/KEY: CDS
<222> LOCATION: (141)...(10730)

<400> SEQUENCE: 7

```
gtggctacag tgtcaatgga ggatctgggg aaaatactta tggtcggaag tcgttggggc      60
aagagctgag ggttaacaat gtgaccagcc ctgagttcac cagtgttcag catggcagtc     120
gtgctttagc caccaaagac atg agg aaa tca cag gag aga tcg atg tct tat    173
                        Met Arg Lys Ser Gln Glu Arg Ser Met Ser Tyr
                        1               5                   10 tct gat gag tct cga ctg tcg aat ctt ctt cgg agg atc acc cgg gaa      221
Ser Asp Glu Ser Arg Leu Ser Asn Leu Leu Arg Arg Ile Thr Arg Glu
            15                  20                  25 gac gac aga gac cga aga ttg gct act gta aag cag ttg aaa gaa ttt      269
Asp Asp Arg Asp Arg Arg Leu Ala Thr Val Lys Gln Leu Lys Glu Phe
        30                  35                  40 att cag caa cca gaa aat aag ctg gta cta gtt aaa caa ttg gat aat      317
Ile Gln Gln Pro Glu Asn Lys Leu Val Leu Val Lys Gln Leu Asp Asn
    45                  50                  55 atc ttg gct gct gta cat gac gtg ctt aat gaa agt agc aaa ttg ctt      365
Ile Leu Ala Ala Val His Asp Val Leu Asn Glu Ser Ser Lys Leu Leu
60                  65                  70                  75 cag gag ttg aga cag gag gga gct tgc tgt ctt ggc ctt ctt tgt gct      413
Gln Glu Leu Arg Gln Glu Gly Ala Cys Cys Leu Gly Leu Leu Cys Ala
                80                  85                  90 tct ctg agc tat gag gct gag aag atc ttc aag tgg att ttt agc aaa      461
Ser Leu Ser Tyr Glu Ala Glu Lys Ile Phe Lys Trp Ile Phe Ser Lys
            95                  100                 105 ttt agc tca tct gca aaa gat gaa gtt aaa ctc ctc tac tta tgt gcc      509
Phe Ser Ser Ser Ala Lys Asp Glu Val Lys Leu Leu Tyr Leu Cys Ala
        110                 115                 120
```

```
acc tac aaa gca cta gag act gta gga gaa aag aaa gcc ttt tca tct    557
Thr Tyr Lys Ala Leu Glu Thr Val Gly Glu Lys Lys Ala Phe Ser Ser
    125                 130                 135 gta atg cag ctt gta atg acc agc ctg cag tct att ctt gaa aat gtg    605
Val Met Gln Leu Val Met Thr Ser Leu Gln Ser Ile Leu Glu Asn Val
140                 145                 150                 155 gat aca cca gaa ttg ctt tgt aaa tgt gtt aag tgc att ctt ttg gtg    653
Asp Thr Pro Glu Leu Leu Cys Lys Cys Val Lys Cys Ile Leu Leu Val
                160                 165                 170 gct cga tgt tac cct cat att ttc agc act aat ttt agg gat aca gtt    701
Ala Arg Cys Tyr Pro His Ile Phe Ser Thr Asn Phe Arg Asp Thr Val
            175                 180                 185 gat ata tta gtt gga tgg cat ata gat cat act cag aaa cct tcg ctc    749
Asp Ile Leu Val Gly Trp His Ile Asp His Thr Gln Lys Pro Ser Leu
        190                 195                 200 acg cag cag gta tct ggg tgg ttg cag agt ttg gag cca ttt tgg gta    797
Thr Gln Gln Val Ser Gly Trp Leu Gln Ser Leu Glu Pro Phe Trp Val
    205                 210                 215 gct gat ctt gca ttt tct act act ctt ctt ggt cag ttt ctg gaa gac    845
Ala Asp Leu Ala Phe Ser Thr Thr Leu Leu Gly Gln Phe Leu Glu Asp
220                 225                 230                 235 atg gaa gca tat gct gag gac ctc agc cat gtg gcc tct ggg gaa tca    893
Met Glu Ala Tyr Ala Glu Asp Leu Ser His Val Ala Ser Gly Glu Ser
                240                 245                 250 gtg gat gaa gat gtc cct cct cca tca gtg tca tta cca aag ctg gct    941
Val Asp Glu Asp Val Pro Pro Pro Ser Val Ser Leu Pro Lys Leu Ala
            255                 260                 265 gca ctt ctc cgg gta ttt agt act gtg gtg agg agc att ggg gaa cgc    989
Ala Leu Leu Arg Val Phe Ser Thr Val Val Arg Ser Ile Gly Glu Arg
        270                 275                 280 ttc agc cca att cgg ggt cct cca att act gag gca tat gta aca gat   1037
Phe Ser Pro Ile Arg Gly Pro Pro Ile Thr Glu Ala Tyr Val Thr Asp
    285                 290                 295 gtt ctg tac aga gta atg aga tgt gtg acg gct gca aac cag gtg ttt   1085
Val Leu Tyr Arg Val Met Arg Cys Val Thr Ala Ala Asn Gln Val Phe
300                 305                 310                 315 ttt tct gag gct gtg ttg aca gct gct aat gag tgt gtt ggt gtt ttg   1133
Phe Ser Glu Ala Val Leu Thr Ala Ala Asn Glu Cys Val Gly Val Leu
                320                 325                 330 ctc ggc agc ttg gat cct agc atg act ata cat tgt gac atg gtc att   1181
Leu Gly Ser Leu Asp Pro Ser Met Thr Ile His Cys Asp Met Val Ile
            335                 340                 345 aca tat gga tta gac caa ctg gag aat tgc cag act tgt ggt acc gat   1229
Thr Tyr Gly Leu Asp Gln Leu Glu Asn Cys Gln Thr Cys Gly Thr Asp
        350                 355                 360 tat atc atc tca gtc ttg aat tta ctc acg ctg att gtt gaa cag ata   1277
Tyr Ile Ile Ser Val Leu Asn Leu Leu Thr Leu Ile Val Glu Gln Ile
    365                 370                 375 aat acg aaa ctg cca tca tca ttt gta gaa aaa ctg ttt ata cca tca   1325
Asn Thr Lys Leu Pro Ser Ser Phe Val Glu Lys Leu Phe Ile Pro Ser
380                 385                 390                 395 tct aaa cta cta ttc ttg cgt tat cat aaa gaa aaa gag gtt gtt gct   1373
Ser Lys Leu Leu Phe Leu Arg Tyr His Lys Glu Lys Glu Val Val Ala
                400                 405                 410 gta gcc cat gct gtt tat caa gca gtg ctc agc ttg aag aat att cct   1421
Val Ala His Ala Val Tyr Gln Ala Val Leu Ser Leu Lys Asn Ile Pro
            415                 420                 425 gtt ttg gag act gcc tat aag tta ata ttg gga gaa atg act tgt gcc   1469
Val Leu Glu Thr Ala Tyr Lys Leu Ile Leu Gly Glu Met Thr Cys Ala
```

```
                430             435             440
cta aac aac ctc cta cac agt cta caa ctt cct gag gcc tgt tct gaa    1517
Leu Asn Asn Leu Leu His Ser Leu Gln Leu Pro Glu Ala Cys Ser Glu
        445             450             455 ata aaa cat gag gct ttt aag aat cat gtg ttc aat gta gac aat gca    1565
Ile Lys His Glu Ala Phe Lys Asn His Val Phe Asn Val Asp Asn Ala
460             465             470             475 aaa ttt gta gtt aaa ttt gac ctc agt gcc ctg act aca att gga aat    1613
Lys Phe Val Val Lys Phe Asp Leu Ser Ala Leu Thr Thr Ile Gly Asn
                480             485             490 gcc aaa aac tca cta ata ggg atg tgg gcg cta tct cca act gtc ttt    1661
Ala Lys Asn Ser Leu Ile Gly Met Trp Ala Leu Ser Pro Thr Val Phe
        495             500             505 gca ctt ctg agt aag aat ctg atg att gtg cac agt gac ctg gct gtt    1709
Ala Leu Leu Ser Lys Asn Leu Met Ile Val His Ser Asp Leu Ala Val
510             515             520 cac ttc cct gcc att cag tat gct gtg ctc tac aca ttg tat tct cat    1757
His Phe Pro Ala Ile Gln Tyr Ala Val Leu Tyr Thr Leu Tyr Ser His
525             530             535 tgt acc agg cat gat cac ttt atc tct agt agc ctc agt tct gcc tct    1805
Cys Thr Arg His Asp His Phe Ile Ser Ser Ser Leu Ser Ser Ala Ser
540             545             550             555 cct tct ttg ttt gat gga gct gtg att agc act gta act acg gct aca    1853
Pro Ser Leu Phe Asp Gly Ala Val Ile Ser Thr Val Thr Thr Ala Thr
                560             565             570 aag aaa cat ttc tca att ata tta aat ctt ctg gga ata tta ctt aag    1901
Lys Lys His Phe Ser Ile Ile Leu Asn Leu Leu Gly Ile Leu Leu Lys
        575             580             585 aaa gat aac ctt aac cag gac acg agg aaa ctg tta atg act tgg gct    1949
Lys Asp Asn Leu Asn Gln Asp Thr Arg Lys Leu Leu Met Thr Trp Ala
590             595             600 ttg gaa gca gct gtt tta atg agg aag tct gaa aca tac gca cct tta    1997
Leu Glu Ala Ala Val Leu Met Arg Lys Ser Glu Thr Tyr Ala Pro Leu
605             610             615 ttc tct ctt ccg tct ttc cat aaa ttt tgc aaa ggc ctt tta gcc aac    2045
Phe Ser Leu Pro Ser Phe His Lys Phe Cys Lys Gly Leu Leu Ala Asn
620             625             630             635 act ctc gtt gaa gat gtg aat atc tgt ctg cag gca tgc agc agt cta    2093
Thr Leu Val Glu Asp Val Asn Ile Cys Leu Gln Ala Cys Ser Ser Leu
                640             645             650 cat gct ctg tcc tct tcc ttg cca gat gat ctt tta cag aga tgt gtc    2141
His Ala Leu Ser Ser Ser Leu Pro Asp Asp Leu Leu Gln Arg Cys Val
        655             660             665 gat gtt tgc cgt gtt caa cta gtg cac agt gga act cgt att cga caa    2189
Asp Val Cys Arg Val Gln Leu Val His Ser Gly Thr Arg Ile Arg Gln
670             675             680 gca ttt gga aaa ctg ttg aaa tca att cct tta gat gtt gtc cta agc    2237
Ala Phe Gly Lys Leu Leu Lys Ser Ile Pro Leu Asp Val Val Leu Ser
685             690             695 aat aac aat cac aca gaa att caa gaa att tct tta gca tta aga agt    2285
Asn Asn Asn His Thr Glu Ile Gln Glu Ile Ser Leu Ala Leu Arg Ser
700             705             710             715 cac atg agt aaa gca cca agt aat aca ttc cac ccc caa gat ttc tct    2333
His Met Ser Lys Ala Pro Ser Asn Thr Phe His Pro Gln Asp Phe Ser
                720             725             730 gat gtt att agt ttt att ttg tat ggg aac tct cat aga aca ggg aag    2381
Asp Val Ile Ser Phe Ile Leu Tyr Gly Asn Ser His Arg Thr Gly Lys
        735             740             745 gac aat tgg ttg gaa aga ctg ttc tat agc tgc cag aga ctg gat aag    2429
Asp Asn Trp Leu Glu Arg Leu Phe Tyr Ser Cys Gln Arg Leu Asp Lys
```

```
                                                                         -continued Asp Asn Trp Leu Glu Arg Leu Phe Tyr Ser Cys Gln Arg Leu Asp Lys
        750                 755                 760 cgt gac cag tca aca att cca cgc aat ctc ctg aag aca gat gct gtc         2477
Arg Asp Gln Ser Thr Ile Pro Arg Asn Leu Leu Lys Thr Asp Ala Val
765                 770                 775 ctt tgg cag tgg gcc ata tgg gaa gct gca caa ttc act gtt ctt tct         2525
Leu Trp Gln Trp Ala Ile Trp Glu Ala Ala Gln Phe Thr Val Leu Ser
780                 785                 790                 795 aag ctg aga acc cca ctg ggc aga gct caa gac acc ttc cag aca att         2573
Lys Leu Arg Thr Pro Leu Gly Arg Ala Gln Asp Thr Phe Gln Thr Ile
            800                 805                 810 gaa ggt atc att cga agt ctc gca gct cac aca tta aac cct gat cag         2621
Glu Gly Ile Ile Arg Ser Leu Ala Ala His Thr Leu Asn Pro Asp Gln
                815                 820                 825 gat gtt agt cag tgg aca act gca gac aat gat gaa ggc cat ggt aac         2669
Asp Val Ser Gln Trp Thr Thr Ala Asp Asn Asp Glu Gly His Gly Asn
        830                 835                 840 aac caa ctt aga ctt gtt ctt ctg cag tat ctg gaa aat ctg gag             2717
Asn Gln Leu Arg Leu Val Leu Leu Gln Tyr Leu Glu Asn Leu Glu
    845                 850                 855 aaa tta atg tat aat gca tac gag gga tgt gct aat gca tta act tca         2765
Lys Leu Met Tyr Asn Ala Tyr Glu Gly Cys Ala Asn Ala Leu Thr Ser
860                 865                 870                 875 cct ccc aag gtc att aga act ttt ttc tat acc aat cgc caa act tgt         2813
Pro Pro Lys Val Ile Arg Thr Phe Phe Tyr Thr Asn Arg Gln Thr Cys
            880                 885                 890 cag gac tgg cta acg cgg att cga ctc tcc atc atg agg gta gga ttg         2861
Gln Asp Trp Leu Thr Arg Ile Arg Leu Ser Ile Met Arg Val Gly Leu
                895                 900                 905 ttg gca ggc cag cct gca gtg aca gtg aga cat ggc ttt gac ttg ctt         2909
Leu Ala Gly Gln Pro Ala Val Thr Val Arg His Gly Phe Asp Leu Leu
        910                 915                 920 aca gag atg aaa aca acc agc cta tct cag ggg aat gaa ttg gaa gta         2957
Thr Glu Met Lys Thr Thr Ser Leu Ser Gln Gly Asn Glu Leu Glu Val
    925                 930                 935 acc att atg atg gtg gta gaa gca tta tgt gaa ctt cat tgt cct gaa         3005
Thr Ile Met Met Val Val Glu Ala Leu Cys Glu Leu His Cys Pro Glu
940                 945                 950                 955 gct ata cag gga att gct gtc tgg tca tca tct att gtt gga aaa aat         3053
Ala Ile Gln Gly Ile Ala Val Trp Ser Ser Ser Ile Val Gly Lys Asn
            960                 965                 970 ctt ctg tgg att aac tca gtg gct caa cag gct gaa ggg agg ttt gaa         3101
Leu Leu Trp Ile Asn Ser Val Ala Gln Gln Ala Glu Gly Arg Phe Glu
                975                 980                 985 aag gcc tct gtg gag tac cag gaa cac ctg tgt gcc atg aca ggt gtt         3149
Lys Ala Ser Val Glu Tyr Gln Glu His Leu Cys Ala Met Thr Gly Val
        990                 995                 1000 gat tgc tgc atc tcc agc ttt gac aaa tcg gtg ctc acc tta gcc aat         3197
Asp Cys Cys Ile Ser Ser Phe Asp Lys Ser Val Leu Thr Leu Ala Asn
        1005                1010                1015 gct ggg cgt aac agt gcc agc ccg aaa cat tct ctg aat ggt gaa tcc         3245
Ala Gly Arg Asn Ser Ala Ser Pro Lys His Ser Leu Asn Gly Glu Ser
1020                1025                1030                1035 aga aaa act gtg ctg tcc aaa ccg act gac tct tcc cct gag gtt ata         3293
Arg Lys Thr Val Leu Ser Lys Pro Thr Asp Ser Ser Pro Glu Val Ile
            1040                1045                1050 aat tat tta gga aat aaa gca tgt gag ttc tac atc tca att gcc gat         3341
Asn Tyr Leu Gly Asn Lys Ala Cys Glu Phe Tyr Ile Ser Ile Ala Asp
            1055                1060                1065
```

-continued

| | |
|---|---|
| tgg gct gct gtg cag gaa tgg cag aac gct atc cat gac ttg aaa aag<br>Trp Ala Ala Val Gln Glu Trp Gln Asn Ala Ile His Asp Leu Lys Lys<br>        1070                         1075                     1080 | 3389 |
| agt acc agt agc act tcc ctc aac ctg aaa gct gac ttc aac tat ata<br>Ser Thr Ser Ser Thr Ser Leu Asn Leu Lys Ala Asp Phe Asn Tyr Ile<br>1085                       1090                     1095 | 3437 |
| aaa tca tta agc agc ttt gag tct gga aaa ttt gtt gaa tgt acc gag<br>Lys Ser Leu Ser Ser Phe Glu Ser Gly Lys Phe Val Glu Cys Thr Glu<br>1100                       1105                     1110                     1115 | 3485 |
| cag tta gaa ttg tta cca gga gaa aat atc aat cta ctt gct gga gga<br>Gln Leu Glu Leu Leu Pro Gly Glu Asn Ile Asn Leu Leu Ala Gly Gly<br>        1120                         1125                     1130 | 3533 |
| tca aaa gaa aaa ata gac atg aaa aaa ctg ctt cct aac atg tta agt<br>Ser Lys Glu Lys Ile Asp Met Lys Lys Leu Leu Pro Asn Met Leu Ser<br>1135                       1140                     1145 | 3581 |
| ccg gat ccg agg gaa ctt cag aaa tcc att gaa gtt caa ttg tta aga<br>Pro Asp Pro Arg Glu Leu Gln Lys Ser Ile Glu Val Gln Leu Leu Arg<br>        1150                         1155                     1160 | 3629 |
| agt tct gtt tgt ttg gca act gct tta aac ccg ata gaa caa gat cag<br>Ser Ser Val Cys Leu Ala Thr Ala Leu Asn Pro Ile Glu Gln Asp Gln<br>1165                       1170                     1175 | 3677 |
| aag tgg cag tct ata act gaa aat gtg gta aag tac ttg aag caa aca<br>Lys Trp Gln Ser Ile Thr Glu Asn Val Val Lys Tyr Leu Lys Gln Thr<br>1180                       1185                     1190                     1195 | 3725 |
| tcc cgc atc gct att gga cct ctg aga ctt tct act tta aca gtt tca<br>Ser Arg Ile Ala Ile Gly Pro Leu Arg Leu Ser Thr Leu Thr Val Ser<br>        1200                         1205                     1210 | 3773 |
| cag tct ttg cca gtt cta agt acc ttg cag ctg tat tgc tca tct gct<br>Gln Ser Leu Pro Val Leu Ser Thr Leu Gln Leu Tyr Cys Ser Ser Ala<br>1215                       1220                     1225 | 3821 |
| ttg gag aac aca gtt tct aac aga ctt tca aca gag gac tgt ctt att<br>Leu Glu Asn Thr Val Ser Asn Arg Leu Ser Thr Glu Asp Cys Leu Ile<br>        1230                         1235                     1240 | 3869 |
| cca ctc ttc agt gaa gct tta cgt tca tgt aaa cag cat gac gtg agg<br>Pro Leu Phe Ser Glu Ala Leu Arg Ser Cys Lys Gln His Asp Val Arg<br>1245                       1250                     1255 | 3917 |
| cca tgg atg cag gca tta agg tat act atg tac cag aat cag ttg ttg<br>Pro Trp Met Gln Ala Leu Arg Tyr Thr Met Tyr Gln Asn Gln Leu Leu<br>1260                       1265                     1270                     1275 | 3965 |
| gag aaa att aaa gaa caa aca gtc cca att aga agc cat ctc atg gaa<br>Glu Lys Ile Lys Glu Gln Thr Val Pro Ile Arg Ser His Leu Met Glu<br>        1280                         1285                     1290 | 4013 |
| tta ggt cta aca gca gca aaa ttt gct aga aaa cga ggg aat gtg tcc<br>Leu Gly Leu Thr Ala Ala Lys Phe Ala Arg Lys Arg Gly Asn Val Ser<br>1295                       1300                     1305 | 4061 |
| ctt gca aca aga ctg ctg gca cag tgc agt gaa gtt cag ctg gga aag<br>Leu Ala Thr Arg Leu Leu Ala Gln Cys Ser Glu Val Gln Leu Gly Lys<br>        1310                         1315                     1320 | 4109 |
| acc acc act gca cag gat tta gtc caa cat ttt aaa aaa cta tca acc<br>Thr Thr Thr Ala Gln Asp Leu Val Gln His Phe Lys Lys Leu Ser Thr<br>1325                       1330                     1335 | 4157 |
| caa ggt caa gtg gat gaa aaa tgg ggg ccc gaa ctt gat att gaa aaa<br>Gln Gly Gln Val Asp Glu Lys Trp Gly Pro Glu Leu Asp Ile Glu Lys<br>1340                       1345                     1350                     1355 | 4205 |
| acc aaa ttg ctt tat aca gca ggc cag tca aca cat gca atg gaa atg<br>Thr Lys Leu Leu Tyr Thr Ala Gly Gln Ser Thr His Ala Met Glu Met<br>        1360                         1365                     1370 | 4253 |
| ttg agt tct tgt gcc ata tct ttc tgc aag tct gtg aaa gct gaa tat<br>Leu Ser Ser Cys Ala Ile Ser Phe Cys Lys Ser Val Lys Ala Glu Tyr<br>1375                       1380                     1385 | 4301 |

```
gca gtt gct aaa tca att ctg aca ctg gct aaa tgg atc cag gca gaa      4349
Ala Val Ala Lys Ser Ile Leu Thr Leu Ala Lys Trp Ile Gln Ala Glu
        1390                1395                1400 tgg aaa gag att tca gga cag ctg aaa cag gtt tac aga gct cag cac      4397
Trp Lys Glu Ile Ser Gly Gln Leu Lys Gln Val Tyr Arg Ala Gln His
    1405                1410                1415 caa cag aac ttc aca ggt ctt tct act ttg tct aaa aac ata ctc act      4445
Gln Gln Asn Phe Thr Gly Leu Ser Thr Leu Ser Lys Asn Ile Leu Thr
1420                1425                1430                1435 cta ata gaa ctg cca tct gtt aat acg atg gaa gaa gag tat cct cgg      4493
Leu Ile Glu Leu Pro Ser Val Asn Thr Met Glu Glu Glu Tyr Pro Arg
            1440                1445                1450 atc gag agt gaa tct aca gtg cat att gga gtt gga gaa cct gac ttc      4541
Ile Glu Ser Glu Ser Thr Val His Ile Gly Val Gly Glu Pro Asp Phe
        1455                1460                1465 att ttg gga cag ttg tat cac ctg tct tca gta cag gca cct gaa gta      4589
Ile Leu Gly Gln Leu Tyr His Leu Ser Ser Val Gln Ala Pro Glu Val
    1470                1475                1480 gcc aaa tct tgg gca gcg ttg gcc agc tgg gct tat agg tgg ggc aga      4637
Ala Lys Ser Trp Ala Ala Leu Ala Ser Trp Ala Tyr Arg Trp Gly Arg
1485                1490                1495 aag gtg gtt gac aat gcc agt cag gga gaa ggt gtt cgt ctg ctg cct      4685
Lys Val Val Asp Asn Ala Ser Gln Gly Glu Gly Val Arg Leu Leu Pro
1500                1505                1510                1515 aga gaa aaa tct gaa gtt cag aat cta ctt cca gac act ata act gag      4733
Arg Glu Lys Ser Glu Val Gln Asn Leu Leu Pro Asp Thr Ile Thr Glu
            1520                1525                1530 gaa gag aaa gag aga ata tat ggt att ctt gga cag gct gtg tgt cgg      4781
Glu Glu Lys Glu Arg Ile Tyr Gly Ile Leu Gly Gln Ala Val Cys Arg
        1535                1540                1545 ccg gcg ggg att cag gat gaa gat ata aca ctt cag ata act gag agt      4829
Pro Ala Gly Ile Gln Asp Glu Asp Ile Thr Leu Gln Ile Thr Glu Ser
    1550                1555                1560 gaa gac aac gaa gaa gat gac atg gtt gat gtt atc tgg cgt cag ttg      4877
Glu Asp Asn Glu Glu Asp Asp Met Val Asp Val Ile Trp Arg Gln Leu
1565                1570                1575 ata tca agc tgc cca tgg ctt tca gaa ctt gat gaa agt gca act gaa      4925
Ile Ser Ser Cys Pro Trp Leu Ser Glu Leu Asp Glu Ser Ala Thr Glu
1580                1585                1590                1595 gga gtt att aaa gtg tgg agg aaa gtt gta gat aga ata ttc agc ctg      4973
Gly Val Ile Lys Val Trp Arg Lys Val Val Asp Arg Ile Phe Ser Leu
            1600                1605                1610 tac aaa ctc tct tgc agt gca tac ttt act ttc ctt aaa ctc aac gct      5021
Tyr Lys Leu Ser Cys Ser Ala Tyr Phe Thr Phe Leu Lys Leu Asn Ala
        1615                1620                1625 ggt caa att cct tta gat gag gat gac cct agg ctg cat tta agt cac      5069
Gly Gln Ile Pro Leu Asp Glu Asp Asp Pro Arg Leu His Leu Ser His
    1630                1635                1640 aga gtg gaa cag agc act gat gac atg att gtg atg gcc aca ttg cgc      5117
Arg Val Glu Gln Ser Thr Asp Asp Met Ile Val Met Ala Thr Leu Arg
1645                1650                1655 ctg ctg cgg ttg ctc gtg aag cat gct ggt gag ctt cgg cag tat ctg      5165
Leu Leu Arg Leu Leu Val Lys His Ala Gly Glu Leu Arg Gln Tyr Leu
1660                1665                1670                1675 gag cac ggc ttg gag aca aca ccc act gca cca tgg agg gga att att      5213
Glu His Gly Leu Glu Thr Thr Pro Thr Ala Pro Trp Arg Gly Ile Ile
            1680                1685                1690 ccg caa ctt ttc tca cgc tta aac cac cct gaa gtg tat gtg cgc caa      5261
Pro Gln Leu Phe Ser Arg Leu Asn His Pro Glu Val Tyr Val Arg Gln
```

```
                1695              1700              1705
agt att tgt aac ctt ctc tgc cgt gtg gct caa gat tcc cca cat ctc    5309
Ser Ile Cys Asn Leu Leu Cys Arg Val Ala Gln Asp Ser Pro His Leu
        1710              1715              1720 ata ttg tat cct gca ata gtg ggt acc ata tcg ctt agt agt gaa tcc    5357
Ile Leu Tyr Pro Ala Ile Val Gly Thr Ile Ser Leu Ser Ser Glu Ser
1725              1730              1735 cag gct tca gga aat aaa ttt tcc act gca att cca act tta ctt ggc    5405
Gln Ala Ser Gly Asn Lys Phe Ser Thr Ala Ile Pro Thr Leu Leu Gly
1740              1745              1750              1755 aat att caa gga gaa gaa ttg ctg gtt tct gaa tgt gag gga gga agt    5453
Asn Ile Gln Gly Glu Glu Leu Leu Val Ser Glu Cys Glu Gly Gly Ser
        1760              1765              1770 cct cct gca tct cag gat agc aat aag gat gaa cct aaa agt gga tta    5501
Pro Pro Ala Ser Gln Asp Ser Asn Lys Asp Glu Pro Lys Ser Gly Leu
    1775              1780              1785 aat gaa gac caa gcc atg atg cag gat tgt tac agc aaa att gta gat    5549
Asn Glu Asp Gln Ala Met Met Gln Asp Cys Tyr Ser Lys Ile Val Asp
        1790              1795              1800 aag ctg tcc tct gca aac ccc acc atg gta tta cag gtt cag atg ctc    5597
Lys Leu Ser Ser Ala Asn Pro Thr Met Val Leu Gln Val Gln Met Leu
    1805              1810              1815 gtg gct gaa ctg cgc agg gtc act gtg ctc tgg gat gag ctc tgg ctg    5645
Val Ala Glu Leu Arg Arg Val Thr Val Leu Trp Asp Glu Leu Trp Leu
1820              1825              1830              1835 gga gtt ttg ctg caa caa cac atg tat gtc ctg aga cga att cag cag    5693
Gly Val Leu Leu Gln Gln His Met Tyr Val Leu Arg Arg Ile Gln Gln
        1840              1845              1850 ctt gaa gat gag gtg aag aga gtc cag aac aac aac acc tta cgc aaa    5741
Leu Glu Asp Glu Val Lys Arg Val Gln Asn Asn Asn Thr Leu Arg Lys
    1855              1860              1865 gaa gag aaa att gca atc atg agg gag agg cac aca gct ttg atg aag    5789
Glu Glu Lys Ile Ala Ile Met Arg Glu Arg His Thr Ala Leu Met Lys
        1870              1875              1880 ccc atc gta ttt gct ttg gag cat gtg agg agt atc aca gcg gct cct    5837
Pro Ile Val Phe Ala Leu Glu His Val Arg Ser Ile Thr Ala Ala Pro
    1885              1890              1895 gca gaa aca cct cat gaa aaa tgg ttt cag gat aac tat ggt gat gcc    5885
Ala Glu Thr Pro His Glu Lys Trp Phe Gln Asp Asn Tyr Gly Asp Ala
1900              1905              1910              1915 att gaa aat gcc cta gaa aaa ctg aag act cca ttg aac cct gca aag    5933
Ile Glu Asn Ala Leu Glu Lys Leu Lys Thr Pro Leu Asn Pro Ala Lys
        1920              1925              1930 cct ggg agc agc tgg att cca ttt aaa gag ata atg cta agt ttg caa    5981
Pro Gly Ser Ser Trp Ile Pro Phe Lys Glu Ile Met Leu Ser Leu Gln
    1935              1940              1945 cag aga gca cag aaa cgt gca agt tac atc ttg cgt ctt gaa gaa atc    6029
Gln Arg Ala Gln Lys Arg Ala Ser Tyr Ile Leu Arg Leu Glu Glu Ile
        1950              1955              1960 agt cca tgg ttg gct gcc atg act aac act gaa att gct ctt cct ggg    6077
Ser Pro Trp Leu Ala Ala Met Thr Asn Thr Glu Ile Ala Leu Pro Gly
1965              1970              1975 gaa gtc tca gcc aga gac act gtc aca atc cat agt gtg ggc gga acc    6125
Glu Val Ser Ala Arg Asp Thr Val Thr Ile His Ser Val Gly Gly Thr
1980              1985              1990              1995 atc aca atc tta ccg act aaa acc aag cca aag aaa ctt ctc ttt ctt    6173
Ile Thr Ile Leu Pro Thr Lys Thr Lys Pro Lys Lys Leu Leu Phe Leu
        2000              2005              2010 gga tca gat ggg aag agc tat cct tat ctt ttc aaa gga ctg gag gat    6221
```

```
Gly Ser Asp Gly Lys Ser Tyr Pro Tyr Leu Phe Lys Gly Leu Glu Asp
            2015                2020                2025 tta cat ctg gat gag aga ata atg cag ttc cta tct att gtg aat acc       6269
Leu His Leu Asp Glu Arg Ile Met Gln Phe Leu Ser Ile Val Asn Thr
            2030                2035                2040 atg ttt gct aca att aat cgc caa gaa aca ccc cgg ttc cat gct cga       6317
Met Phe Ala Thr Ile Asn Arg Gln Glu Thr Pro Arg Phe His Ala Arg
            2045                2050                2055 cac tat tct gta aca cca cta gga aca aga tca gga cta atc cag tgg       6365
His Tyr Ser Val Thr Pro Leu Gly Thr Arg Ser Gly Leu Ile Gln Trp
    2060                2065                2070            2075 gta gat gga gcc aca ccc tta ttt ggt ctt tac aaa cga tgg caa caa       6413
Val Asp Gly Ala Thr Pro Leu Phe Gly Leu Tyr Lys Arg Trp Gln Gln
                2080                2085                2090 cgg gaa gct gcc tta caa gca caa aag gcc caa gat tcc tac caa act       6461
Arg Glu Ala Ala Leu Gln Ala Gln Lys Ala Gln Asp Ser Tyr Gln Thr
            2095                2100                2105 cct cag aat cct gga att gta ccc cgt cct agt gaa ctt tat tac agt       6509
Pro Gln Asn Pro Gly Ile Val Pro Arg Pro Ser Glu Leu Tyr Tyr Ser
            2110                2115                2120 aaa att ggc cct gct ttg aaa aca gtt ggg ctt agc ctg gat gtg tcc       6557
Lys Ile Gly Pro Ala Leu Lys Thr Val Gly Leu Ser Leu Asp Val Ser
            2125                2130                2135 cgt cgg gat tgg cct ctt cat gta atg aag gca gta ttg gaa gag tta       6605
Arg Arg Asp Trp Pro Leu His Val Met Lys Ala Val Leu Glu Glu Leu
2140                2145                2150                2155 atg gag gcc aca ccc ccg aat ctc ctt gcc aaa gag ctc tgg tca tct       6653
Met Glu Ala Thr Pro Pro Asn Leu Leu Ala Lys Glu Leu Trp Ser Ser
                2160                2165                2170 tgc aca aca cct gat gaa tgg tgg aga gtt acg cag tct tat gca aga       6701
Cys Thr Thr Pro Asp Glu Trp Trp Arg Val Thr Gln Ser Tyr Ala Arg
            2175                2180                2185 tct act gca gtc atg tct atg gtt gga tac ata att ggc ctt gga gac       6749
Ser Thr Ala Val Met Ser Met Val Gly Tyr Ile Ile Gly Leu Gly Asp
            2190                2195                2200 aga cat ctg gat aat gtt ctt ata gat atg acg act gga gaa gtt gtt       6797
Arg His Leu Asp Asn Val Leu Ile Asp Met Thr Thr Gly Glu Val Val
    2205                2210                2215 cac ata gat tac aat gtt tgc ttt gaa aaa ggt aaa agc ctt aga gtt       6845
His Ile Asp Tyr Asn Val Cys Phe Glu Lys Gly Lys Ser Leu Arg Val
2220                2225                2230                2235 cct gag aaa gta cct ttt cga atg aca caa aac att gaa aca gca ctg       6893
Pro Glu Lys Val Pro Phe Arg Met Thr Gln Asn Ile Glu Thr Ala Leu
                2240                2245                2250 ggt gta act gga gta gaa ggt gta ttt agg ctt tca tgt gag cag gtt       6941
Gly Val Thr Gly Val Glu Gly Val Phe Arg Leu Ser Cys Glu Gln Val
            2255                2260                2265 tta cac att atg cgg cgt ggc aga gag acc ctg ctg acg ctg ctg gag       6989
Leu His Ile Met Arg Arg Gly Arg Glu Thr Leu Leu Thr Leu Leu Glu
            2270                2275                2280 gcc ttt gtg tac gac cct ctg gtg gac tgg aca gca gga ggc gag gct       7037
Ala Phe Val Tyr Asp Pro Leu Val Asp Trp Thr Ala Gly Gly Glu Ala
            2285                2290                2295 ggg ttt gct ggt gct gtc tat ggt gga ggt ggc cag cag gcc gag agc       7085
Gly Phe Ala Gly Ala Val Tyr Gly Gly Gly Gly Gln Gln Ala Glu Ser
2300                2305                2310                2315 aag cag agc aag aga gag atg gag cga gag atc acc cgc agc ctg ttt       7133
Lys Gln Ser Lys Arg Glu Met Glu Arg Glu Ile Thr Arg Ser Leu Phe
            2320                2325                2330
```

```
                                                        -continued tct tct aga gta gct gag att aag gtg aac tgg ttt aag aat aga gat        7181
Ser Ser Arg Val Ala Glu Ile Lys Val Asn Trp Phe Lys Asn Arg Asp
            2335                2340                2345 gag atg ctg gtt gtg ctt ccc aag ttg gac ggt agc tta gat gaa tac        7229
Glu Met Leu Val Val Leu Pro Lys Leu Asp Gly Ser Leu Asp Glu Tyr
        2350                2355                2360 cta agc ttg caa gag caa ctg aca gat gtg gaa aaa ctg cag ggc aaa        7277
Leu Ser Leu Gln Glu Gln Leu Thr Asp Val Glu Lys Leu Gln Gly Lys
    2365                2370                2375 cta ctg gag gaa ata gag ttt cta gaa gga gct gaa ggg gtg gat cat        7325
Leu Leu Glu Glu Ile Glu Phe Leu Glu Gly Ala Glu Gly Val Asp His
2380                2385                2390                2395 cct tct cat act ctg caa cac agg tat tct gag cac acc caa cta cag        7373
Pro Ser His Thr Leu Gln His Arg Tyr Ser Glu His Thr Gln Leu Gln
                2400                2405                2410 act cag caa aga gct gtt cag gaa gca atc cag gtg aag ctg aat gaa        7421
Thr Gln Gln Arg Ala Val Gln Glu Ala Ile Gln Val Lys Leu Asn Glu
            2415                2420                2425 ttt gaa caa tgg ata aca cat tat cag gct gca ttc aat aat tta gaa        7469
Phe Glu Gln Trp Ile Thr His Tyr Gln Ala Ala Phe Asn Asn Leu Glu
        2430                2435                2440 gca aca cag ctt gca agc ttg ctt caa gag ata agc aca caa atg gac        7517
Ala Thr Gln Leu Ala Ser Leu Leu Gln Glu Ile Ser Thr Gln Met Asp
    2445                2450                2455 ctt ggt cct cca agt tac gtg cca gca aca gcc ttt ctg cag aat gct        7565
Leu Gly Pro Pro Ser Tyr Val Pro Ala Thr Ala Phe Leu Gln Asn Ala
2460                2465                2470                2475 ggt cag gcc cac ttg att agc cag tgc gag cag ctg gag ggg gag gtt        7613
Gly Gln Ala His Leu Ile Ser Gln Cys Glu Gln Leu Glu Gly Glu Val
                2480                2485                2490 ggt gct ctc ctg cag cag agg cgc tcc gtg ctc cgt ggc tgt ctg gag        7661
Gly Ala Leu Leu Gln Gln Arg Arg Ser Val Leu Arg Gly Cys Leu Glu
            2495                2500                2505 caa ctg cat cac tat gca acc gtg gcc ctg cag tat ccg aag gcc ata        7709
Gln Leu His His Tyr Ala Thr Val Ala Leu Gln Tyr Pro Lys Ala Ile
        2510                2515                2520 ttt cag aaa cat cga att gaa cag tgg aag acc tgg atg gaa gag ctc        7757
Phe Gln Lys His Arg Ile Glu Gln Trp Lys Thr Trp Met Glu Glu Leu
    2525                2530                2535 atc tgt aac acc aca gta gag cgt tgt caa gag ctc tat agg aaa tat        7805
Ile Cys Asn Thr Thr Val Glu Arg Cys Gln Glu Leu Tyr Arg Lys Tyr
2540                2545                2550                2555 gaa atg caa tat gct ccc cag cca ccc cca aca gtg tgt cag ttc atc        7853
Glu Met Gln Tyr Ala Pro Gln Pro Pro Pro Thr Val Cys Gln Phe Ile
                2560                2565                2570 act gcc act gaa atg acc ctg cag cga tac gca gca gac atc aac agc        7901
Thr Ala Thr Glu Met Thr Leu Gln Arg Tyr Ala Ala Asp Ile Asn Ser
            2575                2580                2585 aga ctt att aga caa gtg gaa cgc ttg aaa cag gaa gct gtc act gtg        7949
Arg Leu Ile Arg Gln Val Glu Arg Leu Lys Gln Glu Ala Val Thr Val
        2590                2595                2600 cca gtt tgt gaa gat cag ttg aaa gaa att gaa cgt tgc att aaa gtt        7997
Pro Val Cys Glu Asp Gln Leu Lys Glu Ile Glu Arg Cys Ile Lys Val
    2605                2610                2615 ttc ctt cat gag aat gga gaa gaa gga tct ttg agt cta gca agt gtt        8045
Phe Leu His Glu Asn Gly Glu Glu Gly Ser Leu Ser Leu Ala Ser Val
2620                2625                2630                2635 att att tct gcc ctt tgt acc ctt aca agg cgt aac ctg atg atg gaa        8093
Ile Ile Ser Ala Leu Cys Thr Leu Thr Arg Arg Asn Leu Met Met Glu
                2640                2645                2650
```

-continued

| | | |
|---|---|---|
| ggt gca gcg tca agt gct gga gaa cag ctg gtt gat ctg act tct cgg<br>Gly Ala Ala Ser Ser Ala Gly Glu Gln Leu Val Asp Leu Thr Ser Arg<br>        2655                        2660                    2665 | | 8141 |
| gat gga gcc tgg ttc ttg gag gaa ctc tgc agt atg agc gga aac gtc<br>Asp Gly Ala Trp Phe Leu Glu Glu Leu Cys Ser Met Ser Gly Asn Val<br>        2670                        2675                    2680 | | 8189 |
| acc tgc ttg gtt cag tta ctg aag cag tgc cac ctg gtg cca cag gac<br>Thr Cys Leu Val Gln Leu Leu Lys Gln Cys His Leu Val Pro Gln Asp<br>        2685                        2690                    2695 | | 8237 |
| tta gat atc ccg aac ccc atg gaa gcg tct gag aca gtt cac tta gcc<br>Leu Asp Ile Pro Asn Pro Met Glu Ala Ser Glu Thr Val His Leu Ala<br>2700                        2705                    2710                    2715 | | 8285 |
| aat gga gtg tat acc tca ctt cag gaa ttg aat tcg aat ttc cgg caa<br>Asn Gly Val Tyr Thr Ser Leu Gln Glu Leu Asn Ser Asn Phe Arg Gln<br>        2720                        2725                    2730 | | 8333 |
| atc ata ttt cca gaa gca ctt cga tgt tta atg aaa ggg gaa tac acg<br>Ile Ile Phe Pro Glu Ala Leu Arg Cys Leu Met Lys Gly Glu Tyr Thr<br>        2735                        2740                    2745 | | 8381 |
| tta gaa agt atg ctg cat gaa ctg gac ggt ctt att gag cag acc acc<br>Leu Glu Ser Met Leu His Glu Leu Asp Gly Leu Ile Glu Gln Thr Thr<br>        2750                        2755                    2760 | | 8429 |
| gat ggc gtt ccc ctg cag act cta gtg gaa tct ctt cag gcc tac tta<br>Asp Gly Val Pro Leu Gln Thr Leu Val Glu Ser Leu Gln Ala Tyr Leu<br>        2765                        2770                    2775 | | 8477 |
| aga aac gca gct atg gga ctg gaa gaa gaa aca cat gct cat tac atc<br>Arg Asn Ala Ala Met Gly Leu Glu Glu Glu Thr His Ala His Tyr Ile<br>2780                        2785                    2790                    2795 | | 8525 |
| gat gtt gcc aga cta cta cat gct cag tac ggt gaa tta atc caa ccg<br>Asp Val Ala Arg Leu Leu His Ala Gln Tyr Gly Glu Leu Ile Gln Pro<br>                2800                        2805                    2810 | | 8573 |
| aga aat ggt tca gtt gat gaa aca ccc aaa atg tca gct ggc cag atg<br>Arg Asn Gly Ser Val Asp Glu Thr Pro Lys Met Ser Ala Gly Gln Met<br>        2815                        2820                    2825 | | 8621 |
| ctt ttg gta gca ttc gat ggc atg ttt gct caa gtt gaa act gct ttc<br>Leu Leu Val Ala Phe Asp Gly Met Phe Ala Gln Val Glu Thr Ala Phe<br>        2830                        2835                    2840 | | 8669 |
| agc tta tta gtt gaa aag ttg aac aag atg gaa att ccc ata gct tgg<br>Ser Leu Leu Val Glu Lys Leu Asn Lys Met Glu Ile Pro Ile Ala Trp<br>        2845                        2850                    2855 | | 8717 |
| cga aag att gac atc ata agg gaa gcc agg agt act caa gtt aat ttt<br>Arg Lys Ile Asp Ile Ile Arg Glu Ala Arg Ser Thr Gln Val Asn Phe<br>2860                        2865                    2870                    2875 | | 8765 |
| ttt gat gat gat aat cac cgg cag gtg cta gaa gag att ttc ttt cta<br>Phe Asp Asp Asp Asn His Arg Gln Val Leu Glu Glu Ile Phe Phe Leu<br>                2880                        2885                    2890 | | 8813 |
| aaa aga cta cag act att aag gag ttc ttc agg ctc tgt ggt acc ttt<br>Lys Arg Leu Gln Thr Ile Lys Glu Phe Phe Arg Leu Cys Gly Thr Phe<br>        2895                        2900                    2905 | | 8861 |
| tct aaa aca ttg tca gga tca agt tca ctt gaa gat cag aat act gtg<br>Ser Lys Thr Leu Ser Gly Ser Ser Ser Leu Glu Asp Gln Asn Thr Val<br>        2910                        2915                    2920 | | 8909 |
| aat ggg cct gta cag att gtc aat gtg aaa acc ctt ttt aga aac tct<br>Asn Gly Pro Val Gln Ile Val Asn Val Lys Thr Leu Phe Arg Asn Ser<br>        2925                        2930                    2935 | | 8957 |
| tgt ttc agt gaa gac caa atg gcc aaa cct atc aag gca ttc aca gct<br>Cys Phe Ser Glu Asp Gln Met Ala Lys Pro Ile Lys Ala Phe Thr Ala<br>2940                        2945                    2950                    2955 | | 9005 |
| gac ttt gtg agg cag ctc ttg ata ggg cta ccc aac caa gcc ctc gga<br>Asp Phe Val Arg Gln Leu Leu Ile Gly Leu Pro Asn Gln Ala Leu Gly | | 9053 |

-continued

```
                           2960                 2965                 2970
ctc aca ctg tgc agt ttt atc agt gct ctg ggt gta gac atc att gct      9101
Leu Thr Leu Cys Ser Phe Ile Ser Ala Leu Gly Val Asp Ile Ile Ala
            2975                 2980                 2985 caa gta gag gca aag gac ttt ggt gcc gaa agc aaa gtt tct gtt gat      9149
Gln Val Glu Ala Lys Asp Phe Gly Ala Glu Ser Lys Val Ser Val Asp
            2990                 2995                 3000 gat ctc tgt aag aaa gcg gtg gaa cat aac atc cag ata ggg aag ttc      9197
Asp Leu Cys Lys Lys Ala Val Glu His Asn Ile Gln Ile Gly Lys Phe
            3005                 3010                 3015 tct cag ctg gtt atg aac agg gca act gtg tta gca agt tct tac gac      9245
Ser Gln Leu Val Met Asn Arg Ala Thr Val Leu Ala Ser Ser Tyr Asp
            3020                 3025                 3030                 3035 act gcc tgg aag aag cat gac ttg gtg cga agg cta gaa acc agt att      9293
Thr Ala Trp Lys Lys His Asp Leu Val Arg Arg Leu Glu Thr Ser Ile
                    3040                 3045                 3050 tct tct tgt aag aca agc ctg cag cgg gtt cag ctg cat att gcc atg      9341
Ser Ser Cys Lys Thr Ser Leu Gln Arg Val Gln Leu His Ile Ala Met
            3055                 3060                 3065 ttt cag tgg caa cat gaa gat cta ctt atc aat aga cca caa gcc atg      9389
Phe Gln Trp Gln His Glu Asp Leu Leu Ile Asn Arg Pro Gln Ala Met
            3070                 3075                 3080 tca gtc aca cct ccc cca cgg tct gct atc cta acc agc atg aaa aag      9437
Ser Val Thr Pro Pro Pro Arg Ser Ala Ile Leu Thr Ser Met Lys Lys
            3085                 3090                 3095 aag ctg cat acc ctg agc cag att gaa act tct att gcg aca gtt cag      9485
Lys Leu His Thr Leu Ser Gln Ile Glu Thr Ser Ile Ala Thr Val Gln
3100                 3105                 3110                 3115 gag aag cta gct gca ctt gaa tca agt att gaa cag cga ctc aag tgg      9533
Glu Lys Leu Ala Ala Leu Glu Ser Ser Ile Glu Gln Arg Leu Lys Trp
            3120                 3125                 3130 gca ggt ggt gcc aac cct gca ttg gcc cct gta cta caa gat ttt gaa      9581
Ala Gly Gly Ala Asn Pro Ala Leu Ala Pro Val Leu Gln Asp Phe Glu
            3135                 3140                 3145 gca acg ata gct gaa aga aga aat ctt gtc ctt aaa gag agc caa aga      9629
Ala Thr Ile Ala Glu Arg Arg Asn Leu Val Leu Lys Glu Ser Gln Arg
            3150                 3155                 3160 gca agt cag gtc aca ttt ctc tgc agc aat atc att cat ttt gaa agt      9677
Ala Ser Gln Val Thr Phe Leu Cys Ser Asn Ile Ile His Phe Glu Ser
            3165                 3170                 3175 tta cga aca aga act gca gaa gcc tta aac ctg gat gcg gcg tta ttt      9725
Leu Arg Thr Arg Thr Ala Glu Ala Leu Asn Leu Asp Ala Ala Leu Phe
3180                 3185                 3190                 3195 gaa cta atc aag cga tgt cag cag atg tgt tcg ttt gca tca cag ttt      9773
Glu Leu Ile Lys Arg Cys Gln Gln Met Cys Ser Phe Ala Ser Gln Phe
            3200                 3205                 3210 aac agt tca gtg tct gag tta gag ctt cgt tta tta cag aga gtg gac      9821
Asn Ser Ser Val Ser Glu Leu Glu Leu Arg Leu Leu Gln Arg Val Asp
            3215                 3220                 3225 act ggt ctt gaa cat cct att ggc agc tct gaa tgg ctt ttg tca gca      9869
Thr Gly Leu Glu His Pro Ile Gly Ser Ser Glu Trp Leu Leu Ser Ala
            3230                 3235                 3240 cac aaa cag ttg acc cag gat atg tct act cag agg gca att cag aca      9917
His Lys Gln Leu Thr Gln Asp Met Ser Thr Gln Arg Ala Ile Gln Thr
            3245                 3250                 3255 gag aaa gag cag cag ata gaa acg gtc tgt gaa aca att cag aat ctg      9965
Glu Lys Glu Gln Gln Ile Glu Thr Val Cys Glu Thr Ile Gln Asn Leu
3260                 3265                 3270                 3275 gtt gat aat ata aag act gtg ctc act ggt cat aac cga cag ctt gga     10013
```

|   |   |   |   |   |   |   |   |   |   |   |   |   |   |   |
|---|---|---|---|---|---|---|---|---|---|---|---|---|---|---|
| Val | Asp | Asn | Ile | Lys | Thr | Val | Leu | Thr | Gly | His | Asn | Arg | Gln | Leu | Gly |
|  |  | 3280 |  |  |  | 3285 |  |  |  | 3290 |  |  |

```
gat gtc aaa cat ctc ttg aaa gct atg gct aag gat gaa gaa gct gct   10061
Asp Val Lys His Leu Leu Lys Ala Met Ala Lys Asp Glu Glu Ala Ala
            3295                3300                3305 ctg gca gat ggt gaa gat gtt ccc tat gag aac agt gtt agg cag ttt   10109
Leu Ala Asp Gly Glu Asp Val Pro Tyr Glu Asn Ser Val Arg Gln Phe
            3310                3315                3320 ttg ggt gaa tat aaa tca tgg caa gac aac att caa aca gtt cta ttt   10157
Leu Gly Glu Tyr Lys Ser Trp Gln Asp Asn Ile Gln Thr Val Leu Phe
    3325                3330                3335 aca tta gtc cag gct atg ggt cag gtt cga agt caa gaa cac gtt gaa   10205
Thr Leu Val Gln Ala Met Gly Gln Val Arg Ser Gln Glu His Val Glu
3340                3345                3350                3355 atg ctc cag gaa atc act ccc acc ttg aaa gaa ctg aaa aca caa agt   10253
Met Leu Gln Glu Ile Thr Pro Thr Leu Lys Glu Leu Lys Thr Gln Ser
                3360                3365                3370 cag agt atc tat aat aat tta gtg agt ttt gca tca ccc tta gtc acc   10301
Gln Ser Ile Tyr Asn Asn Leu Val Ser Phe Ala Ser Pro Leu Val Thr
            3375                3380                3385 gat gca aca aat gaa tgt tcg agt cca acg tca tct gct act tat cag   10349
Asp Ala Thr Asn Glu Cys Ser Ser Pro Thr Ser Ser Ala Thr Tyr Gln
        3390                3395                3400 cca tcc ttc gct gca gca gtc cgg agt aac act ggc cag aag act cag   10397
Pro Ser Phe Ala Ala Ala Val Arg Ser Asn Thr Gly Gln Lys Thr Gln
    3405                3410                3415 cct gat gtc atg tca cag aat gct aga aag ctg atc cag aaa aat ctt   10445
Pro Asp Val Met Ser Gln Asn Ala Arg Lys Leu Ile Gln Lys Asn Leu
3420                3425                3430                3435 gct aca tca gct gat act cca cca agc acc gtt cca gga act ggc aag   10493
Ala Thr Ser Ala Asp Thr Pro Pro Ser Thr Val Pro Gly Thr Gly Lys
            3440                3445                3450 agt gtt gct tgt agt cct aaa aag gca gtc aga gac cct aaa act ggg   10541
Ser Val Ala Cys Ser Pro Lys Lys Ala Val Arg Asp Pro Lys Thr Gly
        3455                3460                3465 aaa gcg gtg caa gag aga aac tcc tat gca gtg agt gtg tgg aag aga   10589
Lys Ala Val Gln Glu Arg Asn Ser Tyr Ala Val Ser Val Trp Lys Arg
    3470                3475                3480 gtg aaa gcc aag tta gag ggc cga gat gtt gat ccg aat agg agg atg   10637
Val Lys Ala Lys Leu Glu Gly Arg Asp Val Asp Pro Asn Arg Arg Met
3485                3490                3495 tca gtt gct gaa cag gtt gac tat gtc att aag gaa gca act aat cta   10685
Ser Val Ala Glu Gln Val Asp Tyr Val Ile Lys Glu Ala Thr Asn Leu
            3500                3505                3510                3515 gat aac ttg gct cag ctg tat gaa ggt tgg aca gcc tgg gtg tga       10730
Asp Asn Leu Ala Gln Leu Tyr Glu Gly Trp Thr Ala Trp Val *
            3520                3525 atggcaagac agtagatgag tctggttaag cgaggtcaga catccaccag aatcaactca   10790
gcctcaggca tccaaagcca caccacagtc ggtggtgatg caactggggg cttactctga   10850
ggaaacctag gaaatctcgg tgcactagga agtgaatccc gcaggacagc tgcactcagg   10910
gatacgccca acaccatggc ctgcaacccc agggtcaagg gtgaaggaaa gcaaagctca   10970
ccgcctgaac acggagattg tctttctgcc acagaacagc agcagacgtg tcgggaggtt   11030
agctgcggaa agaaatcggg atgccgcgga gcacagagtg atttggaact ccattccacc   11090
tgaccctgtg tgtacaatcc aggaaaaaaa caaaccccac tcagaaacag agaaaactgg   11150
ggtcgcgaag aaatcacagc caaggaagat ttgatgcatt cagattctcg tgtaacactt   11210
```

-continued

```
gttgcttggc aacagtactg gttgggttga ccagtaagta gaaaaaggct aaaggctatg   11270
cgatatgaat ttcagaaatg gactgaaaat ggagagctat gtaacagata cactacagta   11330
gaagaactta cttctgaaat gaagggaaaa aaaccacccc atcgttccct actcctcccc   11390
accacttacc cgttccccct ttacctaatc tagtagatta gccatctttc aaattcactt   11450
ttatttcagt ccttatattt catatacttc cgtctcgatg ctgttaacaa cttctgataa   11510
catggaaaat tcaaggattg tttaaaggtc tgatgatcac acacaaaatg taattccggt   11570
tatttaagtc atttctgtga ttctatcatg tacagtttcc agaattgtca ctgtgcattc   11630
aaaagtaatg aatctaacag acatttgatt taatgtacac tcccttttgc ttatagtgtg   11690 cattttttt ggaggtcatt caaattttcc ctcttctgtg atagctgtag tttctttcat   11750
agaaagtagc taatccagtg taatcttta cctttttaaa aaccaagata gagtatctat   11810
tagagtttta cattgttgat gatagattaa caataaagtg atgttctggt ggaggtagac   11870
tgaaattttt ttaattcatg tttttcattt gatacttta atttacactt agtaaattaa   11930
aagttgttta atttacttgg cattttagga catgtacatg aaacagtgaa atgagatcc   11990 accaacatct tttattaagt tcagttatta gtctgtgaag tgctttactt tttgcacaat   12050
tttaatagct tgctattcag taatacatta tagtgaattc atgatcaagg tttccttaaa   12110
tttagcattg catttcagta ctgactgtgt aagctaaatt gctgatccaa ataaaaaacc   12170
cagactagaa tagggttctt aaaatcaagt atcaatacaa aatagaacac aattaaaatc   12230
ttaattgttg gctgggcaca gtggctcacg cctgtaatcc cagcactttg ggaggccgag   12290
gcgggcggat catgaggtta ggagagcgag accatcctgg ctaacacggt gaaacccgt    12350 ctttactaaa atacaaaaaa aattagccgg gtgtggtggc gggcgcctgt agtcccagct   12410
actcgggagg ctgaggcagg agaatggcgt gaacccagga ggcggagctt gcagtgagcc   12470
gagattgtgc cactgcactc cagcctgggc aacagagcta gactctgtgt caaaaataaa   12530
tgactagat                                                           12539
```

<210> SEQ ID NO 8
<211> LENGTH: 3529
<212> TYPE: PRT
<213> ORGANISM: Homo sapiens

<400> SEQUENCE: 8

```
Met Arg Lys Ser Gln Glu Arg Ser Met Ser Tyr Ser Asp Glu Ser Arg
 1               5                  10                  15

Leu Ser Asn Leu Leu Arg Arg Ile Thr Arg Glu Asp Asp Arg Asp Arg
            20                  25                  30

Arg Leu Ala Thr Val Lys Gln Leu Lys Glu Phe Ile Gln Gln Pro Glu
        35                  40                  45

Asn Lys Leu Val Leu Val Lys Gln Leu Asp Asn Ile Leu Ala Ala Val
    50                  55                  60

His Asp Val Leu Asn Glu Ser Ser Lys Leu Leu Gln Glu Leu Arg Gln
65                  70                  75                  80

Glu Gly Ala Cys Cys Leu Gly Leu Leu Cys Ala Ser Leu Ser Tyr Glu
                85                  90                  95

Ala Glu Lys Ile Phe Lys Trp Ile Phe Ser Lys Phe Ser Ser Ala
            100                 105                 110

Lys Asp Glu Val Lys Leu Leu Tyr Leu Cys Ala Thr Tyr Lys Ala Leu
        115                 120                 125

Glu Thr Val Gly Glu Lys Lys Ala Phe Ser Ser Val Met Gln Leu Val
```

```
                130                 135                 140
Met Thr Ser Leu Gln Ser Ile Leu Glu Asn Val Asp Thr Pro Glu Leu
145                 150                 155                 160

Leu Cys Lys Cys Val Lys Cys Ile Leu Leu Val Ala Arg Cys Tyr Pro
                165                 170                 175

His Ile Phe Ser Thr Asn Phe Arg Asp Thr Val Asp Ile Leu Val Gly
                180                 185                 190

Trp His Ile Asp His Thr Gln Lys Pro Ser Leu Thr Gln Gln Val Ser
                195                 200                 205

Gly Trp Leu Gln Ser Leu Glu Pro Phe Trp Val Asp Leu Ala Phe
210                 215                 220

Ser Thr Thr Leu Leu Gly Gln Phe Leu Glu Asp Met Glu Ala Tyr Ala
225                 230                 235                 240

Glu Asp Leu Ser His Val Ala Ser Gly Glu Ser Val Asp Glu Asp Val
                245                 250                 255

Pro Pro Pro Ser Val Ser Leu Pro Lys Leu Ala Ala Leu Leu Arg Val
                260                 265                 270

Phe Ser Thr Val Val Arg Ser Ile Gly Glu Arg Phe Ser Pro Ile Arg
                275                 280                 285

Gly Pro Pro Ile Thr Glu Ala Tyr Val Thr Asp Val Leu Tyr Arg Val
                290                 295                 300

Met Arg Cys Val Thr Ala Ala Asn Gln Val Phe Ser Glu Ala Val
305                 310                 315                 320

Leu Thr Ala Ala Asn Glu Cys Val Gly Val Leu Leu Gly Ser Leu Asp
                325                 330                 335

Pro Ser Met Thr Ile His Cys Asp Met Val Ile Thr Tyr Gly Leu Asp
                340                 345                 350

Gln Leu Glu Asn Cys Gln Thr Cys Gly Thr Asp Tyr Ile Ile Ser Val
                355                 360                 365

Leu Asn Leu Leu Thr Leu Ile Val Glu Gln Ile Asn Thr Lys Leu Pro
                370                 375                 380

Ser Ser Phe Val Glu Lys Leu Phe Ile Pro Ser Ser Lys Leu Leu Phe
385                 390                 395                 400

Leu Arg Tyr His Lys Glu Lys Glu Val Val Ala Val Ala His Ala Val
                405                 410                 415

Tyr Gln Ala Val Leu Ser Leu Lys Asn Ile Pro Val Leu Glu Thr Ala
                420                 425                 430

Tyr Lys Leu Ile Leu Gly Glu Met Thr Cys Ala Leu Asn Asn Leu Leu
                435                 440                 445

His Ser Leu Gln Leu Pro Glu Ala Cys Ser Glu Ile Lys His Glu Ala
450                 455                 460

Phe Lys Asn His Val Phe Asn Val Asp Asn Ala Lys Phe Val Val Lys
465                 470                 475                 480

Phe Asp Leu Ser Ala Leu Thr Thr Ile Gly Asn Ala Lys Asn Ser Leu
                485                 490                 495

Ile Gly Met Trp Ala Leu Ser Pro Thr Val Phe Ala Leu Leu Ser Lys
                500                 505                 510

Asn Leu Met Ile Val His Ser Asp Leu Ala Val His Phe Pro Ala Ile
                515                 520                 525

Gln Tyr Ala Val Leu Tyr Thr Leu Tyr Ser His Cys Thr Arg His Asp
                530                 535                 540

His Phe Ile Ser Ser Ser Leu Ser Ser Ala Ser Pro Ser Leu Phe Asp
545                 550                 555                 560
```

-continued

```
Gly Ala Val Ile Ser Thr Val Thr Thr Ala Thr Lys Lys His Phe Ser
            565                 570                 575
Ile Ile Leu Asn Leu Leu Gly Ile Leu Leu Lys Lys Asp Asn Leu Asn
        580                 585                 590
Gln Asp Thr Arg Lys Leu Leu Met Thr Trp Ala Leu Glu Ala Ala Val
    595                 600                 605
Leu Met Arg Lys Ser Glu Thr Tyr Ala Pro Leu Phe Ser Leu Pro Ser
610                 615                 620
Phe His Lys Phe Cys Lys Gly Leu Leu Ala Asn Thr Leu Val Glu Asp
625                 630                 635                 640
Val Asn Ile Cys Leu Gln Ala Cys Ser Ser Leu His Ala Leu Ser Ser
            645                 650                 655
Ser Leu Pro Asp Asp Leu Leu Gln Arg Cys Val Asp Val Cys Arg Val
        660                 665                 670
Gln Leu Val His Ser Gly Thr Arg Ile Arg Gln Ala Phe Gly Lys Leu
    675                 680                 685
Leu Lys Ser Ile Pro Leu Asp Val Val Leu Ser Asn Asn Asn His Thr
690                 695                 700
Glu Ile Gln Glu Ile Ser Leu Ala Leu Arg Ser His Met Ser Lys Ala
705                 710                 715                 720
Pro Ser Asn Thr Phe His Pro Gln Asp Phe Ser Asp Val Ile Ser Phe
            725                 730                 735
Ile Leu Tyr Gly Asn Ser His Arg Thr Gly Lys Asp Asn Trp Leu Glu
        740                 745                 750
Arg Leu Phe Tyr Ser Cys Gln Arg Leu Asp Lys Arg Asp Gln Ser Thr
    755                 760                 765
Ile Pro Arg Asn Leu Leu Lys Thr Asp Ala Val Leu Trp Gln Trp Ala
770                 775                 780
Ile Trp Glu Ala Ala Gln Phe Thr Val Leu Ser Lys Leu Arg Thr Pro
785                 790                 795                 800
Leu Gly Arg Ala Gln Asp Thr Phe Gln Thr Ile Glu Gly Ile Ile Arg
            805                 810                 815
Ser Leu Ala Ala His Thr Leu Asn Pro Asp Gln Asp Val Ser Gln Trp
        820                 825                 830
Thr Thr Ala Asp Asn Asp Glu Gly His Gly Asn Asn Gln Leu Arg Leu
    835                 840                 845
Val Leu Leu Gln Tyr Leu Glu Asn Leu Glu Lys Leu Met Tyr Asn
850                 855                 860
Ala Tyr Glu Gly Cys Ala Asn Ala Leu Thr Ser Pro Pro Lys Val Ile
865                 870                 875                 880
Arg Thr Phe Phe Tyr Thr Asn Arg Gln Thr Cys Gln Asp Trp Leu Thr
            885                 890                 895
Arg Ile Arg Leu Ser Ile Met Arg Val Gly Leu Leu Ala Gly Gln Pro
        900                 905                 910
Ala Val Thr Val Arg His Gly Phe Asp Leu Leu Thr Glu Met Lys Thr
    915                 920                 925
Thr Ser Leu Ser Gln Gly Asn Glu Leu Glu Val Thr Ile Met Met Val
930                 935                 940
Val Glu Ala Leu Cys Glu Leu His Cys Pro Glu Ala Ile Gln Gly Ile
945                 950                 955                 960
Ala Val Trp Ser Ser Ile Val Gly Lys Asn Leu Leu Trp Ile Asn
            965                 970                 975
```

```
Ser Val Ala Gln Gln Ala Glu Gly Arg Phe Glu Lys Ala Ser Val Glu
            980                 985                 990

Tyr Gln Glu His Leu Cys Ala Met Thr Gly Val Asp Cys Cys Ile Ser
        995                 1000                1005

Ser Phe Asp Lys Ser Val Leu Thr Leu Ala Asn Ala Gly Arg Asn Ser
    1010                1015                1020

Ala Ser Pro Lys His Ser Leu Asn Gly Glu Ser Arg Lys Thr Val Leu
1025                1030                1035                1040

Ser Lys Pro Thr Asp Ser Ser Pro Glu Val Ile Asn Tyr Leu Gly Asn
            1045                1050                1055

Lys Ala Cys Glu Phe Tyr Ile Ser Ile Ala Asp Trp Ala Val Gln
                1060                1065                1070

Glu Trp Gln Asn Ala Ile His Asp Leu Lys Lys Ser Thr Ser Ser Thr
            1075                1080                1085

Ser Leu Asn Leu Lys Ala Asp Phe Asn Tyr Ile Lys Ser Leu Ser Ser
    1090                1095                1100

Phe Glu Ser Gly Lys Phe Val Glu Cys Thr Glu Gln Leu Glu Leu Leu
1105                1110                1115                1120

Pro Gly Glu Asn Ile Asn Leu Leu Ala Gly Ser Lys Glu Lys Ile
            1125                1130                1135

Asp Met Lys Lys Leu Leu Pro Asn Met Leu Ser Pro Asp Pro Arg Glu
            1140                1145                1150

Leu Gln Lys Ser Ile Glu Val Gln Leu Leu Arg Ser Ser Val Cys Leu
            1155                1160                1165

Ala Thr Ala Leu Asn Pro Ile Glu Gln Asp Gln Lys Trp Gln Ser Ile
            1170                1175                1180

Thr Glu Asn Val Val Lys Tyr Leu Lys Gln Thr Ser Arg Ile Ala Ile
1185                1190                1195                1200

Gly Pro Leu Arg Leu Ser Thr Leu Thr Val Ser Gln Ser Leu Pro Val
                1205                1210                1215

Leu Ser Thr Leu Gln Leu Tyr Cys Ser Ser Ala Leu Glu Asn Thr Val
            1220                1225                1230

Ser Asn Arg Leu Ser Thr Glu Asp Cys Leu Ile Pro Leu Phe Ser Glu
            1235                1240                1245

Ala Leu Arg Ser Cys Lys Gln His Asp Val Arg Pro Trp Met Gln Ala
    1250                1255                1260

Leu Arg Tyr Thr Met Tyr Gln Asn Gln Leu Leu Glu Lys Ile Lys Glu
1265                1270                1275                1280

Gln Thr Val Pro Ile Arg Ser His Leu Met Glu Leu Gly Leu Thr Ala
                1285                1290                1295

Ala Lys Phe Ala Arg Lys Arg Gly Asn Val Ser Leu Ala Thr Arg Leu
            1300                1305                1310

Leu Ala Gln Cys Ser Glu Val Gln Leu Gly Lys Thr Thr Thr Ala Gln
            1315                1320                1325

Asp Leu Val Gln His Phe Lys Lys Leu Ser Thr Gln Gly Gln Val Asp
    1330                1335                1340

Glu Lys Trp Gly Pro Glu Leu Asp Ile Glu Lys Thr Lys Leu Leu Tyr
1345                1350                1355                1360

Thr Ala Gly Gln Ser Thr His Ala Met Glu Met Leu Ser Ser Cys Ala
                1365                1370                1375

Ile Ser Phe Cys Lys Ser Val Lys Ala Glu Tyr Ala Val Ala Lys Ser
            1380                1385                1390

Ile Leu Thr Leu Ala Lys Trp Ile Gln Ala Glu Trp Lys Glu Ile Ser
```

-continued

```
            1395                1400                1405
Gly Gln Leu Lys Gln Val Tyr Arg Ala Gln His Gln Gln Asn Phe Thr
    1410                1415                1420
Gly Leu Ser Thr Leu Ser Lys Asn Ile Leu Thr Leu Ile Glu Leu Pro
1425                1430                1435                1440
Ser Val Asn Thr Met Glu Glu Tyr Pro Arg Ile Glu Ser Glu Ser
            1445                1450                1455
Thr Val His Ile Gly Val Gly Glu Pro Asp Phe Ile Leu Gly Gln Leu
            1460                1465                1470
Tyr His Leu Ser Ser Val Gln Ala Pro Glu Val Ala Lys Ser Trp Ala
            1475                1480                1485
Ala Leu Ala Ser Trp Ala Tyr Arg Trp Gly Arg Lys Val Val Asp Asn
    1490                1495                1500
Ala Ser Gln Gly Glu Gly Val Arg Leu Leu Pro Arg Glu Lys Ser Glu
1505                1510                1515                1520
Val Gln Asn Leu Leu Pro Asp Thr Ile Thr Glu Glu Lys Glu Arg
            1525                1530                1535
Ile Tyr Gly Ile Leu Gly Gln Ala Val Cys Arg Pro Ala Gly Ile Gln
            1540                1545                1550
Asp Glu Asp Ile Thr Leu Gln Ile Thr Glu Ser Glu Asp Asn Glu Glu
            1555                1560                1565
Asp Asp Met Val Asp Val Ile Trp Arg Gln Leu Ile Ser Ser Cys Pro
    1570                1575                1580
Trp Leu Ser Glu Leu Asp Glu Ser Ala Thr Glu Gly Val Ile Lys Val
1585                1590                1595                1600
Trp Arg Lys Val Val Asp Arg Ile Phe Ser Leu Tyr Lys Leu Ser Cys
            1605                1610                1615
Ser Ala Tyr Phe Thr Phe Leu Lys Leu Asn Ala Gly Gln Ile Pro Leu
            1620                1625                1630
Asp Glu Asp Asp Pro Arg Leu His Leu Ser His Arg Val Glu Gln Ser
            1635                1640                1645
Thr Asp Asp Met Ile Val Met Ala Thr Leu Arg Leu Arg Leu Leu
            1650                1655                1660
Val Lys His Ala Gly Glu Leu Arg Gln Tyr Leu Glu His Gly Leu Glu
1665                1670                1675                1680
Thr Thr Pro Thr Ala Pro Trp Arg Gly Ile Ile Pro Gln Leu Phe Ser
            1685                1690                1695
Arg Leu Asn His Pro Glu Val Tyr Val Arg Gln Ser Ile Cys Asn Leu
            1700                1705                1710
Leu Cys Arg Val Ala Gln Asp Ser Pro His Leu Ile Leu Tyr Pro Ala
            1715                1720                1725
Ile Val Gly Thr Ile Ser Leu Ser Ser Glu Ser Gln Ala Ser Gly Asn
            1730                1735                1740
Lys Phe Ser Thr Ala Ile Pro Thr Leu Leu Gly Asn Ile Gln Gly Glu
1745                1750                1755                1760
Glu Leu Leu Val Ser Glu Cys Glu Gly Gly Ser Pro Ala Ser Gln
            1765                1770                1775
Asp Ser Asn Lys Asp Glu Pro Lys Ser Gly Leu Asn Glu Asp Gln Ala
            1780                1785                1790
Met Met Gln Asp Cys Tyr Ser Lys Ile Val Asp Lys Leu Ser Ser Ala
            1795                1800                1805
Asn Pro Thr Met Val Leu Gln Val Gln Met Leu Val Ala Glu Leu Arg
            1810                1815                1820
```

-continued

Arg Val Thr Val Leu Trp Asp Glu Leu Trp Leu Gly Val Leu Leu Gln
1825                1830                1835                1840

Gln His Met Tyr Val Leu Arg Arg Ile Gln Gln Leu Glu Asp Glu Val
            1845                1850                1855

Lys Arg Val Gln Asn Asn Thr Leu Arg Lys Glu Lys Ile Ala
        1860                1865                1870

Ile Met Arg Glu Arg His Thr Ala Leu Met Lys Pro Ile Val Phe Ala
    1875                1880                1885

Leu Glu His Val Arg Ser Ile Thr Ala Ala Pro Ala Glu Thr Pro His
    1890                1895                1900

Glu Lys Trp Phe Gln Asp Asn Tyr Gly Asp Ala Ile Glu Asn Ala Leu
1905                1910                1915                1920

Glu Lys Leu Lys Thr Pro Leu Asn Pro Ala Lys Pro Gly Ser Ser Trp
            1925                1930                1935

Ile Pro Phe Lys Glu Ile Met Leu Ser Leu Gln Gln Arg Ala Gln Lys
        1940                1945                1950

Arg Ala Ser Tyr Ile Leu Arg Leu Glu Glu Ile Ser Pro Trp Leu Ala
        1955                1960                1965

Ala Met Thr Asn Thr Glu Ile Ala Leu Pro Gly Glu Val Ser Ala Arg
    1970                1975                1980

Asp Thr Val Thr Ile His Ser Val Gly Gly Thr Ile Thr Ile Leu Pro
1985                1990                1995                2000

Thr Lys Thr Lys Pro Lys Lys Leu Leu Phe Leu Gly Ser Asp Gly Lys
            2005                2010                2015

Ser Tyr Pro Tyr Leu Phe Lys Gly Leu Glu Asp Leu His Leu Asp Glu
        2020                2025                2030

Arg Ile Met Gln Phe Leu Ser Ile Val Asn Thr Met Phe Ala Thr Ile
        2035                2040                2045

Asn Arg Gln Glu Thr Pro Arg Phe His Ala Arg His Tyr Ser Val Thr
    2050                2055                2060

Pro Leu Gly Thr Arg Ser Gly Leu Ile Gln Trp Val Asp Gly Ala Thr
2065                2070                2075                2080

Pro Leu Phe Gly Leu Tyr Lys Arg Trp Gln Gln Arg Glu Ala Ala Leu
            2085                2090                2095

Gln Ala Gln Lys Ala Gln Asp Ser Tyr Gln Thr Pro Gln Asn Pro Gly
        2100                2105                2110

Ile Val Pro Arg Pro Ser Glu Leu Tyr Tyr Ser Lys Ile Gly Pro Ala
        2115                2120                2125

Leu Lys Thr Val Gly Leu Ser Leu Asp Val Ser Arg Arg Asp Trp Pro
    2130                2135                2140

Leu His Val Met Lys Ala Val Leu Glu Glu Leu Met Glu Ala Thr Pro
2145                2150                2155                2160

Pro Asn Leu Leu Ala Lys Glu Leu Trp Ser Ser Cys Thr Thr Pro Asp
            2165                2170                2175

Glu Trp Trp Arg Val Thr Gln Ser Tyr Ala Arg Ser Thr Ala Val Met
        2180                2185                2190

Ser Met Val Gly Tyr Ile Ile Gly Leu Gly Asp Arg His Leu Asp Asn
        2195                2200                2205

Val Leu Ile Asp Met Thr Thr Gly Glu Val Val His Ile Asp Tyr Asn
    2210                2215                2220

Val Cys Phe Glu Lys Gly Lys Ser Leu Arg Val Pro Glu Lys Val Pro
2225                2230                2235                2240

-continued

```
Phe Arg Met Thr Gln Asn Ile Glu Thr Ala Leu Gly Val Thr Gly Val
            2245                2250                2255
Glu Gly Val Phe Arg Leu Ser Cys Glu Gln Val Leu His Ile Met Arg
            2260                2265                2270
Arg Gly Arg Glu Thr Leu Leu Thr Leu Leu Glu Ala Phe Val Tyr Asp
            2275                2280                2285
Pro Leu Val Asp Trp Thr Ala Gly Gly Glu Ala Gly Phe Ala Gly Ala
            2290                2295                2300
Val Tyr Gly Gly Gly Gln Gln Ala Glu Ser Lys Gln Ser Lys Arg
2305                2310                2315                2320
Glu Met Glu Arg Glu Ile Thr Arg Ser Leu Phe Ser Arg Val Ala
            2325                2330                2335
Glu Ile Lys Val Asn Trp Phe Lys Asn Arg Asp Glu Met Leu Val Val
            2340                2345                2350
Leu Pro Lys Leu Asp Gly Ser Leu Asp Glu Tyr Leu Ser Leu Gln Glu
            2355                2360                2365
Gln Leu Thr Asp Val Glu Lys Leu Gln Gly Lys Leu Leu Glu Glu Ile
            2370                2375                2380
Glu Phe Leu Glu Gly Ala Glu Gly Val Asp His Pro Ser His Thr Leu
2385                2390                2395                2400
Gln His Arg Tyr Ser Glu His Thr Gln Leu Gln Thr Gln Gln Arg Ala
            2405                2410                2415
Val Gln Glu Ala Ile Gln Val Lys Leu Asn Glu Phe Glu Gln Trp Ile
            2420                2425                2430
Thr His Tyr Gln Ala Ala Phe Asn Asn Leu Glu Ala Thr Gln Leu Ala
            2435                2440                2445
Ser Leu Leu Gln Glu Ile Ser Thr Gln Met Asp Leu Gly Pro Pro Ser
            2450                2455                2460
Tyr Val Pro Ala Thr Ala Phe Leu Gln Asn Ala Gly Gln Ala His Leu
2465                2470                2475                2480
Ile Ser Gln Cys Glu Gln Leu Glu Gly Glu Val Gly Ala Leu Leu Gln
            2485                2490                2495
Gln Arg Arg Ser Val Leu Arg Gly Cys Leu Glu Gln Leu His His Tyr
            2500                2505                2510
Ala Thr Val Ala Leu Gln Tyr Pro Lys Ala Ile Phe Gln Lys His Arg
            2515                2520                2525
Ile Glu Gln Trp Lys Thr Trp Met Glu Glu Leu Ile Cys Asn Thr Thr
            2530                2535                2540
Val Glu Arg Cys Gln Glu Leu Tyr Arg Lys Tyr Glu Met Gln Tyr Ala
2545                2550                2555                2560
Pro Gln Pro Pro Thr Val Cys Gln Phe Ile Thr Ala Thr Glu Met
            2565                2570                2575
Thr Leu Gln Arg Tyr Ala Ala Asp Ile Asn Ser Arg Leu Ile Arg Gln
            2580                2585                2590
Val Glu Arg Leu Lys Gln Glu Ala Val Thr Val Pro Val Cys Glu Asp
            2595                2600                2605
Gln Leu Lys Glu Ile Glu Arg Cys Ile Lys Val Phe Leu His Glu Asn
            2610                2615                2620
Gly Glu Glu Gly Ser Leu Ser Leu Ala Ser Val Ile Ile Ser Ala Leu
2625                2630                2635                2640
Cys Thr Leu Thr Arg Arg Asn Leu Met Met Glu Gly Ala Ala Ser Ser
            2645                2650                2655
Ala Gly Glu Gln Leu Val Asp Leu Thr Ser Arg Asp Gly Ala Trp Phe
```

-continued

```
              2660            2665            2670
Leu Glu Glu Leu Cys Ser Met Ser Gly Asn Val Thr Cys Leu Val Gln
        2675            2680            2685
Leu Leu Lys Gln Cys His Leu Val Pro Gln Asp Leu Asp Ile Pro Asn
        2690            2695            2700
Pro Met Glu Ala Ser Glu Thr Val His Leu Ala Asn Gly Val Tyr Thr
2705            2710            2715            2720
Ser Leu Gln Glu Leu Asn Ser Asn Phe Arg Gln Ile Ile Phe Pro Glu
        2725            2730            2735
Ala Leu Arg Cys Leu Met Lys Gly Glu Tyr Thr Leu Glu Ser Met Leu
        2740            2745            2750
His Glu Leu Asp Gly Leu Ile Glu Gln Thr Thr Asp Gly Val Pro Leu
        2755            2760            2765
Gln Thr Leu Val Glu Ser Leu Gln Ala Tyr Leu Arg Asn Ala Ala Met
        2770            2775            2780
Gly Leu Glu Glu Glu Thr His Ala His Tyr Ile Asp Val Ala Arg Leu
2785            2790            2795            2800
Leu His Ala Gln Tyr Gly Glu Leu Ile Gln Pro Arg Asn Gly Ser Val
        2805            2810            2815
Asp Glu Thr Pro Lys Met Ser Ala Gly Gln Met Leu Leu Val Ala Phe
        2820            2825            2830
Asp Gly Met Phe Ala Gln Val Glu Thr Ala Phe Ser Leu Leu Val Glu
        2835            2840            2845
Lys Leu Asn Lys Met Glu Ile Pro Ile Ala Trp Arg Lys Ile Asp Ile
        2850            2855            2860
Ile Arg Glu Ala Arg Ser Thr Gln Val Asn Phe Phe Asp Asp Asn
2865            2870            2875            2880
His Arg Gln Val Leu Glu Glu Ile Phe Phe Leu Lys Arg Leu Gln Thr
        2885            2890            2895
Ile Lys Glu Phe Phe Arg Leu Cys Gly Thr Phe Ser Lys Thr Leu Ser
        2900            2905            2910
Gly Ser Ser Ser Leu Glu Asp Gln Asn Thr Val Asn Gly Pro Val Gln
        2915            2920            2925
Ile Val Asn Val Lys Thr Leu Phe Arg Asn Ser Cys Phe Ser Glu Asp
        2930            2935            2940
Gln Met Ala Lys Pro Ile Lys Ala Phe Thr Ala Asp Phe Val Arg Gln
2945            2950            2955            2960
Leu Leu Ile Gly Leu Pro Asn Gln Ala Leu Gly Leu Thr Leu Cys Ser
        2965            2970            2975
Phe Ile Ser Ala Leu Gly Val Asp Ile Ile Ala Gln Val Glu Ala Lys
        2980            2985            2990
Asp Phe Gly Ala Glu Ser Lys Val Ser Val Asp Asp Leu Cys Lys Lys
        2995            3000            3005
Ala Val Glu His Asn Ile Gln Ile Gly Lys Phe Ser Gln Leu Val Met
        3010            3015            3020
Asn Arg Ala Thr Val Leu Ala Ser Ser Tyr Asp Thr Ala Trp Lys Lys
3025            3030            3035            3040
His Asp Leu Val Arg Arg Leu Glu Thr Ser Ile Ser Ser Cys Lys Thr
        3045            3050            3055
Ser Leu Gln Arg Val Gln Leu His Ile Ala Met Phe Gln Trp Gln His
        3060            3065            3070
Glu Asp Leu Leu Ile Asn Arg Pro Gln Ala Met Ser Val Thr Pro Pro
        3075            3080            3085
```

-continued

```
Pro Arg Ser Ala Ile Leu Thr Ser Met Lys Lys Leu His Thr Leu
    3090                3095                3100
Ser Gln Ile Glu Thr Ser Ile Ala Thr Val Gln Glu Lys Leu Ala Ala
3105                3110                3115                3120
Leu Glu Ser Ser Ile Glu Gln Arg Leu Lys Trp Ala Gly Gly Ala Asn
                3125                3130                3135
Pro Ala Leu Ala Pro Val Leu Gln Asp Phe Glu Ala Thr Ile Ala Glu
        3140                3145                3150
Arg Arg Asn Leu Val Leu Lys Glu Ser Gln Arg Ala Ser Gln Val Thr
            3155                3160                3165
Phe Leu Cys Ser Asn Ile Ile His Phe Glu Ser Leu Arg Thr Arg Thr
    3170                3175                3180
Ala Glu Ala Leu Asn Leu Asp Ala Ala Leu Phe Glu Leu Ile Lys Arg
3185                3190                3195                3200
Cys Gln Gln Met Cys Ser Phe Ala Ser Gln Phe Asn Ser Ser Val Ser
                3205                3210                3215
Glu Leu Glu Leu Arg Leu Leu Gln Arg Val Asp Thr Gly Leu Glu His
        3220                3225                3230
Pro Ile Gly Ser Ser Glu Trp Leu Leu Ser Ala His Lys Gln Leu Thr
            3235                3240                3245
Gln Asp Met Ser Thr Gln Arg Ala Ile Gln Thr Glu Lys Glu Gln Gln
    3250                3255                3260
Ile Glu Thr Val Cys Glu Thr Ile Gln Asn Leu Val Asp Asn Ile Lys
3265                3270                3275                3280
Thr Val Leu Thr Gly His Asn Arg Gln Leu Gly Asp Val Lys His Leu
                3285                3290                3295
Leu Lys Ala Met Ala Lys Asp Glu Glu Ala Ala Leu Ala Asp Gly Glu
        3300                3305                3310
Asp Val Pro Tyr Glu Asn Ser Val Arg Gln Phe Leu Gly Glu Tyr Lys
            3315                3320                3325
Ser Trp Gln Asp Asn Ile Gln Thr Val Leu Phe Thr Leu Val Gln Ala
    3330                3335                3340
Met Gly Gln Val Arg Ser Gln Glu His Val Glu Met Leu Gln Glu Ile
3345                3350                3355                3360
Thr Pro Thr Leu Lys Glu Leu Lys Thr Gln Ser Gln Ser Ile Tyr Asn
                3365                3370                3375
Asn Leu Val Ser Phe Ala Ser Pro Leu Val Thr Asp Ala Thr Asn Glu
        3380                3385                3390
Cys Ser Ser Pro Thr Ser Ser Ala Thr Tyr Gln Pro Ser Phe Ala Ala
            3395                3400                3405
Ala Val Arg Ser Asn Thr Gly Gln Lys Thr Gln Pro Asp Val Met Ser
    3410                3415                3420
Gln Asn Ala Arg Lys Leu Ile Gln Lys Asn Leu Ala Thr Ser Ala Asp
3425                3430                3435                3440
Thr Pro Pro Ser Thr Val Pro Gly Thr Gly Lys Ser Val Ala Cys Ser
                3445                3450                3455
Pro Lys Lys Ala Val Arg Asp Pro Lys Thr Gly Lys Ala Val Gln Glu
        3460                3465                3470
Arg Asn Ser Tyr Ala Val Ser Val Trp Lys Arg Val Lys Ala Lys Leu
            3475                3480                3485
Glu Gly Arg Asp Val Asp Pro Asn Arg Arg Met Ser Val Ala Glu Gln
    3490                3495                3500
```

```
Val Asp Tyr Val Ile Lys Glu Ala Thr Asn Leu Asp Asn Leu Ala Gln
3505                3510                3515                3520

Leu Tyr Glu Gly Trp Thr Ala Trp Val
            3525

<210> SEQ ID NO 9
<211> LENGTH: 13110
<212> TYPE: DNA
<213> ORGANISM: Homo sapiens
<220> FEATURE:
<221> NAME/KEY: CDS
<222> LOCATION: (328)...(11298)

<400> SEQUENCE: 9
ggggaagcag tggccgtgtg agcgtgagga gctgccgcca ccgcctgctc ctcgtcctcc      60
tcgtcctccg gggccccagc gtcgtgggcc gcgcacggcc ctggaagaga cgtcgcctcg     120
ccttcatccg cctctctcac cgcgccgctc cctcgtcctg ccctgcgggc tcaggcggaa     180
cccggaacgg ccgtcctctt cccccgccct ccgccgccgc ctcctcctcc tccttctcgg     240
cttcctcctc agccccgggc cggagcgggg tgtcggcggc ggccggttcg ggcggcggcg     300
```
cttggccatg tcgtgtcggg gaaggta atg agc cgc aga gcc ccg ggg tct cgg    354
                               Met Ser Arg Arg Ala Pro Gly Ser Arg
                                 1               5

| ctg agc agc ggc ggc acc aac tat tcg cgg agc tgg aat gac tgg caa | 402 |
|---|---|
| Leu Ser Ser Gly Gly Thr Asn Tyr Ser Arg Ser Trp Asn Asp Trp Gln | |
| 10              15               20              25 | |

| ccc aga act gat agt gca tca gct gac cca ggt aat tta aaa tat tct | 450 |
|---|---|
| Pro Arg Thr Asp Ser Ala Ser Ala Asp Pro Gly Asn Leu Lys Tyr Ser | |
|             30              35              40 | |

| tca tcc aga gat aga ggt ggt tct tcc tct tac gga ctg caa cct tca | 498 |
|---|---|
| Ser Ser Arg Asp Arg Gly Gly Ser Ser Ser Tyr Gly Leu Gln Pro Ser | |
|         45              50              55 | |

| aat tca gct gtg gtg tct cgg caa agg cac gat gat acc aga gtc cac | 546 |
|---|---|
| Asn Ser Ala Val Val Ser Arg Gln Arg His Asp Asp Thr Arg Val His | |
|     60              65              70 | |

| gct gac ata cag aat gac gaa aag ggt ggc tac agt gtc aat gga gga | 594 |
|---|---|
| Ala Asp Ile Gln Asn Asp Glu Lys Gly Gly Tyr Ser Val Asn Gly Gly | |
| 75              80              85 | |

| tct ggg gaa aat act tat ggt cgg aag tcg ttg ggg caa gag ctg agg | 642 |
|---|---|
| Ser Gly Glu Asn Thr Tyr Gly Arg Lys Ser Leu Gly Gln Glu Leu Arg | |
| 90              95              100             105 | |

| gtt aac aat gtg acc agc cct gag ttc acc agt gtt cag cat ggc agt | 690 |
|---|---|
| Val Asn Asn Val Thr Ser Pro Glu Phe Thr Ser Val Gln His Gly Ser | |
|         110             115             120 | |

| cgt gct tta gcc acc aaa gac atg agg aaa tca cag gag aga tcg atg | 738 |
|---|---|
| Arg Ala Leu Ala Thr Lys Asp Met Arg Lys Ser Gln Glu Arg Ser Met | |
|     125             130             135 | |

| tct tat tct gat gag tct cga ctg tcg aat ctt ctt cgg agg atc acc | 786 |
|---|---|
| Ser Tyr Ser Asp Glu Ser Arg Leu Ser Asn Leu Leu Arg Arg Ile Thr | |
| 140             145             150 | |

| cgg gaa gac gac aga gac cga aga ttg gct act gta aag cag ttg aaa | 834 |
|---|---|
| Arg Glu Asp Asp Arg Asp Arg Arg Leu Ala Thr Val Lys Gln Leu Lys | |
|         155             160             165 | |

| gaa ttt att cag caa cca gaa aat aag ctg gta cta gtt aaa caa ttg | 882 |
|---|---|
| Glu Phe Ile Gln Gln Pro Glu Asn Lys Leu Val Leu Val Lys Gln Leu | |
| 170             175             180             185 | |

| gat aat atc ttg gct gct gta cat gac gtg ctt aat gaa agt agc aaa | 930 |
|---|---|
| Asp Asn Ile Leu Ala Ala Val His Asp Val Leu Asn Glu Ser Ser Lys | |
|             190             195             200 | |

-continued

```
ttg ctt cag gag ttg aga cag gag gga gct tgc tgt ctt ggc ctt ctt        978
Leu Leu Gln Glu Leu Arg Gln Glu Gly Ala Cys Cys Leu Gly Leu Leu
        205                 210                 215 tgt gct tct ctg agc tat gag gct gag aag atc ttc aag tgg att ttt       1026
Cys Ala Ser Leu Ser Tyr Glu Ala Glu Lys Ile Phe Lys Trp Ile Phe
    220                 225                 230 agc aaa ttt agc tca tct gca aaa gat gaa gtt aaa ctc ctc tac tta       1074
Ser Lys Phe Ser Ser Ser Ala Lys Asp Glu Val Lys Leu Leu Tyr Leu
235                 240                 245 tgt gcc acc tac aaa gca cta gag act gta gga gaa aag aaa gcc ttt       1122
Cys Ala Thr Tyr Lys Ala Leu Glu Thr Val Gly Glu Lys Lys Ala Phe
250                 255                 260                 265 tca tct gta atg cag ctt gta atg acc agc ctg cag tct att ctt gaa       1170
Ser Ser Val Met Gln Leu Val Met Thr Ser Leu Gln Ser Ile Leu Glu
                270                 275                 280 aat gtg gat aca cca gaa ttg ctt tgt aaa tgt gtt aag tgc att ctt       1218
Asn Val Asp Thr Pro Glu Leu Leu Cys Lys Cys Val Lys Cys Ile Leu
            285                 290                 295 ttg gtg gct cga tgt tac cct cat att ttc agc act aat ttt agg gat       1266
Leu Val Ala Arg Cys Tyr Pro His Ile Phe Ser Thr Asn Phe Arg Asp
        300                 305                 310 aca gtt gat ata tta gtt gga tgg cat ata gat cat act cag aaa cct       1314
Thr Val Asp Ile Leu Val Gly Trp His Ile Asp His Thr Gln Lys Pro
    315                 320                 325 tcg ctc acg cag cag gta tct ggg tgg ttg cag agt ttg gag cca ttt       1362
Ser Leu Thr Gln Gln Val Ser Gly Trp Leu Gln Ser Leu Glu Pro Phe
330                 335                 340                 345 tgg gta gct gat ctt gca ttt tct act act ctt ctt ggt cag ttt ctg       1410
Trp Val Ala Asp Leu Ala Phe Ser Thr Thr Leu Leu Gly Gln Phe Leu
                350                 355                 360 gaa gac atg gaa gca tat gct gag gac ctc agc cat gtg gcc tct ggg       1458
Glu Asp Met Glu Ala Tyr Ala Glu Asp Leu Ser His Val Ala Ser Gly
            365                 370                 375 gaa tca gtg gat gaa gat gtc cct cct cca tca gtg tca tta cca aag       1506
Glu Ser Val Asp Glu Asp Val Pro Pro Pro Ser Val Ser Leu Pro Lys
        380                 385                 390 ctg gct gca ctt ctc cgg gta ttt agt act gtg gtg agg agc att ggg       1554
Leu Ala Ala Leu Leu Arg Val Phe Ser Thr Val Val Arg Ser Ile Gly
    395                 400                 405 gaa cgc ttc agc cca att cgg ggt cct cca att act gag gca tat gta       1602
Glu Arg Phe Ser Pro Ile Arg Gly Pro Pro Ile Thr Glu Ala Tyr Val
410                 415                 420                 425 aca gat gtt ctg tac aga gta atg aga tgt gtg acg gct gca aac cag       1650
Thr Asp Val Leu Tyr Arg Val Met Arg Cys Val Thr Ala Ala Asn Gln
                430                 435                 440 gtg ttt ttt tct gag gct gtg ttg aca gct gct aat gag tgt gtt ggt       1698
Val Phe Phe Ser Glu Ala Val Leu Thr Ala Ala Asn Glu Cys Val Gly
            445                 450                 455 gtt ttg ctc ggc agc ttg gat cct agc atg act ata cat tgt gac atg       1746
Val Leu Leu Gly Ser Leu Asp Pro Ser Met Thr Ile His Cys Asp Met
        460                 465                 470 gtc att aca tat gga tta gac caa ctg gag aat tgc cag act tgt ggt       1794
Val Ile Thr Tyr Gly Leu Asp Gln Leu Glu Asn Cys Gln Thr Cys Gly
    475                 480                 485 acc gat tat atc atc tca gtc ttg aat tta ctc acg ctg att gtt gaa       1842
Thr Asp Tyr Ile Ile Ser Val Leu Asn Leu Leu Thr Leu Ile Val Glu
490                 495                 500                 505 cag ata aat acg aaa ctg cca tca tca ttt gta gaa aaa ctg ttt ata       1890
Gln Ile Asn Thr Lys Leu Pro Ser Ser Phe Val Glu Lys Leu Phe Ile
                510                 515                 520
```

| | | |
|---|---|---|
| cca tca tct aaa cta cta ttc ttg cgt tat cat aaa gaa aaa gag gtt<br>Pro Ser Ser Lys Leu Leu Phe Leu Arg Tyr His Lys Glu Lys Glu Val<br>525 530 535 | 1938 | |
| gtt gct gta gcc cat gct gtt tat caa gca gtg ctc agc ttg aag aat<br>Val Ala Val Ala His Ala Val Tyr Gln Ala Val Leu Ser Leu Lys Asn<br>540 545 550 | 1986 | |
| att cct gtt ttg gag act gcc tat aag tta ata ttg gga gaa atg act<br>Ile Pro Val Leu Glu Thr Ala Tyr Lys Leu Ile Leu Gly Glu Met Thr<br>555 560 565 | 2034 | |
| tgt gcc cta aac aac ctc cta cac agt cta caa ctt cct gag gcc tgt<br>Cys Ala Leu Asn Asn Leu Leu His Ser Leu Gln Leu Pro Glu Ala Cys<br>570 575 580 585 | 2082 | |
| tct gaa ata aaa cat gag gct ttt aag aat cat gtg ttc aat gta gac<br>Ser Glu Ile Lys His Glu Ala Phe Lys Asn His Val Phe Asn Val Asp<br>590 595 600 | 2130 | |
| aat gca aaa ttt gta gtt aaa ttt gac ctc agt gcc ctg act aca att<br>Asn Ala Lys Phe Val Val Lys Phe Asp Leu Ser Ala Leu Thr Thr Ile<br>605 610 615 | 2178 | |
| gga aat gcc aaa aac tca cta ata ggg atg tgg gcg cta tct cca act<br>Gly Asn Ala Lys Asn Ser Leu Ile Gly Met Trp Ala Leu Ser Pro Thr<br>620 625 630 | 2226 | |
| gtc ttt gca ctt ctg agt aag aat ctg atg att gtg cac agt gac ctg<br>Val Phe Ala Leu Leu Ser Lys Asn Leu Met Ile Val His Ser Asp Leu<br>635 640 645 | 2274 | |
| gct gtt cac ttc cct gcc att cag tat gct gtg ctc tac aca ttg tat<br>Ala Val His Phe Pro Ala Ile Gln Tyr Ala Val Leu Tyr Thr Leu Tyr<br>650 655 660 665 | 2322 | |
| tct cat tgt acc agg cat gat cac ttt atc tct agt agc ctc agt tct<br>Ser His Cys Thr Arg His Asp His Phe Ile Ser Ser Ser Leu Ser Ser<br>670 675 680 | 2370 | |
| gcc tct cct tct ttg ttt gat gga gct gtg att agc act gta act acg<br>Ala Ser Pro Ser Leu Phe Asp Gly Ala Val Ile Ser Thr Val Thr Thr<br>685 690 695 | 2418 | |
| gct aca aag aaa cat ttc tca att ata tta aat ctt ctg gga ata tta<br>Ala Thr Lys Lys His Phe Ser Ile Ile Leu Asn Leu Leu Gly Ile Leu<br>700 705 710 | 2466 | |
| ctt aag aaa gat aac ctt aac cag gac acg agg aaa ctg tta atg act<br>Leu Lys Lys Asp Asn Leu Asn Gln Asp Thr Arg Lys Leu Leu Met Thr<br>715 720 725 | 2514 | |
| tgg gct ttg gaa gca gct gtt tta atg agg aag tct gaa aca tac gca<br>Trp Ala Leu Glu Ala Ala Val Leu Met Arg Lys Ser Glu Thr Tyr Ala<br>730 735 740 745 | 2562 | |
| cct tta ttc tct ctt ccg tct ttc cat aaa ttt tgc aaa ggc ctt tta<br>Pro Leu Phe Ser Leu Pro Ser Phe His Lys Phe Cys Lys Gly Leu Leu<br>750 755 760 | 2610 | |
| gcc aac act ctc gtt gaa gat gtg aat atc tgt ctg cag gca tgc agc<br>Ala Asn Thr Leu Val Glu Asp Val Asn Ile Cys Leu Gln Ala Cys Ser<br>765 770 775 | 2658 | |
| agt cta cat gct ctg tcc tct tcc ttg cca gat gat ctt tta cag aga<br>Ser Leu His Ala Leu Ser Ser Ser Leu Pro Asp Asp Leu Leu Gln Arg<br>780 785 790 | 2706 | |
| tgt gtc gat gtt tgc cgt gtt caa cta gtg cac agt gga act cgt att<br>Cys Val Asp Val Cys Arg Val Gln Leu Val His Ser Gly Thr Arg Ile<br>795 800 805 | 2754 | |
| cga caa gca ttt gga aaa ctg ttg aaa tca att cct tta gat gtt gtc<br>Arg Gln Ala Phe Gly Lys Leu Leu Lys Ser Ile Pro Leu Asp Val Val<br>810 815 820 825 | 2802 | |
| cta agc aat aac aat cac aca gaa att caa gaa att tct tta gca tta<br>Leu Ser Asn Asn Asn His Thr Glu Ile Gln Glu Ile Ser Leu Ala Leu | 2850 | |

-continued

|  |  |  |  |
|---|---|---|---|
| aga agt cac atg agt aaa gca cca agt aat aca ttc cac ccc caa gat<br>Arg Ser His Met Ser Lys Ala Pro Ser Asn Thr Phe His Pro Gln Asp<br>                845                        850                        855 | 2898 |
| ttc tct gat gtt att agt ttt att ttg tat ggg aac tct cat aga aca<br>Phe Ser Asp Val Ile Ser Phe Ile Leu Tyr Gly Asn Ser His Arg Thr<br>              860                        865                        870 | 2946 |
| ggg aag gac aat tgg ttg gaa aga ctg ttc tat agc tgc cag aga ctg<br>Gly Lys Asp Asn Trp Leu Glu Arg Leu Phe Tyr Ser Cys Gln Arg Leu<br>875                        880                        885 | 2994 |
| gat aag cgt gac cag tca aca att cca cgc aat ctc ctg aag aca gat<br>Asp Lys Arg Asp Gln Ser Thr Ile Pro Arg Asn Leu Leu Lys Thr Asp<br>890                        895                        900                        905 | 3042 |
| gct gtc ctt tgg cag tgg gcc ata tgg gaa gct gca caa ttc act gtt<br>Ala Val Leu Trp Gln Trp Ala Ile Trp Glu Ala Ala Gln Phe Thr Val<br>              910                        915                        920 | 3090 |
| ctt tct aag ctg aga acc cca ctg ggc aga gct caa gac acc ttc cag<br>Leu Ser Lys Leu Arg Thr Pro Leu Gly Arg Ala Gln Asp Thr Phe Gln<br>              925                        930                        935 | 3138 |
| aca att gaa ggt atc att cga agt ctc gca gct cac aca tta aac cct<br>Thr Ile Glu Gly Ile Ile Arg Ser Leu Ala Ala His Thr Leu Asn Pro<br>              940                        945                        950 | 3186 |
| gat cag gat gtt agt cag tgg aca act gca gac aat gat gaa ggc cat<br>Asp Gln Asp Val Ser Gln Trp Thr Thr Ala Asp Asn Asp Glu Gly His<br>955                        960                        965 | 3234 |
| ggt aac aac caa ctt aga ctt gtt ctt ctt ctg cag tat ctg gaa aat<br>Gly Asn Asn Gln Leu Arg Leu Val Leu Leu Leu Gln Tyr Leu Glu Asn<br>970                        975                        980                        985 | 3282 |
| ctg gag aaa tta atg tat aat gca tac gag gga tgt gct aat gca tta<br>Leu Glu Lys Leu Met Tyr Asn Ala Tyr Glu Gly Cys Ala Asn Ala Leu<br>              990                        995                        1000 | 3330 |
| act tca cct ccc aag gtc att aga act ttt ttc tat acc aat cgc caa<br>Thr Ser Pro Pro Lys Val Ile Arg Thr Phe Phe Tyr Thr Asn Arg Gln<br>              1005                      1010                      1015 | 3378 |
| act tgt cag gac tgg cta acg cgg att cga ctc tcc atc atg agg gta<br>Thr Cys Gln Asp Trp Leu Thr Arg Ile Arg Leu Ser Ile Met Arg Val<br>1020                        1025                      1030 | 3426 |
| gga ttg ttg gca ggc cag cct gca gtg aca gtg aga cat ggc ttt gac<br>Gly Leu Leu Ala Gly Gln Pro Ala Val Thr Val Arg His Gly Phe Asp<br>              1035                      1040                      1045 | 3474 |
| ttg ctt aca gag atg aaa aca acc agc cta tct cag ggg aat gaa ttg<br>Leu Leu Thr Glu Met Lys Thr Thr Ser Leu Ser Gln Gly Asn Glu Leu<br>1050                        1055                      1060                      1065 | 3522 |
| gaa gta acc att atg atg gtg gta gaa gca tta tgt gaa ctt cat tgt<br>Glu Val Thr Ile Met Met Val Val Glu Ala Leu Cys Glu Leu His Cys<br>              1070                      1075                      1080 | 3570 |
| cct gaa gct ata cag gga att gct gtc tgg tca tca tct att gtt gga<br>Pro Glu Ala Ile Gln Gly Ile Ala Val Trp Ser Ser Ser Ile Val Gly<br>1085                        1090                      1095 | 3618 |
| aaa aat ctt ctg tgg att aac tca gtg gct caa cag gct gaa ggg agg<br>Lys Asn Leu Leu Trp Ile Asn Ser Val Ala Gln Gln Ala Glu Gly Arg<br>              1100                      1105                      1110 | 3666 |
| ttt gaa aag gcc tct gtg gag tac cag gaa cac ctg tgt gcc atg aca<br>Phe Glu Lys Ala Ser Val Glu Tyr Gln Glu His Leu Cys Ala Met Thr<br>1115                        1120                      1125 | 3714 |
| ggt gtt gat tgc tgc atc tcc agc ttt gac aaa tcg gtg ctc acc tta<br>Gly Val Asp Cys Cys Ile Ser Ser Phe Asp Lys Ser Val Leu Thr Leu<br>1130                        1135                      1140                      1145 | 3762 |
| gcc aat gct ggg cgt aac agt gcc agc ccg aaa cat tct ctg aat ggt | 3810 |

```
Ala Asn Ala Gly Arg Asn Ser Ala Ser Pro Lys His Ser Leu Asn Gly
            1150                1155                1160 gaa tcc aga aaa act gtg ctg tcc aaa ccg act gac tct tcc cct gag      3858
Glu Ser Arg Lys Thr Val Leu Ser Lys Pro Thr Asp Ser Ser Pro Glu
        1165                1170                1175 gtt ata aat tat tta gga aat aaa gca tgt gag ttc tac atc tca att      3906
Val Ile Asn Tyr Leu Gly Asn Lys Ala Cys Glu Phe Tyr Ile Ser Ile
    1180                1185                1190 gcc gat tgg gct gct gtg cag gaa tgg cag aac gct atc cat gac ttg      3954
Ala Asp Trp Ala Ala Val Gln Glu Trp Gln Asn Ala Ile His Asp Leu
1195                1200                1205 aaa aag agt acc agt agc act tcc ctc aac ctg aaa gct gac ttc aac      4002
Lys Lys Ser Thr Ser Ser Thr Ser Leu Asn Leu Lys Ala Asp Phe Asn
1210                1215                1220                1225 tat ata aaa tca tta agc agc ttt gag tct gga aaa ttt gtt gaa tgt      4050
Tyr Ile Lys Ser Leu Ser Ser Phe Glu Ser Gly Lys Phe Val Glu Cys
        1230                1235                1240 acc gag cag tta gaa ttg tta cca gga gaa aat atc aat cta ctt gct      4098
Thr Glu Gln Leu Glu Leu Leu Pro Gly Glu Asn Ile Asn Leu Leu Ala
    1245                1250                1255 gga gga tca aaa gaa aaa ata gac atg aaa aaa ctg ctt cct aac atg      4146
Gly Gly Ser Lys Glu Lys Ile Asp Met Lys Lys Leu Leu Pro Asn Met
1260                1265                1270 tta agt ccg gat ccg agg gaa ctt cag aaa tcc att gaa gtt caa ttg      4194
Leu Ser Pro Asp Pro Arg Glu Leu Gln Lys Ser Ile Glu Val Gln Leu
1275                1280                1285 tta aga agt tct gtt tgt ttg gca act gct tta aac ccg ata gaa caa      4242
Leu Arg Ser Ser Val Cys Leu Ala Thr Ala Leu Asn Pro Ile Glu Gln
1290                1295                1300                1305 gat cag aag tgg cag tct ata act gaa aat gtg gta aag tac ttg aag      4290
Asp Gln Lys Trp Gln Ser Ile Thr Glu Asn Val Val Lys Tyr Leu Lys
        1310                1315                1320 caa aca tcc cgc atc gct att gga cct ctg aga ctt tct act tta aca      4338
Gln Thr Ser Arg Ile Ala Ile Gly Pro Leu Arg Leu Ser Thr Leu Thr
    1325                1330                1335 gtt tca cag tct ttg cca gtt cta agt acc ttg cag ctg tat tgc tca      4386
Val Ser Gln Ser Leu Pro Val Leu Ser Thr Leu Gln Leu Tyr Cys Ser
1340                1345                1350 tct gct ttg gag aac aca gtt tct aac aga ctt tca aca gag gac tgt      4434
Ser Ala Leu Glu Asn Thr Val Ser Asn Arg Leu Ser Thr Glu Asp Cys
    1355                1360                1365 ctt att cca ctc ttc agt gaa gct tta cgt tca tgt aaa cag cat gac      4482
Leu Ile Pro Leu Phe Ser Glu Ala Leu Arg Ser Cys Lys Gln His Asp
1370                1375                1380                1385 gtg agg cca tgg atg cag gca tta agg tat act atg tac cag aat cag      4530
Val Arg Pro Trp Met Gln Ala Leu Arg Tyr Thr Met Tyr Gln Asn Gln
        1390                1395                1400 ttg ttg gag aaa att aaa gaa caa aca gtc cca att aga agc cat ctc      4578
Leu Leu Glu Lys Ile Lys Glu Gln Thr Val Pro Ile Arg Ser His Leu
    1405                1410                1415 atg gaa tta ggt cta aca gca gca aaa ttt gct aga aaa cga ggg aat      4626
Met Glu Leu Gly Leu Thr Ala Ala Lys Phe Ala Arg Lys Arg Gly Asn
1420                1425                1430 gtg tcc ctt gca aca aga ctg ctg gca cag tgc agt gaa gtt cag ctg      4674
Val Ser Leu Ala Thr Arg Leu Leu Ala Gln Cys Ser Glu Val Gln Leu
    1435                1440                1445 gga aag acc acc act gca cag gat tta gtc caa cat ttt aaa aaa cta      4722
Gly Lys Thr Thr Thr Ala Gln Asp Leu Val Gln His Phe Lys Lys Leu
1450                1455                1460                1465
```

-continued

```
tca acc caa ggt caa gtg gat gaa aaa tgg ggg ccc gaa ctt gat att      4770
Ser Thr Gln Gly Gln Val Asp Glu Lys Trp Gly Pro Glu Leu Asp Ile
            1470                1475                1480 gaa aaa acc aaa ttg ctt tat aca gca ggc cag tca aca cat gca atg      4818
Glu Lys Thr Lys Leu Leu Tyr Thr Ala Gly Gln Ser Thr His Ala Met
        1485                1490                1495 gaa atg ttg agt tct tgt gcc ata tct ttc tgc aag tct gtg aaa gct      4866
Glu Met Leu Ser Ser Cys Ala Ile Ser Phe Cys Lys Ser Val Lys Ala
    1500                1505                1510 gaa tat gca gtt gct aaa tca att ctg aca ctg gct aaa tgg atc cag      4914
Glu Tyr Ala Val Ala Lys Ser Ile Leu Thr Leu Ala Lys Trp Ile Gln
1515                1520                1525 gca gaa tgg aaa gag att tca gga cag ctg aaa cag gtt tac aga gct      4962
Ala Glu Trp Lys Glu Ile Ser Gly Gln Leu Lys Gln Val Tyr Arg Ala
1530                1535                1540                1545 cag cac caa cag aac ttc aca ggt ctt tct act ttg tct aaa aac ata      5010
Gln His Gln Gln Asn Phe Thr Gly Leu Ser Thr Leu Ser Lys Asn Ile
            1550                1555                1560 ctc act cta ata gaa ctg cca tct gtt aat acg atg gaa gaa gag tat      5058
Leu Thr Leu Ile Glu Leu Pro Ser Val Asn Thr Met Glu Glu Glu Tyr
        1565                1570                1575 cct cgg atc gag agt gaa tct aca gtg cat att gga gtt gga gaa cct      5106
Pro Arg Ile Glu Ser Glu Ser Thr Val His Ile Gly Val Gly Glu Pro
    1580                1585                1590 gac ttc att ttg gga cag ttg tat cac ctg tct tca gta cag gca cct      5154
Asp Phe Ile Leu Gly Gln Leu Tyr His Leu Ser Ser Val Gln Ala Pro
1595                1600                1605 gaa gta gcc aaa tct tgg gca gcg ttg gcc agc tgg gct tat agg tgg      5202
Glu Val Ala Lys Ser Trp Ala Ala Leu Ala Ser Trp Ala Tyr Arg Trp
1610                1615                1620                1625 ggc aga aag gtg gtt gac aat gcc agt cag gga gaa ggt gtt cgt ctg      5250
Gly Arg Lys Val Val Asp Asn Ala Ser Gln Gly Glu Gly Val Arg Leu
            1630                1635                1640 ctg cct aga gaa aaa tct gaa gtt cag aat cta ctt cca gac act ata      5298
Leu Pro Arg Glu Lys Ser Glu Val Gln Asn Leu Leu Pro Asp Thr Ile
        1645                1650                1655 act gag gaa gag aaa gag aga ata tat ggt att ctt gga cag gct gtg      5346
Thr Glu Glu Glu Lys Glu Arg Ile Tyr Gly Ile Leu Gly Gln Ala Val
    1660                1665                1670 tgt cgg ccg gcg ggg att cag gat gaa gat ata aca ctt cag ata act      5394
Cys Arg Pro Ala Gly Ile Gln Asp Glu Asp Ile Thr Leu Gln Ile Thr
1675                1680                1685 gag agt gaa gac aac gaa gaa gat gac atg gtt gat gtt atc tgg cgt      5442
Glu Ser Glu Asp Asn Glu Glu Asp Asp Met Val Asp Val Ile Trp Arg
1690                1695                1700                1705 cag ttg ata tca agc tgc cca tgg ctt tca gaa ctt gat gaa agt gca      5490
Gln Leu Ile Ser Ser Cys Pro Trp Leu Ser Glu Leu Asp Glu Ser Ala
            1710                1715                1720 act gaa gga gtt att aaa gtg tgg agg aaa gtt gta gat aga ata ttc      5538
Thr Glu Gly Val Ile Lys Val Trp Arg Lys Val Val Asp Arg Ile Phe
        1725                1730                1735 agc ctg tac aaa ctc tct tgc agt gca tac ttt act ttc ctt aaa ctc      5586
Ser Leu Tyr Lys Leu Ser Cys Ser Ala Tyr Phe Thr Phe Leu Lys Leu
    1740                1745                1750 aac gct ggt caa att cct tta gat gag gat gac cct agg ctg cat tta      5634
Asn Ala Gly Gln Ile Pro Leu Asp Glu Asp Asp Pro Arg Leu His Leu
1755                1760                1765 agt cac aga gtg gaa cag agc act gat gac atg att gtg atg gcc aca      5682
Ser His Arg Val Glu Gln Ser Thr Asp Asp Met Ile Val Met Ala Thr
1770                1775                1780                1785
```

```
                                                       -continued ttg cgc ctg ctg cgg ttg ctc gtg aag cat gct ggt gag ctt cgg cag       5730
Leu Arg Leu Leu Arg Leu Leu Val Lys His Ala Gly Glu Leu Arg Gln
            1790                1795                1800 tat ctg gag cac ggc ttg gag aca aca ccc act gca cca tgg agg gga       5778
Tyr Leu Glu His Gly Leu Glu Thr Thr Pro Thr Ala Pro Trp Arg Gly
        1805                1810                1815 att att ccg caa ctt ttc tca cgc tta aac cac cct gaa gtg tat gtg       5826
Ile Ile Pro Gln Leu Phe Ser Arg Leu Asn His Pro Glu Val Tyr Val
    1820                1825                1830 cgc caa agt att tgt aac ctt ctc tgc cgt gtg gct caa gat tcc cca       5874
Arg Gln Ser Ile Cys Asn Leu Leu Cys Arg Val Ala Gln Asp Ser Pro
1835                1840                1845 cat ctc ata ttg tat cct gca ata gtg ggt acc ata tcg ctt agt agt       5922
His Leu Ile Leu Tyr Pro Ala Ile Val Gly Thr Ile Ser Leu Ser Ser
1850                1855                1860                1865 gaa tcc cag gct tca gga aat aaa ttt tcc act gca att cca act tta       5970
Glu Ser Gln Ala Ser Gly Asn Lys Phe Ser Thr Ala Ile Pro Thr Leu
                1870                1875                1880 ctt ggc aat att caa gga gaa gaa ttg ctg gtt tct gaa tgt gag gga       6018
Leu Gly Asn Ile Gln Gly Glu Glu Leu Leu Val Ser Glu Cys Glu Gly
            1885                1890                1895 gga agt cct cct gca tct cag gat agc aat aag gat gaa cct aaa agt       6066
Gly Ser Pro Pro Ala Ser Gln Asp Ser Asn Lys Asp Glu Pro Lys Ser
        1900                1905                1910 gga tta aat gaa gac caa gcc atg atg cag gat tgt tac agc aaa att       6114
Gly Leu Asn Glu Asp Gln Ala Met Met Gln Asp Cys Tyr Ser Lys Ile
    1915                1920                1925 gta gat aag ctg tcc tct gca aac ccc acc atg gta tta cag gtt cag       6162
Val Asp Lys Leu Ser Ser Ala Asn Pro Thr Met Val Leu Gln Val Gln
1930                1935                1940                1945 atg ctc gtg gct gaa ctg cgc agg gtc act gtg ctc tgg gat gag ctc       6210
Met Leu Val Ala Glu Leu Arg Arg Val Thr Val Leu Trp Asp Glu Leu
                1950                1955                1960 tgg ctg gga gtt ttg ctg caa caa cac atg tat gtc ctg aga cga att       6258
Trp Leu Gly Val Leu Leu Gln Gln His Met Tyr Val Leu Arg Arg Ile
            1965                1970                1975 cag cag ctt gaa gat gag gtg aag aga gtc cag aac aac aac acc tta       6306
Gln Gln Leu Glu Asp Glu Val Lys Arg Val Gln Asn Asn Asn Thr Leu
        1980                1985                1990 cgc aaa gaa gag aaa att gca atc atg agg gag agg cac aca gct ttg       6354
Arg Lys Glu Glu Lys Ile Ala Ile Met Arg Glu Arg His Thr Ala Leu
    1995                2000                2005 atg aag ccc atc gta ttt gct ttg gag cat gtg agg agt atc aca gcg       6402
Met Lys Pro Ile Val Phe Ala Leu Glu His Val Arg Ser Ile Thr Ala
2010                2015                2020                2025 gct cct gca gaa aca cct cat gaa aaa tgg ttt cag gat aac tat ggt       6450
Ala Pro Ala Glu Thr Pro His Glu Lys Trp Phe Gln Asp Asn Tyr Gly
                2030                2035                2040 gat gcc att gaa aat gcc cta gaa aaa ctg aag act cca ttg aac cct       6498
Asp Ala Ile Glu Asn Ala Leu Glu Lys Leu Lys Thr Pro Leu Asn Pro
            2045                2050                2055 gca aag cct ggg agc agc tgg att cca ttt aaa gag ata atg cta agt       6546
Ala Lys Pro Gly Ser Ser Trp Ile Pro Phe Lys Glu Ile Met Leu Ser
        2060                2065                2070 ttg caa cag aga gca cag aaa cgt gca agt tac atc ttg cgt ctt gaa       6594
Leu Gln Gln Arg Ala Gln Lys Arg Ala Ser Tyr Ile Leu Arg Leu Glu
    2075                2080                2085 gaa atc agt cca tgg ttg gct gcc atg act aac act gaa att gct ctt       6642
Glu Ile Ser Pro Trp Leu Ala Ala Met Thr Asn Thr Glu Ile Ala Leu
```

-continued

| | | | | |
|---|---|---|---|---|
| 2090 | 2095 | 2100 | 2105 | | cct ggg gaa gtc tca gcc aga gac act gtc aca atc cat agt gtg ggc   6690
Pro Gly Glu Val Ser Ala Arg Asp Thr Val Thr Ile His Ser Val Gly
                2110                2115                2120 gga acc atc aca atc tta ccg act aaa acc aag cca aag aaa ctt ctc   6738
Gly Thr Ile Thr Ile Leu Pro Thr Lys Thr Lys Pro Lys Lys Leu Leu
                2125                2130                2135 ttt ctt gga tca gat ggg aag agc tat cct tat ctt ttc aaa gga ctg   6786
Phe Leu Gly Ser Asp Gly Lys Ser Tyr Pro Tyr Leu Phe Lys Gly Leu
            2140                2145                2150 gag gat tta cat ctg gat gag aga ata atg cag ttc cta tct att gtg   6834
Glu Asp Leu His Leu Asp Glu Arg Ile Met Gln Phe Leu Ser Ile Val
            2155                2160                2165 aat acc atg ttt gct aca att aat cgc caa gaa aca ccc cgg ttc cat   6882
Asn Thr Met Phe Ala Thr Ile Asn Arg Gln Glu Thr Pro Arg Phe His
2170                2175                2180                2185 gct cga cac tat tct gta aca cca cta gga aca aga tca gga cta atc   6930
Ala Arg His Tyr Ser Val Thr Pro Leu Gly Thr Arg Ser Gly Leu Ile
                2190                2195                2200 cag tgg gta gat gga gcc aca ccc tta ttt ggt ctt tac aaa cga tgg   6978
Gln Trp Val Asp Gly Ala Thr Pro Leu Phe Gly Leu Tyr Lys Arg Trp
            2205                2210                2215 caa caa cgg gaa gct gcc tta caa gca caa aag gcc caa gat tcc tac   7026
Gln Gln Arg Glu Ala Ala Leu Gln Ala Gln Lys Ala Gln Asp Ser Tyr
            2220                2225                2230 caa act cct cag aat cct gga att gta ccc cgt cct agt gaa ctt tat   7074
Gln Thr Pro Gln Asn Pro Gly Ile Val Pro Arg Pro Ser Glu Leu Tyr
            2235                2240                2245 tac agt aaa att ggc cct gct ttg aaa aca gtt ggg ctt agc ctg gat   7122
Tyr Ser Lys Ile Gly Pro Ala Leu Lys Thr Val Gly Leu Ser Leu Asp
2250                2255                2260                2265 gtg tcc cgt cgg gat tgg cct ctt cat gta atg aag gca gta ttg gaa   7170
Val Ser Arg Arg Asp Trp Pro Leu His Val Met Lys Ala Val Leu Glu
                2270                2275                2280 gag tta atg gag gcc aca ccc ccg aat ctc ctt gcc aaa gag ctc tgg   7218
Glu Leu Met Glu Ala Thr Pro Pro Asn Leu Leu Ala Lys Glu Leu Trp
            2285                2290                2295 tca tct tgc aca aca cct gat gaa tgg tgg aga gtt acg cag tct tat   7266
Ser Ser Cys Thr Thr Pro Asp Glu Trp Trp Arg Val Thr Gln Ser Tyr
            2300                2305                2310 gca aga tct act gca gtc atg tct atg gtt gga tac ata att ggc ctt   7314
Ala Arg Ser Thr Ala Val Met Ser Met Val Gly Tyr Ile Ile Gly Leu
            2315                2320                2325 gga gac aga cat ctg gat aat gtt ctt ata gat atg acg act gga gaa   7362
Gly Asp Arg His Leu Asp Asn Val Leu Ile Asp Met Thr Thr Gly Glu
2330                2335                2340                2345 gtt gtt cac ata gat tac aat gtt tgc ttt gaa aaa ggt aaa agc ctt   7410
Val Val His Ile Asp Tyr Asn Val Cys Phe Glu Lys Gly Lys Ser Leu
                2350                2355                2360 aga gtt cct gag aaa gta cct ttt cga atg aca caa aac att gaa aca   7458
Arg Val Pro Glu Lys Val Pro Phe Arg Met Thr Gln Asn Ile Glu Thr
            2365                2370                2375 gca ctg ggt gta act gga gta gaa ggt gta ttt agg ctt tca tgt gag   7506
Ala Leu Gly Val Thr Gly Val Glu Gly Val Phe Arg Leu Ser Cys Glu
            2380                2385                2390 cag gtt tta cac att atg cgg cgt ggc aga gag acc ctg ctg acg ctg   7554
Gln Val Leu His Ile Met Arg Arg Gly Arg Glu Thr Leu Leu Thr Leu
            2395                2400                2405 ctg gag gcc ttt gtg tac gac cct ctg gtg gac tgg aca gca gga ggc   7602

| | | |
|---|---|---|
| Leu Glu Ala Phe Val Tyr Asp Pro Leu Val Asp Trp Thr Ala Gly Gly<br>2410               2415               2420               2425 | | |
| gag gct ggg ttt gct ggt gct gtc tat ggt gga ggt ggc cag cag gcc<br>Glu Ala Gly Phe Ala Gly Ala Val Tyr Gly Gly Gly Gly Gln Gln Ala<br>               2430               2435               2440 | 7650 | |
| gag agc aag cag agc aag aga gag atg gag cga gag atc acc cgc agc<br>Glu Ser Lys Gln Ser Lys Arg Glu Met Glu Arg Glu Ile Thr Arg Ser<br>        2445               2450               2455 | 7698 | |
| ctg ttt tct tct aga gta gct gag att aag gtg aac tgg ttt aag aat<br>Leu Phe Ser Ser Arg Val Ala Glu Ile Lys Val Asn Trp Phe Lys Asn<br>        2460               2465               2470 | 7746 | |
| aga gat gag atg ctg gtt gtg ctt ccc aag ttg gac ggt agc tta gat<br>Arg Asp Glu Met Leu Val Val Leu Pro Lys Leu Asp Gly Ser Leu Asp<br>2475               2480               2485 | 7794 | |
| gaa tac cta agc ttg caa gag caa ctg aca gat gtg gaa aaa ctg cag<br>Glu Tyr Leu Ser Leu Gln Glu Gln Leu Thr Asp Val Glu Lys Leu Gln<br>2490               2495               2500               2505 | 7842 | |
| ggc aaa cta ctg gag gaa ata gag ttt cta gaa gga gct gaa ggg gtg<br>Gly Lys Leu Leu Glu Glu Ile Glu Phe Leu Glu Gly Ala Glu Gly Val<br>               2510               2515               2520 | 7890 | |
| gat cat cct tct cat act ctg caa cac agg tat tct gag cac acc caa<br>Asp His Pro Ser His Thr Leu Gln His Arg Tyr Ser Glu His Thr Gln<br>        2525               2530               2535 | 7938 | |
| cta cag act cag caa aga gct gtt cag gaa gca atc cag gtg aag ctg<br>Leu Gln Thr Gln Gln Arg Ala Val Gln Glu Ala Ile Gln Val Lys Leu<br>               2540               2545               2550 | 7986 | |
| aat gaa ttt gaa caa tgg ata aca cat tat cag gct gca ttc aat aat<br>Asn Glu Phe Glu Gln Trp Ile Thr His Tyr Gln Ala Ala Phe Asn Asn<br>        2555               2560               2565 | 8034 | |
| tta gaa gca aca cag ctt gca agc ttg ctt caa gag ata agc aca caa<br>Leu Glu Ala Thr Gln Leu Ala Ser Leu Leu Gln Glu Ile Ser Thr Gln<br>2570               2575               2580               2585 | 8082 | |
| atg gac ctt ggt cct cca agt tac gtg cca gca aca gcc ttt ctg cag<br>Met Asp Leu Gly Pro Pro Ser Tyr Val Pro Ala Thr Ala Phe Leu Gln<br>2590               2595               2600 | 8130 | |
| aat gct ggt cag gcc cac ttg att agc cag tgc gag cag ctg gag ggg<br>Asn Ala Gly Gln Ala His Leu Ile Ser Gln Cys Glu Gln Leu Glu Gly<br>        2605               2610               2615 | 8178 | |
| gag gtt ggt gct ctc ctg cag cag agg cgc tcc gtg ctc cgt ggc tgt<br>Glu Val Gly Ala Leu Leu Gln Gln Arg Arg Ser Val Leu Arg Gly Cys<br>        2620               2625               2630 | 8226 | |
| ctg gag caa ctg cat cac tat gca acc gtg gcc ctg cag tat ccg aag<br>Leu Glu Gln Leu His His Tyr Ala Thr Val Ala Leu Gln Tyr Pro Lys<br>        2635               2640               2645 | 8274 | |
| gcc ata ttt cag aaa cat cga att gaa cag tgg aag acc tgg atg gaa<br>Ala Ile Phe Gln Lys His Arg Ile Glu Gln Trp Lys Thr Trp Met Glu<br>2650               2655               2660               2665 | 8322 | |
| gag ctc atc tgt aac acc aca gta gag cgt tgt caa gag ctc tat agg<br>Glu Leu Ile Cys Asn Thr Thr Val Glu Arg Cys Gln Glu Leu Tyr Arg<br>        2670               2675               2680 | 8370 | |
| aaa tat gaa atg caa tat gct ccc cag cca ccc cca aca gtg tgt cag<br>Lys Tyr Glu Met Gln Tyr Ala Pro Gln Pro Pro Pro Thr Val Cys Gln<br>        2685               2690               2695 | 8418 | |
| ttc atc act gcc act gaa atg acc ctg cag cga tac gca gca gac atc<br>Phe Ile Thr Ala Thr Glu Met Thr Leu Gln Arg Tyr Ala Ala Asp Ile<br>2700               2705               2710 | 8466 | |
| aac agc aga ctt att aga caa gtg gaa cgc ttg aaa cag gaa gct gtc<br>Asn Ser Arg Leu Ile Arg Gln Val Glu Arg Leu Lys Gln Glu Ala Val<br>        2715               2720               2725 | 8514 | |

| | |
|---|---:|
| act gtg cca gtt tgt gaa gat cag ttg aaa gaa att gaa cgt tgc att<br>Thr Val Pro Val Cys Glu Asp Gln Leu Lys Glu Ile Glu Arg Cys Ile<br>2730                        2735                  2740                 2745 | 8562 |
| aaa gtt ttc ctt cat gag aat gga gaa gaa gga tct ttg agt cta gca<br>Lys Val Phe Leu His Glu Asn Gly Glu Glu Gly Ser Leu Ser Leu Ala<br>                 2750                 2755                  2760 | 8610 |
| agt gtt att att tct gcc ctt tgt acc ctt aca agg cgt aac ctg atg<br>Ser Val Ile Ile Ser Ala Leu Cys Thr Leu Thr Arg Arg Asn Leu Met<br>             2765                 2770                  2775 | 8658 |
| atg gaa ggt gca gcg tca agt gct gga gaa cag ctg gtt gat ctg act<br>Met Glu Gly Ala Ala Ser Ser Ala Gly Glu Gln Leu Val Asp Leu Thr<br>2780                        2785                  2790 | 8706 |
| tct cgg gat gga gcc tgg ttc ttg gag gaa ctc tgc agt atg agc gga<br>Ser Arg Asp Gly Ala Trp Phe Leu Glu Glu Leu Cys Ser Met Ser Gly<br>             2795                 2800                  2805 | 8754 |
| aac gtc acc tgc ttg gtt cag tta ctg aag cag tgc cac ctg gtg cca<br>Asn Val Thr Cys Leu Val Gln Leu Leu Lys Gln Cys His Leu Val Pro<br>2810                        2815                  2820                 2825 | 8802 |
| cag gac tta gat atc ccg aac ccc atg gaa gcg tct gag aca gtt cac<br>Gln Asp Leu Asp Ile Pro Asn Pro Met Glu Ala Ser Glu Thr Val His<br>                    2830                 2835                  2840 | 8850 |
| tta gcc aat gga gtg tat acc tca ctt cag gaa ttg aat tcg aat ttc<br>Leu Ala Asn Gly Val Tyr Thr Ser Leu Gln Glu Leu Asn Ser Asn Phe<br>             2845                 2850                  2855 | 8898 |
| cgg caa atc ata ttt cca gaa gca ctt cga tgt tta atg aaa ggg gaa<br>Arg Gln Ile Ile Phe Pro Glu Ala Leu Arg Cys Leu Met Lys Gly Glu<br>2860                        2865                  2870 | 8946 |
| tac acg tta gaa agt atg ctg cat gaa ctg gac ggt ctt att gag cag<br>Tyr Thr Leu Glu Ser Met Leu His Glu Leu Asp Gly Leu Ile Glu Gln<br>             2875                 2880                  2885 | 8994 |
| acc acc gat ggc gtt ccc ctg cag act cta gtg gaa tct ctt cag gcc<br>Thr Thr Asp Gly Val Pro Leu Gln Thr Leu Val Glu Ser Leu Gln Ala<br>2890                        2895                  2900                 2905 | 9042 |
| tac tta aga aac gca gct atg gga ctg gaa gaa gaa aca cat gct cat<br>Tyr Leu Arg Asn Ala Ala Met Gly Leu Glu Glu Glu Thr His Ala His<br>                    2910                 2915                  2920 | 9090 |
| tac atc gat gtt gcc aga cta cta cat gct cag tac ggt gaa tta atc<br>Tyr Ile Asp Val Ala Arg Leu Leu His Ala Gln Tyr Gly Glu Leu Ile<br>             2925                 2930                  2935 | 9138 |
| caa ccg aga aat ggt tca gtt gat gaa aca ccc aaa atg tca gct ggc<br>Gln Pro Arg Asn Gly Ser Val Asp Glu Thr Pro Lys Met Ser Ala Gly<br>2940                        2945                  2950 | 9186 |
| cag atg ctt ttg gta gca ttc gat ggc atg ttt gct caa gtt gaa act<br>Gln Met Leu Leu Val Ala Phe Asp Gly Met Phe Ala Gln Val Glu Thr<br>             2955                 2960                  2965 | 9234 |
| gct ttc agc tta tta gtt gaa aag ttg aac aag atg gaa att ccc ata<br>Ala Phe Ser Leu Leu Val Glu Lys Leu Asn Lys Met Glu Ile Pro Ile<br>2970                        2975                  2980                 2985 | 9282 |
| gct tgg cga aag att gac atc ata agg gaa gcc agg agt act caa gtt<br>Ala Trp Arg Lys Ile Asp Ile Ile Arg Glu Ala Arg Ser Thr Gln Val<br>                    2990                 2995                  3000 | 9330 |
| aat ttt ttt gat gat gat aat cac cgg cag gtg cta gaa gag att ttc<br>Asn Phe Phe Asp Asp Asp Asn His Arg Gln Val Leu Glu Glu Ile Phe<br>             3005                 3010                  3015 | 9378 |
| ttt cta aaa aga cta cag act att aag gag ttc ttc agg ctc tgt ggt<br>Phe Leu Lys Arg Leu Gln Thr Ile Lys Glu Phe Phe Arg Leu Cys Gly<br>3020                        3025                  3030 | 9426 |
| acc ttt tct aaa aca ttg tca gga tca agt tca ctt gaa gat cag aat<br>Thr Phe Ser Lys Thr Leu Ser Gly Ser Ser Ser Leu Glu Asp Gln Asn<br>             3035                 3040                  3045 | 9474 |

-continued

| | |
|---|---|
| act gtg aat ggg cct gta cag att gtc aat gtg aaa acc ctt ttt aga<br>Thr Val Asn Gly Pro Val Gln Ile Val Asn Val Lys Thr Leu Phe Arg<br>3050     3055     3060     3065 | 9522 |
| aac tct tgt ttc agt gaa gac caa atg gcc aaa cct atc aag gca ttc<br>Asn Ser Cys Phe Ser Glu Asp Gln Met Ala Lys Pro Ile Lys Ala Phe<br>   3070     3075     3080 | 9570 |
| aca gct gac ttt gtg agg cag ctc ttg ata ggg cta ccc aac caa gcc<br>Thr Ala Asp Phe Val Arg Gln Leu Leu Ile Gly Leu Pro Asn Gln Ala<br>3085     3090     3095 | 9618 |
| ctc gga ctc aca ctg tgc agt ttt atc agt gct ctg ggt gta gac atc<br>Leu Gly Leu Thr Leu Cys Ser Phe Ile Ser Ala Leu Gly Val Asp Ile<br>   3100     3105     3110 | 9666 |
| att gct caa gta gag gca aag gac ttt ggt gcc gaa agc aaa gtt tct<br>Ile Ala Gln Val Glu Ala Lys Asp Phe Gly Ala Glu Ser Lys Val Ser<br>3115     3120     3125 | 9714 |
| gtt gat gat ctc tgt aag aaa gcg gtg gaa cat aac atc cag ata ggg<br>Val Asp Asp Leu Cys Lys Lys Ala Val Glu His Asn Ile Gln Ile Gly<br>3130     3135     3140     3145 | 9762 |
| aag ttc tct cag ctg gtt atg aac agg gca act gtg tta gca agt tct<br>Lys Phe Ser Gln Leu Val Met Asn Arg Ala Thr Val Leu Ala Ser Ser<br>   3150     3155     3160 | 9810 |
| tac gac act gcc tgg aag aag cat gac ttg gtg cga agg cta gaa acc<br>Tyr Asp Thr Ala Trp Lys Lys His Asp Leu Val Arg Arg Leu Glu Thr<br>3165     3170     3175 | 9858 |
| agt att tct tct tgt aag aca agc ctg cag cgg gtt cag ctg cat att<br>Ser Ile Ser Ser Cys Lys Thr Ser Leu Gln Arg Val Gln Leu His Ile<br>   3180     3185     3190 | 9906 |
| gcc atg ttt cag tgg caa cat gaa gat cta ctt atc aat aga cca caa<br>Ala Met Phe Gln Trp Gln His Glu Asp Leu Leu Ile Asn Arg Pro Gln<br>3195     3200     3205 | 9954 |
| gcc atg tca gtc aca cct ccc cca cgg tct gct atc cta acc agc atg<br>Ala Met Ser Val Thr Pro Pro Pro Arg Ser Ala Ile Leu Thr Ser Met<br>3210     3215     3220     3225 | 10002 |
| aaa aag aag ctg cat acc ctg agc cag att gaa act tct att gcg aca<br>Lys Lys Lys Leu His Thr Leu Ser Gln Ile Glu Thr Ser Ile Ala Thr<br>   3230     3235     3240 | 10050 |
| gtt cag gag aag cta gct gca ctt gaa tca agt att gaa cag cga ctc<br>Val Gln Glu Lys Leu Ala Ala Leu Glu Ser Ser Ile Glu Gln Arg Leu<br>3245     3250     3255 | 10098 |
| aag tgg gca ggt ggt gcc aac cct gca ttg gcc cct gta cta caa gat<br>Lys Trp Ala Gly Gly Ala Asn Pro Ala Leu Ala Pro Val Leu Gln Asp<br>   3260     3265     3270 | 10146 |
| ttt gaa gca acg ata gct gaa aga aga aat ctt gtc ctt aaa gag agc<br>Phe Glu Ala Thr Ile Ala Glu Arg Arg Asn Leu Val Leu Lys Glu Ser<br>3275     3280     3285 | 10194 |
| caa aga gca agt cag gtc aca ttt ctc tgc agc aat atc att cat ttt<br>Gln Arg Ala Ser Gln Val Thr Phe Leu Cys Ser Asn Ile Ile His Phe<br>3290     3295     3300     3305 | 10242 |
| gaa agt tta cga aca aga act gca gaa gcc tta aac ctg gat gcg gcg<br>Glu Ser Leu Arg Thr Arg Thr Ala Glu Ala Leu Asn Leu Asp Ala Ala<br>   3310     3315     3320 | 10290 |
| tta ttt gaa cta atc aag cga tgt cag cag atg tgt tcg ttt gca tca<br>Leu Phe Glu Leu Ile Lys Arg Cys Gln Gln Met Cys Ser Phe Ala Ser<br>3325     3330     3335 | 10338 |
| cag ttt aac agt tca gtg tct gag tta gag ctt cgt tta tta cag aga<br>Gln Phe Asn Ser Ser Val Ser Glu Leu Glu Leu Arg Leu Leu Gln Arg<br>   3340     3345     3350 | 10386 |
| gtg gac act ggt ctt gaa cat cct att ggc agc tct gaa tgg ctt ttg<br>Val Asp Thr Gly Leu Glu His Pro Ile Gly Ser Ser Glu Trp Leu Leu | 10434 |

|  |  |
|---|---|
| tca gca cac aaa cag ttg acc cag gat atg tct act cag agg gca att<br>Ser Ala His Lys Gln Leu Thr Gln Asp Met Ser Thr Gln Arg Ala Ile<br>3370                 3375                 3380                 3385 | 10482 |
| cag aca gag aaa gag cag cag ata gaa acg gtc tgt gaa aca att cag<br>Gln Thr Glu Lys Glu Gln Gln Ile Glu Thr Val Cys Glu Thr Ile Gln<br>               3390                 3395                 3400 | 10530 |
| aat ctg gtt gat aat ata aag act gtg ctc act ggt cat aac cga cag<br>Asn Leu Val Asp Asn Ile Lys Thr Val Leu Thr Gly His Asn Arg Gln<br>3405                 3410                 3415 | 10578 |
| ctt gga gat gtc aaa cat ctc ttg aaa gct atg gct aag gat gaa gaa<br>Leu Gly Asp Val Lys His Leu Leu Lys Ala Met Ala Lys Asp Glu Glu<br>               3420                 3425                 3430 | 10626 |
| gct gct ctg gca gat ggt gaa gat gtt ccc tat gag aac agt gtt agg<br>Ala Ala Leu Ala Asp Gly Glu Asp Val Pro Tyr Glu Asn Ser Val Arg<br>3435                 3440                 3445 | 10674 |
| cag ttt ttg ggt gaa tat aaa tca tgg caa gac aac att caa aca gtt<br>Gln Phe Leu Gly Glu Tyr Lys Ser Trp Gln Asp Asn Ile Gln Thr Val<br>3450                 3455                 3460                 3465 | 10722 |
| cta ttt aca tta gtc cag gct atg ggt cag gtt cga agt caa gaa cac<br>Leu Phe Thr Leu Val Gln Ala Met Gly Gln Val Arg Ser Gln Glu His<br>               3470                 3475                 3480 | 10770 |
| gtt gaa atg ctc cag gaa atc act ccc acc ttg aaa gaa ctg aaa aca<br>Val Glu Met Leu Gln Glu Ile Thr Pro Thr Leu Lys Glu Leu Lys Thr<br>3485                 3490                 3495 | 10818 |
| caa agt cag agt atc tat aat aat tta gtg agt ttt gca tca ccc tta<br>Gln Ser Gln Ser Ile Tyr Asn Asn Leu Val Ser Phe Ala Ser Pro Leu<br>               3500                 3505                 3510 | 10866 |
| gtc acc gat gca aca aat gaa tgt tcg agt cca acg tca tct gct act<br>Val Thr Asp Ala Thr Asn Glu Cys Ser Ser Pro Thr Ser Ser Ala Thr<br>3515                 3520                 3525 | 10914 |
| tat cag cca tcc ttc gct gca gca gtc cgg agt aac act ggc cag aag<br>Tyr Gln Pro Ser Phe Ala Ala Ala Val Arg Ser Asn Thr Gly Gln Lys<br>3530                 3535                 3540                 3545 | 10962 |
| act cag cct gat gtc atg tca cag aat gct aga aag ctg atc cag aaa<br>Thr Gln Pro Asp Val Met Ser Gln Asn Ala Arg Lys Leu Ile Gln Lys<br>               3550                 3555                 3560 | 11010 |
| aat ctt gct aca tca gct gat act cca cca agc acc gtt cca gga act<br>Asn Leu Ala Thr Ser Ala Asp Thr Pro Pro Ser Thr Val Pro Gly Thr<br>3565                 3570                 3575 | 11058 |
| ggc aag agt gtt gct tgt agt cct aaa aag gca gtc aga gac cct aaa<br>Gly Lys Ser Val Ala Cys Ser Pro Lys Lys Ala Val Arg Asp Pro Lys<br>               3580                 3585                 3590 | 11106 |
| act ggg aaa gcg gtg caa gag aga aac tcc tat gca gtg agt gtg tgg<br>Thr Gly Lys Ala Val Gln Glu Arg Asn Ser Tyr Ala Val Ser Val Trp<br>3595                 3600                 3605 | 11154 |
| aag aga gtg aaa gcc aag tta gag ggc cga gat gtt gat ccg aat agg<br>Lys Arg Val Lys Ala Lys Leu Glu Gly Arg Asp Val Asp Pro Asn Arg<br>3610                 3615                 3620                 3625 | 11202 |
| agg atg tca gtt gct gaa cag gtt gac tat gtc att aag gaa gca act<br>Arg Met Ser Val Ala Glu Gln Val Asp Tyr Val Ile Lys Glu Ala Thr<br>               3630                 3635                 3640 | 11250 |
| aat cta gat aac ttg gct cag ctg tat gaa ggt tgg aca gcc tgg gtg<br>Asn Leu Asp Asn Leu Ala Gln Leu Tyr Glu Gly Trp Thr Ala Trp Val<br>3645                 3650                 3655 | 11298 |
| tgaatggcaa gacagtagat gagtctggtt aagcgaggtc agacatccac cagaatcaac | 11358 |
| tcagcctcag gcatccaaag ccacaccaca gtcggtggtg atgcaactgg ggcttactgc | 11418 |
| tgaggaaacc taggaaatct cggtgcacta ggaagtgaat cccgcaggac agctgcactc | 11478 |

-continued

```
agggatacgc ccaacaccat ggcctgcaac cccagggtca agggtgaagg aaagcaaagc   11538
tcaccgcctg aacacggaga ttgtctttct gccacagaac agcagcagac gtgtcgggag   11598
gttagctgcg gaaagaaatc gggatgccgc ggagcacaga gtgatttgga actccattcc   11658 acctgacccct gtgtgtacaa tccaggaaaa aaacaaaccc cactcagaaa cagagaaaac   11718
tggggtcgcg aagaaatcac agccaaggaa gatttgatgc attcagattc tcgtgtaaca   11778
cttgttgctt ggcaacagta ctggttgggt tgaccagtaa gtagaaaaag gctaaaggct   11838
atgcgatatg aatttcagaa atggactgaa atggagagc tatgtaacag atacactaca   11898
gtagaagaac ttacttctga aatgaaggga aaaaaaccac cccatcgttc cctactcctc   11958
cccaccactt acccgttccc cctttaccta atctagtaga ttagccatct ttcaaattca   12018
cttttatttc agtccttata tttcatatac ttccgtctcg atgctgttaa caacttctga   12078
taacatggaa aattcaagga ttgtttaaag gtctgatgat cacacacaaa atgtaattcc   12138
ggttatttaa gtcatttctg tgattctatc atgtacagtt tccagaattg tcactgtgca   12198
ttcaaaagta atgaatctaa cagacatttg atttaatgta cactcccttt tgcttatagt   12258
gtgcattttt tttggaggtc attcaaattt tccctcttct gtgatagctg tagtttcttt   12318
catagaaagt agctaatcca gtgtaatctt ttacctttt aaaaaccaag atagagtatc   12378
tattagagtt ttacattgtt gatgatagat taacaataaa gtgatgttct ggtggaggta   12438
gactgaaatt tttttaattc atgtttttca tttgatactt ttaatttaca cttagtaaat   12498
taaaagttgt ttaatttact tggcatttta ggacatgtac atgaaacagt gaaaatgaga   12558
tccaccaaca tcttttatta agttcagtta ttagtctgtg aagtgcttta cttttttgcac   12618 aattttaata gcttgctatt cagtaataca ttatagtgaa ttcatgatca aggtttcctt   12678
aaatttagca ttgcatttca gtactgactg tgtaagctaa attgctgatc caaaataaaa   12738
acccagacta gaatagggtt cttaaaatca agtatcaata caaaatagaa cacaattaaa   12798
atcttaattg ttggctgggc acagtggctc acgcctgtaa tcccagcact ttgggaggcc   12858
gaggcgggcg gatcatgagg ttaggagagc gagaccatcc tggctaacac ggtgaaaccc   12918
cgtctttact aaaatacaaa aaaattagc cgggtgtggt ggcgggcgcc tgtagtccca   12978
gctactcggg aggctgaggc aggagaatgg cgtgaaccca ggaggcggag cttgcagtga   13038
gccgagattg tgccactgca ctccagcctg ggcaacagag ctagactctg tgtcaaaaat   13098
aaatgactag at                                                      13110
```

<210> SEQ ID NO 10
<211> LENGTH: 3657
<212> TYPE: PRT
<213> ORGANISM: Homo sapiens

<400> SEQUENCE: 10

```
Met Ser Arg Arg Ala Pro Gly Ser Arg Leu Ser Ser Gly Gly Thr Asn
1               5                   10                  15

Tyr Ser Arg Ser Trp Asn Asp Trp Gln Pro Arg Thr Asp Ser Ala Ser
            20                  25                  30

Ala Asp Pro Gly Asn Leu Lys Tyr Ser Ser Ser Arg Asp Arg Gly Gly
        35                  40                  45

Ser Ser Ser Tyr Gly Leu Gln Pro Ser Asn Ser Ala Val Val Ser Arg
    50                  55                  60

Gln Arg His Asp Asp Thr Arg Val His Ala Asp Ile Gln Asn Asp Glu
65                  70                  75                  80
```

-continued

```
Lys Gly Gly Tyr Ser Val Asn Gly Gly Ser Glu Asn Thr Tyr Gly
                 85                  90                  95
Arg Lys Ser Leu Gly Gln Glu Leu Arg Val Asn Asn Val Thr Ser Pro
                100                 105                 110
Glu Phe Thr Ser Val Gln His Gly Ser Arg Ala Leu Ala Thr Lys Asp
                115                 120                 125
Met Arg Lys Ser Gln Glu Arg Ser Met Ser Tyr Ser Asp Glu Ser Arg
    130                 135                 140
Leu Ser Asn Leu Leu Arg Arg Ile Thr Arg Glu Asp Arg Asp Arg
145                 150                 155                 160
Arg Leu Ala Thr Val Lys Gln Leu Lys Glu Phe Ile Gln Gln Pro Glu
                165                 170                 175
Asn Lys Leu Val Leu Val Lys Gln Leu Asp Asn Ile Leu Ala Ala Val
                180                 185                 190
His Asp Val Leu Asn Glu Ser Ser Lys Leu Leu Gln Glu Leu Arg Gln
                195                 200                 205
Glu Gly Ala Cys Cys Leu Gly Leu Leu Cys Ala Ser Leu Ser Tyr Glu
    210                 215                 220
Ala Glu Lys Ile Phe Lys Trp Ile Phe Ser Lys Phe Ser Ser Ser Ala
225                 230                 235                 240
Lys Asp Glu Val Lys Leu Leu Tyr Leu Cys Ala Thr Tyr Lys Ala Leu
                245                 250                 255
Glu Thr Val Gly Glu Lys Lys Ala Phe Ser Val Met Gln Leu Val
                260                 265                 270
Met Thr Ser Leu Gln Ser Ile Leu Glu Asn Val Asp Thr Pro Glu Leu
    275                 280                 285
Leu Cys Lys Cys Val Lys Cys Ile Leu Leu Val Ala Arg Cys Tyr Pro
    290                 295                 300
His Ile Phe Ser Thr Asn Phe Arg Asp Thr Val Asp Ile Leu Val Gly
305                 310                 315                 320
Trp His Ile Asp His Thr Gln Lys Pro Ser Leu Thr Gln Gln Val Ser
                325                 330                 335
Gly Trp Leu Gln Ser Leu Glu Pro Phe Trp Val Ala Asp Leu Ala Phe
                340                 345                 350
Ser Thr Thr Leu Leu Gly Gln Phe Leu Glu Asp Met Glu Ala Tyr Ala
    355                 360                 365
Glu Asp Leu Ser His Val Ala Ser Gly Glu Ser Val Asp Glu Asp Val
    370                 375                 380
Pro Pro Pro Ser Val Ser Leu Pro Lys Leu Ala Ala Leu Leu Arg Val
385                 390                 395                 400
Phe Ser Thr Val Val Arg Ser Ile Gly Glu Arg Phe Ser Pro Ile Arg
                405                 410                 415
Gly Pro Pro Ile Thr Glu Ala Tyr Val Thr Asp Val Leu Tyr Arg Val
                420                 425                 430
Met Arg Cys Val Thr Ala Ala Asn Gln Val Phe Phe Ser Glu Ala Val
    435                 440                 445
Leu Thr Ala Ala Asn Glu Cys Val Gly Val Leu Leu Gly Ser Leu Asp
    450                 455                 460
Pro Ser Met Thr Ile His Cys Asp Met Val Ile Thr Tyr Gly Leu Asp
465                 470                 475                 480
Gln Leu Glu Asn Cys Gln Thr Cys Gly Thr Asp Tyr Ile Ile Ser Val
                485                 490                 495
```

```
Leu Asn Leu Leu Thr Leu Ile Val Glu Gln Ile Asn Thr Lys Leu Pro
            500                 505                 510

Ser Ser Phe Val Glu Lys Leu Phe Ile Pro Ser Ser Lys Leu Leu Phe
            515                 520                 525

Leu Arg Tyr His Lys Glu Lys Glu Val Ala Val Ala His Ala Val
            530                 535                 540

Tyr Gln Ala Val Leu Ser Leu Lys Asn Ile Pro Val Leu Glu Thr Ala
545                 550                 555                 560

Tyr Lys Leu Ile Leu Gly Glu Met Thr Cys Ala Leu Asn Asn Leu Leu
            565                 570                 575

His Ser Leu Gln Leu Pro Glu Ala Cys Ser Glu Ile Lys His Glu Ala
            580                 585                 590

Phe Lys Asn His Val Phe Asn Val Asp Asn Ala Lys Phe Val Val Lys
            595                 600                 605

Phe Asp Leu Ser Ala Leu Thr Thr Ile Gly Asn Ala Lys Asn Ser Leu
            610                 615                 620

Ile Gly Met Trp Ala Leu Ser Pro Thr Val Phe Ala Leu Leu Ser Lys
625                 630                 635                 640

Asn Leu Met Ile Val His Ser Asp Leu Ala Val His Phe Pro Ala Ile
            645                 650                 655

Gln Tyr Ala Val Leu Tyr Thr Leu Tyr Ser His Cys Thr Arg His Asp
            660                 665                 670

His Phe Ile Ser Ser Ser Leu Ser Ser Ala Ser Pro Ser Leu Phe Asp
            675                 680                 685

Gly Ala Val Ile Ser Thr Val Thr Thr Ala Thr Lys Lys His Phe Ser
            690                 695                 700

Ile Ile Leu Asn Leu Leu Gly Ile Leu Lys Lys Asp Asn Leu Asn
705                 710                 715                 720

Gln Asp Thr Arg Lys Leu Leu Met Thr Trp Ala Leu Glu Ala Ala Val
            725                 730                 735

Leu Met Arg Lys Ser Glu Thr Tyr Ala Pro Leu Phe Ser Leu Pro Ser
            740                 745                 750

Phe His Lys Phe Cys Lys Gly Leu Leu Ala Asn Thr Leu Val Glu Asp
            755                 760                 765

Val Asn Ile Cys Leu Gln Ala Cys Ser Ser Leu His Ala Leu Ser Ser
770                 775                 780

Ser Leu Pro Asp Asp Leu Leu Gln Arg Cys Val Asp Val Cys Arg Val
785                 790                 795                 800

Gln Leu Val His Ser Gly Thr Arg Ile Arg Gln Ala Phe Gly Lys Leu
            805                 810                 815

Leu Lys Ser Ile Pro Leu Asp Val Val Leu Ser Asn Asn Asn His Thr
            820                 825                 830

Glu Ile Gln Glu Ile Ser Leu Ala Leu Arg Ser His Met Ser Lys Ala
            835                 840                 845

Pro Ser Asn Thr Phe His Pro Gln Asp Phe Ser Asp Val Ile Ser Phe
850                 855                 860

Ile Leu Tyr Gly Asn Ser His Arg Thr Gly Lys Asp Asn Trp Leu Glu
865                 870                 875                 880

Arg Leu Phe Tyr Ser Cys Gln Arg Leu Asp Lys Arg Asp Gln Ser Thr
            885                 890                 895

Ile Pro Arg Asn Leu Leu Lys Thr Asp Ala Val Leu Trp Gln Trp Ala
            900                 905                 910

Ile Trp Glu Ala Ala Gln Phe Thr Val Leu Ser Lys Leu Arg Thr Pro
```

-continued

```
                915                 920                 925
Leu Gly Arg Ala Gln Asp Thr Phe Gln Thr Ile Glu Gly Ile Ile Arg
    930                 935                 940
Ser Leu Ala Ala His Thr Leu Asn Pro Asp Gln Asp Val Ser Gln Trp
945                 950                 955                 960
Thr Thr Ala Asp Asn Asp Glu Gly His Gly Asn Asn Gln Leu Arg Leu
                965                 970                 975
Val Leu Leu Leu Gln Tyr Leu Glu Asn Leu Glu Lys Leu Met Tyr Asn
            980                 985                 990
Ala Tyr Glu Gly Cys Ala Asn Ala Leu Thr Ser Pro Pro Lys Val Ile
        995                 1000                1005
Arg Thr Phe Phe Tyr Thr Asn Arg Gln Thr Cys Gln Asp Trp Leu Thr
    1010                1015                1020
Arg Ile Arg Leu Ser Ile Met Arg Val Gly Leu Leu Ala Gly Gln Pro
1025                1030                1035                1040
Ala Val Thr Val Arg His Gly Phe Asp Leu Leu Thr Glu Met Lys Thr
                1045                1050                1055
Thr Ser Leu Ser Gln Gly Asn Glu Leu Glu Val Thr Ile Met Met Val
            1060                1065                1070
Val Glu Ala Leu Cys Glu Leu His Cys Pro Glu Ala Ile Gln Gly Ile
        1075                1080                1085
Ala Val Trp Ser Ser Ser Ile Val Gly Lys Asn Leu Leu Trp Ile Asn
    1090                1095                1100
Ser Val Ala Gln Gln Ala Glu Gly Arg Phe Glu Lys Ala Ser Val Glu
1105                1110                1115                1120
Tyr Gln Glu His Leu Cys Ala Met Thr Gly Val Asp Cys Cys Ile Ser
                1125                1130                1135
Ser Phe Asp Lys Ser Val Leu Thr Leu Ala Asn Ala Gly Arg Asn Ser
            1140                1145                1150
Ala Ser Pro Lys His Ser Leu Asn Gly Glu Ser Arg Lys Thr Val Leu
        1155                1160                1165
Ser Lys Pro Thr Asp Ser Ser Pro Glu Val Ile Asn Tyr Leu Gly Asn
    1170                1175                1180
Lys Ala Cys Glu Phe Tyr Ile Ser Ile Ala Asp Trp Ala Val Gln
1185                1190                1195                1200
Glu Trp Gln Asn Ala Ile His Asp Leu Lys Lys Ser Thr Ser Ser Thr
                1205                1210                1215
Ser Leu Asn Leu Lys Ala Asp Phe Asn Tyr Ile Lys Ser Leu Ser Ser
            1220                1225                1230
Phe Glu Ser Gly Lys Phe Val Glu Cys Thr Glu Gln Leu Glu Leu Leu
        1235                1240                1245
Pro Gly Glu Asn Ile Asn Leu Leu Ala Gly Gly Ser Lys Glu Lys Ile
    1250                1255                1260
Asp Met Lys Lys Leu Leu Pro Asn Met Leu Ser Pro Asp Pro Arg Glu
1265                1270                1275                1280
Leu Gln Lys Ser Ile Glu Val Gln Leu Leu Arg Ser Ser Val Cys Leu
                1285                1290                1295
Ala Thr Ala Leu Asn Pro Ile Glu Gln Asp Gln Lys Trp Gln Ser Ile
            1300                1305                1310
Thr Glu Asn Val Val Lys Tyr Leu Lys Gln Thr Ser Arg Ile Ala Ile
        1315                1320                1325
Gly Pro Leu Arg Leu Ser Thr Leu Thr Val Ser Gln Ser Leu Pro Val
    1330                1335                1340
```

```
Leu Ser Thr Leu Gln Leu Tyr Cys Ser Ser Ala Leu Glu Asn Thr Val
1345                1350                1355                1360

Ser Asn Arg Leu Ser Thr Glu Asp Cys Leu Ile Pro Leu Phe Ser Glu
            1365                1370                1375

Ala Leu Arg Ser Cys Lys Gln His Asp Val Arg Pro Trp Met Gln Ala
            1380                1385                1390

Leu Arg Tyr Thr Met Tyr Gln Asn Gln Leu Leu Glu Lys Ile Lys Glu
            1395                1400                1405

Gln Thr Val Pro Ile Arg Ser His Leu Met Glu Leu Gly Leu Thr Ala
1410                1415                1420

Ala Lys Phe Ala Arg Lys Arg Gly Asn Val Ser Leu Ala Thr Arg Leu
1425                1430                1435                1440

Leu Ala Gln Cys Ser Glu Val Gln Leu Gly Lys Thr Thr Thr Ala Gln
            1445                1450                1455

Asp Leu Val Gln His Phe Lys Lys Leu Ser Thr Gln Gly Gln Val Asp
            1460                1465                1470

Glu Lys Trp Gly Pro Glu Leu Asp Ile Glu Lys Thr Lys Leu Leu Tyr
            1475                1480                1485

Thr Ala Gly Gln Ser Thr His Ala Met Glu Met Leu Ser Ser Cys Ala
            1490                1495                1500

Ile Ser Phe Cys Lys Ser Val Lys Ala Glu Tyr Ala Val Ala Lys Ser
1505                1510                1515                1520

Ile Leu Thr Leu Ala Lys Trp Ile Gln Ala Glu Trp Lys Glu Ile Ser
            1525                1530                1535

Gly Gln Leu Lys Gln Val Tyr Arg Ala Gln His Gln Gln Asn Phe Thr
            1540                1545                1550

Gly Leu Ser Thr Leu Ser Lys Asn Ile Leu Thr Leu Ile Glu Leu Pro
            1555                1560                1565

Ser Val Asn Thr Met Glu Glu Glu Tyr Pro Arg Ile Glu Ser Glu Ser
            1570                1575                1580

Thr Val His Ile Gly Val Gly Glu Pro Asp Phe Ile Leu Gly Gln Leu
1585                1590                1595                1600

Tyr His Leu Ser Ser Val Gln Ala Pro Glu Val Ala Lys Ser Trp Ala
            1605                1610                1615

Ala Leu Ala Ser Trp Ala Tyr Arg Trp Gly Arg Lys Val Val Asp Asn
            1620                1625                1630

Ala Ser Gln Gly Glu Gly Val Arg Leu Leu Pro Arg Glu Lys Ser Glu
            1635                1640                1645

Val Gln Asn Leu Leu Pro Asp Thr Ile Thr Glu Glu Lys Glu Arg
1650                1655                1660

Ile Tyr Gly Ile Leu Gly Gln Ala Val Cys Arg Pro Ala Gly Ile Gln
1665                1670                1675                1680

Asp Glu Asp Ile Thr Leu Gln Ile Thr Glu Ser Glu Asp Asn Glu Glu
            1685                1690                1695

Asp Asp Met Val Asp Val Ile Trp Arg Gln Leu Ile Ser Ser Cys Pro
            1700                1705                1710

Trp Leu Ser Glu Leu Asp Glu Ser Ala Thr Glu Gly Val Ile Lys Val
            1715                1720                1725

Trp Arg Lys Val Val Asp Arg Ile Phe Ser Leu Tyr Lys Leu Ser Cys
            1730                1735                1740

Ser Ala Tyr Phe Thr Phe Leu Lys Leu Asn Ala Gly Gln Ile Pro Leu
1745                1750                1755                1760
```

```
                            -continued

Asp Glu Asp Asp Pro Arg Leu His Leu Ser His Arg Val Glu Gln Ser
            1765                1770                1775

Thr Asp Asp Met Ile Val Met Ala Thr Leu Arg Leu Leu Arg Leu Leu
            1780                1785                1790

Val Lys His Ala Gly Glu Leu Arg Gln Tyr Leu Glu His Gly Leu Glu
            1795                1800                1805

Thr Thr Pro Thr Ala Pro Trp Arg Gly Ile Ile Pro Gln Leu Phe Ser
            1810                1815                1820

Arg Leu Asn His Pro Glu Val Tyr Val Arg Gln Ser Ile Cys Asn Leu
1825                1830                1835                1840

Leu Cys Arg Val Ala Gln Asp Ser Pro His Leu Ile Leu Tyr Pro Ala
            1845                1850                1855

Ile Val Gly Thr Ile Ser Leu Ser Ser Glu Ser Gln Ala Ser Gly Asn
            1860                1865                1870

Lys Phe Ser Thr Ala Ile Pro Thr Leu Leu Gly Asn Ile Gln Gly Glu
            1875                1880                1885

Glu Leu Leu Val Ser Glu Cys Glu Gly Gly Ser Pro Pro Ala Ser Gln
            1890                1895                1900

Asp Ser Asn Lys Asp Glu Pro Lys Ser Gly Leu Asn Glu Asp Gln Ala
1905                1910                1915                1920

Met Met Gln Asp Cys Tyr Ser Lys Ile Val Asp Lys Leu Ser Ser Ala
            1925                1930                1935

Asn Pro Thr Met Val Leu Gln Val Gln Met Leu Val Ala Glu Leu Arg
            1940                1945                1950

Arg Val Thr Val Leu Trp Asp Glu Leu Trp Leu Gly Val Leu Leu Gln
            1955                1960                1965

Gln His Met Tyr Val Leu Arg Arg Ile Gln Gln Leu Glu Asp Glu Val
            1970                1975                1980

Lys Arg Val Gln Asn Asn Asn Thr Leu Arg Lys Glu Glu Lys Ile Ala
1985                1990                1995                2000

Ile Met Arg Glu Arg His Thr Ala Leu Met Lys Pro Ile Val Phe Ala
            2005                2010                2015

Leu Glu His Val Arg Ser Ile Thr Ala Ala Pro Ala Glu Thr Pro His
            2020                2025                2030

Glu Lys Trp Phe Gln Asp Asn Tyr Gly Asp Ala Ile Glu Asn Ala Leu
            2035                2040                2045

Glu Lys Leu Lys Thr Pro Leu Asn Pro Ala Lys Pro Gly Ser Ser Trp
2050                2055                2060

Ile Pro Phe Lys Glu Ile Met Leu Ser Leu Gln Gln Arg Ala Gln Lys
2065                2070                2075                2080

Arg Ala Ser Tyr Ile Leu Arg Leu Glu Glu Ile Ser Pro Trp Leu Ala
            2085                2090                2095

Ala Met Thr Asn Thr Glu Ile Ala Leu Pro Gly Glu Val Ser Ala Arg
            2100                2105                2110

Asp Thr Val Thr Ile His Ser Val Gly Gly Thr Ile Thr Ile Leu Pro
            2115                2120                2125

Thr Lys Thr Lys Pro Lys Lys Leu Leu Phe Leu Gly Ser Asp Gly Lys
            2130                2135                2140

Ser Tyr Pro Tyr Leu Phe Lys Gly Leu Glu Asp Leu His Leu Asp Glu
2145                2150                2155                2160

Arg Ile Met Gln Phe Leu Ser Ile Val Asn Thr Met Phe Ala Thr Ile
            2165                2170                2175

Asn Arg Gln Glu Thr Pro Arg Phe His Ala Arg His Tyr Ser Val Thr
```

-continued

```
            2180                2185                2190
Pro Leu Gly Thr Arg Ser Gly Leu Ile Gln Trp Val Asp Gly Ala Thr
            2195                2200                2205
Pro Leu Phe Gly Leu Tyr Lys Arg Trp Gln Gln Arg Glu Ala Ala Leu
            2210                2215                2220
Gln Ala Gln Lys Ala Gln Asp Ser Tyr Gln Thr Pro Gln Asn Pro Gly
2225                2230                2235                2240
Ile Val Pro Arg Pro Ser Glu Leu Tyr Tyr Ser Lys Ile Gly Pro Ala
                2245                2250                2255
Leu Lys Thr Val Gly Leu Ser Leu Asp Val Ser Arg Arg Asp Trp Pro
            2260                2265                2270
Leu His Val Met Lys Ala Val Leu Glu Glu Leu Met Glu Ala Thr Pro
            2275                2280                2285
Pro Asn Leu Leu Ala Lys Glu Leu Trp Ser Ser Cys Thr Thr Pro Asp
            2290                2295                2300
Glu Trp Trp Arg Val Thr Gln Ser Tyr Ala Arg Ser Thr Ala Val Met
2305                2310                2315                2320
Ser Met Val Gly Tyr Ile Ile Gly Leu Gly Asp Arg His Leu Asp Asn
                2325                2330                2335
Val Leu Ile Asp Met Thr Thr Gly Glu Val Val His Ile Asp Tyr Asn
                2340                2345                2350
Val Cys Phe Glu Lys Gly Lys Ser Leu Arg Val Pro Glu Lys Val Pro
                2355                2360                2365
Phe Arg Met Thr Gln Asn Ile Glu Thr Ala Leu Gly Val Thr Gly Val
            2370                2375                2380
Glu Gly Val Phe Arg Leu Ser Cys Glu Gln Val Leu His Ile Met Arg
2385                2390                2395                2400
Arg Gly Arg Glu Thr Leu Leu Thr Leu Leu Glu Ala Phe Val Tyr Asp
                2405                2410                2415
Pro Leu Val Asp Trp Thr Ala Gly Gly Glu Ala Gly Phe Ala Gly Ala
                2420                2425                2430
Val Tyr Gly Gly Gly Gly Gln Gln Ala Glu Ser Lys Gln Ser Lys Arg
            2435                2440                2445
Glu Met Glu Arg Glu Ile Thr Arg Ser Leu Phe Ser Ser Arg Val Ala
            2450                2455                2460
Glu Ile Lys Val Asn Trp Phe Lys Asn Arg Asp Glu Met Leu Val Val
2465                2470                2475                2480
Leu Pro Lys Leu Asp Gly Ser Leu Asp Glu Tyr Leu Ser Leu Gln Glu
                2485                2490                2495
Gln Leu Thr Asp Val Glu Lys Leu Gln Gly Lys Leu Glu Glu Ile
            2500                2505                2510
Glu Phe Leu Glu Gly Ala Glu Gly Val Asp His Pro Ser His Thr Leu
            2515                2520                2525
Gln His Arg Tyr Ser Glu His Thr Gln Leu Gln Thr Gln Gln Arg Ala
            2530                2535                2540
Val Gln Glu Ala Ile Gln Val Lys Leu Asn Glu Phe Glu Gln Trp Ile
2545                2550                2555                2560
Thr His Tyr Gln Ala Ala Phe Asn Asn Leu Glu Ala Thr Gln Leu Ala
                2565                2570                2575
Ser Leu Leu Gln Glu Ile Ser Thr Gln Met Asp Leu Gly Pro Pro Ser
            2580                2585                2590
Tyr Val Pro Ala Thr Ala Phe Leu Gln Asn Ala Gly Gln Ala His Leu
            2595                2600                2605
```

```
Ile Ser Gln Cys Glu Gln Leu Glu Gly Glu Val Gly Ala Leu Leu Gln
    2610                2615                2620

Gln Arg Arg Ser Val Leu Arg Gly Cys Leu Glu Gln Leu His His Tyr
2625                2630                2635                2640

Ala Thr Val Ala Leu Gln Tyr Pro Lys Ala Ile Phe Gln Lys His Arg
                2645                2650                2655

Ile Glu Gln Trp Lys Thr Trp Met Glu Leu Ile Cys Asn Thr Thr
            2660                2665                2670

Val Glu Arg Cys Gln Glu Leu Tyr Arg Lys Tyr Glu Met Gln Tyr Ala
            2675                2680                2685

Pro Gln Pro Pro Thr Val Cys Gln Phe Ile Thr Ala Thr Glu Met
            2690                2695                2700

Thr Leu Gln Arg Tyr Ala Ala Asp Ile Asn Ser Arg Leu Ile Arg Gln
2705                2710                2715                2720

Val Glu Arg Leu Lys Gln Glu Ala Val Thr Val Pro Val Cys Glu Asp
                2725                2730                2735

Gln Leu Lys Glu Ile Glu Arg Cys Ile Lys Val Phe Leu His Glu Asn
                2740                2745                2750

Gly Glu Glu Gly Ser Leu Ser Leu Ala Ser Val Ile Ser Ala Leu
        2755                2760                2765

Cys Thr Leu Thr Arg Arg Asn Leu Met Met Glu Gly Ala Ala Ser Ser
2770                2775                2780

Ala Gly Glu Gln Leu Val Asp Leu Thr Ser Arg Asp Gly Ala Trp Phe
2785                2790                2795                2800

Leu Glu Glu Leu Cys Ser Met Ser Gly Asn Val Thr Cys Leu Val Gln
                2805                2810                2815

Leu Leu Lys Gln Cys His Leu Val Pro Gln Asp Leu Asp Ile Pro Asn
                2820                2825                2830

Pro Met Glu Ala Ser Glu Thr Val His Leu Ala Asn Gly Val Tyr Thr
            2835                2840                2845

Ser Leu Gln Glu Leu Asn Ser Asn Phe Arg Gln Ile Ile Phe Pro Glu
    2850                2855                2860

Ala Leu Arg Cys Leu Met Lys Gly Glu Tyr Thr Leu Glu Ser Met Leu
2865                2870                2875                2880

His Glu Leu Asp Gly Leu Ile Glu Gln Thr Thr Asp Gly Val Pro Leu
                2885                2890                2895

Gln Thr Leu Val Glu Ser Leu Gln Ala Tyr Leu Arg Asn Ala Ala Met
        2900                2905                2910

Gly Leu Glu Glu Glu Thr His Ala His Tyr Ile Asp Val Ala Arg Leu
            2915                2920                2925

Leu His Ala Gln Tyr Gly Glu Leu Ile Gln Pro Arg Asn Gly Ser Val
    2930                2935                2940

Asp Glu Thr Pro Lys Met Ser Ala Gly Gln Met Leu Leu Val Ala Phe
2945                2950                2955                2960

Asp Gly Met Phe Ala Gln Val Glu Thr Ala Phe Ser Leu Leu Val Glu
                2965                2970                2975

Lys Leu Asn Lys Met Glu Ile Pro Ile Ala Trp Arg Lys Ile Asp Ile
            2980                2985                2990

Ile Arg Glu Ala Arg Ser Thr Gln Val Asn Phe Phe Asp Asp Asn
        2995                3000                3005

His Arg Gln Val Leu Glu Glu Ile Phe Phe Leu Lys Arg Leu Gln Thr
    3010                3015                3020
```

```
Ile Lys Glu Phe Phe Arg Leu Cys Gly Thr Phe Ser Lys Thr Leu Ser
3025                3030                3035                3040

Gly Ser Ser Ser Leu Glu Asp Gln Asn Thr Val Asn Gly Pro Val Gln
            3045                3050                3055

Ile Val Asn Val Lys Thr Leu Phe Arg Asn Ser Cys Phe Ser Glu Asp
        3060                3065                3070

Gln Met Ala Lys Pro Ile Lys Ala Phe Thr Ala Asp Phe Val Arg Gln
    3075                3080                3085

Leu Leu Ile Gly Leu Pro Asn Gln Ala Leu Gly Leu Thr Leu Cys Ser
    3090                3095                3100

Phe Ile Ser Ala Leu Gly Val Asp Ile Ala Gln Val Glu Ala Lys
3105                3110                3115                3120

Asp Phe Gly Ala Glu Ser Lys Val Ser Val Asp Asp Leu Cys Lys Lys
            3125                3130                3135

Ala Val Glu His Asn Ile Gln Ile Gly Lys Phe Ser Gln Leu Val Met
        3140                3145                3150

Asn Arg Ala Thr Val Leu Ala Ser Ser Tyr Asp Thr Ala Trp Lys Lys
    3155                3160                3165

His Asp Leu Val Arg Arg Leu Glu Thr Ser Ile Ser Ser Cys Lys Thr
    3170                3175                3180

Ser Leu Gln Arg Val Gln Leu His Ile Ala Met Phe Gln Trp Gln His
3185                3190                3195                3200

Glu Asp Leu Leu Ile Asn Arg Pro Gln Ala Met Ser Val Thr Pro Pro
            3205                3210                3215

Pro Arg Ser Ala Ile Leu Thr Ser Met Lys Lys Leu His Thr Leu
        3220                3225                3230

Ser Gln Ile Glu Thr Ser Ile Ala Thr Val Gln Glu Lys Leu Ala Ala
    3235                3240                3245

Leu Glu Ser Ser Ile Glu Gln Arg Leu Lys Trp Ala Gly Gly Ala Asn
    3250                3255                3260

Pro Ala Leu Ala Pro Val Leu Gln Asp Phe Glu Ala Thr Ile Ala Glu
3265                3270                3275                3280

Arg Arg Asn Leu Val Leu Lys Glu Ser Gln Arg Ala Ser Gln Val Thr
            3285                3290                3295

Phe Leu Cys Ser Asn Ile Ile His Phe Glu Ser Leu Arg Thr Arg Thr
        3300                3305                3310

Ala Glu Ala Leu Asn Leu Asp Ala Ala Leu Phe Glu Leu Ile Lys Arg
    3315                3320                3325

Cys Gln Gln Met Cys Ser Phe Ala Ser Gln Phe Asn Ser Ser Val Ser
    3330                3335                3340

Glu Leu Glu Leu Arg Leu Leu Gln Arg Val Asp Thr Gly Leu Glu His
3345                3350                3355                3360

Pro Ile Gly Ser Ser Glu Trp Leu Leu Ser Ala His Lys Gln Leu Thr
            3365                3370                3375

Gln Asp Met Ser Thr Gln Arg Ala Ile Gln Thr Glu Lys Glu Gln Gln
        3380                3385                3390

Ile Glu Thr Val Cys Glu Thr Ile Gln Asn Leu Val Asp Asn Ile Lys
    3395                3400                3405

Thr Val Leu Thr Gly His Asn Arg Gln Leu Gly Asp Val Lys His Leu
    3410                3415                3420

Leu Lys Ala Met Ala Lys Asp Glu Glu Ala Leu Ala Asp Gly Glu
3425                3430                3435                3440

Asp Val Pro Tyr Glu Asn Ser Val Arg Gln Phe Leu Gly Glu Tyr Lys
```

```
                    3445              3450              3455
Ser Trp Gln Asp Asn Ile Gln Thr Val Leu Phe Thr Leu Val Gln Ala
            3460              3465              3470

Met Gly Gln Val Arg Ser Gln Glu His Val Glu Met Leu Gln Glu Ile
        3475              3480              3485

Thr Pro Thr Leu Lys Glu Leu Lys Thr Gln Ser Gln Ser Ile Tyr Asn
    3490              3495              3500

Asn Leu Val Ser Phe Ala Ser Pro Leu Val Thr Asp Ala Thr Asn Glu
3505              3510              3515              3520

Cys Ser Ser Pro Thr Ser Ser Ala Thr Tyr Gln Pro Ser Phe Ala Ala
            3525              3530              3535

Ala Val Arg Ser Asn Thr Gly Gln Lys Thr Gln Pro Asp Val Met Ser
            3540              3545              3550

Gln Asn Ala Arg Lys Leu Ile Gln Lys Asn Leu Ala Thr Ser Ala Asp
        3555              3560              3565

Thr Pro Pro Ser Thr Val Pro Gly Thr Gly Lys Ser Val Ala Cys Ser
    3570              3575              3580

Pro Lys Lys Ala Val Arg Asp Pro Lys Thr Gly Lys Ala Val Gln Glu
3585              3590              3595              3600

Arg Asn Ser Tyr Ala Val Ser Val Trp Lys Arg Val Lys Ala Lys Leu
            3605              3610              3615

Glu Gly Arg Asp Val Asp Pro Asn Arg Arg Met Ser Val Ala Glu Gln
            3620              3625              3630

Val Asp Tyr Val Ile Lys Glu Ala Thr Asn Leu Asp Asn Leu Ala Gln
            3635              3640              3645

Leu Tyr Glu Gly Trp Thr Ala Trp Val
    3650              3655

<210> SEQ ID NO 11
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 11
agcaagctcc ctcctgtctc                                              20
```

ATM RELATED KINASE ATX, NUCLEIC ACIDS ENCODING SAME AND METHODS OF USE

This application is based on, and claims the benefit of, U.S. Provisional Application Ser. No. 60/813,607, filed Jun. 6, 2002, which was converted from U.S. Ser. No. 10/165, 216, and which is incorporated herein by reference.

This invention was made with government support under grant number CA76193 awarded by the National Institutes of Health. The United States Government has certain rights in this invention.

BACKGROUND OF THE INVENTION

This invention relates generally to the fields of molecular biology and molecular medicine and more specifically to the identification of phosphoinositide 3-kinase related kinases (PIKKs) involved in cell cycle control and mRNA surveillance pathways.

The mitotic cell cycle is the process by which a cell creates an exact copy of its chromosomes and then segregates each copy into two cells. The sequence of events of the cell cycle is regulated such that cell division does not occur until the cell has completed accurate DNA replication. To ensure that cells pass accurate copies of their genomes on to the next generation, evolution has overlaid the core cell cycle machinery with a series of surveillance pathways termed cell cycle checkpoints. The overall function of these checkpoints is to detect damaged or abnormally structured DNA, and to coordinate cell cycle progression with DNA repair.

Members of the phosphoinositide 3-kinase related kinases (PIKK) family of kinases are involved in cell cycle checkpoints and DNA damage repair. The PIKK family members identified to date express a carboxylterminal domain that displays significant sequence homology to the catalytic domains of phosphoinositide (PI) 3-kinases. Indeed, many, but not all of the PIKKs have been shown to possess protein serine-threonine kinase activities (McMahon et al., *Cell* 94:363–374 (1998); Vassilev et al., *Cell* 2:869–875 (1998); Grant et al., *Cell* 2:863–867 (1998); Hunter, *Cell* 83:1–4 (1995); Tibbetts and Abraham, *Signaling Networks and Cell Cycle: Themolecular Basis of Cancer and Other Diseases* pp. 267–301 (2000)). In mammalian cells, three PIKK family members, ATM, ATR, and DNA-dependent protein kinase (DNA-PK), serve as proximal signal transducers in cell-cycle checkpoint and DNA repair pathways (Abraham, *Genes & Dev.* 15:2177–2196 (2001); Durocher and Jackson, *Curr. Opin. Cell Biol.* 13:2225–231 (2001)). The critical roles of ATM in orchestrating cellular responses to various forms of stress are underscored by the diverse pathologies associated with the hereditary disorder, ataxiatelangiectasia (A-T) (Crawford, *Seminarsin Ped. Neuro.* 5:287–294 (1998); Rotman and Shiloh, *Human Mol. Gen.* 7:1555–1563 (1998); Rotman and Shiloh, *Oncogene* 18:6135–6144 (1999)). A-T patients lack functional ATM and develop symptoms including extreme sensitivity to irradiation, cerebellar degeneration, oculocutaneous telangiectasias, gonadal deficiencies, immunodeficiencies, and increased risk of cancer (Lehman and Carr, *Trends in Genet.* 11:375–377 (1995)). Fibroblasts derived from these patients show defects in cell cycle checkpoints and are defective in their response to irradiation (Painter and Young, *Proc. Natl. Acad. Sci.* (USA) 77:7315–7317 (1980)).

In general, the proteins in the PIKK family of kinases play important roles in mRNA surveillance and cell cycle progression in order to insure genetic integrity from generation to generation. Compounds that modulate PIKK polypeptides can result in altered progression through the cell cycle leading to increased or decreased cell survival. For example, a PIKK-modulatory compound can make a cell more or less susceptible to cell death in the presence of radiation or a cytotoxic agent.

All cancer cells have a dysfunctional cell cycle and continue through the cell cycle in an inappropriate manner, either by failing to respond to negative growth signals or by failing to die in response to the appropriate signal. In addition, most cancer cells lack genomic integrity and often have an increased chromosome count compared to normal cells. Therefore, compounds that inhibit cell cycle checkpoints or DNA damage repair, in combination with the cytotoxic agents, can cause cancer cell death by forcing cancer cells to progress through the cell cycle in the presence of DNA damaging agents such that they undergo events that lead to cell death.

Thus, there exists a need to identify additional members of the PIKK family of kinases and compounds that modulate these kinases. The present invention satisfies this need and provides related advantages as well.

SUMMARY OF THE INVENTION

The invention provides an isolated nucleic acid molecule having substantially the same nucleotide sequence as SEQ ID NO:1. Also provided is an isolated oligonucleotide having at least 15 contiguous nucleotides of a nucleotide sequence referenced as SEQ ID NO:11. An isolated polypeptide having substantially the same amino acid sequence as SEQ ID NO:2 is further provided as well as an antibody, or antigen binding fragment thereof, which specifically binds to an ATX polypeptide and has an amino acid sequence as referenced in SEQ ID NO:2. A method for identifying an ATX-modulatory compound is additionally provided. The method consists of measuring the level of an ATX polypeptide in the presence of a test compound, wherein a difference in the level of said ATX polypeptide in the presence of said test compound compared to in the absence of said test compound indicating that said test compound is an ATX-modulatory compound, and wherein said ATX-modulatory compound is not caffeine or wortmannin.

DETAILED DESCRIPTION OF THE INVENTION

Figure 1:
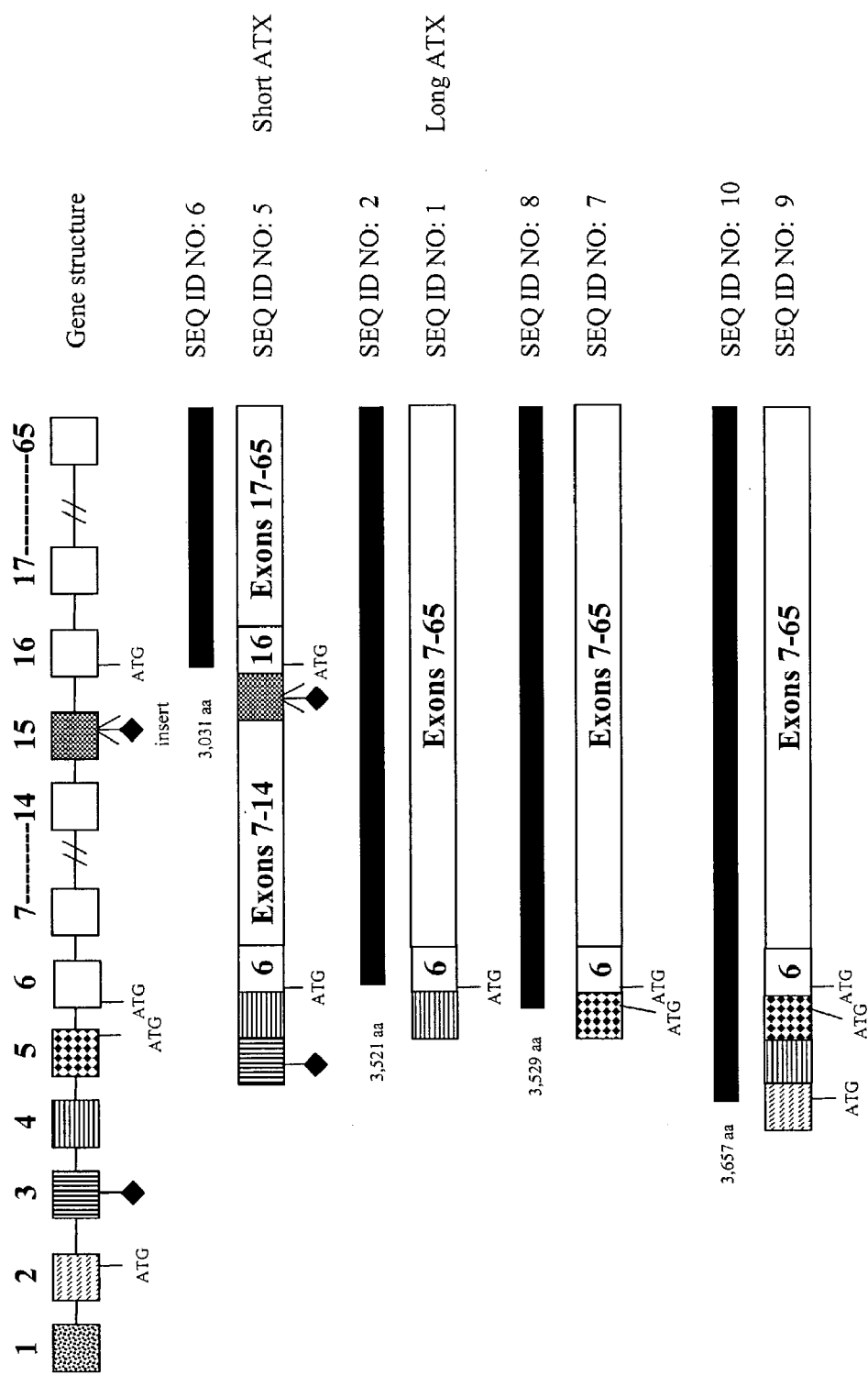
FIG. 1A shows the genomic structure of the ATX locus along with clones isolated to date. The black diamonds denote the locations of translational stop codons and black bars indicate open reading frames that give rise to various ATX polypeptides. The lines and symbols below exon 15 indicate an allelic variant that contains a 27 bp insertion having two in-frame stop codons.
FIG. 1B shows the location of N-terminal homology 1 (NH1), NH2, PI3-K catalytic (PI3-Kc), PKC-λ/ι-interacting protein (LIP), and FAT-C(C) domains. The numbers shown indicate % identity/similarity and shading highlights amino acid identity with ATX. A sequence alignment of the PI 3-Kc domains of ATX, CeSMG-1, mTOR, and ATM is shown.
FIG. 1C shows immune complex kinase assays with GST-p53$_{1-70}$, GST-p53$_{1-70}$(S15A), or with GSThUpf11019-1118 as substrates. The reaction products were immunoblotted with α-HA (lower panel).
FIG. 1D shows immune complex assays with cells or α-HA-ATX immunoprecipitates treated with wortmannin.
Figure 1:
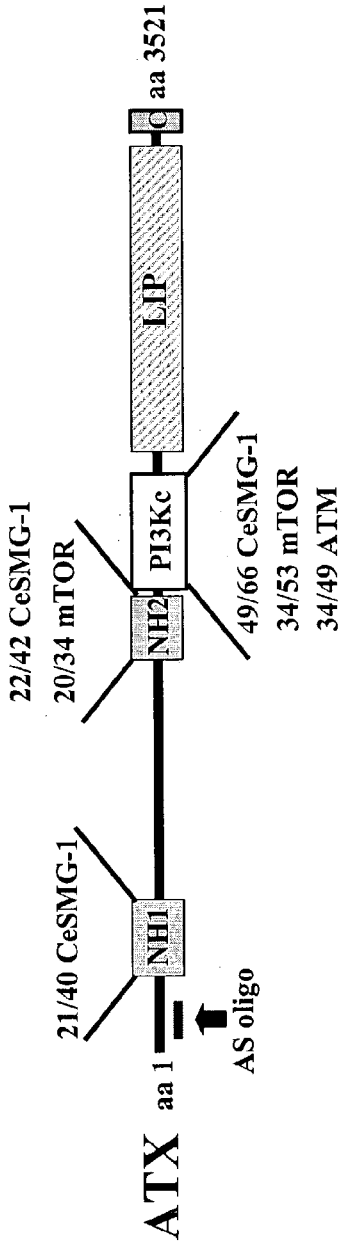
Figure 1:
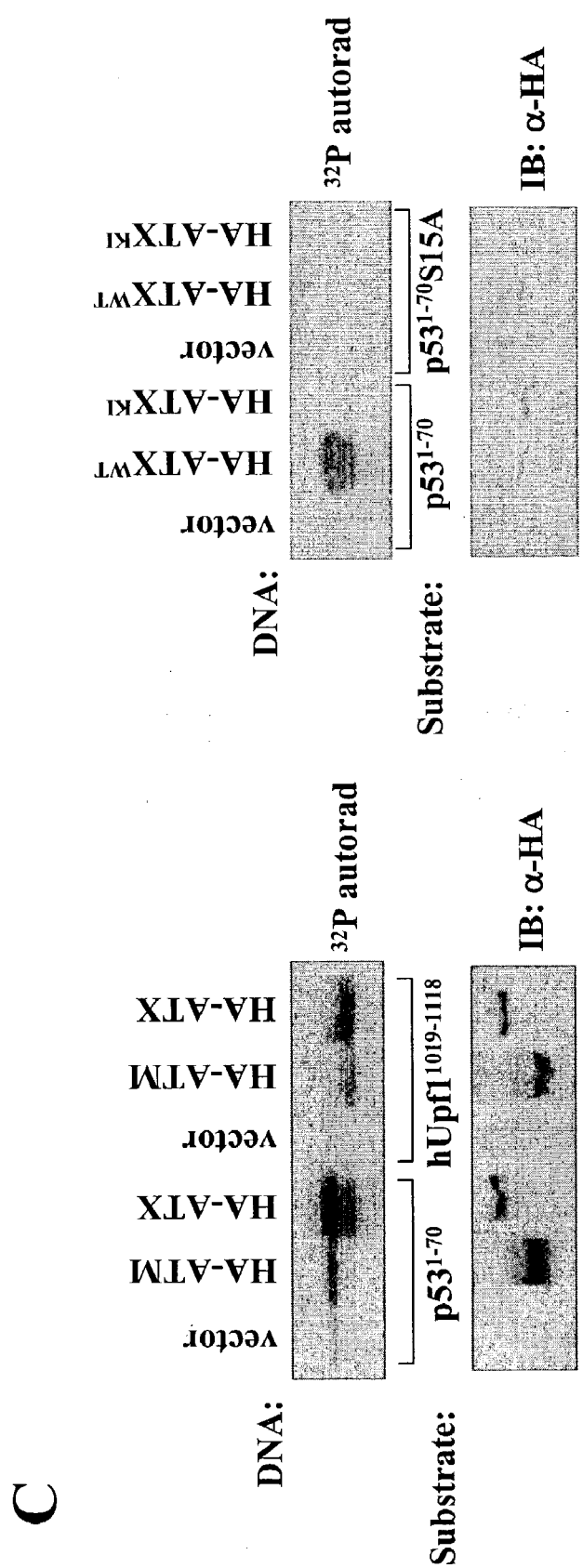
Figure 1:
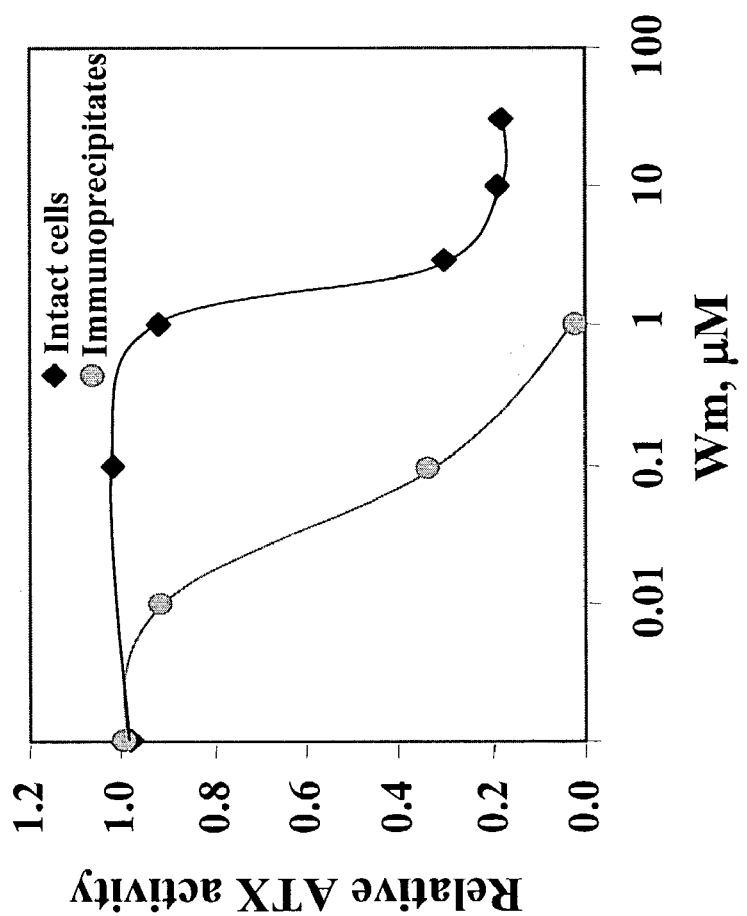

This invention is directed to isolated ATX nucleic acids and polypeptides. ATX is a novel PIKK kinase family member that participates in stress-induced p53 and cell cycle checkpoint activation in cells exposed to DNA damaging agents. In addition, ATX can activate the intrinsic non-sense mediated mRNA decay (NMD) pathway in these cells. The invention is also directed to methods of identifying ATX-modulatory compounds and using these compounds to modulate cell survival. Compounds that modulate cellular survival can be useful in the treatment of diseases characterized by excessive cell growth or excessive cell death.

In one embodiment, an expressed sequence tag (EST) with homology to a conserved region in the catalytic domains of PIKK family members was used to isolate a full-length cDNA encoding a novel member of the PIKK family, termed ATX. The ATX polypeptide was detected in both the nucleus and cytoplasm of human cells, and formed nuclear foci upon exposure to UV light. In addition, the cell cycle regulatory proteins p53 and hUpf1 were found to be phosphorylated by ATX. Furthermore, the reduction of endogenous ATX in a cell using anti-sense oligonucleotides resulted in decreased survival of cells, and decreased phosphorylation and stabilization of p53 in cells exposed to UV light. Similar to other PIKK family members, ATX activity was inhibited by wortmannin and caffeine.

As used herein, the term "ATX polypeptide" refers to a polypeptide with substantially the same amino acid sequence as that shown in SEQ ID NO:2 (human ATX). "Substantially the same amino acid sequence" is intended to mean an amino acid sequence contains a considerable degree of sequence identity or similarity, such as at least 70%, 80%, 90%, 95%, 98%, or 100% sequence identity or similarity, to a reference amino acid sequence. Substantially the same amino acid sequence includes conservative and non-conservative amino acid changes, gaps, and insertions to an amino acid sequence. Conservative and non-conservative amino acid changes, gaps, and insertions to an amino acid sequence can be compared to a reference sequence using available algorithms and programs such as the Smith-Waterman algorithm and the BLAST homology search program (Altschul et al., *J. Mol. Biol.* 215:403–410 (1990)).

It is understood that a fragment of ATX can be sufficient in order to produce an ATX activity. Activities associated with ATX include, for example, kinase activity, cell cycle checkpoint activity, and NMD activity. For example, fragments of ATX which retain substantially an activity of the entire polypeptide are included within the definition. Fragments can include, for example, amino terminal, carboxyl terminal, or internal deletions of a full length ATX polypeptide. In addition, fragments can include domains of a full length ATX polypeptide, such as for example, a kinase domain, NH1 domain, NH2 domain, or LIP domain. A fragment can contain, for example, at least about 10, 100, 500, 1,000, 1,500, 2,000, 2,500, 3,000, 3,500 or more contiguous or non-contiguous amino acid residues of a full-length ATX polypeptide. ATX polypeptide fragments include the fragments described above, but excludes fragments KIAA0421 (Accession number AB007881), KIAA0220 (Accession number D86974), and LIP (Accession number U32581), which are present in databases. Polypeptide fragments can be generated using a variety of methods. For example, polypeptide fragments can be generated using recombinant DNA methods, enzymatic cleavage, or chemical cleavage of larger polypeptides.

It is understood that limited modifications to the ATX polypeptide can be made without destroying an activity of ATX. For example, ATX is intended to include other ATX family members such as those polypeptides that are found to exhibit the above sequence homologies. Such members include, for example, homologs of ATX that can be cloned from other organisms such as monkeys, cows, rats, mice, chickens, frogs, flies or worms. The sequence of possible homologs of human ATX are available in nucleotide databases.

Various modifications of the ATX primary amino acid sequence can result in polypeptides having substantially equivalent, decreased, or enhanced function as compared to the sequence set forth as SEQ ID NO:2. Those skilled in the art recognize that such modifications can be desirable at times in order to enhance the bioactivity, bioavailability or stability of ATX, or to facilitate its synthesis or purification. Contemplated amino acid substitutions to the native sequence of ATX can include, for example, conservative changes, wherein a substituted amino acid has similar structural or chemical properties such as replacement of a polar amino acid with another polar amino acid or replacement of a charged amino acid with a similarly charged amino acid. Those skilled in the art also recognize that nonconservative changes such as replacement of an uncharged polar amino acid with an non-polar amino acid or replacement of a charged amino acid with an uncharged polar amino acid, can also be made without affecting a function of ATX. In addition, a variety of polypeptide modifications are known in the art for constraining the structure of polypeptides to enhance stability or binding (Cabezas and Satterthwait, *J. Am. Chem. Soc.* 121:3862–3875 (1999); Stanfield et al., *Structure* 7:131–142 (1999)).

A polypeptide can be modified by naturally occurring modifications such as post-translational modifications, including phosphorylation, lipidation, prenylation, sulfation, hydroxylation, acetylation, addition of carbohydrate, addition of prosthetic groups or cofactors, formation of disulfide bonds, proteolysis, assembly into macromolecular complexes, and the like. Chemical modifications of the polypeptide such as, for example, alkylation, acylation, carbamylation, and iodination can also be used to modify an ATX polypeptide. In addition, various molecules, such as other polypeptides, carbohydrates, or lipids, or small molecules can be attached to ATX including fragments of ATX. For example, ATX can contain a label moiety, a sequence such as a FLAG epitope, or be fused to another polypeptide such as a DNA binding domain.

Those skilled in the art can determine which residues and which regions of a ATX sequence are likely to be tolerant of modification and still retain an activity associated with ATX. For example, amino acid substitutions or chemical or enzymatic modifications at residues that are less well conserved between species are more likely to be tolerated than substitutions at highly conserved residues. Accordingly, an alignment can be performed among ATX sequences of various species to determine residues and regions in which modifications are likely to be tolerated (FIG. 1B). Additional guidance for determining residues and regions of ATX likely to be tolerant of modification is provided by studies of ATX fragments and variants. In addition, it can be useful to modify ATX in a way that destroys an activity associated with ATX. For example, as disclosed herein, the mutation of an aspartic acid to an alanine at conserved residue Asp-2195 in the ATX kinase domain generates a kinase-inactive version of ATX.

As used herein, the term "level" in reference to a level of an ATX nucleic acid or polypeptide refers to the amount, accumulation, or rate of synthesis of a molecule or to the amount or rate of an activity associated with the molecule. A level can be represented, for example, by the amount or synthesis rate of messenger RNA (mRNA) encoded by a gene, the amount or synthesis rate of polypeptide corresponding to a given amino acid sequence encoded by a gene, or the amount or synthesis rate of a biochemical form of a molecule accumulated in a cell, including, for example, the amount of particular post-synthetic modifications of a molecule such as a polypeptide or nucleic acid. In addition, a level can be represented, for example, by the extent of phosphorylation of a substrate molecule or by the amount of an activity such as cell cycle checkpoint activity, NMD activity or ability to induce cell death or cell survival. The term can be used to refer to an absolute amount of a molecule or activity in a sample or to a relative amount of the molecule or activity, including amounts and activities determined under steady-state or non-steady-state conditions. For example, the expression level of a molecule can be determined relative to a control component molecule in a sample.

As used herein, the term "p53" is intended to mean a polypeptide with substantially the same amino acid sequence as that shown in SEQ ID NO:4 (human p53). As described above for ATX, it is understood that p53 includes fragments of the full length p53 polypeptide. For example, the amino terminal 70 amino acids of p53 (p53 1–70) can be used in the methods of the invention as a substrate for ATX kinase activity. Also, for example, a fragment of p53 that includes the LSQE sequence located at amino acids 14 to 17 of p53 can be used as a substrate for ATX kinase activity. In addition, as described above for ATX, a p53 polypeptide includes p53 from species other than humans, and includes modifications to the p53 polypeptide including conservative and non-conservative amino acid changes, post-translational modifications and chemical modification. Also, as described for ATX, a p53 polypeptide can contain additional sequences such as a known epitope or a label moiety.

The term "specifically binds" is intended to mean the molecule will have an affinity for the target molecule that is measurably higher than its affinity for a non-specific interaction. For example, a nucleic acid can specifically bind to another nucleic acid by complementary base pairing between the nucleotides. In addition, a polypeptide such as an antibody that specifically binds another polypeptide will have an affinity for the target polypeptide or antigen that is measurably higher than its affinity for a non-specific interaction. Furthermore, a compound such as a small organic molecule can specifically bind to a target molecule with an affinity that is measurably higher than its affinity for a non-specific interaction. Binding affinity can be low or high affinity so long as the binding is sufficient to be detectable. For example, a compound can bind ATX with a binding affinity (Kd) of about $10^{-4}$ M or less, $10^{-5}$ M or less, $10^{-6}$ M or less, about $10^{-7}$ M or less, including about $10^{-8}$ M or less, such as $10^{-9}$ M or less. Several methods for detecting or measuring nucleotide, polypeptide, and other compound binding are well known in the art and disclosed herein.

As used herein, the term "compound" is intended to mean an isolated macromolecule of natural or synthetic origin that can be assayed using the methods of the invention. A compound includes, for example, a polypeptide, peptidomimetic, non-peptidyl compound, carbohydrate, lipid, an antibody or antibody fragment, a small organic or inorganic molecule, or a nucleotide sequence including an aptamer, antisense oligonucleotide, interfering RNA or ribozyme. For example, a compound can be an isolated cDNA sequence. A compound can have a known or unknown structure. A compound can be isolated or be part of a population of compounds such as a library. For example, a compound can be a small organic compound obtained from a combinatorial chemical library. A library of compounds can be a random collection of compounds or can be rationally designed based on a physical characteristic. A compound which is assayed in the methods of the invention can be called a "test compound" and if the test compound has the ability to modulate the level of ATX it can be called an "ATX-modulatory compound." One compound or more than one compound can be used in the methods of the invention.

As used herein, a "stressor agent" is any agent that can induce a stress response pathway within a cell. Several stressor agents are known in the art such as UV light, ionizing radiation, reactive oxygen intermediates, cytotoxic agents, and replicational stress imposed by DNA replication inhibitors including, for example, hydroxyurea and aphidicolin. In addition, environmental conditions such as excessive heat can induce a stress response pathway within a cell resulting in, for example, the induction of heat shock proteins. Stress response pathways include DNA repair pathways, non-sense mediated mRNA decay (NMD), heat shock pathways, the induction of apoptosis, activation of the NFkB transcription factor, activation of the stress-activated MAP kinase pathways including, for example, JNK and p38 pathways, and activation of ubiquitin-dependent proteolysis.

As used herein, the term "non-sense mediated messenger RNA (mRNA) decay (NMD)" is intended to mean the surveillance mechanism within cells whereby imperfect mRNAs that contain premature translation termination codons are preferentially degraded. These imperfect mRNAs can result in polypeptides that are nonfunctional or have altered function such as gain-of function or dominant negative mutations.

As used herein, the term an "amount effective" or "effective amount" when used in reference to a compound that modulates cell survival or growth is intended to mean an amount of the compound or molecule sufficient to increase or decrease cell survival or growth. Modulation also includes induction of cell survival or growth or complete blockage of cell survival or growth. In addition, an effective amount of a compound is intended to mean an amount of the compound that is sufficient to treat or reduce the severity of a condition in an affected subject.

The invention provides an isolated nucleic acid molecule having substantially the same nucleotide sequence as SEQ ID NO:1. In addition, the invention provides an isolated nucleic acid molecule having substantially the same nucleotide sequence as SEQ ID NO:1 where the nucleic acid molecule encodes an ATX polypeptide containing an amino acid sequence shown in SEQ ID NO:2. For example, the invention provides an isolated nucleic acid molecule containing the sequence shown in SEQ ID NO:1.

Substantially the same nucleic acid sequence is intended to mean a nucleic acid sequence contains a considerable degree of sequence identity or similarity, such as at least 70%, 80%, 90%, 95%, 98%, or 100% sequence identity or similarity, to a reference nucleic acid sequence. Substantially the same nucleic acid sequence includes nucleic acid changes, gaps, and insertions to an nucleic sequence. Nucleic acid changes, gaps, and insertions to a nucleic acid sequence can be compared to a reference sequence using available algorithms and programs such as the Smith-Waterman algorithm and the BLAST homology search program (Altschul et al., *J. Mol. Biol.* 215:403–410 (1990)).

Isolated nucleic acid molecules include DNA sequences and RNA transcripts, both sense and complementary antisense strands, including splice variants thereof encoding ATX polypeptides. An isolated nucleic acid molecule can contain a double stranded molecules or single stranded molecules, including RNA as well as coding and noncoding DNA. DNA sequences of the invention include genomic and cDNA sequences as well as wholly or partially chemically synthesized DNA sequences. Genomic DNA of the invention comprises the protein coding region for a polypeptide of the invention and includes allelic variants of the preferred nucleic acid of the invention. Genomic DNA of the invention is distinguishable from genomic DNAs encoding polypeptides other than ATX in that it includes an ATX protein coding region found in ATX-encoding cDNA of the invention. Genomic DNA of the invention can be transcribed into RNA, and the resulting RNA transcript can undergo one or more splicing events wherein one or more introns of the transcript are removed, or "spliced out." Peptide nucleic acids (PNAs) encoding a polypeptide of the invention are also contemplated (Corey, TIBTech 15:224–229 (1997)). PNAs are DNA analogs containing neutral amide backbone linkages that are resistant to DNA degradation enzymes and which bind to complementary sequences at higher affinity than analogous DNA sequences as a result of the neutral charge on the backbone of the molecule.

RNA transcripts that can be spliced by alternative mechanisms, and therefore be subject to removal of different RNA sequences but still encode an ATX polypeptide, are referred to in the art as splice variants which are embraced by the invention. Splice variants comprehended by the invention therefore are encoded by the same DNA sequences but arise from distinct mRNA transcripts. Allelic variants are known in the art to be modified forms of a wild type gene sequence, the modification resulting from recombination during chromosomal segregation or exposure to conditions which give rise to genetic mutation. Allelic variants, like wild type genes, are inherently naturally occurring sequences (as opposed to non-naturally occurring variants which arise from in vitro manipulation).

An allelic variant of ATX is disclosed herein as SEQ ID NO:5. This form of ATX is produced as the result of allelic variation in exon 15 which leads to the insertion of 27 nucleotides beginning at nucleotide 1427 (FIG. 1A). This sequence alteration causes the insertion of two in-frame stop codons and the use of the next available ATG codon in exon 16 as the translational stat site, resulting in an amino-terminally truncated or short form of ATX. A form of ATX that is similar to the long form of ATX disclosed herein (SEQ ID NO:1) is referenced as SEQ ID NO:7. This form of ATX has exon 5 spliced to exon 6 which results in a different N-terminus and 8 additional amino acids in the resulting polypeptide (FIG. 1A). In the experiments disclosed herein clones that were isolated with exon 5 frequently contained exon 3 which place an in-frame stop codon at the 3' end of this DNA (Example 1). The longest form of ATX (SEQ ID NO:9) was isolated, however the exon 3 associated stop codon was present in this transcript as well.

In addition to genomic DNA, isolated nucleic acids include cDNA. cDNA can be obtained through reverse transcription of an RNA nucleic acid encoding ATX, followed by second strand synthesis of a complementary strand to provide a double stranded DNA. In addition, nucleic acid molecules can be chemically synthesized meaning produced by purely chemical, as opposed to enzymatic, methods. Wholly chemically synthesized DNA sequences are produced entirely by chemical means, and partially synthesized DNAs are those where only portions of the resulting DNA were produced by chemical means.

ATX nucleic acid molecules include homologs of the human ATX sequence. Species homologs in general share at least 50%, at least 60%, at least 70%, at least 80%, at least 90%, at least 95% or at least 99% homology with a human DNA of the invention. ATX nucleic acids include species homologs of the human ATX sequence, but exclude a mouse EST that contains a sequence homologous to the 3' part of ATX is (GenBank Accession Number BC024431) and a Macaca fascicularis brain cDNA clone Qf1A-15747 (accession number AB056380).

The invention also provides anti-sense oligonucleotides based on SEQ ID NO:1. For example, the invention provides an isolated oligonucleotide having at least 15 contiguous nucleotides of the nucleotide sequence 5'-AGCAAGCTC-CCTCCTGTCTC-31 (SEQ ID NO:11). The oligonucleotide shown in SEQ ID NO:11 is an ATX anti-sense oligonucleotide that has been shown herein to decrease the level of ATX in a cell (Example 5).

Nucleic acids of the invention also permit identification and isolation of nucleic acid encoding related ATX polypeptides by well known techniques including Southern hybridization, Northern hybridization, and polymerase chain reaction (PCR). Examples of related nucleic acids include human and non-human nucleic acid sequences, including allelic variants, as well as nucleic acids encoding polypeptides homologous to ATX and structurally related polypeptides sharing one or more biological, immunological, or physical properties of ATX.

The invention provides a method for detecting an ATX nucleic acid molecule in a sample, by contacting the sample with an ATX nucleic acid molecule under conditions that allow specific hybridization to ATX nucleic acid, and detecting the specific hybridization. In addition, the invention provides a method for detecting an ATX nucleic acid molecule in a sample, by contacting a nucleic acid fraction derived from the sample with a PCR primer pair set under conditions that allow amplification of an ATX nucleic acid, and detecting amplified ATX nucleic acid. Kits for detecting ATX nucleic acids based on these methods are provided as well.

Fragments of ATX nucleic acid molecules are useful in the invention, for example, as probes for detection of full length or other fragment ATX nucleic acids. A nucleic acid fragment can include for example 5', 3', or internal deletions of a full length ATX nucleic acid sequence. For example, the invention provides an isolated ATX nucleic acid molecule as referenced in SEQ ID NO:5. Alternatively, the invention provides ATX nucleic acid fragments other than the fragment as referenced in SEQ ID NO:5. For example, the invention provides ATX nucleic acid fragments that contain carboxyl terminal deletions of a full length ATX polypeptide. In addition, fragments can include domains of a full length ATX nucleic acid sequence, for example, a kinase domain, NH1 domain, NH2 domain, or LIP domain. A fragment can contain, for example, at least about 10, 100, 1,000, 2,500, 5,000, 7,500, 10,000, 12,500 or more contiguous or non-contiguous nucleic acid residues of a full-length ATX nucleic acid sequence. ATX nucleic acid fragments include the fragments described above, but excludes fragments KIAA0421 (Accession number AB007881), KIAA0220 (Accession number D86974), and LIP (Accession number U32581), which are present in databases. One or more fragment nucleic acids can be included in kits that are used to detect the presence of a nucleic acids encoding ATX, or used to detect variations in a nucleic acid sequence encoding ATX, including polymorphisms, for example, single nucleotide polymorphisms.

The nucleic acids of the invention can contain heterologous sequences that are not part of the ATX-encoding sequences in nature. The heterologous nucleic acid sequence can be separated from the ATX-coding sequence by an encoded cleavage site that will permit removal of non-ATX polypeptide sequences from the expressed fusion protein. Heterologous nucleic acids sequences can include sequences encoding epitopes, such as poly-histidine sequences, FLAG tags, glutathione-S-transferase, thioredoxin, and maltose binding protein domains, that facilitate purification of the fusion protein. In addition heterologous nucleic acids can encode domains, such as leucine zipper motifs, that promote multimer formation between the fusion protein and itself or other proteins or immunoglobulins or fragments thereof that can enhance circulatory half-life of the encoded protein.

The nucleic acid molecules of the invention also include DNA sequences encoding ATX species that hybridize under highly or moderately stringent conditions to the non-coding strand, or complement, of the nucleic acid in SEQ ID NO: 1. ATX-encoding nucleic acids of the invention include a) the nucleic acid sequence set out in SEQ ID NO: 1; b) nucleic acids encoding a polypeptide encoded by the nucleic acid of (a), and c) nucleic acids that hybridize to the complement of the nucleic acids of (a) or (b) under moderately or highly stringent conditions. Exemplary high stringency conditions include a final wash in 0.2×SSC/0.1% SDS at 65° C. to 75° C., and exemplary moderate stringency conditions include a final wash at 2× to 3×SSC/0.1% SDS at 65° C. to 75° C. It is understood in the art that conditions of equivalent stringency can be achieved through variation of temperature and buffer, or salt concentration as described in Ausubel, et al. (Eds.), Protocols in Molecular Biology, John Wiley & Sons (1994). Modifications in hybridization conditions can be empirically determined or precisely calculated based on the length and the percentage of guanosine/cytosine (GC) base pairing of the probe.

The invention also provides a vector containing the isolated ATX nucleic acid molecules described above. For example, the invention provides a vector containing an isolated nucleic acid molecule having substantially the same nucleotide sequence as SEQ ID NO:1.

Vectors include autonomously replicating recombinant expression constructs such as plasmid and viral DNA vectors. The invention includes vectors where ATX-encoding nucleic acids are operatively linked to an endogenous or exogenous promoter, enhancer, or operator sequence and a transcription terminator sequence. Promoter and enhancer sequences are generally selected for the ability to increase gene expression, while operator sequences are generally selected for the ability to regulate gene expression. It is understood in the art that the choice of host cell is relevant to selection of an appropriate regulatory sequence. Vectors used in the invention can also include sequences encoding one or more selectable markers that permit identification of host cells bearing the construct. Vectors can also include sequences that facilitate homologous recombination in a host cell.

Suitable vectors for expression in prokaryotic or eukaryotic cells are well known to those skilled in the art (see, for example, Ausubel et al., supra, 1999). Vectors useful for expression in eukaryotic cells can include, for example, regulatory elements including the SV40 early promoter, the cytomegalovirus (CMV) promoter, the mouse mammary tumor virus (MMTV) steroid-inducible promoter, Moloney murine leukemia virus (MMLV) promoter, and the like. A vector can include, for example, viral vectors such as a bacteriophage, a baculovirus or a retrovirus; cosmids or plasmids; and, particularly for cloning large nucleic acid molecules, bacterial artificial chromosome vectors (BACs)

and yeast artificial chromosome vectors (YACs). Such vectors are commercially available, and their uses are well known in the art. One skilled in the art will know or can readily determine an appropriate promoter for expression in a particular host cell. For example, as disclosed herein, the long form of ATX can be sub-cloned into pcDNA 3.1 with an HA tag and transfected using Fugene 6 into human embryonic kidney 293T cells (Example 2 and Example 5).

Vectors useful for expression of an ATX polypeptide can contain a regulatory element that provides tissue specific or inducible expression of an operatively linked nucleic acid. Such inducible systems, include, for example, tetracycline inducible system (Gossen & Bizard, *Proc. Natl. Acad. Sci. USA*, 89:5547–5551 (1992); Gossen et al., *Science*, 268:1766–1769 (1995); Clontech, Palo Alto, Calif.)); metallothionein promoter induced by heavy metals; insect steroid hormone responsive to ecdysone or related steroids such as muristerone (No et al., *Proc. Natl. Acad. Sci. USA*, 93:3346–3351 (1996); Yao et al., *Nature*, 366:476–479 (1993); Invitrogen, Carlsbad, Calif.); mouse mammory tumor virus (MMTV) induced by steroids such as glucocortocoid and estrogen (Lee et al., *Nature*, 294:228–232 (1981); and heat shock promoters inducible by temperature changes.

In addition, viral vectors such as retroviral, adenovirus, adeno-associated virus, lentivirus, and herpesvirus vectors can be used to express ATX polypeptides into a cell. Viral based systems provide the advantage of being able to introduce relatively high levels of a heterologous nucleic acid into a variety of cells. Additionally, such viruses can introduce heterologous DNA into nondividing cells. Viral vectors include, for example, Herpes simplex virus vectors (U.S. Pat. No. 5,501,979), Vaccinia virus vectors (U.S. Pat. No. 5,506,138), Cytomegalovirus vectors (U.S. Pat. No. 5,561,063), Modified Moloney murine leukemia virus vectors (U.S. Pat. No. 5,693,508), adenovirus vectors (U.S. Pat. Nos. 5,700,470 and 5,731,172), adeno-associated virus vectors (U.S. Pat. No. 5,604,090), constitutive and regulatable retrovirus vectors (U.S. Pat. Nos. 4,405,712; 4,650,764 and 5,739,018, respectively), papilloma virus vectors (U.S. Pat. Nos. 5,674,703 and 5,719,054), and the like.

The invention further provides a host cell containing an ATX-encoding vector as described above. For example, the invention provides a host cell that contains a vector which contains an isolated nucleic acid molecule having substantially the same nucleotide sequence as SEQ ID NO:1. Host cells include prokaryotic and eukaryotic cells. Nucleic acids of the invention can be introduced into the host cell as part of a circular plasmid, or as linear DNA having an isolated protein coding region or a viral vector. Methods for introducing DNA into the host cell are well known in the art and include transformation, transfection, electroporation, nuclear injection, or fusion with carriers such as liposomes, micelles, ghost cells, protoplasts, and other transformed cells. Detailed procedures for these methods can be found in Sambrook et al., *Molecular Cloning: A Laboratory Manual* (Cold Spring Harbor Laboratory Press, 1989) and the references cited therein). Expression systems of the invention include bacterial, yeast, fungal, plant, insect, invertebrate, and mammalian cells systems.

Useful mammalian expression vectors and methods of introducing such vectors into mammalian cells either ex vivo or in vivo, for expression of the encoded polypeptide, are well known in the art. For example, a plasmid expression vector can be introduced into a cell by calcium-phosphate mediated transfection, DEAE-Dextran-mediated transfection, lipofection, polybrene- or polylysine-mediated transfection, electroporation, or by conjugation to an antibody, gramacidin S, artificial viral envelopes or other intracellular carriers. A viral expression vector can be introduced into a cell in an expressible form by infection or transduction, for example, or by encapsulation in a liposome.

The invention also provides a method of producing an ATX polypeptide by a) growing the host cell described above under conditions appropriate for expression of the ATX polypeptide, and b) isolating the ATX polypeptide from the host cell or host cell growth medium. This method can be used to produce ATX polypeptide, for example, as a source of immunogen for the development of antibodies specifically reactive with ATX.

ATX polypeptide isolated from the cells or from the medium in which the cells are grown by purification methods known in the art, for example, conventional chromatographic methods including immunoaffinity chromatography, receptor affinity chromatography, hydrophobic interaction chromatography, lectin affinity chromatography, size exclusion filtration, cation or anion exchange chromatography, high pressure liquid chromatography (HPLC), reverse phase HPLC, and the like. Still other methods of purification include those wherein the desired protein is expressed and purified as a fusion protein having a specific tag, label, or chelating moiety that is recognized by a specific binding partner or agent. The purified protein can be cleaved to yield the desired protein, or be left as an intact fusion protein.

The DNA sequence information provided by the present invention also makes possible the development through, for example, homologous recombination or "knock-out" strategies of animals that fail to express functional ATX or that express a variant of ATX (Capecchi, *Science* 244:1288–1292 (1989)). Such animals are useful as models for studying the in vivo activities of ATX and modulators of ATX.

The invention provides an isolated polypeptide containing substantially the same amino acid sequence as SEQ ID NO:2. For example, the invention provides a polypeptide containing an amino acid sequence as referenced in SEQ ID NO:2. The sequence shown in SEQ ID NO:2 corresponds to the "long form" of ATX (FIG. 1A).

As described further above, an isolated ATX polypeptide includes conservative and non-conservative amino acid changes to the sequence shown in SEQ ID NO:2. In addition, an isolated ATX polypeptide includes species homologs and fragments of ATX. For example, the invention provides an isolated ATX polypeptide fragment as referenced in SEQ ID NO:6. Alternatively, the invention provides ATX polypeptide fragments other than the fragment as referenced in SEQ ID NO:6. For example, the invention provides ATX polypeptide fragments that contain carboxyl terminal deletions of a full length ATX polypeptide. Furthermore, an ATX polypeptide can contain polypeptide modifications or heterologous sequences such as an epitope tag. Polypeptides of the invention can be isolated from natural cell sources, chemically synthesized, or produced by recombinant procedures involving the host cells of the invention.

The invention provides an antibody, or antigen binding fragment thereof, which specifically binds to an ATX polypeptide containing an amino acid sequence as referenced in SEQ ID NO:2. Antibodies include, for example, monoclonal and polyclonal antibodies, single chain antibodies, chimeric antibodies, bifunctional or bispecific antibodies, humanized antibodies, human antibodies, and complementary determining region (CDR)-grafted antibodies, including compounds which include CDR or antigen-binding sequences, which specifically bind to a polypeptide of the invention. Antibody fragments, including Fab, Fab', F(ab')$_2$, and Fv, are also provided by the invention. Screening assays to determine binding specificity or exclusivity of an antibody of the invention are well known in the art (see Harlow et al. (Eds), Antibodies A Laboratory Manual; Cold Spring Harbor Laboratory; Cold Spring Harbor, N.Y. (1988)).

Antibodies that recognize and bind fragments of the ATX polypeptides of the invention are also contemplated, provided that the antibodies specifically bind ATX polypeptides. As with antibodies that are specific for full length ATX polypeptides, antibodies of the invention that recognize ATX fragments are those which can distinguish ATX polypeptides from other PIKK polypeptides despite inherent sequence identity, homology, or similarity found in the family of proteins.

Antibodies of the invention can be produced using any method well known in the art, using any polypeptide, or immunogenic fragment thereof, of the invention. Immunogenic polypeptides can be isolated from natural sources, from recombinant host cells, or can be chemically synthesized. For example, as disclosed herein, antibodies specifically reactive with ATX were generated using glutathione S-transferase (GST) fusion proteins containing ATX amino acids 2281–2339 (anti-ATX-Ab-1) or amino acids 1691–1790 (anti-ATX-Ab-2) (Example 2). Polypeptide of the invention can also be conjugated to a hapten such as keyhole limpet hemocyanin (KLH) in order to increase immunogenicity. Methods for synthesizing such peptides are known in the art, for example, as in R. P. Merrifield, J. *Amer. Chem. Soc.* 85: 2149–2154 (1963); J. L. Krstenansky, et al., *FEBS Lett.* 211:10 (1987). Antibodies to a polypeptide of the invention can also be prepared through immunization using a nucleic acid of the invention, as described in Fan et al., *Nat. Biotech.* 17:870–872 (1999). DNA encoding a polypeptide can be used to generate antibodies against the encoded polypetide following topical administration of naked plasmid DNA or following injection, for example, intramuscular injection, of the DNA.

Non-human antibodies can be humanized by any methods known in the art. In one method, the non-human CDRs are inserted into a human antibody or consensus antibody framework sequence. Further changes can then be introduced into the antibody framework to modulate affinity or immunogenicity. Antibodies of the invention further include plastic antibodies or molecularly imprinted polymers (MIPs) (Haupt and Mosbauch, *TIBTech* 16:468–475 (1998)). Antibodies of this type can be useful in immunoaffinity separation, chromatography, solid phase extraction, immunoassays, for use as immunosensors, and for screening chemical or biological libraries. Advantages of antibodies of this type are that no animal immunization is required, the antibodies are relatively inexpensive to produce, they are resistant to organic solvents, and they are reusable over long period of time.

The invention provides a method for detecting ATX polypeptide in a sample by contacting the sample with an ATX antibody under conditions that allow specific binding of the antibody to the polypeptide and detecting the bound antibody. Antibodies of the invention can also include one or more labels that permit detection of the antibody and antibody binding. Labels can include, for example, radioactivity, fluorescence (or chemiluminescence), one of a high affinity binding pair (such as biotin/avidin), enzymes, or combinations of one or more of these labels. Antibodies of the invention are also useful, for example, for therapeutic purposes (by modulating activity of ATX), diagnostic purposes to detect or quantitate ATX, as well as purification of ATX. Kits containing an antibody or antibodies of the invention are also provided.

The DNA and amino acid sequence information provided by the present invention also makes possible the systematic analysis of the structure and function of ATX. DNA and amino acid sequence information for ATX also permits identification of compounds with which an ATX polypeptide or nucleic acid will interact. Methods to identify compounds that bind to ATX include solution assays, in vitro assays where ATX polypeptides are immobilized, and cell based assays. Identification of compounds that bind ATX polypeptides provides potential targets for therapeutic or prophylactic intervention in pathologies associated with ATX biological activity.

The invention provides a method for identifying a compound that specifically binds to an ATX polypeptide of the invention, by a) contacting the ATX polypeptide with a compound, and b) determining specific binding of the compound to said ATX polypeptide. As described further above, the term compound includes macromolecules of natural or synthetic origin including, for example, a polypeptide, peptidomimetic, non-peptidyl compound, carbohydrate, lipid, and antibody or antibody fragment, a small organic or inorganic molecule, or a nucleic acid including an aptamer.

Identification of compounds that bind the ATX polypeptide can be achieved by isolating the ATX polypeptide/binding complex, and separating the ATX polypeptide from the binding compound. An additional step of characterizing the physical, biological, or biochemical properties of the binding compound can also be performed. In one embodiment, the ATX polypeptide/binding complex can be isolated using a antibody immunospecific for either the ATX polypeptide or the candidate binding compound. In another embodiment, the complex can be isolated using a second binding compound that interacts with either the ATX polypeptide or the candidate binding compound. In still another embodiment, either the polypeptide ATX or the candidate binding compound comprises a label or tag that facilitates its isolation, and methods of the invention to identify binding compounds include a step of isolating the ATX polypeptide/binding complex through interaction with the label or tag. An exemplary tag of this type is a polyhistidine sequence, generally around six histidine residues, that permits isolation of a compound so labeled using nickel chelation. Other labels and tags, such as the FLAG tag, thioredoxin, and GST, each of which is well known in the art.

An in vitro assay can be performed where the ATX polypeptide can be immobilized and then contacted with a candidate binding compound. In an alternative embodiment, the candidate binding compound can be immobilized and binding of the ATX polypeptide is detected. Immobilization can be accomplished using any of the methods well known in the art, including covalent bonding to a support, a bead, or a chromatographic resin, as well as non-covalent, high affinity interaction such as antibody binding, or use of streptavidin/biotin binding wherein the immobilized compound includes a biotin or streptavidin moiety. Detection of binding can be accomplished, for example, (i) using a radioactive label on the compound that is not immobilized, (ii) using of a fluorescent label on the non-immobilized compound, (iii) using an antibody immunospecific for the non-immobilized compound, (iv) using a label on the non-immobilized compound that excites a fluorescent support to which the immobilized compound is attached, as well as other techniques well known in the art.

A cell based assay that can be used in the method of the invention for detecting an ATX binding compound is a yeast or mammalian two-hybrid assay (Fields and Song, *Nature* 340:245–246 (1989); Fields, *Methods: A Companion to Methods in Enzymology* 5:116–124 (1993); U.S. Pat. No. 5,283,173 issued Feb. 1, 1994 to Fields, et al.). Modifications and variations on the two-hybrid assay have previously been described (Colas and Brent, *TIBTECH* 16:355–363 (1998)).

The invention also provides a method for identifying an ATX-modulatory compound by measuring the level of an ATX polypeptide in the presence of a test compound, where a difference in the level of the ATX polypeptide in the presence of the test compound compared to in the absence of the test compound indicating that the test compound is an ATX-modulatory compound. In addition, the invention provides a method for identifying an ATX-modulatory compound by measuring the level of an ATX polypeptide in the presence of a test compound, where a difference in the level of the ATX polypeptide in the presence of the test compound compared to in the absence of the test compound indicating that the test compound is an ATX-modulatory compound, and where the ATX-modulatory compound is not caffeine or wortmannin. The ATX-modulatory compound can decrease or increase the level of ATX polypeptide.

Agents that modulate, for example, increase, decrease, or block the level of ATX can be identified by incubating a test compound with an ATX polypeptide or nucleic acid and determining the effect of the test compound on ATX activity or expression. The level of ATX can include the expression level of ATX or an activity level of ATX. The selectivity, or specificity, of an ATX-modulatory compound can be evaluated by comparing its effects on ATX or an ATX-encoding nucleic acids to its effect on other polypeptides or compounds. Cell based methods, such as two-hybrid assays to identify DNAs encoding binding compounds and split hybrid assays to identify inhibitors of ATX polypeptide interaction with a known binding polypeptide, as well as in vitro methods, including assays where an ATX polypeptide, ATX-encoding nucleic acid, or a binding compound are immobilized, and solution assays are included in this method of the invention.

As understood by those of skill in the art, assay methods for identifying compounds that modulate an activity generally require comparison to a "control." One type of a control is a reaction or cell that is treated substantially the same as the test reaction or cell exposed to the compound, with the distinction that the control reaction or cell is not exposed to the compound.

As disclosed herein, the compounds wortmannin and caffeine can modulate (inhibit) the level of ATX (Example 3 and Example 7). Wortmannin is known to inhibit ATM kinase and is an irreversible inhibitor of PIKKs. Caffeine is a known inhibitor of the G2 cell cycle checkpoint. As disclosed herein, caffeine reversed the accumulation of G2/M phase cells induced by ATX anti-sense treatment, indicating that ATX deficiency can trigger the activation of a caffeine-sensitive G2 checkpoint (Example 7).

The invention provides a method for identifying an ATX-modulatory compound where the level of ATX polypeptide is measured by determining the kinase activity of the ATX polypeptide. The kinase activity of ATX can be measured using methods well known in the art such as kinase assays and immune complex kinase assays as performed herein in Example 3. These assays contain ATX, a substrate, and a suitable buffer including [g-32 P]ATP and $Mn^{2+}$. Phosphorylated substrates can also be detected using phospho-specific antibodies.

In addition, the invention provides a method for identifying an ATX-modulatory compound where the level of ATX polypeptide is measured by determining the phosphorylation of a p53 polypeptide or fragment. For example, a GST fusion protein containing the first 70 amino acids of p53 ($GST-p53_{1-70}$) can be used as a substrate to measure the level of ATX polypeptide by its kinase activity (Example 3). In addition to p53, the phosphorylation of hUpf1, a helicase, can be used to measure the level of ATX polypeptide (Example 3).

The invention also provides a method for identifying an ATX-modulatory compound where the level of ATX polypeptide is measured by determining the level of p53 polypeptide accumulation. As shown herein, a decrease in ATX polypeptide, such as results from the use of an anti-sense oligonucleotide, leads to a reduction in p53 polypeptide accumulation (Example 6). Thus, the level of p53 can be used as a measure of ATX polypeptide level.

The invention further provides a method for identifying an ATX-modulatory compound where the level of ATX polypeptide is measured by determining the level of non-sense mediated messenger RNA (mRNA) decay (NMD). NMD is a surveillance mechanism within cells whereby imperfect mRNAs that contain premature translation termination codons are preferentially degraded. As disclosed herein, treatment of cells with an ATX anti-sense oligonucleotide, which reduced endogenous ATX expression, demonstrated that ATX expression is required for maximal NMD activity (Example 9). The level of NMD is correlated to the level of ATX in the cell and so the level of NMD can be used as a measure of ATX polypeptide level.

ATX-modulatory compounds can be identified that decrease or increase the level of ATX polypeptide or nucleic acid. A decrease in the level of ATX can be a partial reduction or a total blockage of the level of ATX, and an increase in the level of ATX can be a partial increase or an induction of the level of ATX from a previously undetectable level. For example, an ATX-modulatory compound can increase the level of NMD activity in a cell. It can be desirable to increase the level of NMD activity in a cell in order to protect the cell from deleterious gain-of-function mutations caused by truncated polypeptides resulting from the translation of imperfect mRNAs that contain premature translation termination. Alternatively, an ATX-modulatory compound can decrease the level of NMD activity in a cell. It can be desirable to decrease the level of NMD activity in a cell in some cases where the truncated polypeptide does not have a deleterious effect but instead retains some activity that can compensate for the normal gene function.

ATX-modulatory compounds can include, for example, antibodies and other proteins or peptides which specifically bind to an ATX polypeptide or an ATX-encoding nucleic acid, oligonucleotides which bind to an ATX polypeptide or an ATX gene sequence, and other non-peptide compounds, for example, isolated or synthetic organic and inorganic molecules, which specifically react with an ATX polypeptide or underlying nucleic acid. ATX-modulatory compounds of the invention can interact specifically or exclusively to an ATX polypeptide or ATX-encoding nucleic acid, however, modulators that interact with an ATX polypeptide or an ATX-encoding nucleic acid with higher affinity or avidity compared to other compounds are also included in the invention. Mutant ATX polypeptides which affect the enzymatic activity or cellular localization of the wild-type ATX polypeptides are also contemplated by the invention. Targets for the development of ATX-modulatory compounds can include, for example: (1) regions of an ATX polypeptide which contact other proteins, (2) regions that localize an ATX polypeptide within a cell, (3) regions of an ATX polypeptide which bind substrate, (4) allosteric regulatory binding site(s) of an ATX polypeptide, (5) phosphorylation site(s) of an ATX polypeptide as well as other regions of the protein where covalent modification regulates biological activity and (6) regions of an ATX polypeptide which are involved in multimerization of subunits. Still other ATX-modulatory compounds include those that recognize specific ATX-encoding and regulatory nucleic acid sequences. ATX-modulatory compounds that modulate the level of ATX can be therapeutically useful in treatment of diseases and physiological conditions in which ATX is known or suspected to be involved.

Methods of the invention to identify ATX-modulatory compounds include variations on any of the methods described above to identify ATX binding compounds, the variations including techniques where a binding compound has been identified and the binding assay is carried out in the presence and absence of a candidate ATX-modulatory compound. A modulatory compound is identified in those instances where the level of binding between an ATX polypeptide and a binding compound changes in the presence of the candidate modulatory compound compared to the level of binding in the absence of the candidate modulatory compound. An ATX-modulatory compound that increases binding between an ATX polypeptide and the binding compound is described as an enhancer or activator, and a modulatory compound that decreases binding between the ATX polypeptide and the binding compound is described as an inhibitor. In vitro methods of the invention are amenable to high throughput assays as described below.

In addition to the assays described above which can be modified to identify binding compounds, other methods are contemplated to identify modulatory compounds. In one embodiment, methods of the invention can include use of the split hybrid assay as generally described in WO98/13502 and variations on this method as described in WO95/20652.

The methods of the invention can also utilize high throughput screening (HTS) assays to identify compounds that interact with or inhibit biological activity of an ATX polypeptide. HTS assays permit screening of large numbers of compounds in an efficient manner. Cell-based HTS systems include melanophore assays, yeast-based assay systems, and mammalian cell expression systems (Jayawickreme and Kost, Curr. Opin. Biotechnol. 8:629–634 (1997)). Automated (robotic) and miniaturized HTS assays are also embraced (Houston and Banks, Curr. Opin. Biotechnol. 8:734–740 (1997)). HTS assays are designed to identify "hits" or "lead compounds" having the desired property, from which modifications can be designed to improve the desired property. Chemical modification of the "hit" or "lead compound" is often based on an identifiable structure/activity relationship (SAR) between the "hit" and the ATX polypeptide.

There are a number of different libraries used for the identification of small molecule modulators, including, (1) chemical libraries, (2) natural product libraries, and (3) combinatorial libraries comprised of random peptides, oligonucleotides or organic molecules.

Chemical libraries consist of structural analogs of known compounds or compounds that are identified as "hits" or "leads" via natural product screening. Natural product libraries are collections from microorganisms, animals, plants, or marine organisms which are used to create mixtures for screening by, for example, (1) fermentation and extraction of broths from soil, plant or marine microorganisms or (2) extraction of plants or marine organisms. Natural product libraries include polyketides, non-ribosomal peptides, and variants (non-naturally occurring) variants thereof. Combinatorial libraries are composed of large numbers of peptides, oligonucleotides or organic compounds as a mixture. They can be prepared by traditional automated synthesis methods, PCR, cloning or proprietary synthetic methods. Libraries that can be utilized by the invention include peptide and oligonucleotide combinatorial libraries. Still other libraries of interest include protein, peptidomimetic, multiparallel synthetic collection, recombinatorial, and polypeptide libraries. For a review of combinatorial chemistry and libraries created therefrom, see Myers, *Curr. Opin. Biotechnol.* 8:701–707 (1997). Identification of modulators through use of the various libraries described herein permits modification of the candidate "hit" (or "lead") to optimize the capacity of the "hit" to modulate activity.

Anti-sense oligonucleotides which recognize and hybridize to nucleic acid encoding ATX can also be utilized by the methods of the invention. Full length and fragment anti-sense oligonucleotides are provided. One skilled in the art of will appreciate that fragment anti-sense molecules of the invention include (i) those which specifically or exclusively recognize and hybridize to ATX-encoding RNA (as determined by sequence comparison of DNA encoding ATX to DNA encoding other molecules) as well as (ii) those which recognize and hybridize to RNA encoding variants of the ATX family of proteins. Antisense oligonucleotides that hybridize to RNA encoding other members of the PIKK family of proteins are also identifiable through sequence comparison to identify characteristic, or signature, sequences for the family of molecules. Identification of sequences unique to ATX-encoding nucleic acids, as well as sequences common to the family of PIKK-encoding nucleic acids, can be deduced through use of any publicly available sequence database, or through use of commercially available sequence comparison programs. After identification of the desired sequences, isolation through restriction digestion or amplification using any of the various polymerase chain reaction techniques well known in the art can be performed. Anti-sense oligonucleotides can be used for regulating expression of ATX by those cells expressing ATX mRNA. Antisense molecules are generally from about 5 to about 100 nucleotide in length, and preferably are about 10 to 20 nucleotides in length. Antisense nucleic acids capable of specifically binding to ATX expression control sequences or ATX RNA are introduced into cells, for example, by a viral vector or colloidal dispersion system such as a liposome.

The anti-sense nucleic acid binds to the ATX-encoding target nucleotide sequence in the cell and prevents transcription or translation of the target sequence. Phosphorothioate and methylphosphonate anti-sense oligonucleotides are specifically contemplated for therapeutic use by the invention. The anti-sense oligonucleotides may be further modified by poly-L-lysine, transferrin polylysine, or cholesterol moieties at their 5' end.

The invention also provides methods to modulate ATX expression through the use of RNA interference (RNAi) (Brummelkamp et al., *Science* 296:550–553 (2002); Elbashir et al., *Nature* 411:494–498 (2002)). RNAi is a process of sequence-specific gene silencing by post-transcriptional RNA degradation, which is initiated by double-stranded RNA (dsRNA) homologous in sequence to the silenced gene. A double-stranded RNA (dsRNA) that is used for RNAi is referred to herein as an "interfering RNA." For example, a suitable dsRNA for RNAi can contain sense and antisense strands of about 21 contiguous nucleotides corresponding to the gene to be targeted that form 19 RNA base pairs, leaving overhangs of two nucleotides at each 3' end (Elbashir et al., supra; Bass, *Nature* 411:428–429 (2001); Zamore, *Nat. Struct. Biol.* 8:746–750 (2001)). dsRNAs of about 25–30 nucleotides have also been used successfully for RNAi (Karabinos et al., *Proc. Natl. Acad. Sci.* 98:7863–7868 (2001). dsRNA can be synthesized in vitro and introduced into a cell by methods known in the art. By using RNAi methods, the targeted RNA is degraded, and translation of the target polypeptide is decreased or abolished.

The invention further provides methods to modulate ATX expression through the use of ribozymes (Gibson and Shillitoe, *Mol. Biotech.* 7:125–137 (1997)). Ribozyme technology can be utilized to inhibit translation of ATX mRNA in a sequence specific manner through (i) the hybridization of a complementary RNA to a target mRNA and (ii) cleavage of the hybridized mRNA through nuclease activity inherent to the complementary strand. Ribozymes can be identified by empirical methods or be specifically designed based on accessible sites on the target mRNA (Bramlage, et al., *Trends in Biotech* 16:434–438 (1998)). Delivery of ribozymes to target cells can be accomplished using either exogenous or endogenous delivery techniques well known in the art. Exogenous delivery methods can include use of targeting liposomes or direct local injection. Endogenous methods include use of viral vectors and non-viral plasmids. Ribozymes can be ATX-modulatory compounds and specifically modulate expression of ATX when designed to be complementary to regions unique to a nucleic acid encoding ATX. Specifically modulate means that ribozymes of the invention exclusively recognize a nucleic acid encoding ATX.

The invention further provides methods to modulate transcription of ATX through use of oligonucleotide-directed triple helix formation (Lavrovsky, et al., *Biochem. Mol. Med.* 62:11–22 (1997)). Triple helix formation is accomplished using sequence specific oligonucleotides which hybridize to double stranded DNA in the major groove as defined in the Watson-Crick model. Hybridization of a sequence specific oligonucleotide can thereafter modulate activity of DNA-binding proteins, including, for example, transcription factors and polymerases. Target sequences for hybridization include promoter and enhancer regions to permit transcriptional regulation of ATX expression. In addition to use of oligonucleotides, triple helix formation techniques of the invention also include use of peptide nucleic acids as described in Corey, *TIBTECH* 15:224–229 (1997). Oligonucleotides which are capable of triple helix formation are also useful for site-specific covalent modification of target DNA sequences. Oligonucleotides useful for covalent modification can be coupled to various DNA damaging agents as described in Lavrovsky, et al. (supra).

Mutations in the ATX gene can result in loss of normal function of the ATX gene product and underlie ATX-related human disease states. The invention therefore provides gene therapy methods to restore ATX activity in treating those disease states described herein. Delivery of a functional ATX gene to appropriate cells is effected ex vivo, in situ, or in vivo by use of vectors, for example, viral vectors such as adenovirus, adeno-associated virus, or a retrovirus, or ex vivo by use of physical DNA transfer methods such as liposomes or chemical treatments (Anderson, *Nature*, supplement to vol. 392, no. 6679, pp. 25–20 (1998)). Alternatively, in some human disease states, preventing the expression of, or inhibiting the activity of, ATX can be useful in treating the disease states. In this case, anti-sense therapy or gene therapy, for example, where a dominant negative ATX mutant is introduced into a target cell type, can be applied to negatively regulate the expression of ATX.

The invention provides a method for modulating cell survival by introducing an ATX-modulatory compound identified by the methods described above into a cell in an amount effective to modulate survival of the cell. For example, the ATX-modulatory compound can decrease or increase cell survival.

A level of cell death or cell survival can be measured by any of a variety of methods known to one skilled in the art. For example, trypan blue staining can be used to measure the level of cell death in a cell. In addition, clonogenic assays, as described herein, can be used (Example 5). Other staining methods, for example, propidium iodide and Alomar Blue, also can be used to measure cell death. The stained cells can be visualized in any way that is convenient, for example, by microscopy or flow cytometry (FACS). In addition, cell viability and cell proliferation assays such as the lactose dehydrogenase (LDH) assay and the MTT (3-(4,5-dimethylthiazolyl-2)-2,5-diphenyltetrazolium bromide) assay are commercially available and can be used to measure cell viability. In addition, the uptake of 3H thymidine can be used to access the viability of cells.

The invention further provides a method for modulating cell survival by introducing an ATX-modulatory compound into a cell where the cell is exposed to a stressor agent. As described further above, a stressor agent is any agent that can induce a stress response pathway within a cell. A stressor agent can include, for example, UV light, ionizing radiation, reactive oxygen intermediates, or a chemical agent such as a cytotoxic or chemotherapeutic agent. In addition, environmental conditions such as excessive heat can induce a stress response pathway within a cell resulting in, for example, the induction of heat shock proteins. Stress response pathways include DNA repair pathways, non-sense mediated mRNA decay (NMD), heat shock pathways, the induction of apoptosis, activation of the NFkB transcription factor, activation of the stress-activated MAP kinase pathways including, for example, JNK and p38 pathways, and activation of ubiquitin-dependent proteolysis.

An example of an ATX-modulatory compound of the invention is an antisense oligonucleotide. The invention provides a method for decreasing cell survival by introducing an antisense oligonucleotide, such as SEQ ID NO: 11 into a cell in an amount effective to decrease survival of the cell.

Association of ATX with cell cycle progression makes compositions of the invention, including for example an ATX polypeptide, an inhibitor thereof, an antibody, or other modulator of ATX expression or biological activity, useful for treating a number of conditions. For example, the invention provides a method for treating a condition characterized by excessive cell survival or cell growth by administering to a patient having such a condition an effective amount of an ATX-modulatory compound where the effective amount of the compound increases cell death. For example, an ATX-modultory compound can be given to a patient with a neoplastic condition.

An ATX-modulatory compound that decreases the level of ATX can enhance the radiosensitivity or chemosensitivity of neoplastic cells. Therefore, it is contemplated that an ATX-modulatory compound can be given alone or in combination with another agent such as a cytotoxic or chemotherapeutic agent. Several cytotoxic agents, such as radiation, and chemotherapeutic agents, such as cis-platin, are well known in the art. An appropriate agent can be chosen based on several factors, such as the particular type of neoplastic condition at issue or the ability of the patient to tolerate the agent. For example, focused radiation therapy, including brachytherapy, can be used in conjunction with an ATX inhibitory compound in order to induce tumor cell death while minimizing cytotoxic effects on normal tissue.

A "neoplastic condition," refers to a condition associated with hyperproliferation of cells and includes benign and malignant expanding lesions of proliferating cells. Neoplastic conditions include benign and malignant hyperproliferative disorders. A benign neoplasm grows in an expansile manner, displacing or compressing surrounding tissues rather than invading them. A malignant neoplasm refers to a large group of diseases characterized by uncontrolled growth and spread of abnormal cells. Cancer, for example, is a malignant neoplastic condition that encompasses many sub-conditions that are characterized by insufficient death of abnormal cells. Tumors of the colon, prostate, lung, cervix, stomach, breast and skin are examples of neoplastic conditions.

Aberrant ATX activity can be associated with various forms of cancer in, for example, adult and pediatric oncology, including growth of solid tumors/malignancies, myxiod and round cell carcinoma, locally advanced tumors, metastatic cancer, human soft tissue sarcomas, cancer metastases, including lymphatic metastases, squamous cell carcinoma of the head and neck, esophageal squamous cell carcinoma, oral carcinoma, blood cell malignancies, including multiple myeloma, leukemias, effusion lymphomas (body cavity based lymphomas), thymic lymphoma lung cancer, including small cell carcinoma, non-small cell cancers, breast cancer, including small cell carcinoma and ductal carcinoma, gastrointestinal cancers, including stomach cancer, colon cancer, colorectal cancer, polyps associated with colorectal neoplasia, pancreatic cancer, liver cancer, urological cancers, including bladder cancer, including primary superficial bladder tumors, invasive transitional cell carcinoma of the bladder, and muscle-invasive bladder cancer, prostate cancer, malignancies of the female genital tract, including ovarian carcinoma, primary peritoneal epithelial neoplasms, cervical carcinoma, uterine endometrial cancers, and solid tumors in the ovarian follicle, kidney cancer, including renal cell carcinoma, brain cancer, including intrinsic brain tumors, neuroblastoma, astrocytic brain tumors, gliomas, metastatic tumor cell invasion in the central nervous system, bone cancers, including osteomas, skin cancers, including malignant melanoma, tumor progression of human skin keratinocytes, and squamous cell cancer, hemangiopericytoma, and Kaposi's sarcoma.

Aberrant ATX activity also can be associated with other conditions which include aberrant apoptotic mechanisms, including abnormal caspase activity; aberrant enzyme activity associated with cell cycle progression, including for example cyclins A, B, D and E; alterations in viral (such as Epstein-Barr virus, papillomavirus) replication in latently infected cells; chromosome structure abnormalities, including genomic stability in general, unrepaired chromosome damage, telomere erosion (and telomerase activity), breakage syndromes including for example, Sjogren's syndrome and Nijimegen breakage syndrome; embryonic stem cell lethality; abnormal embyonic development; sensitivity to ionizing radiation; acute immune complex alveolitis; and Fanconi anemia. ATX-modulatory compounds can be used alone or in combination with another agent in the treatment of these conditions.

The invention also provides a method for treating a condition characterized by excessive cell death by administering to a patient having such a condition an effective amount of an ATX-modulatory compound where the effective amount of the compound increases cell survival. For example, an ATX-modultory compound can be given to a patient with a neurodegenerative condition in order to increase neuronal cell survival. In addition the invention provides a method of prolonging the in vivo survival of transplanted cells for the treatment of a disease or pathological condition. Also, for example, a compound that increases the level of ATX can be given to a patient who is exposed to stressors such as UV light in order to protect against genetic mutations.

The effective compounds of the invention described herein can optionally be formulated together with a pharmaceutically acceptable carrier for delivery to a cultured cell or to a subject. Suitable pharmaceutically acceptable carriers are well known in the art and include, for example, aqueous or organic solvents such as physiologically buffered saline, glycols, glycerol, oils or injectable organic esters. A pharmaceutically acceptable carrier can also contain a physiologically acceptable compound that acts, for example, to stabilize or increase the solubility of a pharmaceutical composition. Such a physiologically acceptable compound can be, for example, a carbohydrate, such as glucose, sucrose or dextrans; an antioxidant, such as ascorbic acid or glutathione; a chelating agent; a low molecular weight polypeptide; or another stabilizer or excipient. Pharmaceutically acceptable carriers, including solvents, stabilizers, solubilizers and preservatives, are described, for example, in Martin, *Remington's Pharm. Sci.*, 15th Ed. (Mack Publ. Co., Easton, 1975).

Those skilled in the art can formulate the therapeutic molecules to ensure proper distribution in vivo. For example, the blood-brain barrier (BBB) excludes many highly hydrophilic compounds. To ensure that the effective compounds of the invention cross the BBB, if desired, they can be formulated, for example, in liposomes, or chemically derivatized. For a review of strategies for increasing bioavailability of polypeptide drugs in the brain, and of methods for determining the permeability of polypeptides through the BBB using in vitro and in vivo assays, see Engleton et al., *Peptides* 9:1431–1439 (1997). Strategies that have been successfully used to increase the permeability of other neuropeptides through the BBB are particularly contemplated. Modifications to a polypeptide of the invention that can increase its BBB penetration include conjugating the peptide to a lipophilic moiety, such as a lipophilic amino acid or methyldihydropyridine. Similar modifications to invention polypeptides or peptidomimetics are likewise expected to be advantageous.

Methods of ensuring appropriate distribution in vivo can also be provided by rechargeable or biodegradable devices, particularly where gradients of concentrations of drug in a tissue are desired. Various slow release polymeric devices are known in the art for the controlled delivery of drugs, and include both biodegradable and non-degradable polymers and hydrogels. Those skilled in the art understand that the choice of the pharmaceutical formulation and the appropriate preparation of the composition will depend on the intended use and mode of administration.

The effective compounds of the invention can be administered to a subject by any effective route. Suitable routes for delivering the therapeutic molecules of the invention include topically, intraocularly, intradermally, parenterally, orally, intranasally, intravenously, intramuscularly, intraspinally, intracerebrally and subcutaneously. The present invention also provides compounds containing an acceptable carrier such as any of the standard pharmaceutical carriers, including phosphate buffered saline solution, water and emulsions such as an oil and water emulsion, and various types of wetting agents.

An effective dose of an effective compound of the invention can be determined, for example, by extrapolation from the concentration required in the ATX binding or ATX activity assays described herein; or from the dose required to modulate cell proliferation. An effective dose of an effective compound of the invention for the treatment of a pathology can also be determined from appropriate animal models, such as transgenic mice. Animal models for pathologies such as tumors are well-known in the art. An effective dose for treating this disease is a dose that results in either partial or complete regression of the tumor, reduction in metastasis, reduced discomfort, or prolonged life span. The appropriate dose for treatment of a human subject with a therapeutic molecule of the invention can be determined by those skilled in the art, and is dependent on the nature and bioactivity of the particular compound, the desired route of administration, the gender, age and health of the individual, the number of doses and duration of treatment, and the particular condition being treated.

It is understood that modifications which do not substantially affect the activity of the various embodiments of this invention are also included within the definition of the invention provided herein. Accordingly, the following examples are intended to illustrate but not limit the present invention.

EXAMPLE 1

Molecular Cloning of ATX

This example shows the cloning of ATX nucleic acids. During a BLAST search for mTOR-related proteins, it was noted that an expressed sequence tag (EST) (KIAA0421) contained a 5'-terminus with an open reading frame (ORF) that bore clear homology to a conserved region in the catalytic domains of PIKK family members. To access the full-length cDNA, the EST was used to generate a primer for 5'-RACE with human brain cDNA as the template. The initial 5'-RACE product extended the region of homology with the PIKK catalytic domain. Sequential screens of human brain (Clontech #HL1128a) and Jurkat T cell cDNA libraries (Stratagene #936219), combined with 5'-RACE of brain and Jurkat cDNA, resulted in the isolation of several overlapping DNA fragments that were assembled into approximately 12 kb of contiguous nucleotide sequence. This cDNA contains an ORF of 10,563 nucleotides with an additional 1.8 kb of 3'-UTR, and encodes a 3,521 amino acid polypeptide with a deduced molecular mass of 395 kDa. The first nucleotide of the ATG translation initiation codon in exon 6 as has been designated as nucleotide "1", and nucleotides upstream of this ATG are identified in the 3' to 5' direction with negative numbers. The conclusion that this sequence was derived from a single mRNA transcript was confirmed by PCR with primers that were complementary to the extreme 5'-terminus (nucleotides −90 to −67) and 3'-terminus (nucleotides 10,553 to 10,570) of the corresponding cDNA. The cloned cDNA sequence is contained in a genomic BAC clone (AC020716), which allowed localization of the gene encoding this putative PIKK family member to human chromosome 16. Based on its functional overlap with ATM, this new PIKK family member was named "ATX".

The collective results of the 5'-RACE and RT-PCR assays of mRNA derived from Jurkat T cell, human brain, and other human cell lines indicated that the ATX locus gives rise to several mRNA transcripts (FIG. 1A). One repetitively isolated ATX cDNA clone contains exon 4 spliced directly to exon 6, and yields the 3,521 amino acid polypeptide described above. This mRNA transcript and encoded polypeptide has been designated "long ATX", to distinguish it from a "short ATX" polypeptide (3,031 amino acids) produced as a result of allelic variation in exon 15, which leads to the insertion of 27 nucleotides beginning at nucleotide 1427 (FIG. 1A). This sequence alteration causes the insertion of two in-frame stop codons, and use of the next available ATG codon (in exon 16) as the translational start site gives rise to the amino-terminally truncated, short form of ATX. The 5' end of the ATX allele that encodes short ATX is contained within a second genomic BAC clone (AC003007) derived from human chromosome 16. Yamashita et al. have identified two human cDNA clones, both designated hSMG-1, one of which (FIG. 1A, second from bottom, SEQ ID NO: 7) was similar to the long ATX cDNA clone (SEQ ID NO:1) (Yamashita et al., *Genes and Development* 15:2215–2228 (2001)). Exon 5 was not included in our long cDNA clone due to the infrequent appearance of this exon during our 5'-RACE and RT-PCR analyses of human cell line-derived mRNA. Furthermore, the minority of cDNAs that did include the exon 5 sequence frequently contained exon 3, which placed an in-frame stop codon at the 5'-end of this cDNA (FIG. 1A). The longest ATX cDNA clone (ORF beginning at exon 2, SEQ ID NO:9) identified by Yamashita et al. (Yamashita et al., supra, 2001) was also isolated in our screening procedure. However, it was repeatedly found that the exon 3-associated stop codon was present in this transcript.

EXAMPLE 2

Expression of Endogenous and Recombinant ATX

In order to examine the expression of ATX mRNA in various tissues, a multiple tissue Northern blot was hybridized with a 32P-labelled, ATX cDNA probe that spanned exons 38–39(nucleotides 5,071–5,370). The ATX probe detected a major mRNA species that, based on its electrophoretic mobility, was significantly larger the 9.5 kb calibration marker, and could reasonably accommodate the predicted ORF (10.5 kb) of long ATX (data not shown). This ATX transcript was widely expressed in human tissues, with the highest levels observed in heart and skeletal muscle. These results are consistent with those obtained in immunoblot analyses with ATX-specific antibodies, which showed that ATX protein was uniformly expressed in hematopoietic, mesenchymal, and epithelial cell lines (data not shown). Database searches with the ATX amino acid sequence revealed the highest degree of homology to *C. elegans* SMG1, a protein required for NMD in the worm. Both ATX and CeSMG1 contain the PI 3-kinase related catalytic domain, which identifies these proteins as members of the PIKK family (FIG. 1B). Outside of the catalytic domain, the regional sequence homology between ATX and other PIKK family members was limited to the FKBP-12●rapamycin binding (FRB, designated NH2 in FIG. 1B) domain of mTOR, and to the NH1 and NH2 domains of CeSMG1. The FRB domain mediates the high-affinity interaction between mTOR and the antiproliferative FKBP12●rapamycin complex (Chen et al., *Proc. Natl. Acad. Sci. USA*, 92:4947–4951 (1995)). However, the FRB-related domain of ATX does not confer any detectable binding affinity for FKBP12●rapamycin (data not shown); hence, it is unlikely that ATX is a relevant target for rapamycin in intact cells. The expression of the short and long forms of ATX were compared after transient transfection of the respective cDNAs into human embryonic kidney 293T cells. The short ATX polypeptide was poorly expressed relative to long ATX (data not shown). However, these results do not exclude the possibility that the shorter form of ATX is expressed and contributes to the overall functions of ATX in mammalian cells.

In order to compare the translation product derived from the long ATX cDNA with the endogenously expressed ATX polypeptide, HEK 293T cells were transfected with HA-tagged expression plasmids encoding either wild-type ATX (HA-ATXWT) or a catalytically inactive ATX mutant (HA-ATXKI). The HA-ATXKI mutant contains an Asp>Ala substitution at a conserved residue (Asp-2195) in the ATX catalytic domain. Similar mutations in the catalytic domains of ATM, ATR, and DNA-PKCS have been shown to generate kinase-inactive (KI) versions of these PIKK family members (Canman et al., *Science*, 281:1677–1679 (1998); Cliby et al., *EMBO Journal*, 17:159–169 (1998); Hunter, supra, 1995).

For analyses of the endogenous ATX protein, two different rabbit polyclonal antibodies were prepared against GST fusion proteins containing peptide fragments derived from ATX. The first antibody (α-ATX Ab-1) was generated against a GST fusion protein containing amino acids 2281–2339 of ATX, while the second (α-ATX Ab-2) was obtained from immunizations with GST fused to amino acids 1691–1790 of ATX. The α-ATX Ab1 immunoblot analyses of whole cell extracts from non-transfected or HA-ATX-transfected HEK 293T cells revealed a single major immunoreactive band migrating at the predicted molecular mass of ~395 kDa (data not shown). An immunoreactive protein bearing a nearly identical electrophoretic mobility was detected in α-HA immunoprecipitates from transfected 293T cells. These results indicate that the molecular mass of the recombinant protein produced from the long ATX cDNA corresponds closely to that of the endogenous ATX protein. Consistent with the predicted size of ATX, the band recognized by the α-ATX antibodies migrated with a significantly lower electrophoretic mobility than either ATM (molecular mass, 370 kDa) or ATR (molecular mass, 305 kDa).

Methods:

Cloning

The longer ATX ORF was appended with an amino-terminal hemagglutinin (HA) epitope tag sequence (CYPYDVPD-YASL), and was subsequently amplified as two partially overlapping fragments from Jurkat cDNA. The nucleotide at position 4,620 was mutated in each of the two PCR products to create a SacII site that could be utilized to ligate the two ATX fragments, which were inserted into the XhoI and NotI sites of pcDNA3.1 (Invitrogen) (HA-ATX). The mutation used to generate the SacII did not alter the ATX polypeptide sequence. The expression vector encoding the catalytically inactive ATX mutant (HA-ATXKI) contains an Ala substitution at Asp-2195, which was generated by site-directed mutagenesis with the QuickChange kit (Stratagene). All plasmid constructs were sequenced to insure the fidelity of the PCR and cloning procedures.

Cell Lines

U2OS osterosarcoma and human embryonic kidney (HEK) 293T cells were cultured in low-glucose Dulbecco's Modified Eagle's Medium (DMEM), supplemented with 10% fetal bovine serum. The ATM-deficient human fibroblast line, AT4BI, was maintained in DMEM/F-12 medium supplemented with 10% fetal bovine serum. Where indicated, cells were γ-irradiated with a 137Cs source or UV irradiated with a UV-B source (λmax, 305 nm).

Antibodies

ATX-specific antibodies were raised by immunizing rabbits (Cocalico Biologicals, Inc.) with the indicated glutathione S-transferase (GST) fusion protein. Anti-ATX Ab-1 was raised against a GST fusion protein containing ATX amino acids 2281–2339, and α-ATX Ab-2 was raised against a GST fusion protein containing ATX amino acids 1691–1790. For purification of α-ATX Ab-2, GST-reactive antibodies were first absorbed on GSH-agarose. The flow-through fraction was then affinity purified over Affi-Gel 15 (BIO-RAD) coupled to the GST-ATX1691–1790 fusion protein. The α-PLC-γ1 antiserum was prepared as described (Secrist et al., *J. Biol. Chem.*, 268: 5886–5893 (1993)). The α-ATM (Ab-3), α-ATR (Ab-1), α-phospho-Ser15-p53, and α-p53 (Ab-6) reagents were obtained from Oncogene Science Research Products. Additional antibodies were obtained from (sources in parentheses): α-HA (clone 12CA5; BabCo), α-FLAG-M2 and α-tubulin (Sigma), α-Cds1/Chk2 (Upstate Biotechnology), and α-GAL4 (clone RK5C1; Santa Cruz Biotechnology).

Two-Dimensional PAGE

HEK 293 cells were lysed and protein analyzed as described {Pal, 2001 #1360}, except that cellular extracts were incubated for 2 h with α-FLAG-M2 mAb, followed by 2 h with protein G agarose (Sigma) to immunoprecipitate the FLAG-hUpf1 protein. Prior to elution, the immunoprecipitates were washed in lysis buffer as described {Pal et al., *Rna* 7:5–15 (2001) #1360}.

Immunofluorescence

For immunofluorescence microscopy of endogenous ATX, $6 \times 10^4$ U2OS cells were plated onto 22-mm2 glass coverslips. After 40 h, cells were exposed to 400 J/m2 UV-B, then fixed 1, 4 or 8 hrs later in phosphate-buffered saline (PBS) containing 4% paraformaldehyde for 20 min, and incubated in methanol at −20° for 15 min. The coverslips were rehydrated in phosphate-buffered saline (PBS) and incubated overnight at 4° C. in blocking solution (PBS containing 3% BSA and 2% goat serum). Coverslips were subsequently overlayed for 1 h with affinity purified A-ATX Ab-2 (1 μg per ml) in blocking solution at room temperature. Coverslips were washed with PBS, 0.2% Tween-20, and overlayed for 45 min at room temperature with fluorescein isothiocyanate (FITC)-conjugated goat anti-rabbit IgG (Caltag) (1:2000 in blocking solution). Samples were then washed and incubated with 100 μg per ml RNaseA in PBS for 30 min, followed by 1 μg per ml propidium iodide for 5 min. After extensive washing in PBS containing 0.2% Tween-20, coverslips were mounted on slides with an aqueous anti-fade mounting reagent (Vectashield, Vector Laboratories). Immunofluorescence images were generated with a Carl Zeiss LSM410 scanning laser confocal microscope.

EXAMPLE 3

Characterization of ATX Kinase Activity

With the exception of the TOR proteins, the PIKK family members that bear functional catalytic domains phosphorylate substrates bearing the Ser/Thr-Gln motif (Tibbetts and Abraham, supra, 2000). To determine whether the ATX kinase domain displayed a similar phosphorylation site selectivity, HEK 293T cells were transfected with a plasmid vector encoding HA-tagged ATXWT, ATXKI, or, for comparative purposes, HA-ATMWT. Detergent extracts from the transfected cell populations were immunoprecipitated with α-HA antibody, and protein kinase assays were performed in buffer containing Mn2+, [γ-32P]ATP, and a GST fusion protein containing the first 70 amino acids of p53 (GST-p53$_{1-70}$) as the substrate (FIG. 1C) The GST-p53$_{1-70}$ protein was previously identified as a substrate for ATM and ATR in immune complex kinase assays (Tibbetts et al., *Genes and Development* 13:152–157 (1999)). Interestingly, the specific kinase activity of HA-ATXWT towards GST-p53$_{1-70}$ was significantly higher than that of HA-ATM (FIG. 1C, left panel). Based on the ratios of 32P incorporation into substrate to levels of HA-tagged protein kinase, it can be estimated that the specific kinase activity of ATXWT was approximately 3.5-fold higher than that of ATMWT. As observed with ATM as the test kinase (Banin et al., *Science* 281:1674–1677 (1998); Canman et al., *Science* 281:1677–1679 (1998); Tibbetts et al., supra, 1999), phosphorylation of GST-p53$_{1-70}$ by ATXWT was nearly abolished by substitution of the Ser-15 residue in p53 with Ala (FIG. 1C, right panel). Because Ser-15 resides in the optimal sequence (LSQE) for phosphorylation by ATM (O'Neill et al., *J. Biol. Chem.* 275:22719–22727 (2000)), this finding indicates that ATX is a Ser/Thr-Gln-directed kinase, with the potential to phosphorylate a set of substrates that overlaps with those modified by ATM. In contrast to the amino-terminal fragment of p53, the PHAS-I/4E-BP1 protein, which is the prototypical substrate for mTOR, was poorly phosphorylated by HA-ATXWT in immune complex kinase assays (data not shown).

The amino acid sequences surrounding the four phosphorylation sites (LSQP, LSQD, LSQD, and LSQY) identified in this study resemble the consensus site for phosphorylation by ATM (O'Neill et al., supra, 2000). A GST fusion protein that contained the carboxyl-terminal region of hupf1 (amino acids 1019–1118), including all four of the ATX phosphorylation sites was constructed. This GST-hUpf11019–1118 protein was tested as a substrate for HA-ATXWT versus HA-ATMWT in immune complex kinase assays. Once again, this substrate was phosphorylated by both ATM and ATX, with the latter protein kinase showing the higher specific catalytic activity under these in vitro assay conditions (FIG. 1C, left panel). Furthermore, the results of repeated assays indicated that GST-p53$_{1-70}$ was more avidly phosphorylated by ATX than was the GST-hUpf11019–1118 substrate.

The protein kinase activities of the mammalian PIKKs characteristically display a strong dependence on Mn2+ as a cofactor for the phosphotransferase reaction, and variable sensitivity to inhibition by wortmannin (Abraham, *Genes and Development* 15:2177–2196 (2001)). In our studies, the protein kinase activity of ATX was also dependent on the addition of Mn2+ to the kinase reaction buffer (data not shown). In addition, pretreatment of the immunoprecipitated HA-ATXWT protein with wortmannin resulted in a concentration-dependent inhibition of GST-p53$_{1-70}$ phosphorylation. The drug concentration required for 50% inhibition (IC50) of ATX activity in vitro was between 10 and 100 nM (FIG. 1D), which is comparable to the previously published IC50 (80 nM) for wortmannin as an ATM inhibitor (Sarkaria et al., *Cancer Res.* 58:4375–4382 (1998)). Wortmannin is an irreversible inhibitor of PIKKs (Walker et al., *Molecular Cells* 6:909–919 (2000)) and can be used to assess the potency of this drug as an ATX inhibitor in intact cells. To this end, U2OS osteosarcoma cells were pretreated for 30 min with the indicated concentrations of wortmannin, followed by the preparation of cellular extracts for immunoprecipitation of endogenous ATX with A-ATX Ab-2. Under these conditions, wortmannin inhibited ATX kinase activity with an IC50 of 1–3 μM; which is considerably higher than that observed following direct treatment of the immunoprecipitated protein kinase with this drug (FIG. 1D). A similarly dramatic decrease in the inhibitory potency of wortmannin was observed with ATM as the target enzyme in intact cells (Sarkaria et al., supra, 1998).

Immune Complex Kinase Assays

Native or recombinant ATX proteins were immunoprecipitated from cell extracts as described above, and the immunoprecipitates were washed twice in lysis buffer, once in high-salt buffer (100 mM Tris-HCl, pH 7.4, 500 mM LiCl) and once in kinase buffer (10 mM Hepes, pH 7.4, 50 mM NaCl, 50 mM β-glycerol phosphate). Forty μl kinase buffer (containing 10% glycerol, 1 mM DTT, 10 mM MnCl$_2$, 20 nM microcystin, protease inhibitors, 1 μg of the indicated substrate, 10 μM ATP, and 10 μCi [γ-32P]ATP (6000 Ci/mmole) (NEN)] was added to each sample, and kinase reactions were performed for 30 min at 30° C. Reactions were terminated by addition of 40 μl of 4×-SDS-PAGE sample buffer, and heating to 100° C.

EXAMPLE 4

Subcellular Localization of ATX

The subcellular localization of ATX was examined by biochemical fractionation of U2OS cells, followed by immunoprecipitation of crude nuclear and cytoplasmic fractions with α-ATX Ab-2. Comparable levels of ATX were found in the nuclear and cytoplasmic extracts from U2OS cells (data not shown). The integrity of these subcellular fractions was confirmed by immunoprecipitation and immunoblotting of parallel samples with antibodies specific for PLCγ1 and ATR, which are localized to the cytoplasm and nucleus, respectively. The presence of ATX in both the cytoplasmic and nuclear compartments was further documented by immunostaining of U2OS cells with affinity-purified A-ATX Ab-2. Exposure of cells to genotoxic agents-triggers the appearance of DNA damage-induced nuclear foci containing either ATM or ATR (Andegeko et al., *J. Biol. Chem.* 276:38334–38230 (2001); Tibbetts et al., *Genes and Development* 14:2989–3002 (2000)). To determine whether ATX undergoes similar changes in subcellular localization in response to genotoxic stress, U2OS cells were treated with 400 J/m2 UV-B, and stained with α-ATX Ab-2. Exposure to UV triggered the appearance of ATX-containing nuclear foci. The ATX-positive foci were evident within 1 h after UV treatment, and continued to accumulate in the cells until at least 8 h post-treatment, at which time greater than 50% of the cells exhibited multiple ATX-containing foci. In contrast, the formation of ATX foci after treatment of U2OS cells with 20 Gy IR was not detected.

In addition, the effect of genotoxic stress on the protein kinase activity of ATX in immune complex assays was determined. Consistent with the results of the immunofluorescence staining experiments, treatment of the cells with IR failed to induce a reproducible increase in the protein kinase activity observed in α-ATX immunoprecipitates (data not shown). On the other hand, UV exposure caused a modest but consistent increase in ATX kinase activity that reached a maximal level at 4 h post-irradiation. Collectively, the results of the nuclear localization and protein kinase activity studies indicated that, like ATM and ATR, ATX participated in cellular responses to DNA damage or other forms of stress induced by UV irradiation.

Methods:

Cell Fractionation, Immunoprecipitation, and Immunoblotting.

For subcellular fractionations, U2OS cells were resuspended in cold homogenization buffer (25 mM Hepes, pH 7.4, 250 mM sucrose, 1 mM EGTA, 5 mM MgCl2, 50 mM NaF, 1 mM DTT, plus protease inhibitors) and Dounce homogenized on ice with 40 strokes in a Tefloncoated homogenizer. The nuclei were pelleted at 500×g, and the supernatant was collected as the crude cytoplasmic fraction. Prior to immunoprecipitation, 150 mM NaCl and 1% (wt/vol) NP-40 (final concentration) were added to the crude cytoplasmic fractions. Nuclear extracts were prepared by suspending the nuclear pellets in extraction buffer (50 mM Tris-HCl, pH 7.4, 150 mM NaCl, 1% NP-40, 1 mM dithiothreitol), supplemented with protease inhibitors (10 μg per ml leupeptin, 10 μg per ml aprotinin, 1 μM pepstatin). After 15 min on ice, the samples were centrifuged, and the supernatant was collected for analysis. For immunoprecipitations, cell extracts were prepared by resuspending washed cell pellets in lysis buffer (50 mM Tris-HCl, pH 7.4, 150 mM NaCl, 1% NP-40, 1 mM dithiothreitol) plus protease inhibitors. When samples were prepared for immune complex kinase assays, the lysis buffer was modified to contain 1% Tween-20 detergent in place of NP-40, and additional phosphatase inhibitors (20 mM β-glycerol phosphate and 50 nM microcystin). Samples were incubated on ice for 15 min, and then clarified by centrifugation. HA-tagged recombinant proteins were immunoprecipitated from cell extracts with 4 μg of α-HA antibody. Endogenous ATX protein was immunoprecipitated with 8 μg of α-ATX Ab-2. After separation by SDS-PAGE, the proteins were detected by autoradiography (for kinase reaction products) or by immunoblotting. Proteins immunoblotted with rabbit and mouse antibodies were detected with protein A-horseradish peroxidase (HRP) (Amersham), and sheep anti-mouse IgG-HRP (Amersham), respectively. Immunoreactive proteins were illuminated with Renaissance chemiluminescence system (NEN).

EXAMPLE 5

Effect of Decreased ATX Function on Cellular Sensitivity to UV and IR

In order to gain further insights into the role of ATX in stress responses, U2OS cells were transfected with the kinase-inactive ATXKI mutant, and the UV- and IR-sensitivities of the transfected cells in clonogenic survival assays was examined. Control cell populations were transfected with either empty plasmid (pcDNA3.1) or with ATXWT-encoding plasmid. At 48 h post-transfection, the cells were treated with various doses of UV-B (FIG. 2A) or IR (FIG. 2B). The treated cells were then cultured in G418-containing medium in order to select for stably transfected cells. Cellular survival was determined after 10 days in culture by staining emergent colonies with Coomassie blue, followed by calorimetric quantitation of the amount of dye-bound protein present in each sample. Expression of ATXKI, but not ATXWT, reduced the basal survival of otherwise untreated U2OS cells (FIG. 2B, top panel). These results indicate that endogenous ATX function is required for the maintenance of normal cell viability or growth in culture. Furthermore, expression of ATXKI dramatically increased the sensitivity of U2OS cells to the cytostatic/cytotoxic effects of both UV and IR in these clonogenic survival assays.

Figure 2:
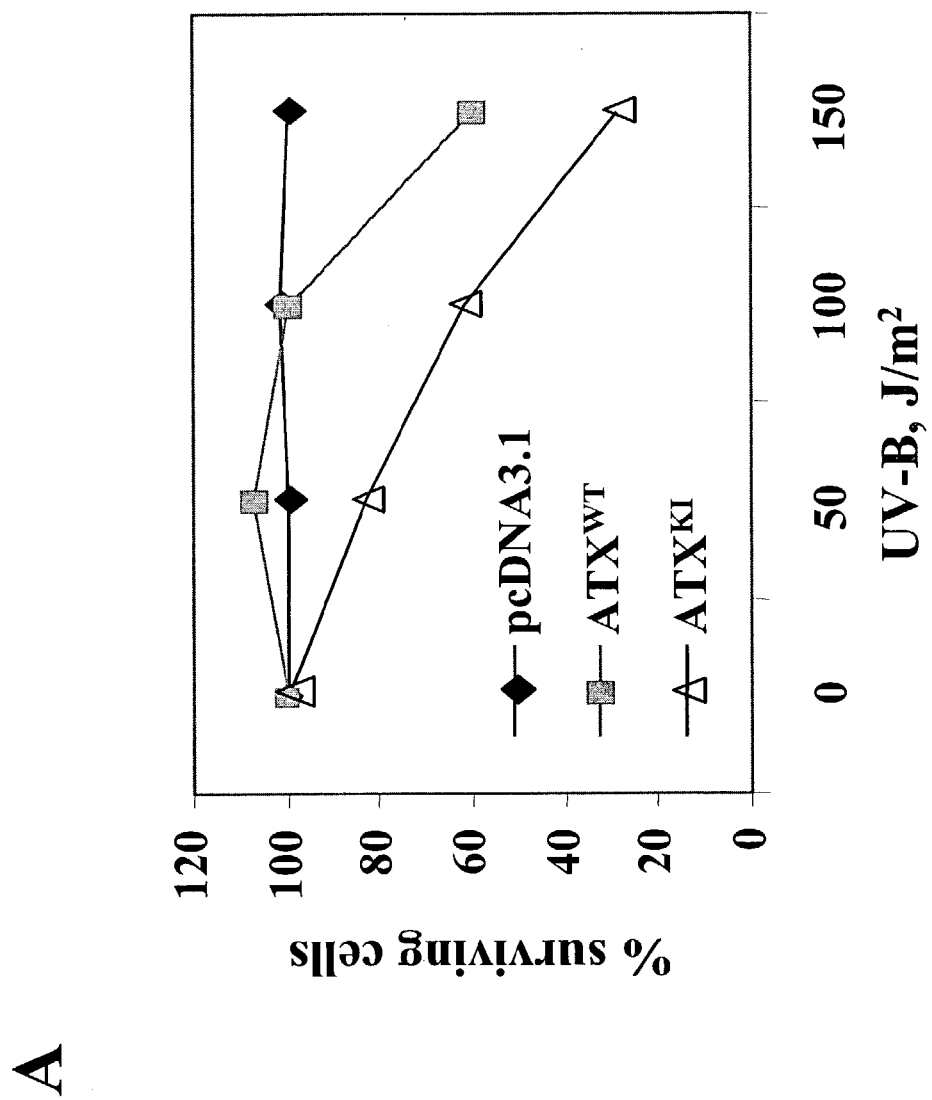
FIG. 2A shows clonogenic survival assays after UV exposure.
FIG. 2B shows clonogenic survival assays after IR exposure. The upper panel displays colony outgrowth results from cells transfected with the indicated plasmids, and not exposed to IR.
FIG. 2C shows clonogenic survival assays of cells treated with ATX-directed antisense oligonucleotides (AS). The right panel displays colony survival results from non-irradiated cells treated with the indicated oligonucleotides.
Figure 2:
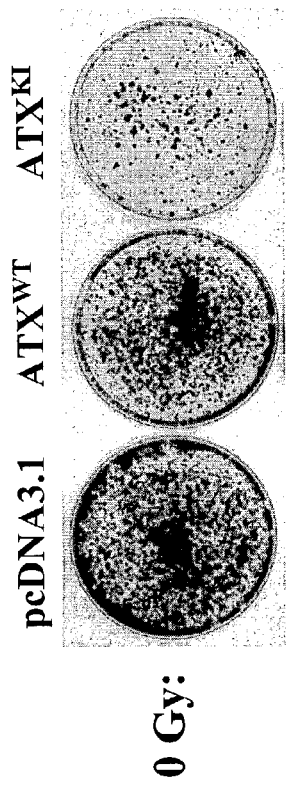
Figure 2:
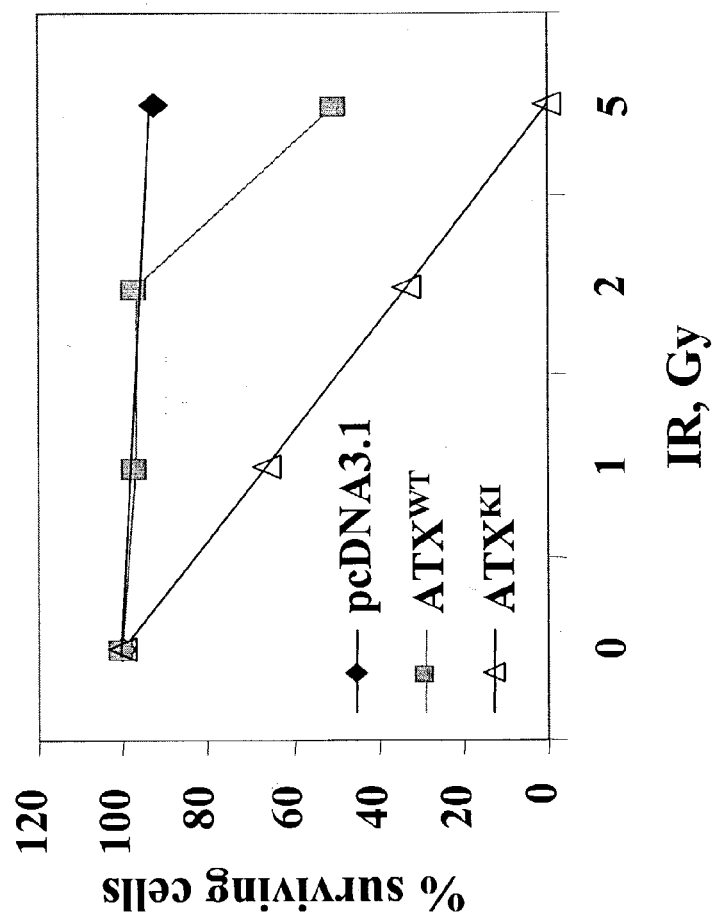
Figure 2:
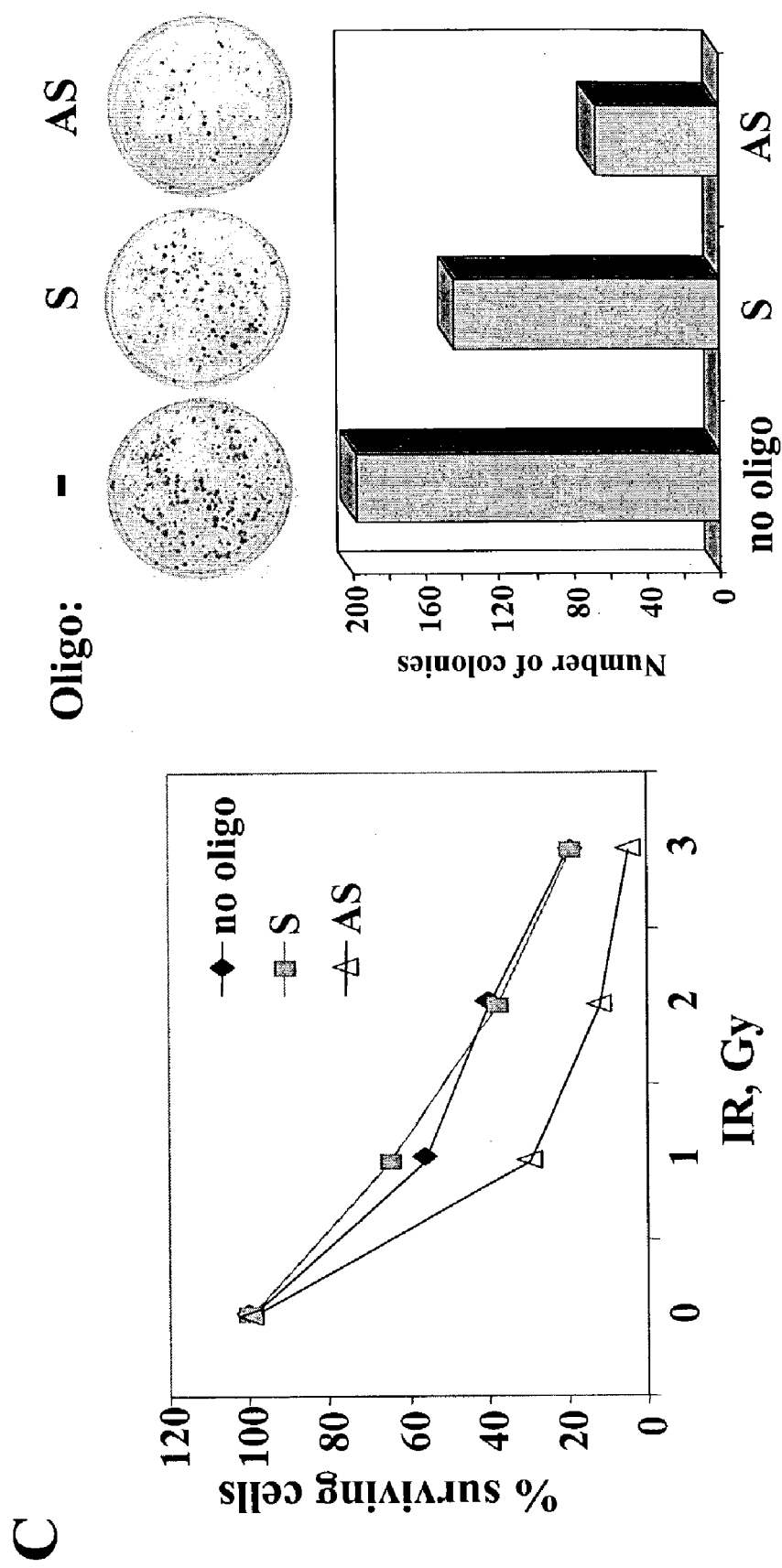

To address concerns related to potential non-specific effects of ATXKI expression on cellular functions, an antisense oligonucleotide-based approach to reduce the level of ATX expression in U2OS cells was developed. The cells were mock transfected, or transfected with sense (S) or antisense (AS) oligonucleotides, and then treated for 24 h with various genotoxic agents. The cells were then trypsinized and replated, and clonogenic survival was analyzed after 10 days in culture. The results obtained with AS-treated cells were strikingly similar to those obtained with the ATXKI-expressing cells (FIGS. 2 A–C). While transfection of U2OS cells with the S oligonucleotide reduced the basal level of colony outgrowth by 25%, treatment with the AS oligonucleotide decreased basal clonogenic activity by 75% (FIG. 2C, right panel). Hence, the AS-induced decrease in ATX protein expression was accompanied by a reduction in cell viability or proliferation in the absence of environmental stress. Furthermore, the AS-treated cells were significantly more sensitive to the suppressive effects of IR (FIG. 2C, left panel) and UV treatments (data not shown) on clonogenic survival. The reduction in ATX protein caused by AS treatment ranged from 50–90% in over 10 independent trials.

Methods:

Cell Transfections

To prepare recombinant HA-tagged ATX and ATM proteins, HEK 293T cells were plated onto 60-mm dishes (9×105 cells per dish), and were transfected with 5 μg pcDNA3.1 (empty vector), HA-ATXWT, HA-ATXKI, or HA-ATMWT plasmid DNAs. Transfections were performed with the Fugene 6 transfection reagent (Roche), according to the manufacturer's instructions. For NMD assays (see Example 9, below), U2OS cells were seeded onto 100 mm dishes (1×106 cells per dish). After 20 h, cells were transfected with 1.5 μg of pmCMV-Gl test plasmid, either Norm or 39Ter (Ishigaki et al., 2001); 1.5 μg of phCMV-MUP reference plasmid (Ishigaki et al., Cell 106:607–617 (2001)); and 7 μg of empty plasmid (pcDNA 3.1), plasmids encoding HA-ATMWT, HA-ATMKI, HA-ATXWT or HA-ATXKI. For antisense transfection experiments, U2OS cells were seeded onto 60 mm dishes (1×10$^5$ cells per dish) in complete medium supplemented with penicillin/streptomycin. After 30 h, cells were either mock transfected or transfected with sense (S) or antisense (AS) phosphorothioate oligonucleotides (Genset Oligos, La Jolla, Calif.). The S oligonucleotide spans ATX nucleotides 210–229 (5'-GAGACAG-GAGGGAGCTTGCT-3'), and the AS oligonucleotide is complementary to this sequence (5'-AGCAAGCTCCCTC-CTGTCTC-3'). The cells were transfected with oligonucleotides at final concentrations of 8 μg/ml, with Fugene 6:DNA ratio of 1.6:1. Forty-eight hours after transfection, dishes were exposed to IR, UV-B, or 5-FU, and then harvested for immunoblotting, cell-cycle distribution, or cell survival assays. To examine ATX protein levels in oligonucleotide-treated cells, whole cell extracts were resolved by SDS-PAGE and immunoblotted with A-ATX Ab-1. When oligonucleotide-transfected cells were used for NMD assays, U2OS cells were seeded in culture dishes as described above. The cells were transfected using the Fugene reagent, with 1.5 μg of pmCMV-Gl test plasmid, 0.7 μg of phCMV-MUP reference plasmid, and 24 μg of S or AS oligonucleotide.

Clonogenic and G418 Survival Assays

U2OS cells were seeded into 60 mm dishes (1×105 cells per dish) in complete medium. After 48 h, cells were transfected as described above. Forty-eight hours after transfection, dishes were exposed to IR or UV-B, and G418 was added at 1 mg per ml in complete medium. G418-resistant cells were stained 10 days later with Coomassie Blue. To quantitate the outgrowth of drug-resistant cells, the Coomassie Blue-bound protein was solubilized at 37° C. with 0.1 M NaOH, and the soluble material was analyzed by absorbance spectroscopy at a wavelength of 590 nm. For AT4BI cell survival assays, cells were transfected with pcDNA3.1, pcDNA3.1-FLAG-ATM, or HA-ATX. After 48 h, the transfected cells were exposed to the indicated doses of IR, and G418 was added at 8 hours post-irradiation. Drug-resistant colonies were stained with Coomassie Blue after 10 days in culture, and the samples were analyzed with Image Pro Plus software to quantitate cell density. For clonogenic assays where oligonucleotides were used, the cells were plated and transfected with S or AS oligonucleotides as described above. Forty-eight hours after transfection, cells were exposed to IR or UV. Twenty-four hours after exposure to damaging agents, cells were replated at 1000 cells per 60 mm dish and colonies allowed to form for 10 days. Dishes were stained with Coomassie Blue, and the number of colonies (minimum size, 50 cells per colony) was counted by visual examination.

EXAMPLE 6

Role of ATX in p53 Activation

Figure 3:
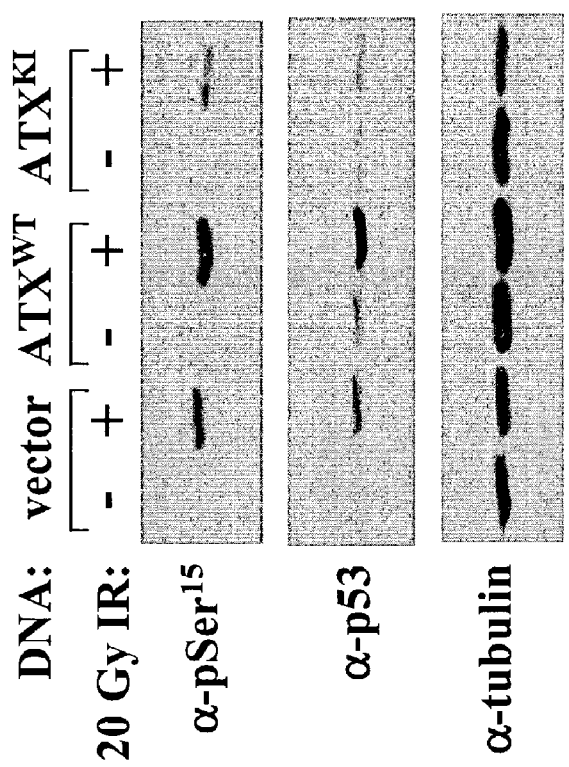
FIG. 3A shows whole cell extracts resolved by SDS-PAGE and sequentially immunblotted with the indicated antibodies.
FIG. 3B shows extracts of transfected cells separated by SDS-PAGE and sequentially immunoblotted with the indicated antibodies. The p53 phosphoserine-15 specific antibody is designated α-pSer15.
FIG. 3C shows extracts of cells treated with S or AS oligonucleotides and analyzed as described in panel A.
FIG. 3D shows cell cycle progression in AS-transfected cells examined by flow cytometry. The table shows the percentages of cells in each cell cycle phase. The right panel shows immunoblot analyses from the same cell population.
FIG. 3E shows an effect of caffeine on AS-induced cell cycle defects. The table shows percentages of cells in each cell-cycle phase, plus the ratio of G2/M to G1 cells for each sample. The right panel shows immunoblotting results from the same cell populations.
Figure 3:
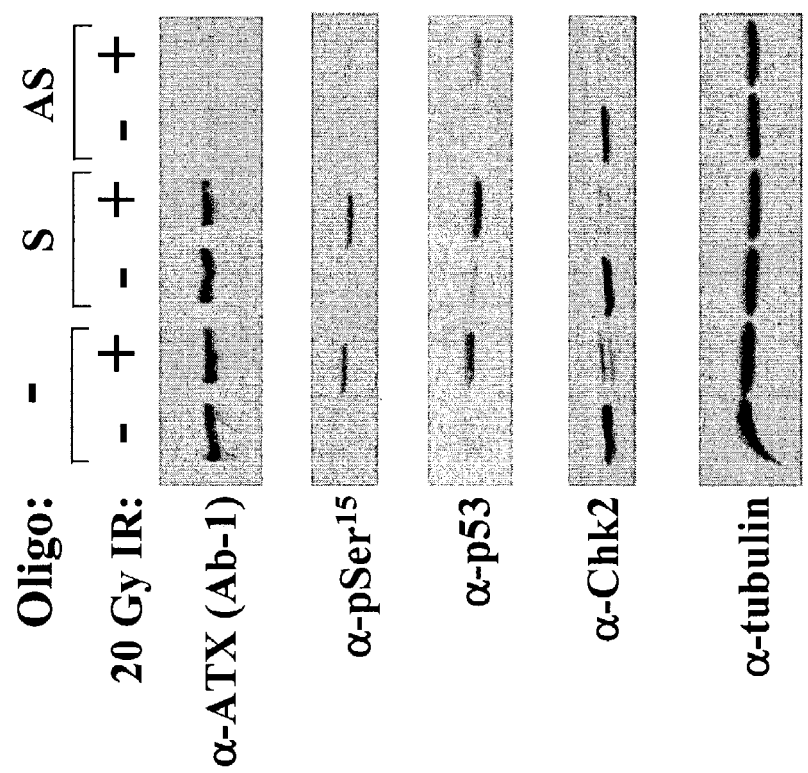
Figure 3:
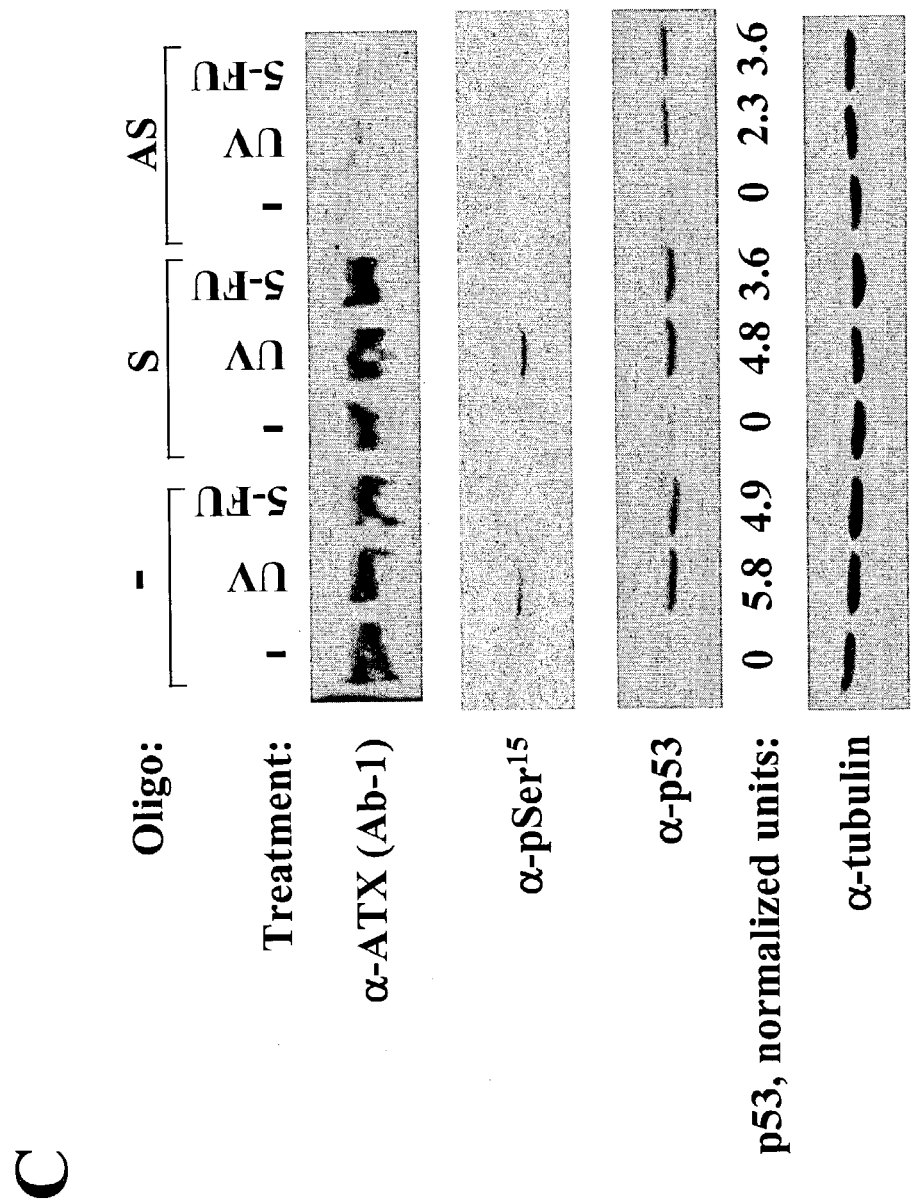
Figure 3:
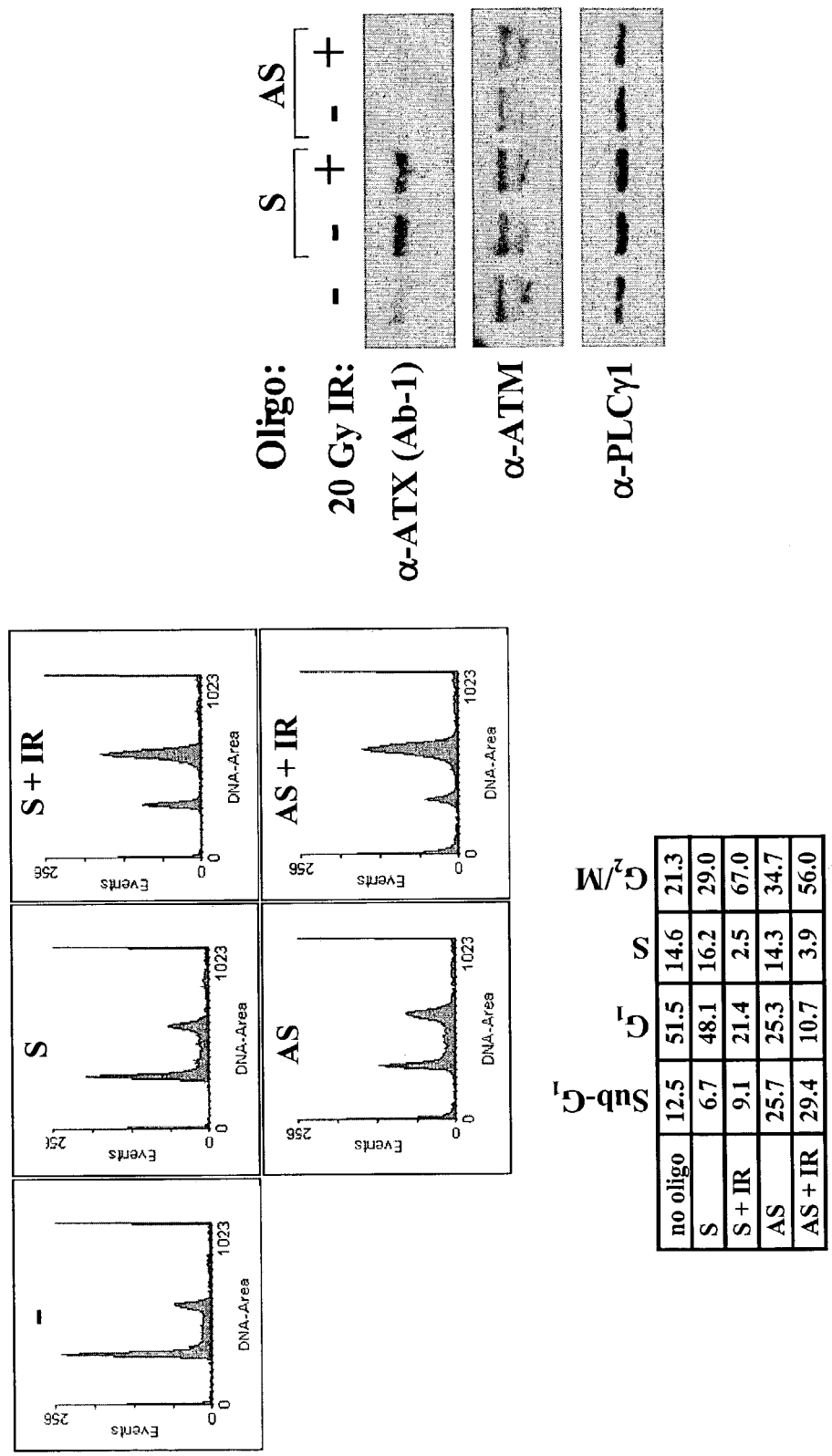
Figure 3:
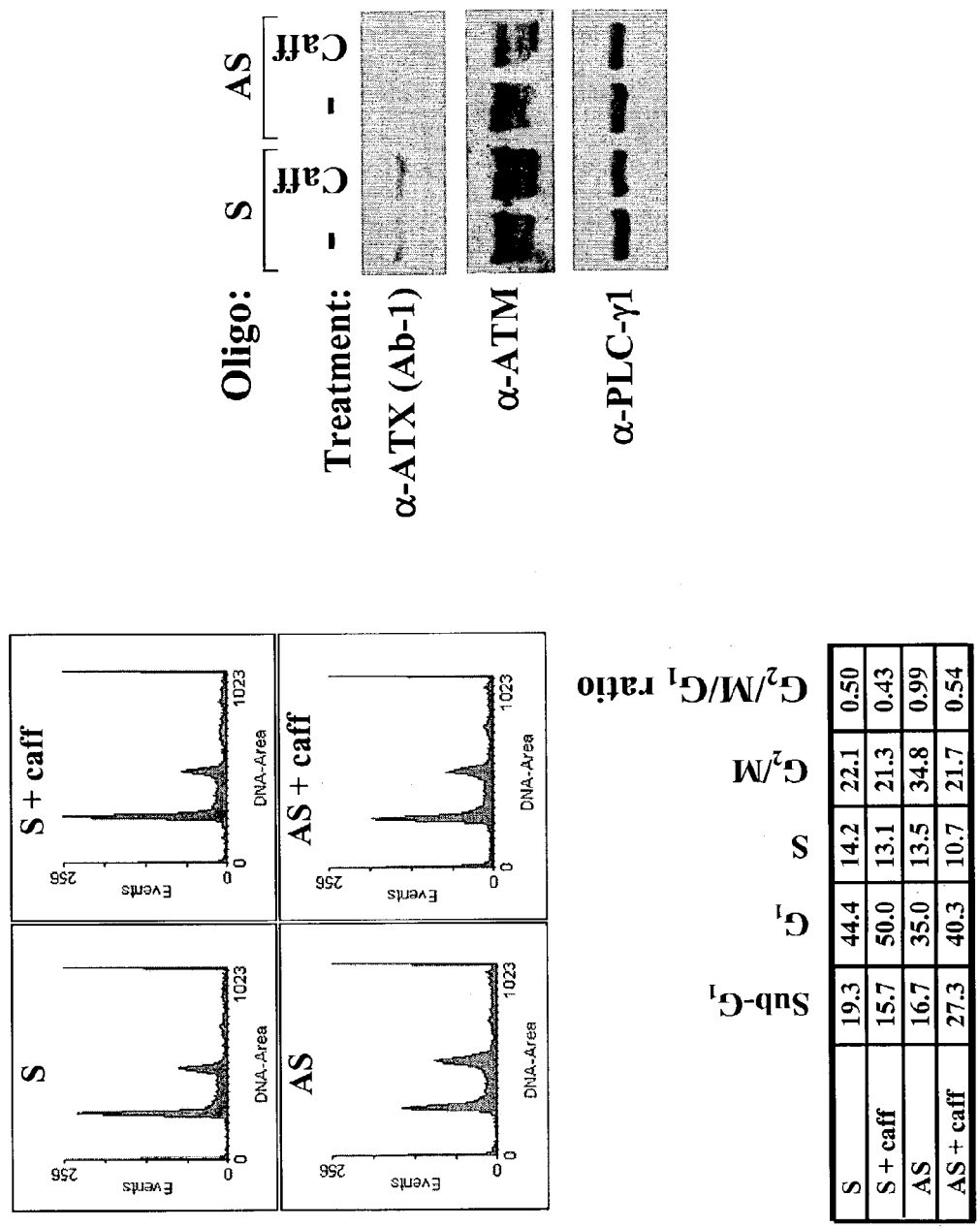

A major mediator of stress-induced signaling in mammalian cells is the tumor suppressor protein, p53 (Ko and Prives, *Genes and Development* 10:1054–1072, (1996); Ryan et al., *Curr. Opin. Cell Biol.* 13:332–337 (2001)). ATX phosphorylates p53 on Ser-15 (FIG. 1C), a site implicated in the regulation of p53 stability and transcriptional activity (Dumaz and Meek, *Curr. Opin. Cell Biol.* 13:225–231 (1999); Zhang and Xiong, *Science* 292:1910–1915 (2001)). Therefore, the possibility that these two proteins are functionally linked during cellular stress responses was investigated. U2OS cells were transiently transfected with a HA-ATXWT or HA-ATXKI expression plasmid, together with a GFP-encoding plasmid to allow for FACS-based enrichment of the transfected cells. The GFP+ cells were then examined for IR-induced stabilization of p53, as well as for specific phosphorylation of this protein on Ser-15. Expression of ATXKI strongly suppressed both the phosphorylation of Ser-15 and the overall accumulation of p53 in IR-treated cells (FIG. 3A). In contrast, overexpression of ATXWT enhanced both of these responses in cells exposed to IR. Consistent with findings presented above, treatment of U2OS cells with the AS oligonucleotide led to a decrease in endogenous ATX expression, and concomitantly reduced both the phosphorylation and stabilization of p53 induced by IR exposure (FIG. 3B). These results indicated that ATX exhibits functional overlap with ATM during IR-induced p53 activation.

Recent findings point toward ATM as a critical upstream regulator of the activity of the checkpoint kinase, hChk2, in IR-damaged cells (Ahn et al., *Cancer Res.* 60:5934–5936 (2000); Melchionna et al., *Nat. Cell Biol.* 2:762–765 (2000)). To determine whether ATX was also involved in hChk2 activation, the effect of AS oligonucleotide treatment on the IR-dependent phosphorylation of hChk2 was examined. In contrast to the p53 results, the AS-treated cells retained the ability to phosphorylate hChk2 in response to IR-induced stress (FIG. 3B). These results indicate that, while ATM and ATX serve as positive regulators of p53 function, ATX plays no identifiable role as an upstream activator of a distinct ATM target protein, the hChk2 kinase. Moreover, the differential effects of AS treatment on p53 expression versus hChk2 activation argue against the possibility that AS exposure leads to nonspecific inhibition of checkpoint signaling responses to IR-induced DNA damage.

Additional studies with AS oligonucleotide-treated cells demonstrated that, in contrast to ATM (Canman et al., *Science* 281, 1677–1679. 1998; Siliciano et al., *Genes Dev* 11, 3471–3481 (1997)), ATX plays a role in the phosphorylation and stabilization of p53 in cells exposed to UV light (FIG. 3C). As observed with IR as the stress-inducing agent, a reduction in ATX protein expression severely impaired both Ser-15 phosphorylation and p53 protein accumulation in UV-damaged cells. The recognition of UV light-induced DNA damage occurs primarily during S phase, when pyrimidine dimers and other bulky lesions interfere with replication fork progression (Friedberg, *DNA Repair and Mutagenesis* (Washington, D.C., ASM Press) (1995); Lindahl and Wood, *Cell* 103:1121–1131 (1999)).

In order to further define the potential linkage between DNA replicational stress and ATX, the response of AS-treated cells to 5-fluorouracil (5-FU), an S-phase specific cytotoxic agent was examined (Danenberg et al., *Seminars in Oncology* 26:621–631 (1999); Grem, *Investigational New Drugs* 18:299–313 (2000)). Previous findings indicated that the cytotoxic effects of 5-FU are strongly p53-dependent (Bunz et al., *J. Clin. Invest.* 104:263–269 (1999)). Treatment of U2OS cells with 5-FU increased p53 expression to levels similar to those observed in UV-irradiated cells (FIG. 3C). However, the accumulation of p53 induced by 5-FU exposure was not accompanied by an increase in Ser-15 phosphorylation. These findings indicate that the mechanism of p53 stabilization triggered by 5-FU does not involve upstream protein kinases that modify the Ser-15 site. Consistent with this conclusion, the level of p53 induction by 5-FU in AS-treated cells was identical to that observed in their S-treated counterparts. These results indicate that the inhibitory effect of the AS treatment on p53 activation is selective for those forms of stress that induce the phosphorylation of p53 at Ser-15.

Changes in phosphorylation at Ser-15 are typically accompanied by alterations in the expression of the p53 protein, which complicates the interpretation of results obtained by immunoblotting of whole cell extracts with phospho-Ser-15-specific antibodies. In order to confirm that reduced ATX expression interferes with stress-induced Ser-15 phosphorylation, U2OS cells were transfected with either the S or AS oligonucleotide, and then were pretreated with the proteasome inhibitor, LLnV, to stabilize p53. In the presence of LLnV, the p53 level in each test population was relatively unaffected by UV exposure (data not shown).

However, the ratio of phospho-Ser-15 to total p53 protein was increased by UV irradiation of both the mock-transfected and S oligonucleotide-treated cells. Although AS treatment partially interfered with the accumulation of p53 under these conditions, the reduction in ATX expression effectively blocked the stoichiometric increase in Ser-15 phosphorylation triggered by UV-induced stress.

EXAMPLE 7

Role of ATX in IR-Induced Cell Cycle Arrest

Since p53 plays a central role in activation of the G1 checkpoint, and influences S, G2, and M checkpoints as well (Giaccia and Kastan, *Genes & Development* 12:2973–2983 (1998); Ko and Prives, supra, 1996), a functional deficiency of ATX might alter the cell-cycle arrest responses to IR and other genotoxic agents. To test this possibility, U2OS cells were pre-treated with S or AS oligonucleotides, exposed to IR, and cell-cycle distributions at 24 h post-irradiation were determined. In the absence of IR, AS treatment led to a reduction in the percentage of G1 phase cells, and a concomitant accumulation of G2/M phase cells, when compared to their S oligonucleotide-treated counterparts (FIG. 3D). The AS-treated cells also contained an increased subpopulation with <2N DNA content, which is indicative of apoptotic cells. After IR exposure, cells treated with the S oligonucleotide accumulated in both G1 and G2/M phases and were cleared out of S phase, a profile typical of p53-positive cells that retain G1 checkpoint function. In contrast, the AS-treated cells arrested primarily in G2/M phase after IR exposure. The cell-cycle distribution of the AS-treated cells was reminiscent of that observed in cells that have lost p53-dependent checkpoint function (North and Hainaut, *Pathol. Biol.* 48:255–270 (2000); Waldman et al., *Cancer Res.* 55:5187–5190 (1995)). Immunoblot analyses of the same cell populations confirmed that AS exposure led to a profound reduction in ATX protein levels in U2OS cells. In contrast, AS exposure caused no significant change in the expression levels of two control proteins, ATM and PLC-γ1.

The cell-cycle distribution results described in FIG. 3D demonstrated that ATX-deficient cells accumulate with 4N DNA content under both basal culture conditions and after IR-induced stress. This arrest state could reflect the activation of either a G2 or a mitotic checkpoint (or both checkpoints). To distinguish between these possibilities, the effects of caffeine, a known inhibitor of the G2 checkpoint (Powell et al., *Cancer Res.* 55:1643–1648 (1995); Russell et al., *Cancer Res.* 55:1639–1642 (1995); Yao et al., *Nat, Med.* 2:1140–1143 (1996)), on the cell cycle distribution of the AS-treated cells were examined. The G2 checkpoint inhibitor was added to the culture medium at 8 h prior to harvest for determination of cell-cycle distributions (FIG. 3E, left panel), and immunoblotting for ATX expression (right panel). Caffeine completely reversed the accumulation of G2/M phase cells induced by AS treatment, indicating that ATX deficiency triggered the activation of a caffeine-sensitive G2 checkpoint. The immunoblotting results confirmed that AS-treated cells displayed a marked, specific reduction in ATX protein expression. In addition, treatment of the AS cells with caffeine also resulted in an increase in the percentage of hypodiploid cells, which indicates that an intact G2 checkpoint partially protects the ATX-deficient cells from apoptotic death, for example, by preventing a catastrophic entry into M phase.

EXAMPLE 8

ATX Overexpression Complements IR Sensitivity in ATM-Deficient Cells

Figure 4:
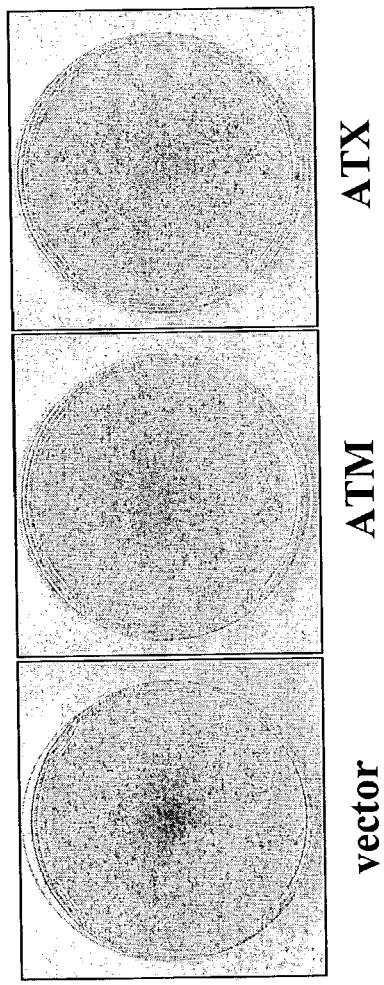
FIG. 4A shows an effect of ATX overexpression on basal viability. Cell densities of the scanned images from each sample were obtained with the ImagePro Plus software program.
FIG. 4B shows an effect of ATX overexpression on radiosensitivity. Surviving cells were quantitated as described in panel except that arbitrary unit values for each group were normalized to the corresponding nonirradiated control.
Figure 4:
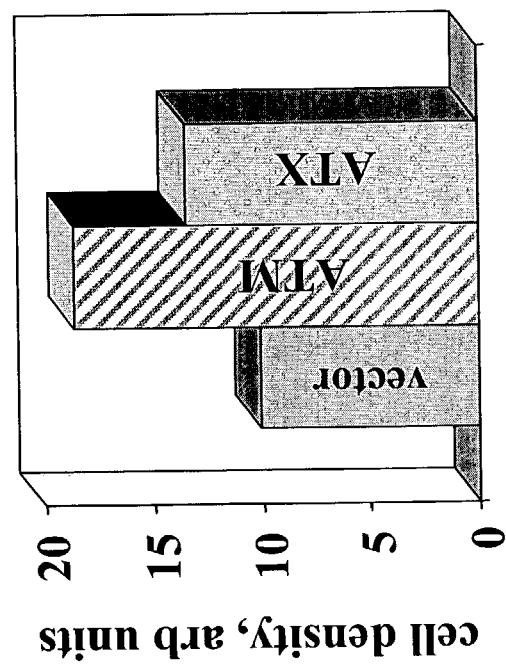
Figure 4:
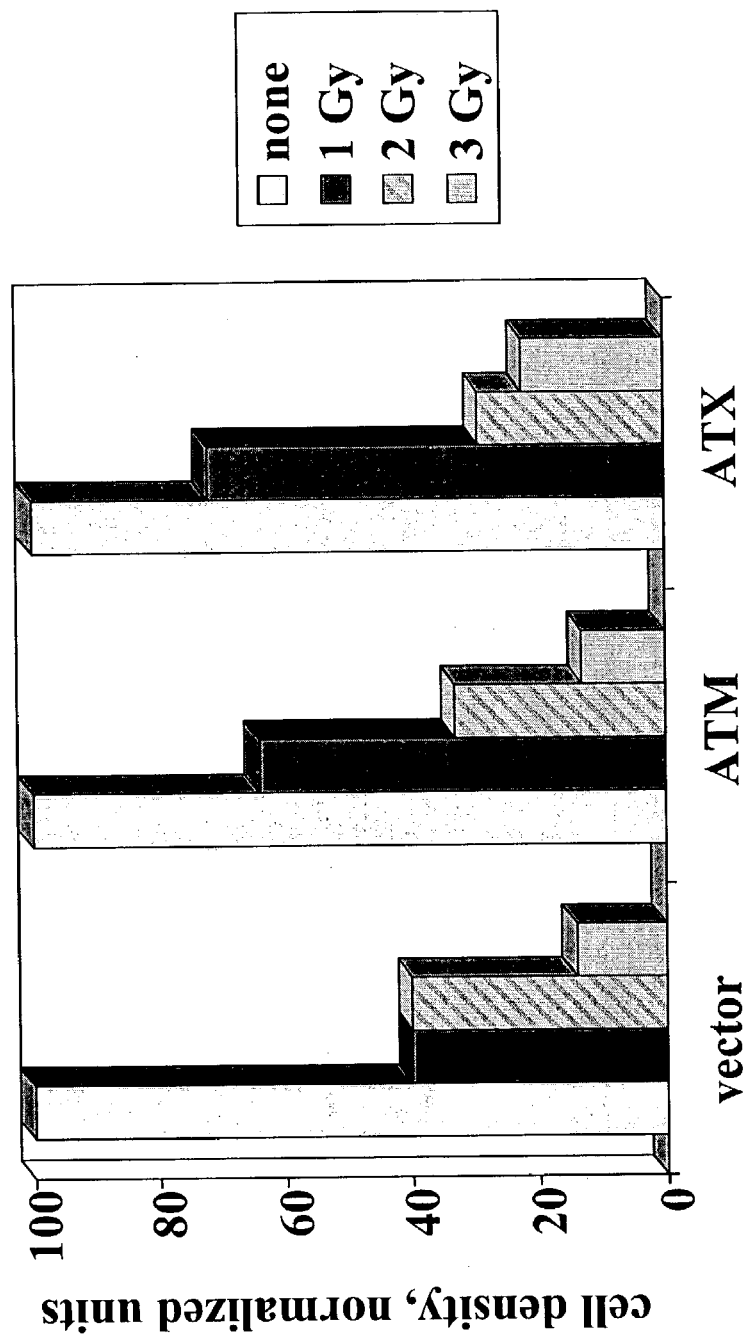

Based on the finding that ATM and ATX display overlapping functions as activators of p53, it was investigated whether ATX overexpression can complement the phenotypic defects found in cells from A-T patients. One characteristic defect of cells from A-T patients is reduced clonogenic survival in culture, even in the absence of DNA dsb-inducing agents (Rotman and Shiloh, *Oncogene* 18:6135–6144 (1998)). As shown in FIG. 4 A, transient transfection of ATM-null AT4BI cells with an ATM expression plasmid increased the outgrowth of G418-resistant colonies by approximately 2-fold, relative to cells transfected with empty vector. The clonogenic defect of AT4BI cells was partially rescued (approximately 1.5-fold increase in colony survival) by transient expression of ATX. Thus, ATX overexpression partially complements the intrinsic clonogenic survival defect of ATM-null cells. Furthermore, low-dose (1 Gy) IR treatment sharply reduced the clonogenic survival of mock-transfected AT4BI cells, and this radiosensitive phenotype was rescued to equivalent degrees by transfection of the cells with ATM or ATX (FIG. 4B). Thus, overexpression of ATX complements, at least in part, the stress response defects observed in cells from A-T patients.

EXAMPLE 9

Roles of ATX and ATM in hUpf1 Phosphorylation and NMD

The Upf1 helicase undergoes serum-inducible phosphorylation in intact cells, as demonstrated by two-dimensional (2-D) gel electrophoresis (Pal et al., supra, 2001). Based on the evidence disclosed herein that ATX is a UV-responsive kinase, the possibility that UV light exposure triggers the phosphorylation of hUpf1 in ATXWT-transfected U2OS cells was investigated. Serum stimulation or UV treatment induced virtually identical shifts in the 2-D electrophoretic mobility of hUpf1, which indicates that these agents provoke the phosphorylation of this protein at similar sites (data not shown). In contrast, expression of the catalytically-inactive ATXKI protein blocked the appearance of the most highly shifted form of hUpf1, and caused the accumulation of a broad band with intermediate electrophoretic mobility. The latter hupf1 species can be less phosphorylated forms of the protein. Thus, overexpression of ATXKI interferes with both the serum- and UV-induced phosphorylation of hupf1; however, these results also indicate that the hUpf1 is targeted by at least one additional protein kinase in these cells.

Figure 5:
FIG. 5A shows cells transfected with GAL4 or GAL4-hUpf11019-1118 expression constructs with the indicated samples treated with wortmannin. The right panel shows phosphatase treatment. The soluble proteins were separated by SDS-PAGE and immunoblotted with α-GAL4 mAb. The arrow indicates the uppermost band of the phosphorylated GAL4-hUpf11019-1118 reporter protein.
FIG. 5B shows an effect of ATMKI or ATXKI expression on UV stimulation of GAL4-hUpf1 phosphorylation.
Figure 5:
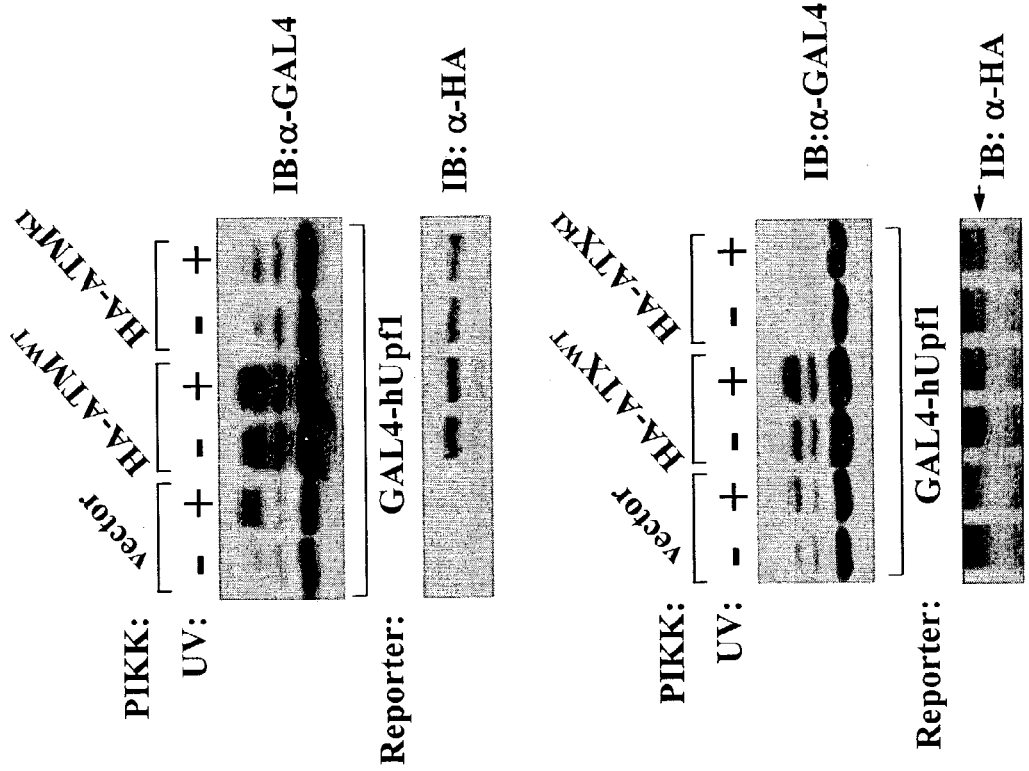

Based on the functional overlap between ATM and ATX during stress-induced p53 activation, it was possible that these PIKKs might also share the ability to regulate the RNA surveillance pathway leading to NMD. To focus our studies of hUpf1 phosphorylation on the Ser-Gln-rich region, a mammalian expression vector encoding GAL4 fused to the carboxyl terminus (amino acids 1019–1118) of hupf1 (GAL4-hUpf11019–1118) was generated. Expression of GAL4-hUpf11019–1118 in U2OS cells generates a major immunoreactive band that migrates with a molecular mass of ~35 kDa in serum-starved cells. Stimulation of the transfected cells with 10% fetal bovine serum or UV light leads to the increased expression of forms of GAL4 hUpf11019–1118 that display reduced electrophoretic mobility (FIG. 5A, left panel). In this experiment, cells were harvested at 6 h after serum or UV exposure; however, the GAL4-hUpf11019–1118 mobility shifts could be detected as early as 2 h after cellular stimulation with either agent. The appearance of these shifted GAL4-hUpf11019–1118 bands is due to phosphorylation, as treatment of the cell extracts with λphosphatase collapses the complex pattern of α-Gal4-reactive species into the major ~35 kDa band, which represents non-phosphorylated GAL4-hUpf11019–1118 (FIG. 5A, right panel). Moreover, the observed GAL4-hUpf11019–1118 mobility shifts were due to phosphorylation of the hUpf1 fragment, as the electrophoretic mobility GAL4 alone was not altered by cellular exposure to serum or UV (FIG. 5A, lower panel). In the experiment shown in FIG. 5A (left panel), selected samples were pretreated with 20 µM wortmannin in order to inhibit endogenous ATX and ATM kinase activities (Sarkaria et al., supra, 1998)). In the wortmannin-treated cells, the FBS- or UV-induced generation of the most slowly migrating form of GAL4-hUpf11019–1118 (indicated with an arrow) was preferentially inhibited. This drug effect was accompanied by an increase in the abundance of the less shifted bands, which can represent less phosphorylated forms of GAL4-hUpf11019–1118. These results indicate that, although a wortmannin-sensitive protein kinase(s) contributes to the inducible phosphorylation of the GAL4-hUpf11019–1118 reporter protein, the hupf1 carboxyl-terminal region is also targeted for modification by at least one additional, wortmannin-resistant protein kinase.

To further examine the contributions of ATM and ATX to the phosphorylation of GAL4-hUpf11019–1118, U2OS cells were cotransfected with wild-type (WT) or kinase-inactive (KI) versions of HA-ATM or HA-ATX. Expression of either HA-ATMKI or HA-ATXKI strongly suppressed the phosphorylation of GAL4-hUpf11019–1118 in cells treated with UV light (FIG. 5B) or serum (data not shown). Expression of the catalytically active HA-ATMWT or HA-ATXWT proteins enhanced the phosphorylation of GAL4-hUpf11019–1118 in both unstimulated and stimulated cells. The latter results add further support to the notion that ATX and ATM are capable of phosphorylating hupf1 carboxyl-terminal region in intact cells. In these experiments, the HA-tagged ATM and ATX proteins were overexpressed by approximately 2- and 1.5-fold, respectively, when compared to their endogenous counterparts (data not shown).

Figure 6:
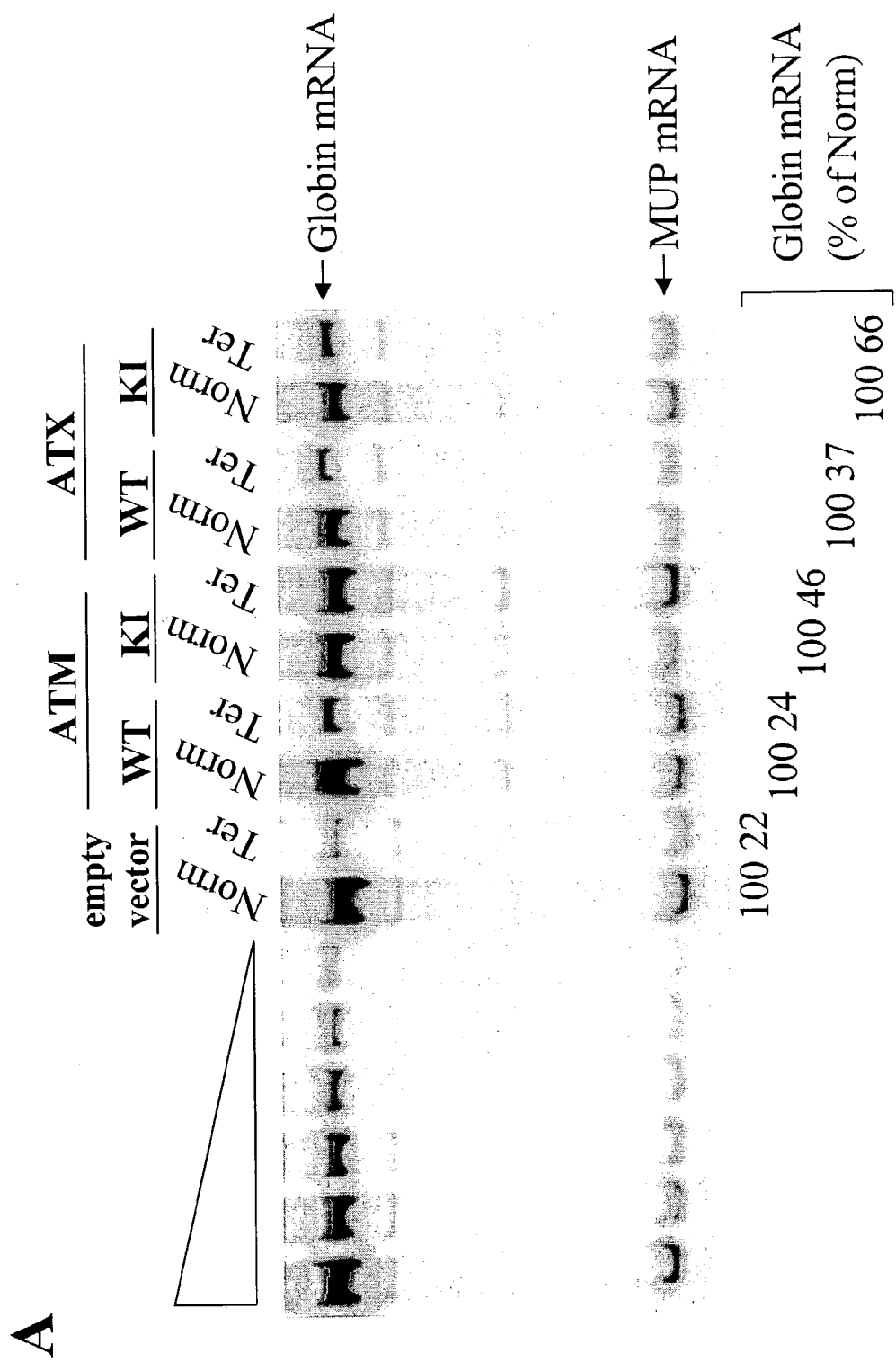
FIG. 6A shows an effect of HA-ATXKI or HAATMKI expression on NMD. Nuclear RNA was isolated from transfected cells and β-globin and MUP mRNAs were quantitated by RT-PCR and PhosphorImaging. For each pair of transfections, the level of Globin mRNA was normalized to the level of MUP mRNA and expressed below each lane as a percentage of the normalized level of Globin Norm mRNA, which was defined as 100.
FIG. 6B shows an effect of ATX AS oligonucleotide on NMD.
Figure 6:
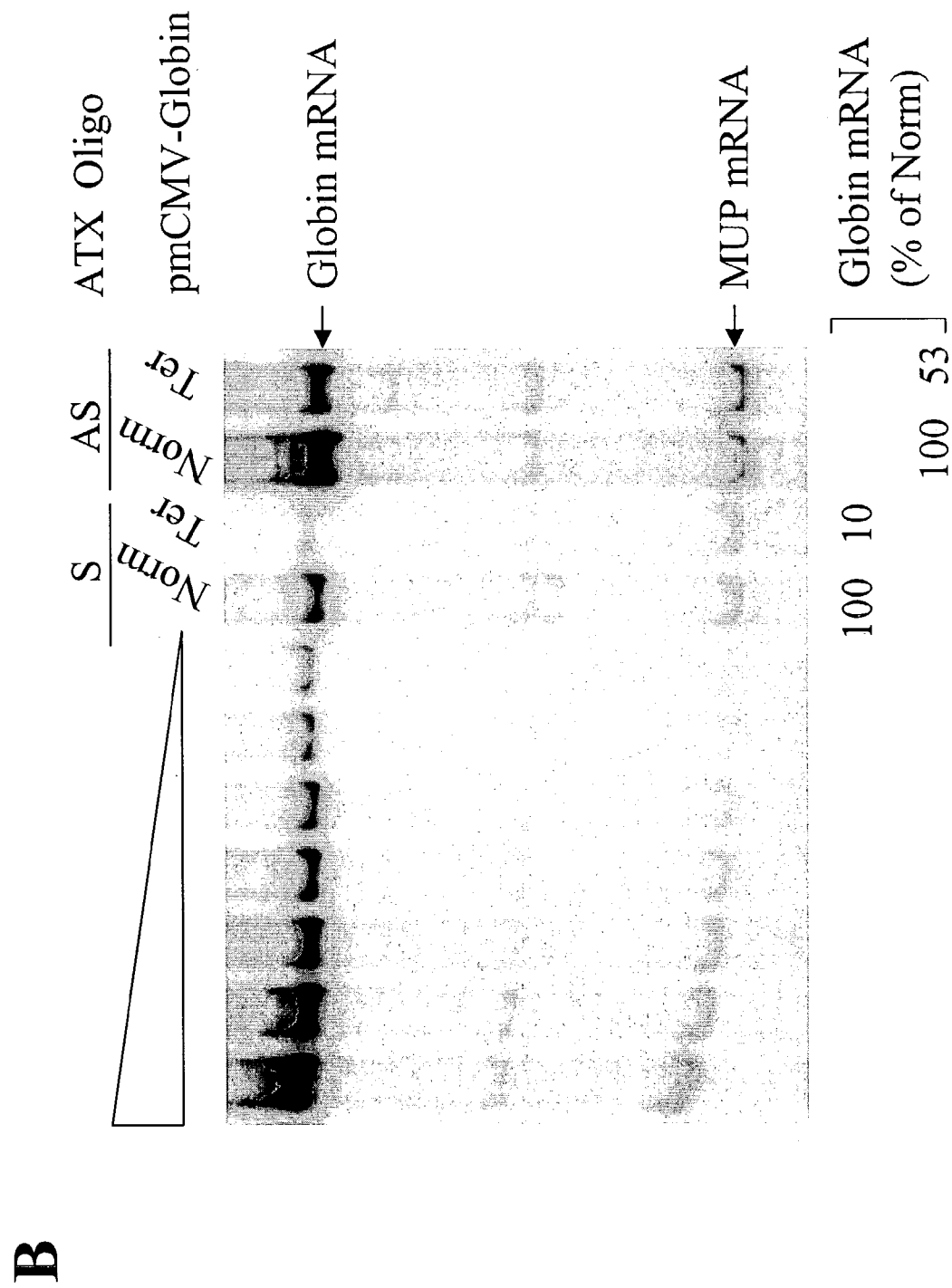

In addition, the effects of HA-ATXKI and HA-ATMKI overexpression on NMD were comparatively examined using an established assay (Sun et al., Proc. Natl. Acad. Sci. USA 95:10009–1998). U2OS cells were transfected with a plasmid encoding either the normal human β-globin gene (Norm) or a mutated β-globin gene bearing a premature termination codon (Ter), together with a reference plasmid encoding the mouse urinary protein (MUP). Where indicated, the cells were co-transfected with empty vector, or expression vectors encoding wild-type or kinase-inactive versions of ATM (HA-ATMWT, HA-ATMKI) or ATX (HA-ATXWT, HA-ATXKI) (FIG. 6A). Expression of the kinase-inactive HA-ATMKI or HA-ATXKI proteins abrogated NMD of the Ter-containing β-globin mRNA. Furthermore, treatment of the cells with the AS oligonucleotide to reduce endogenous ATX expression confirmed that ATX expression is required for maximal NMD activity under these assay conditions (FIG. 6B). Collectively, these results indicate that ATM and ATX function as shared components of the pathways leading to both NMD and p53 activation during UV- and IR-induced stress.

Methods:

Construction of GST and GAL4-hUpf1 Fusion Proteins

The hUpf11019–1118-BamHI fragment was generated by PCR amplification of full-length hUpf1 using the following primers: 5'-AGGAGGGGATCCGGACGCCAGAAGAAC-CGCTTTGGG-31, 5'-AGGAGGGGATCCATACTGGGA-CAGCCCCGTCAC-3'. This fragment was subcloned into the BamHI site of pGEX-2T and pCMX-GAL4(N) to generate the GSThUpf11019–1118 and GAL4-hUpf11019–1118 fusion proteins, respectively.

GAL4-hUpf1 Mobility Shift Assays

U2OS cells were plated in 60 mm dishes (4×105 cells per dish), and then transfected with 0.5 µg pCMX-GAL4 or pCMX-GAL4-hUpf11019–1118, together with 4.5 µg pcDNA3.1-HA-ATXWT, HA-ATXKI, HA-ATMWT, or HA-ATMKI plasmid DNAs. The HA-ATMKI protein contains an Asp-2870>Ala mutation that inactivates the kinase domain. Twenty hours after transfection, serum was removed from the medium, and the cells were cultured for an additional 24 h. The cells were then treated with 10% fetal bovine serum or 100 J/m2 UV-B. Where indicated, the serum-starved cells were pretreated for 30 min with 20 µM wortmannin prior to treatment with serum or UV. Cells were harvested in lysis buffer containing 25 mM Hepes, pH 7.4, 300 mM NaCl, 1.5 mM MgCl2, 1 mM EGTA, 1% Triton X-100, 20 mM β-glycerophosphate, 20 nM microcystin, 0.1 mM sodium orthovanadate, 1 mM DTT, plus protease inhibitors. For phosphatase treatment, 600 U λ phosphatase was added to cellular extracts (New England Biolabs). Cell extracts were resolved on by SDS-PAGE, and were immunoblotted with α-GAL4 antibody.

RNA Isolation and Assays of NMD

Total or nuclear RNA was isolated using Trizol (Invitrogen) or the NE-PER kit (Pierce), respectively. The extent of NMD was determined by using RT-PCR to quantitate the levels of Globin and MUP mRNA as described previously (Ishigaki et al., Cell 83: 1–4 (2001)), except that 21 cycles of PCR were used when analyzing the effects of ATX-specific S and AS oligonucleotides.

EXAMPLE 10

Decreased Expression of ATX Results in Spontaneously Increased DNA Damage

Figure 7:
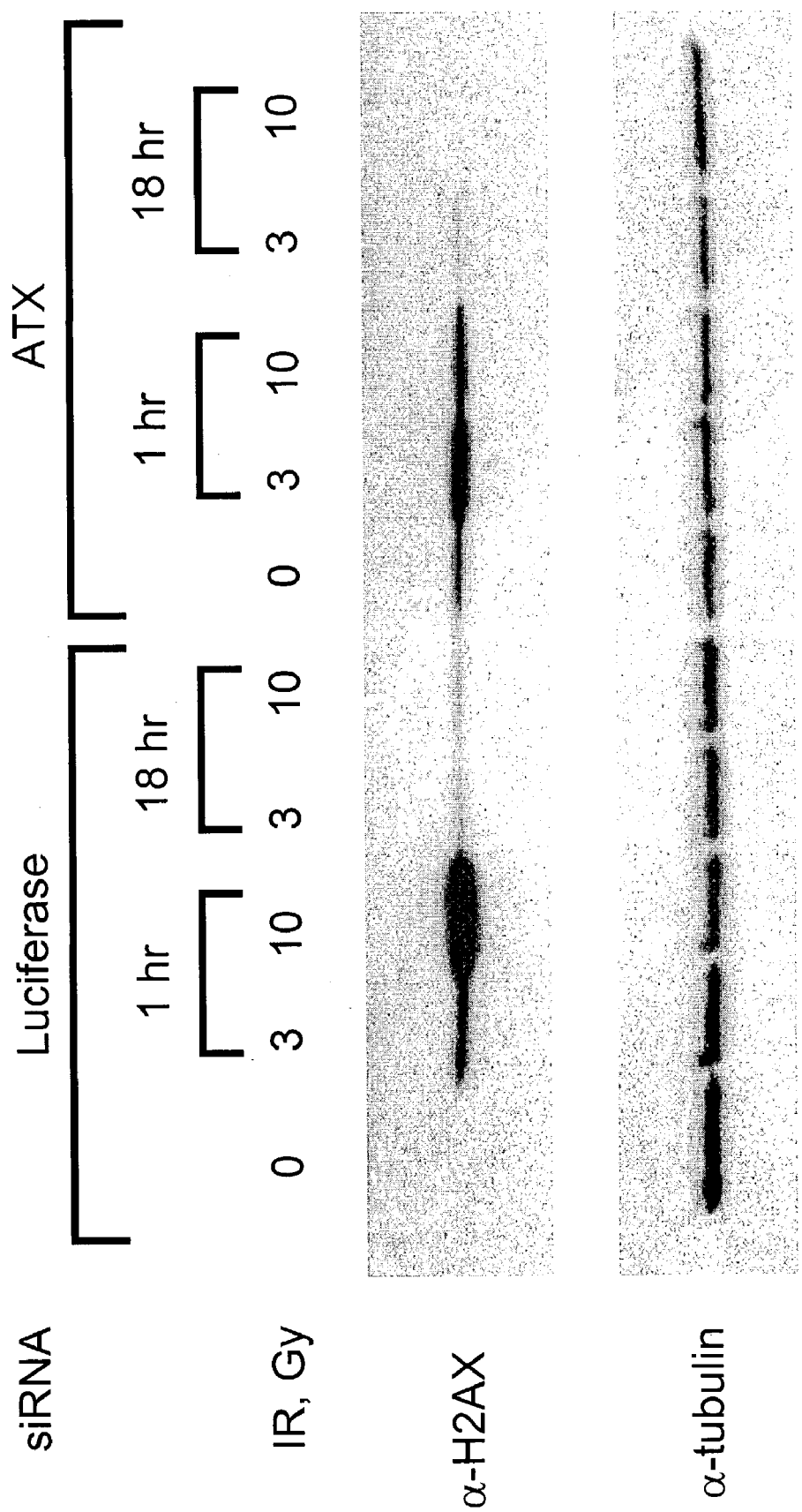
FIG. 7 shows the effect of small-interfering (si) RNA reduction of ATX on response to ionizing radiation (IR). U2OS cells transfected with si RNA directed against luciferase (control) or ATX were treated with different doses of ionizing radiation and lysed after 1 hour or 18 hours. Cellular extracts were separated by SDS-PAGE and immunoblotted with an anti-phospho-Histone H2AX antibody. The level of a control polypeptide, α-tubulin, is shown in the lower panel for comparison.

U2OS osteosarcoma cells were treated with small-interfering (si) RNA directed against luciferase (control) or ATX. The siRNA consistently induces a >80% decrease in the expression of ATX protein at day 3 post-transfection. The transfected cells were treated with 0, 3, or 10 Gy ionizing radiation (IR), and then lysed after either 1 hour or 18 hours. The cell extracts were separated by SDS-PAGE and immunoblotted with an anti-phospho-Histone H2AX antibody. A significant increase in phospho-Histone H2AX immunoreactivity in 0 Gy IR-treated cells exposed to the ATX siRNA relative to the corresponding luciferase siRNA-transfected control cells was detected (see FIG. 7). The level of a control polypeptide, α-tubulin, was also determined to show equal loading of each lane.

The appearance of phospho-Histone H2AX marks DNA double-strand breaks or other forms of DNA damage, as indicated by the strong induction of immunoreactivity in IR-treated cells. These results indicate that ATX-deficient cells can spontaneously develop DNA damage. Furthermore, the compromised phosphorylation of Histone H2AX observed in IR-treated, ATX-deficient cells indicates that loss of ATX function can also compromise DNA damage recognition and/or repair in mammalian cells.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention.

What is claimed is:

1. An isolated nucleic acid molecule, comprising a nucleotide sequence referenced as SEQ ID NO: 1.

2. The isolated nucleic acid molecule of claim 1, wherein said nucleic acid molecule encodes a polypeptide comprising an amino acid sequence shown in SEQ ID NO:2.

3. A vector, comprising the isolated nucleic acid molecule of claim 1.

4. A host cell, comprising the vector of claim 3.

5. A method of producing a polypeptide comprising:
a) growing the host cell according to claim 4 under conditions appropriate for expression of the polypeptide, and
b) isolating the polypeptide from the host cell or host cell growth medium.

6. An isolated oligonucleotide, consisting of at least contiguous nucleotides of a nucleotide sequence referenced as SEQ ID NO: 11.

* * * * *

UNITED STATES PATENT AND TRADEMARK OFFICE
CERTIFICATE OF CORRECTION

| | | |
|---|---|---|
| PATENT NO. | : 7,166,716 B2 | Page 1 of 1 |
| APPLICATION NO. | : 10/456238 | |
| DATED | : January 23, 2007 | |
| INVENTOR(S) | : Robert T. Abraham et al. | |

It is certified that error appears in the above-identified patent and that said Letters Patent is hereby corrected as shown below:

Column 206, claim 6, line 1, after "least" and before "contiguous" please insert --15 --.

Signed and Sealed this

Third Day of July, 2007

JON W. DUDAS
*Director of the United States Patent and Trademark Office*

UNITED STATES PATENT AND TRADEMARK OFFICE
CERTIFICATE OF CORRECTION

PATENT NO. : 7,166,716 B2  Page 1 of 1
APPLICATION NO. : 10/456238
DATED : January 23, 2007
INVENTOR(S) : Robert T. Abraham et al.

It is certified that error appears in the above-identified patent and that said Letters Patent is hereby corrected as shown below:

Title Page;
At Assignee (73) on the cover sheet, please correct the Assignee data to read as follows:

The Burnham Institute, La Jolla, CA (US)
Duke University, Durham, NC (US)

Signed and Sealed this

Eighth Day of September, 2009

David J. Kappos
*Director of the United States Patent and Trademark Office*